(12) United States Patent
Lewis et al.

(10) Patent No.: US 12,331,100 B2
(45) Date of Patent: *Jun. 17, 2025

(54) EXOSOMES FOR IMMUNO-ONCOLOGY AND ANTI-INFLAMMATORY THERAPY

(71) Applicant: LONZA SALES AG, Basel (CH)

(72) Inventors: Nuruddeen D. Lewis, Andover, MA (US); Yu Zhou, Somerville, MA (US); Sriram Sathyanarayanan, Lexington, MA (US); John Kulman, Belmont, MA (US); Douglas E. Williams, Boston, MA (US); Leonid A. Gaydukov, Tewksbury, MA (US); Ke Xu, Belmont, MA (US); Shelly Martin, Stoneham, MA (US)

(73) Assignee: LONZA SALES AG, Basel (CH)

( * ) Notice: Subject to any disclaimer, the term of this patent is extended or adjusted under 35 U.S.C. 154(b) by 63 days.

This patent is subject to a terminal disclaimer.

(21) Appl. No.: 18/049,999

(22) Filed: Oct. 26, 2022

(65) Prior Publication Data

US 2024/0010705 A1 Jan. 11, 2024

Related U.S. Application Data

(60) Division of application No. 16/921,351, filed on Jul. 6, 2020, now Pat. No. 12,030,924, which is a continuation of application No. 16/236,246, filed on Dec. 28, 2018, now Pat. No. 10,723,782.

(60) Provisional application No. 62/723,267, filed on Aug. 27, 2018, provisional application No. 62/611,140, filed on Dec. 28, 2017.

(51) Int. Cl.
| | |
|---|---|
| *C07K 14/52* | (2006.01) |
| *A61K 39/00* | (2006.01) |
| *C07K 14/47* | (2006.01) |
| *C07K 14/475* | (2006.01) |
| *C07K 14/54* | (2006.01) |
| *C07K 14/57* | (2006.01) |
| *C07K 14/705* | (2006.01) |
| *C07K 14/715* | (2006.01) |
| *C07K 16/28* | (2006.01) |

(52) U.S. Cl.
CPC ...... *C07K 14/7151* (2013.01); *C07K 14/4703* (2013.01); *C07K 14/475* (2013.01); *C07K 14/52* (2013.01); *C07K 14/5418* (2013.01); *C07K 14/5434* (2013.01); *C07K 14/5443* (2013.01); *C07K 14/57* (2013.01); *C07K 14/70532* (2013.01); *C07K 14/70575* (2013.01); *C07K 14/70578* (2013.01); *C07K 14/7155* (2013.01); *C07K 16/2809* (2013.01); *C07K 16/2818* (2013.01); *A61K 2039/505* (2013.01); *A61K 2039/6018* (2013.01); *A61K 2039/627* (2013.01); *C07K 2317/622* (2013.01); *C07K 2317/76* (2013.01); *C07K 2319/00* (2013.01); *C07K 2319/02* (2013.01); *C07K 2319/03* (2013.01); *C07K 2319/31* (2013.01); *C07K 2319/60* (2013.01)

(58) Field of Classification Search
None
See application file for complete search history.

(56) References Cited

U.S. PATENT DOCUMENTS

| | | |
|---|---|---|
| 5,747,660 A | 5/1998 | Orlicky |
| 7,704,964 B2 | 4/2010 | Delcayre et al. |
| 9,518,125 B2 | 12/2016 | Yong et al. |
| 10,195,290 B1 | 2/2019 | Dooley |
| 10,561,740 B2 | 2/2020 | Dooley |
| 10,723,782 B2 | 7/2020 | Lewis et al. |
| 2004/0049010 A1 | 3/2004 | Warren et al. |
| 2005/0119215 A1 | 6/2005 | Al-Mahmood et al. |
| 2013/0156801 A1 | 6/2013 | Bond et al. |
| 2013/0280265 A1 | 10/2013 | Rolland et al. |
| 2014/0179006 A1 | 6/2014 | Zhang |
| 2015/0174166 A1 | 6/2015 | Giampapa |
| 2015/0190429 A1 | 7/2015 | Beelen et al. |
| 2015/0290343 A1 | 10/2015 | Lotvall et al. |
| 2015/0301058 A1 | 10/2015 | Schettini et al. |
| 2017/0173076 A1 | 6/2017 | Greco et al. |
| 2017/0182182 A1 | 6/2017 | Seow et al. |
| 2017/0258845 A1 | 9/2017 | Lim |
| 2017/0333479 A1 | 11/2017 | Copik et al. |
| 2017/0335281 A1 | 11/2017 | Loew et al. |
| 2018/0042847 A1 | 2/2018 | Ross |
| 2018/0128833 A1 | 5/2018 | Selvaraj et al. |

FOREIGN PATENT DOCUMENTS

| | | |
|---|---|---|
| WO | 2001093836 A3 | 10/2002 |
| WO | 2007053648 A2 | 5/2007 |
| WO | 2007126386 A1 | 11/2007 |
| WO | 2012048372 A1 | 4/2012 |
| WO | 2014138793 A1 | 9/2014 |

(Continued)

OTHER PUBLICATIONS

Bellavia, D. et al., "Interleukin 3-receptor targeted exosomes inhibit in vitro and in vivo Chronic Myelogenous Leukemia cell growth," Theranostics 7(5):1333-1345 (2017).

(Continued)

*Primary Examiner* — Daniel C Gamett
(74) *Attorney, Agent, or Firm* — MEDLER FERRO WOODHOUSE & MILLS PLLC

(57) ABSTRACT

Disclosed herein are extracellular vesicles comprising an immunomodulating component. Also provided are methods for producing the extracellular vesicles and methods for using the extracellular vesicles for treating cancer, GvHD, and autoimmune diseases.

20 Claims, 53 Drawing Sheets
Specification includes a Sequence Listing.

(56) References Cited

FOREIGN PATENT DOCUMENTS

| | | | |
|---|---|---|---|
| WO | 2016057755 A1 | 4/2016 | |
| WO | 2016077639 A2 | 5/2016 | |
| WO | 2016168860 A1 | 10/2016 | |
| WO | 2017078385 A1 | 5/2017 | |
| WO | 2017117585 A1 | 7/2017 | |
| WO | 2017161010 A1 | 9/2017 | |
| WO | 2018226758 A2 | 12/2018 | |
| WO | 2019040920 A1 | 2/2019 | |
| WO | 2019133934 A2 | 7/2019 | |

OTHER PUBLICATIONS

Chen, G. et al., "Exosomal PD-L 1 contributes to immunosuppression and is associated with anti-PD-1 response," Nature 560(7718)382-386 (2018).

Corpet, F., "Multiple sequence alignment with hierarchical clustering," Nuc Acids Res 16(22):10881-10890 (1988).

Ding, X. et al., "Chapter 47—Extended-Release and Targeted Drug Delivery Systems" in Remington: The Science and Practice of Pharmacy, Troy, D., Ed., 2151 Edition, pp. 939, 950-953, Lippincott Williams & Wilkins, United States (Jul. 2005).

Ghazawi, F.M. et al., "IL-7 downregulates IL-7Ra expression in human CDS T cells by two independent mechanisms," Immunology and Cell Biology 91(2):149-158 (2013).

Higgins, D.G., and Sharp, P.M., "Clustal: a package for performing multiple sequence alignment on a microcomputer," Gene 73(1):237-244 (1988).

Huang, X. et al., "Parallelization of a local similarity algorithm," Computer Applications in the BioSciences (CABIOS) 8:155-165 (1992).

International Search Report and Written Opinion for International Application No. PCT/US2018/068062, ISA, United States, mailed Jul. 12, 2019, 11 pages.

Kooijmans, S.A.A. et al., "Modulation of tissue tropism and biological activity of exosomes and other extracellular vesicles: New nanotools for cancer treatment," Pharmacological Research 111:487-500 (2016).

Kordelas et al., "MSC-derived exosomes: a novel tool to treat therapy-refractory graft-versus-host disease," Leukemia 28:970-973 (2014).

Kuypers, F.A., et al., "Survival of Rabbit and Horse Erythrocytes in Vivo after Changing the Fatty Acyl Composition of their Phosphatidylcholine," Biochimica et Biophysica Acta 819(2):170-178 (1985).

Lai, R.C. et al., "Mesenchymal Stem Cell Exosome: a Novel Stem Cell Based Therapy for Cardiovascular Disease," Regenerative Medicine 6(4):481-492 (2011).

Lehninger, A.L., "Chapter 7—Proteins: Purification and Characterization" in Biochemistry: The Molecular Basis of Cell Structure and Function, 2nd Edition, pp. 157-182, Worth Publishers Inc., United States (Jul. 1975).

Leonard, J.P et al., "Effects of single-dose interleukin-12 exposure on interleukin-12-associated toxicity and interferon-y production," Blood 90(7):2541-2548 (1997).

Moss, M. et al. "Shedding of Membrane Proteins by ADAM Family Proteases." Essays In Biochemistry 38:141-154 (2002).

Needleman, S.B. and Wunsch, C.D., "A General Method Applicable to the Search for Similarities in the Amino Acid Sequence of Two Proteins," Journal of Molecular Biology 48(3):443-453 (1970).

Office Action mailed Mar. 28, 2019 in U.S. Appl. No. 16/231,012, Dooley, Kevin P., et al., filed Dec. 21, 2018, 4 pages.

Papapetrou, E.P. et al., "Genetic Modification of Hematopoietic Stem Cells With Nonviral Systems: Past Progress and Future Prospects", Gene Therapy 12(Supplement 1):S118-S130 (2005).

PCT International Search Report and Written Opinion, PCT Application No. PCT/US2018/048026, Oct. 30, 2018, 23 pages.

Pearson, W.R., and Lipman, D.J., "Improved tools for biological sequence comparison," PNAS 85(8):2444-2448 (1988).

Raposo, G. et al. "B Lymphocytes Secrete Antigen-presenting Vesicles", Journal of Experimental Medicine 183(3):1161-1172 (1996).

Senti G., et al. "Intralymphatic Allergen Administration Renders Specific Immunotherapy Faster and Safer: a Randomized Controlled Trial," Proc Natl Acad Sci USA 105(46): 17908-17912, National Academy of Sciences, United States (Apr. 2008).

Smith, T.F., and Waterman, M.S., "Comparison of biosequences," Advances in Applied Mathematics 2(4):482-498 (1981).

Yang, J. et al., "Exosome Mediated Delivery of miR-124 Promotes Neurogenesis after Ischemia," Molecular Therapy Nucleic Acids 7:278-287 (2017).

Zhu, X., et al., "Novel human interleukin-15 agonists," J Immunol 183(6):3598-3607 (2009).

Zitvogel, L. et al. "Eradication of established murine tumors using a novel cell-free vaccine: dendritic cell-derived exosomes", Nature Medicine, 4(5):594-600 (1998).

Hiraiwa, H. et al., "Elucidation of correspondence between swine chromosome 4 and human chromosome 1 by assigning 27 genes to the ImpRH map, and development of microsatellites in the proximity of 14 genes", Cytogenetic and Genome Research 101(1):84-89 (2003).

Luan, X. et al. "Engineering exosomes as refined biological nanoplatforms for drug delivery", Acta pharmacologica Sinica (38)6:754-763 (2017).

Sterzenbach, U et al., "Engineered Exosomes as Vehicles for Biologically Active Proteins", Molecular Therapy 25(6):1269-1278 (2017).

Venter, J.C., et al. "Prostaglandin F2 receptor negative regulator, isoform CRA_a [*Homo sapiens*]", GenBank Accession No. EAW56662.1 (2015).

Xie, Y. et al., "A novel T cell-based vaccine capable of stimulating long-term functional CTL memory against B16 melanoma via CD40L signaling", Cellular and Molecular Immunology 10(1):72-77 (2013).

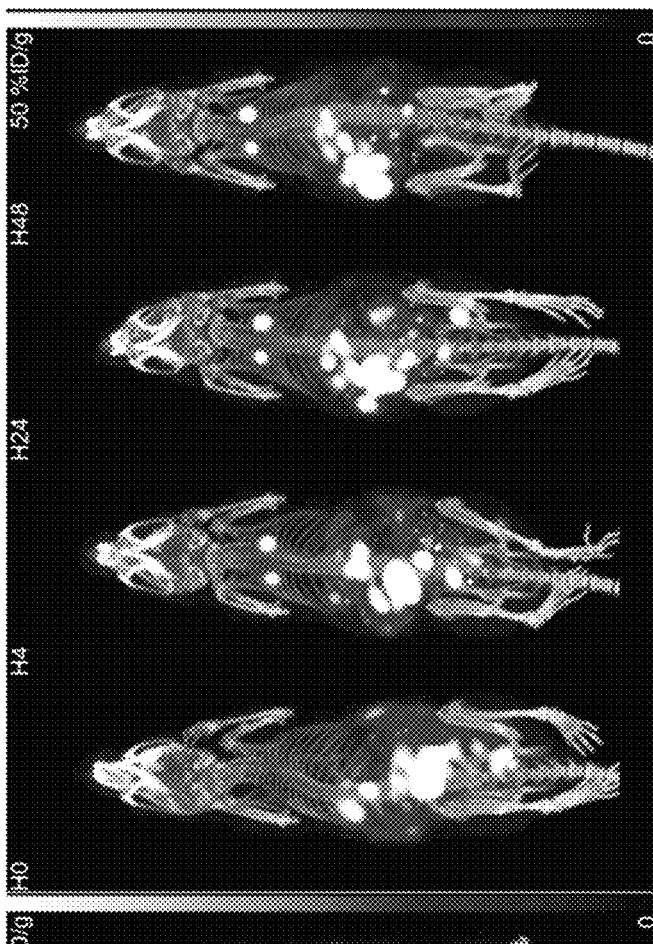
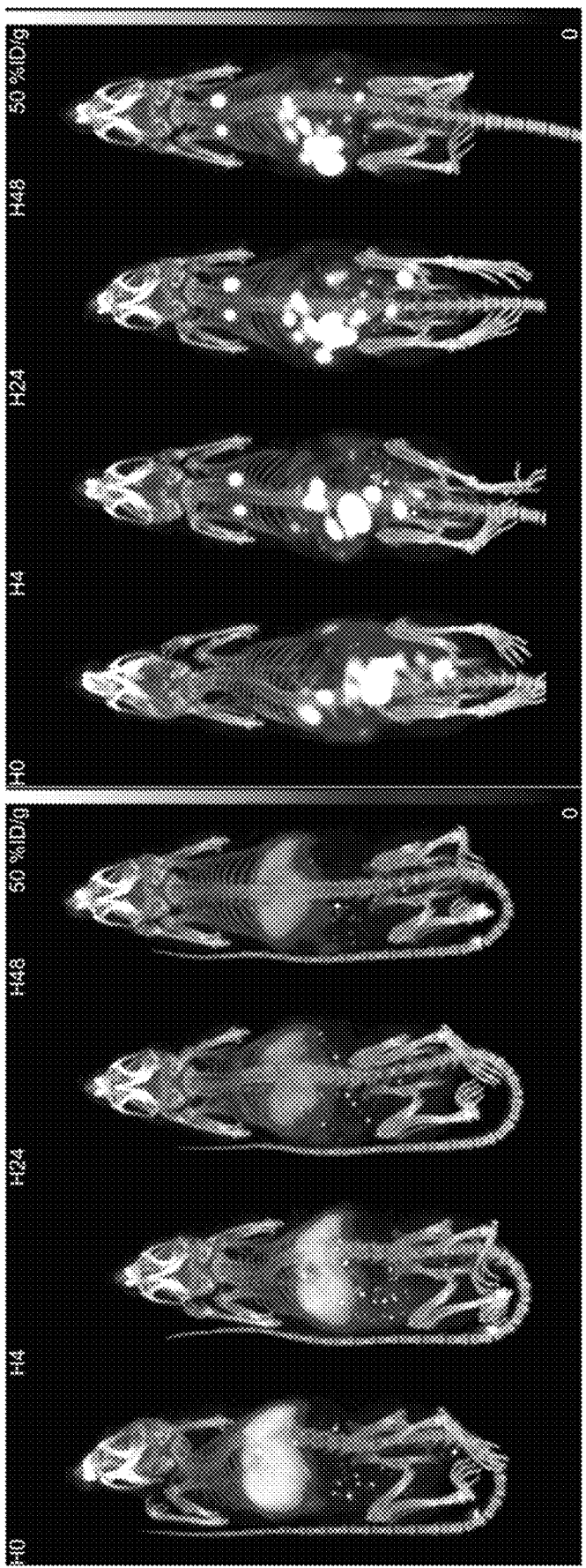
FIGURE 1B
FIGURE 1A

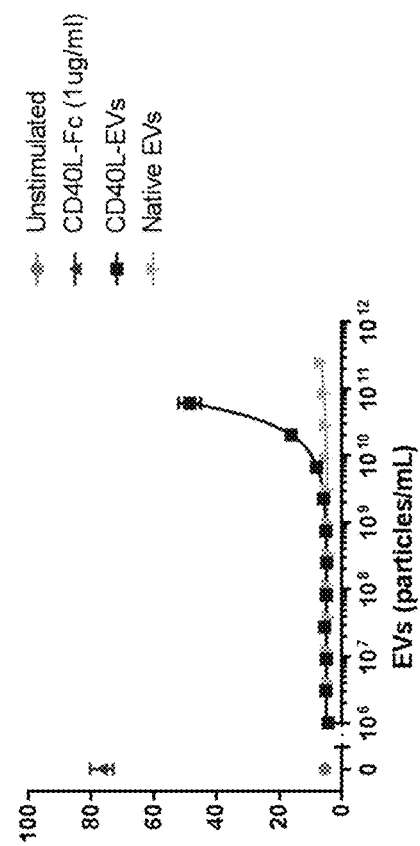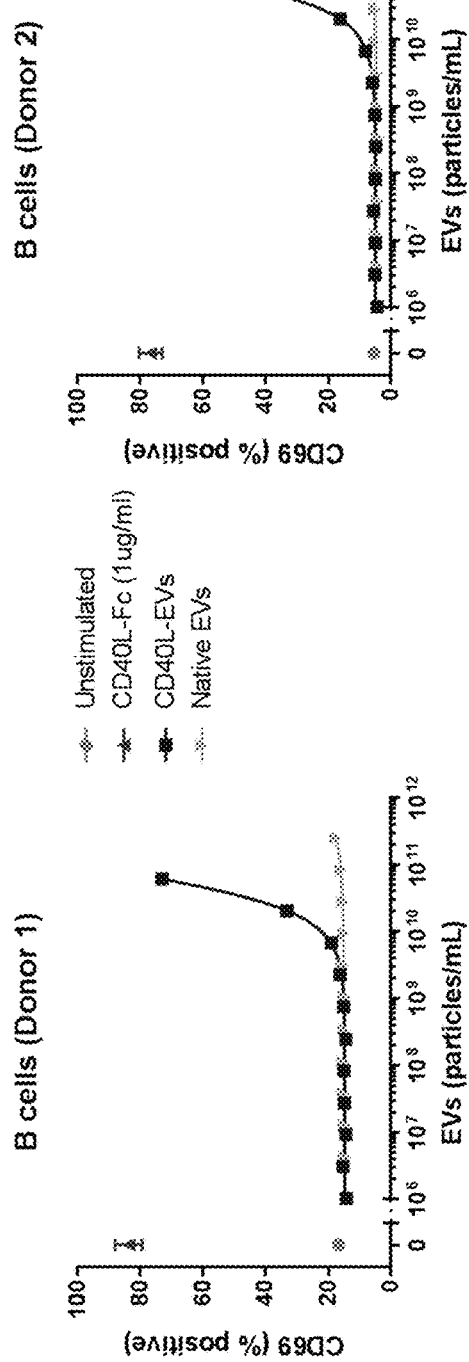
FIGURE 3B
FIGURE 3A

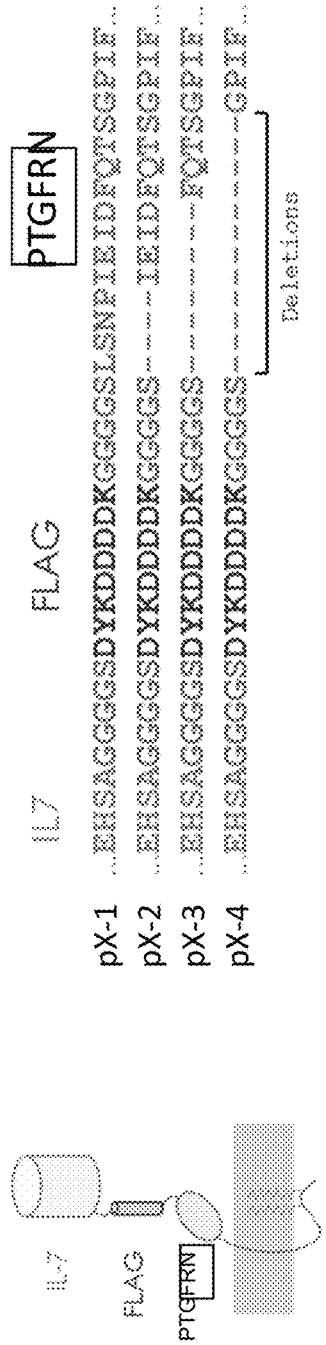

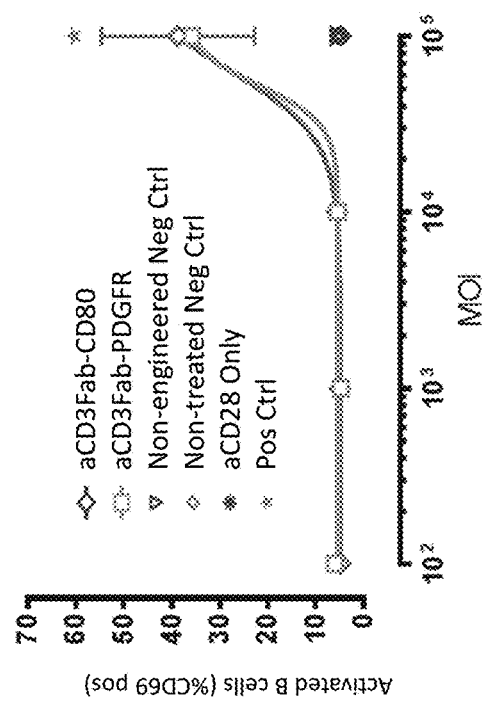
FIGURE 20A
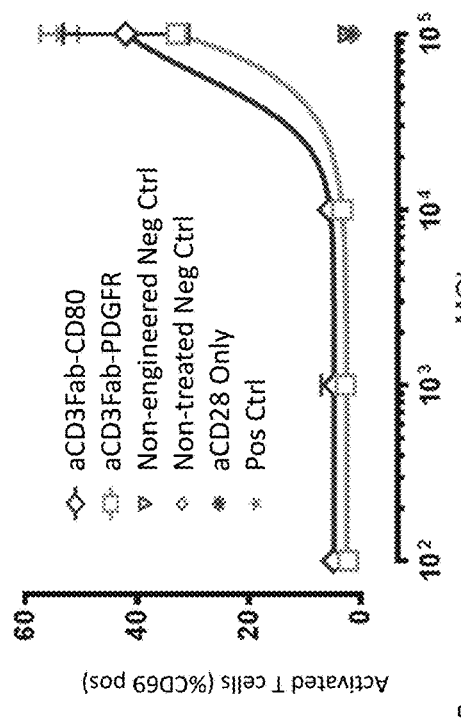
FIGURE 20B
aCD3-Fab Exosomes (with a-CD28 co-stimulation)
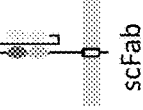

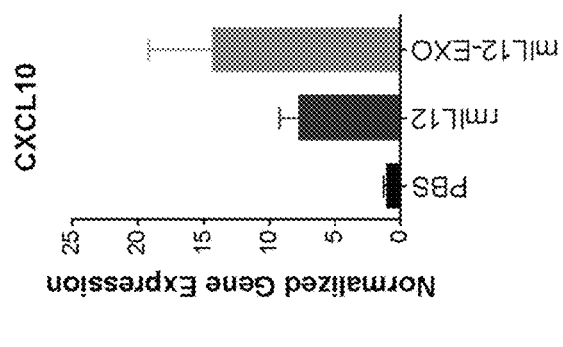
FIGURE 29D
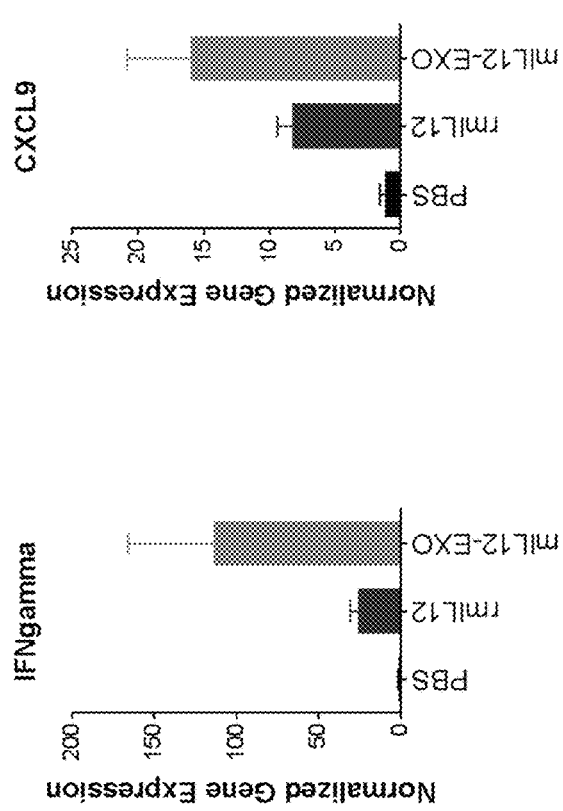
FIGURE 29C
FIGURE 29B
FIGURE 29A

PTGFRN-IFNγ Monomer

PTGFRN-IFNγ Tandem Dimer

FIGURE 48

| EC50 (ng/mL) | rhIL12 | rhIL12+rhCD40L | Exo-hIL12 | Exo-hIL12/CD40L (179) | Exo-hIL12+Exo-hCD40L |
|---|---|---|---|---|---|
| Donor 1 | 0.111 | 0.466 | 0.038 | 0.085 | 0.065 |
| Donor 2 | 0.124 | 0.233 | 0.034 | 0.047 | 0.058 |
| Average | 0.117 | 0.349 | 0.041 | 0.066 | 0.062 |

FIGURE 50

| EC50 (ng/mL) | hCD40L | hIL12+hCD40L* | Exo-hCD40L | Exo-hIL12/CD40L (1:79) | Exo-hIL12+Exo-hCD40L* |
|---|---|---|---|---|---|
| Donor 1 | 70.08 | 124.9 | 2.518 | 1.034 | 2.441 |
| Donor 2 | 91.75 | 64.76 | 2.946 | 1.053 | 2.939 |
| Average | 80.915 | 94.830 | 2.732 | 1.044 | 2.690 |

EXOSOMES FOR IMMUNO-ONCOLOGY AND ANTI-INFLAMMATORY THERAPY

CROSS REFERENCE TO RELATED APPLICATIONS

This application is a division of U.S. application Ser. No. 16/921,351, filed Jul. 6, 2020, which is a continuation application of U.S. application Ser. No. 16/236,246, filed Dec. 28, 2018 (now U.S. Pat. No. 10,723,782, issued on Jul. 28, 2020), which claims the benefit of U.S. Provisional Application Nos. 62/723,267, filed Aug. 27, 2018; and 62/611,140, filed Dec. 28, 2017, each of which is hereby incorporated by reference in its entirety.

REFERENCE TO SEQUENCE LISTING SUBMITTED ELECTRONICALLY VIA EFS-WEB

The content of the electronically submitted sequence listing (Name: 0132-0252US3_ST26.xml, Size: 44,265 bytes; and Date of Creation: Sep. 25, 2023) submitted in this application is incorporated herein by reference in its entirety.

FIELD OF THE INVENTION

The invention relates to compositions for interacting and modulating the human immune system, methods of making the compositions, and methods of using the compositions to treat cancer, GvHD, and autoimmune diseases.

BACKGROUND

Immunotherapy is the treatment of disease by inducing, enhancing, or suppressing the immune response. Immunotherapy can stimulate the patient's own immune system to attack cancer cells. Cancer immunotherapy usually has fewer side effects than traditional cancer therapies, such as chemotherapy and radiation therapy. Anti-inflammatory immunotherapy can down-regulate the patient's immune system for treating autoimmune diseases and graft-versus-host disease (GvHD). What is needed are improved methods for delivering immunomodulatory molecules to cells and tissues of the body.

SUMMARY

As drug delivery vehicles, extracellular vesicles offer many advantages over traditional drug delivery methods, especially for gene therapy. Systemic delivery of extracellular vesicles results in distribution of these lipid nanoparticles to various tissues. Studies have shown that extracellular vesicles can interact with various cells involved with the modulation of the human immune system. Extracellular vesicles that are selected, enriched, or engineered to deliver therapeutic molecules to activate, suppress, or influence the human immune system can be potent therapeutics for cancer and other immune system related diseases.

Provided herein are compositions comprising extracellular vesicles selected, enriched, or engineered with immunomodulating components that can up-regulate or down-regulate the human immune system, boosting the patient's immune system to fight cancer or suppressing the patient's immune system to alleviate the symptoms of GvHD and autoimmune diseases.

Also provided are methods of producing and utilizing the extracellular vesicles for modulating the human immune system.

Accordingly, in a first aspect, provided herein is a composition, comprising: an extracellular vesicle comprising a cell membrane bounding an enclosed volume, the cell membrane having an interior surface and an exterior surface; and a first immunomodulating component associated with the cell membrane or enclosed within the enclosed volume.

In various embodiments, the first immunomodulating component is an inhibitor for a negative checkpoint regulator or an inhibitor for a binding partner of a negative checkpoint regulator. In some of these embodiments, the negative checkpoint regulator is selected from the group consisting of: cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, and CD73.

In various embodiments, the first immunomodulating component is an activator for a positive co-stimulatory molecule or an activator for a binding partner of a positive co-stimulatory molecule. In some embodiments, the positive co-stimulatory molecule is a TNF receptor superfamily member. In some of these embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TALI, BAFF receptor, ATAR, CD271, CD269, AITR, TROY, CD358, TRAMP, and XEDAR. In some embodiments, the activator for a positive co-stimulatory molecule is a TNF superfamily member. In some of these embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2. In certain embodiments, the TNF superfamily member is CD40L. In certain embodiments, the TNF superfamily member is CD27L. In certain embodiments, the TNF superfamily member is OX40L.

In some embodiments, the positive co-stimulatory molecule is a CD28-superfamily co-stimulatory molecule. In some of these embodiments, the CD28-superfamily co-stimulatory molecule is ICOS or CD28. In some embodiments, the activator for a positive co-stimulatory molecule is ICOSL, CD80, or CD86. In certain embodiments, the activator for a positive co-stimulatory molecule is CD80.

In some embodiments, the first immunomodulating component is a cytokine or a binding partner of a cytokine. In some embodiments, the cytokine is selected from the group consisting of: IL-2, IL-7, IL-10, IL-12, and IL-15. In certain embodiments, the cytokine is IL-7. In certain embodiment, the cytokine is IL-12. In certain embodiments, the cytokine is IL-15.

In some embodiments, the first immunomodulating component is a T-cell receptor (TCR), a T-cell co-receptor, a major histocompatibility complex (MHC), a human leukocyte antigen (HLA), or a derivative thereof.

In some embodiments, the first immunomodulating component is an activator of a T-cell receptor or co-receptor. In certain embodiments, the activator of a T-cell receptor or co-receptor is an activator of CD3, optionally an agonist antibody of CD3.

In some embodiments, the first immunomodulating component is a tumor antigen. In some embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived from a genome sequence of a subject.

In some embodiments, the first immunomodulating component is an agonist or an antagonist of a selected target or activity.

In some embodiments, the first immunomodulating component is an antibody or an antigen-binding fragment.

In some embodiments, the first immunomodulating component is a polynucleotide. In some of these embodiments, the polynucleotide is selected from the group consisting of: an mRNA, a miRNA, an siRNA, an antisense RNA, an shRNA, a lncRNA, and a dsDNA.

In some embodiments, the first immunomodulating component is a protein, a peptide, a glycolipid, or a glycoprotein.

In some embodiments, the first immunomodulating component is expressed as a fusion protein displayed on the exterior surface of said extracellular vesicle. In some embodiments, the fusion protein comprises PTGFRN or a fragment or a variant thereof. In some embodiments, the sequence of the fusion protein is SEQ ID NO: 3.

In some embodiments, the extracellular vesicle is an exosome. In some other embodiments, the extracellular vesicle is a nanovesicle.

In certain embodiments, the composition further comprises a pharmaceutically-acceptable carrier.

In some embodiments, the extracellular vesicle additionally comprises a second immunomodulating component.

In various embodiments, the second immunomodulating component is an inhibitor for a negative checkpoint regulator or an inhibitor for a binding partner of a negative checkpoint regulator. In some of these embodiments, the negative checkpoint regulator is selected from the group consisting of: cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, and CD73.

In various embodiments, the second immunomodulating component is an activator for a positive co-stimulatory molecule or an activator for a binding partner of a positive co-stimulatory molecule. In some embodiments, the positive co-stimulatory molecule is a TNF receptor superfamily member. In some of these embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR. In some embodiments, the activator for a positive co-stimulatory molecule is a TNF superfamily member. In some of these embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2. In certain embodiments, the TNF superfamily member is CD40L. In certain embodiments, the TNF superfamily member is CD27L. In certain embodiments, the TNF superfamily member is OX40L.

In some embodiments, the positive co-stimulatory molecule is a CD28-superfamily co-stimulatory molecule. In some of these embodiments, the CD28-superfamily co-stimulatory molecule is ICOS or CD28. In some embodiments, the activator for a positive co-stimulatory molecule is ICOSL, CD80, or CD86. In certain embodiments, the activator for a positive co-stimulatory molecule is CD80.

In some embodiments, the second immunomodulating component is a cytokine or a binding partner of a cytokine. In some embodiments, the cytokine is selected from the group consisting of: IL-2, IL-7, IL-10, IL-12, and IL-15. In certain embodiments, the cytokine is IL-7. In certain embodiment, the cytokine is IL-12. In certain embodiment, the cytokine is IL-15.

In some embodiments, the second immunomodulating component is a T-cell receptor (TCR), a T-cell co-receptor, a major histocompatibility complex (MHC), a human leukocyte antigen (HLA), or a derivative thereof.

In some embodiments, the second immunomodulating component is an activator of a T-cell receptor or co-receptor. In certain embodiments, the activator of a T-cell receptor or co-receptor is an activator of CD3, optionally an agonist antibody of CD3.

In some embodiments, the second immunomodulating component is a tumor antigen. In some embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived from a genome sequence of a subject.

In some embodiments, the second immunomodulating component is an agonist or an antagonist of a selected target or activity.

In some embodiments, the second immunomodulating component is an antibody or an antigen-binding fragment.

In some embodiments, the second immunomodulating component is a polynucleotide. In some of these embodiments, the polynucleotide is selected from the group consisting of: an mRNA, a miRNA, an siRNA, an antisense RNA, an shRNA, a lncRNA, and a dsDNA.

In some embodiments, the second immunomodulating component is a protein, a peptide, a glycolipid, or a glycoprotein.

In some embodiments, the second immunomodulating component is expressed as a fusion protein displayed on the exterior surface of said extracellular vesicle. In some embodiments, the fusion protein comprises PTGFRN or a fragment or a variant thereof. In some embodiments, the sequence of said fusion protein is SEQ ID NO: 3.

In some embodiments, the second immunomodulating component is different from said first immunomodulating component.

In some embodiments, the extracellular vesicle additionally comprises a third immunomodulating component. In some embodiments, the third immunomodulating component is different from said first and second immunomodulating components.

In another aspect, provided herein is a method of producing the composition. In some embodiments, the method comprises modifying a producer cell with the first, second, and/or third immunomodulating components; obtaining the extracellular vesicle from the producer cell; and optionally isolating the obtained extracellular vesicles. In some other embodiments the method comprises obtaining the extracellular vesicle from a producer cell; isolating the obtained extracellular vesicles; and modifying the isolated extracellular vesicle with the first, second, and/or third immunomodulating components. In certain embodiments, the method further comprises formulating the isolated extracellular vesicles into a pharmaceutical composition.

In another aspect, provided herein is a method of treating cancer in a subject. The method comprises administering to the subject a therapeutically effective amount of the composition, wherein the composition is capable of up-regulating an immune response in the subject, thereby enhancing the tumor targeting of the subject's immune system.

In another aspect, provided herein is a method of treating graft-versus-host disease (GvHD) in a subject. The method comprises administering to the subject a therapeutically effective amount of the composition, wherein the composition is capable of down-regulating an immune response in the subject, thereby alleviating the symptoms of GvHD.

In another aspect, provided herein is a method of treating an autoimmune disease in a subject. The method comprises administering to the subject a therapeutically effective amount of the composition, wherein the composition is capable of down-regulating an immune response in the subject, thereby suppressing the immune activity of the subject.

In another aspect, provided herein is a method of treating or preventing cancer in a subject comprising administering to the subject a therapeutically effective amount of the composition comprising a tumor antigen, wherein the composition is capable of potentiating an immune response to the tumor antigen, thereby enhancing the immune response of the subject to cancer.

In some embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In certain embodiments, the tumor antigen is derived from a reference genome sequence. In certain embodiments, the tumor antigen is derived from a genome sequence of a subject.

BRIEF DESCRIPTION OF THE DRAWINGS

FIGS. 1A and 1B show a time course of mice injected with radio-labeled exosomes. FIG. 1A shows the intravenous route of administration. FIG. 1B shows the intraperitoneal route of administration.

FIGS. 3A and 3B show the effects of B-cell activation in peripheral blood mononuclear cells (PBMCs) from two human donors after incubation with CD40L-expressing exosomes.

FIG. 6A shows the effect of CD80-expressing exosomes on the number of $CD8^+$ T-cells. FIG. 6B shows the effect of CD80-expressing exosomes on the number of $CD4^+$ T-cells.

FIG. 15A shows the effects of IL-7- expressing exosomes on CD8+ T-cell. FIG. 15B shows the effects of IL-7-expressing exosomes on memory CD8+ T-cell.

FIG. 16A shows the effects of IL-7-expressing exosomes on CD8+ T-cell. FIG. 16B shows the effects of IL-7-expressing exosomes on memory CD8+ T-cell.

FIG. 17A shows a schematic of a PTGFRN/IL-7 fusion protein expressed at high density on the surface of an exosome, and variants of the fusion protein. FIG. 17B is the sequence of the optimized PTGFRN/IL-7 fusion protein.

FIG. 20A shows the effects of anti-CD3 scFab exosomes on T-cell activation in PBMCs. FIG. 20B shows the effects of anti-CD3 scFab exosomes on B-cell activation in PBMCs.

FIG. 29A shows the levels of IFNγ gene expression in tumors of mice treated with PBS, rIL-12 or IL-12-PTGFRN exosomes. FIG. 29B shows the levels of CXCL9 gene expression in tumors of mice treated with PBS, rIL-12 or IL-12-PTGFRN exosomes. FIG. 29C shows the levels of CXCL10 gene expression in tumors of mice treated with PBS, rIL-12 or IL-12-PTGFRN exosomes. FIG. 29D shows the levels of TGFβ gene expression in tumors of mice treated with PBS, rIL-12 or IL-12-PTGFRN exosomes.

FIG. 48 shows $EC_{50}$ of the IFNγ response in Donor 1 and Donor 2 human PBMCs after addition of recombinant IL-12, recombinant IL-12 mixed with recombinant CD40L, PTGFRN-IL-12 exosomes, double-positive PTGFRN-CD40L/IL-12 exosomes, and a mixture of PTGFRN-IL-12 exosomes and PTGFRN-CD40L exosomes, respectively.

FIG. 50 shows $EC_{50}$ of the IFNγ response in Donor 1 and Donor 2 human PBMCs after addition of recombinant CD40L, recombinant IL-12 mixed with recombinant CD40L, PTGFRN-CD40L exosomes, double-positive PTGFRN-CD40L/IL-12 exosomes, and a mixture of PTGFRN-IL-12 exosomes and PTGFRN-CD40L exosomes, respectively.

DETAILED DESCRIPTION

Figure 2:
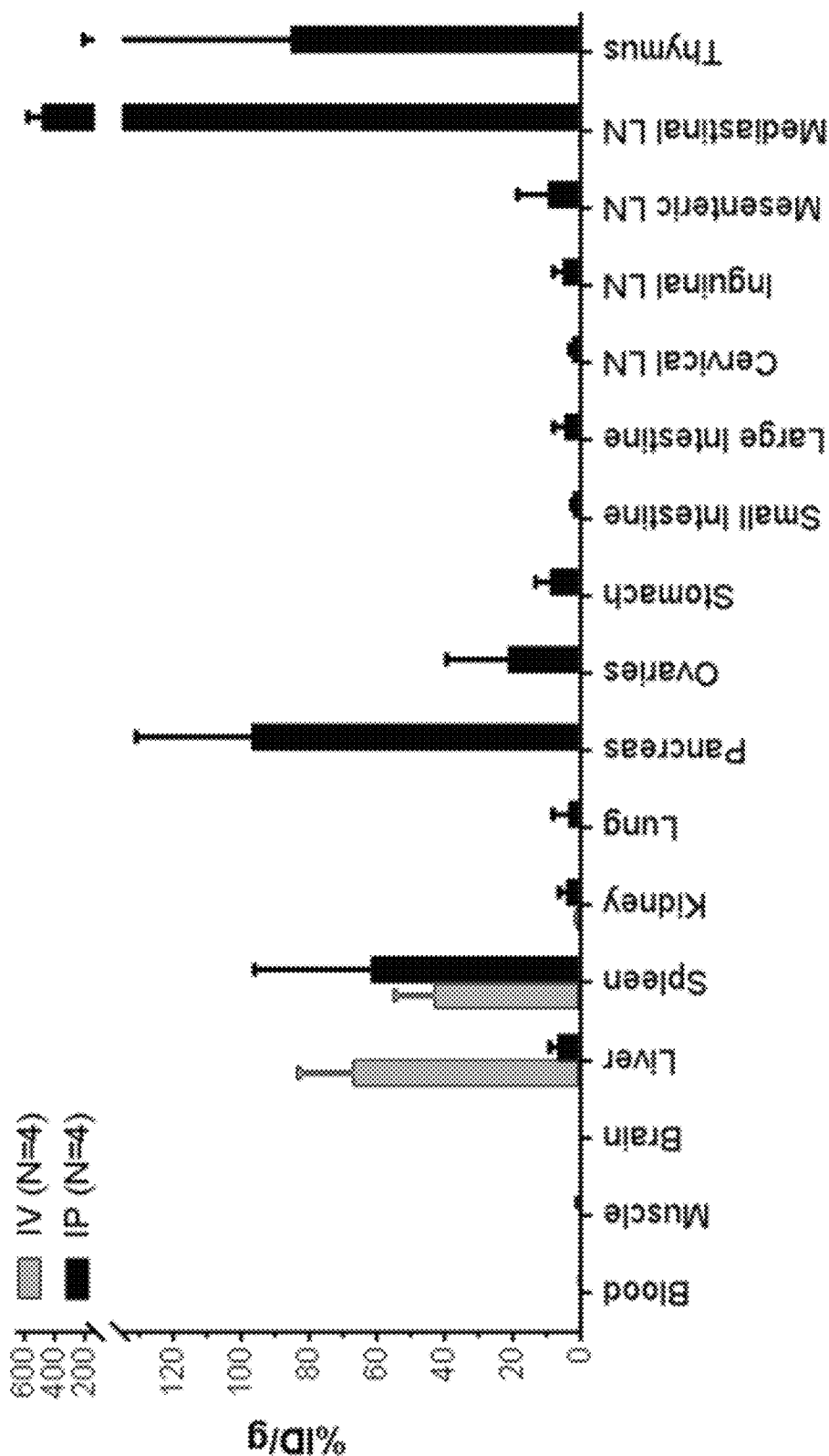
FIG. 2 is a quantitation of exosome distribution in different mouse tissues after intravenous and intraperitoneal administration of radiolabeled exosomes.

Disclosed herein are extracellular vesicles capable of modulating human immune system. Also provided are methods for producing the extracellular vesicles, and methods of using these extracellular vesicles to treat cancer and other immune system related diseases.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject systems for use in practicing the subject methods will be discussed in greater detail, followed by a review of associated methods.

As used herein, the term "extracellular vesicle" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. The cargo can comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells.

As used herein the term "exosome" refers to a cell-derived small (between 20-300 nm in diameter, more preferably 40-200 nm in diameter) vesicle comprising a membrane that encloses an internal space, and which is generated from the cell by direct plasma membrane budding or by fusion of the late endosome with the plasma membrane. The exosome is a species of extracellular vesicle. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof.

As used herein, the term "nanovesicle" refers to a cell-derived small (between 20-250 nm in diameter, more preferably 30-150 nm in diameter) vesicle comprising a membrane that encloses an internal space, and which is generated from the cell by direct or indirect manipulation such that the nanovesicle would not be produced by the producer cell without the manipulation. Appropriate manipulations of the producer cell include but are not limited to serial extrusion, treatment with alkaline solutions, sonication, or combinations thereof. The production of nanovesicles can, in some instances, result in the destruction of the producer cell. Preferably, populations of nanovesicles are substantially free of vesicles that are derived from producer cells by way of direct budding from the plasma membrane or fusion of the late endosome with the plasma membrane. The nanovesicle is a species of extracellular vesicle. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The nanovesicle, once it is derived from a producer cell according to the manipulation, can be isolated from the producer cell based on its size, density, biochemical parameters, or a combination thereof.

The term "extracellular vesicle delivery" or "delivery of extracellular vesicles" refers to the administration and localization of extracellular vesicles to target tissues, cells, and/or organs of the subject. In some embodiments, the immunomodulating component can be delivered to the cytoplasm of a target cell. In other embodiments, the immunomodulating component is delivered to the membrane of the target cell. In some embodiments, the membrane of the extracellular vesicle fuses with a membrane of a target cell.

As used herein, the term "producer cell" refers to any cell from which an extracellular vesicle can be isolated. A producer cell is a cell which serves as a source for the extracellular vesicle. A producer cell can share a protein, lipid, sugar, or nucleic acid component with the extracellular vesicle. In some embodiments, the producer cell is a modified or synthetic cell. In some embodiments, the producer cell is a cultured or isolated cell. In certain embodiments, the producer cell is a cell line. In certain other embodiments, the producer cell is a primary cell. In some particular embodiments, the producer cell is an immune cell.

"Membrane" as used herein is a boundary layer that separates an interior space from an exterior space comprising one or more biological compounds, typically lipids, and optionally polypeptides and/or carbohydrates. In some embodiments, the membrane comprises lipids and fatty acids. In some embodiments, the membrane comprises phospholipids, glycolipids, fatty acids, sphingolipids, phosphoglycerides, sterols, cholesterols, and phosphatidylserines. In some of these embodiments, the membrane further comprises one or more polypeptide and/or one or more polysaccharide, such as glycan. The extracellular vesicle comprises a membrane as defined herein.

As used herein, the term "immunomodulating component" refers to a therapeutic agent that acts on a target (e.g., a target cell) that is contacted with the extracellular vesicle, and regulates the immune system. The immunomodulating component that can be introduced into an extracellular vesicle and/or a producer cell include therapeutic agents such as, modulators of checkpoint inhibitors or ligands of checkpoint inhibitors, surface antigens and derivatives thereof, cytokines and derivatives thereof. The immunomodulating component can also include an agonist, an antagonist, an antibody, and an antigen-binding fragment, or a polynucleotide, such as siRNA, miRNA, lncRNA, and DNA.

The term "receiver" refers to a molecule that directs the extracellular vesicle to a target and/or promotes the interaction of extracellular vesicle with the target in the subject. In some embodiments, the receiver is a polypeptide. In some embodiments, the receiver is capable of increasing the concentration of the immunomodulating component in the tissue of the subject. Examples of receivers include, but are not limited to, examples listed in Table 3.

The term "target" refers to, a cell, a pathogen, a metabolite, a polypeptide complex or any molecule or structure that resides in a tissue or circulates in the circulatory system or lymphatic system of the subject, such as an immune cell or a cancer cell. Examples of targets include, but are not limited to, examples listed in Table 4.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibody includes bispecific antibodies and multispecific antibodies so long as they exhibit the desired biological activity or function.

The term "antigen-binding fragment" used herein refers to fragments of an intact immunoglobulin, and any part of a polypeptide including antigen binding regions having the ability to specifically bind to the antigen. For example, the antigen-binding fragment can be a F(ab')$_2$ fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment differs from a Fab fragment in that the Fab' fragment additionally includes the hinge region of the heavy chain, including at least one cysteine residue at the C-terminal of the heavy chain CH1 region. The F(ab')$_2$ fragment is produced whereby cysteine residues of the Fab' fragment are joined by a disulfide bond at the hinge region. An Fv fragment is the minimal antibody fragment having only heavy chain variable regions and light chain variable regions, and a recombinant technique for producing the Fv fragment is well-known in the art. Two-chain Fv fragments can have a structure in which heavy chain variable regions are linked to light chain variable regions by a non-covalent bond. Single-chain Fv (scFv) fragments generally can have a dimer structure as in the two-chain Fv fragments in which heavy chain variable regions are covalently bound to light chain variable regions via a peptide linker or heavy and light chain variable regions are directly linked to each other at the C-terminal thereof. The antigen-binding fragment can be obtained using a protease (for example, a whole antibody is digested with papain to obtain Fab fragments, and is digested with pepsin to obtain F(ab')$_2$ fragments), and can be prepared by a genetic recombinant technique. A dAb fragment consists of a VH domain. Single-chain antibody molecules can comprise a polymer with a number of individual molecules, for example, dimer, trimer or other polymers.

The phrase "nucleic acid molecule" refers to a single or double-stranded polymer of deoxyribonucleotide or ribonucleotide bases. It includes chromosomal DNA and self-replicating plasmids, vectors, mRNA, tRNA, siRNA, miRNA, etc. The nucleic acid molecule can be recombinant and exogenous polypeptides can be expressed when the nucleic acid is introduced into a cell.

The term "agonist" refers to a molecule that binds to a receptor and activates the receptor to produce a biological response. Receptors can be activated by either an endogenous or an exogenous agonist. Non-limiting examples of endogenous agonist include hormones and neurotransmitters. Non-limiting examples of exogenous agonist include drugs. The agonist can be a full, partial, or inverse agonist.

The term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, beta-blocker, and calcium channel blockers. The antagonist can be a competitive, non-competitive, or uncompetitive antagonist.

As used herein the term "a fragment" of a protein refers to a protein that is N- and/or C-terminally deleted in comparison to the naturally occurring protein. Preferably, a fragment of PTGFRN, BSG, IGSF2, IGSF3, IGSF8, ITGB1, ITGA4, SLC3A2, or ATP transporter retains the ability to be specifically targeted to exosomes. Such a fragment is also referred to as "functional fragment". Whether a fragment is a functional fragment in that sense can be assessed by any art known methods to determine the protein content of exosomes including Western Blots, FACS analysis and fusions of the fragments with autofluorescent proteins like, e.g. GFP. In a particular embodiment the fragment of PTGFRN, BSG, IGSF2, IGSF3, IGSF8, ITGB1, ITGA4, SLC3A2, ATP transporter retains at least 50%, 60%, 70%, 80%, 90% or 100% of the ability of the naturally occurring PTGFRN, BSG, IGSF2, IGSF3, IGSF8, ITGB1, ITGA4, SLC3A2, or ATP transporter to be specifically targeted to exosomes.

As used herein the term "variant" of a protein refers to a protein that shares a certain amino acid sequence identity with another protein upon alignment by a method known in the art. A variant of a protein can include a substitution, insertion, deletion, frameshift or rearrangement in another protein. In a particular embodiment, the variant is a variant having at least 70% identity to PTGFRN, BSG, IGSF2, IGSF3, IGSF8, ITGB1, ITGA4, SLC3A2, ATP transporter or a fragment of PTGFRN, BSG, IGSF2, IGSF3, IGSF8, ITGB1, ITGA4, SLC3A2, or ATP transporter. In some embodiments variants or variants of fragments of PTGFRN share at least 70%, 80%, 85%, 90%, 95% or 99% sequence identity with PTGFRN according to SEQ ID NO: 1 or with a functional fragment thereof. In some embodiments variants or variants of fragments of BSG share at least 70%, 80%, 85%, 90%, 95% or 99% sequence identity with BSG according to SEQ ID NO: 9 or with a functional fragment thereof. In some embodiments variants or variants of fragments of IGSF2 share at least 70%, 80%, 85%, 90%, 95% or 99% sequence identity with IGSF2 according to SEQ ID NO: 34 or with a functional fragment thereof. In some embodiments variants or variants of fragments of IGSF3 share at least 70%, 80%, 85%, 90%, 95% or 99% sequence identity with IGSF3 according to SEQ ID NO: 20 or with a functional fragment thereof. In some embodiments variants or variants of fragments of IGSF8 share at least 70%, 80%, 85%, 90%, 95% or 99% sequence identity with IGSF8 according to SEQ ID NO: 14 or with a functional fragment thereof. In some embodiments variants or variants of fragments of ITGB1 share at least 70%, 80%, 85%, 90%, 95% or 99% sequence identity with ITGB1 according to SEQ ID NO: 21 or with a functional fragment thereof. In some embodiments variants or variants of fragments of ITGA4 share at least 70%, 80%, 85%, 90%, 95% or 99% sequence identity with ITGA4 according to SEQ ID NO: 22 or with a functional fragment thereof. In some embodiments variants or variants of fragments of SLC3A2 share at least 70%, 80%, 85%, 90%, 95% or 99% sequence identity with SLC3A2 according to SEQ ID NO: 23 or with a functional fragment thereof. In some embodiments variants or variants of fragments of ATP1A1 share at least 70%, 80%, 85%, 90%, 95% or 99% sequence identity with ATP1A1 according to SEQ ID NO: 24 or with a functional fragment thereof. In some embodiments variants or variants of fragments of ATP1A2 share at least 70%, 80%, 85%, 90%, 95% or 99% sequence identity with ATP1A2 according to SEQ ID NO: 25 or with a functional fragment thereof. In some embodiments variants or variants of fragments of ATP1A3 share at least 70%, 80%, 85%, 90%, 95% or 99% sequence identity with ATP1A3 according to SEQ ID NO: 26 or with a functional fragment thereof. In some embodiments variants or variants of fragments of ATP1A4 share at least 70%, 80%, 85%, 90%, 95% or 99% sequence identity with ATP1A4 according to SEQ ID NO: 27 or with a functional fragment thereof. In some embodiments variants or variants of fragments of ATP1B3 share at least 70%, 80%, 85%, 90%, 95% or 99% sequence identity with ATP1B3 according to SEQ ID NO: 28 or with a functional fragment thereof. In some embodiments variants or variants of fragments of ATP2B1 share at least 70%, 80%, 85%, 90%, 95% or 99% sequence identity with ATP2B1 according to SEQ ID NO: 29 or with a functional fragment thereof. In some embodiments variants or variants of fragments of ATP2B2 share at least 70%, 80%, 85%, 90%, 95% or 99% sequence identity with ATP2B2 according to SEQ ID NO: 30 or with a functional fragment thereof. In some embodiments variants or variants of fragments of ATP2B3 share at least 70%, 80%, 85%, 90%, 95% or 99% sequence identity with ATP2B3 according to SEQ ID NO: 31 or with a functional fragment thereof. In some embodiments variants or variants of fragments of ATP2B4 share at least 70%, 80%, 85%, 90%, 95% or 99% sequence identity with ATP2B4 according to SEQ ID NO: 32 or with a functional fragment thereof. In each of above cases, it is preferred that the variant or variant of a fragment retains the ability to be specifically targeted to exosomes.

Methods of alignment of sequences for comparison are well-known in the art. Various programs and alignment algorithms are described in: Smith and Waterman, Adv. Appl. Math. 2: 482 (1981); Needleman and Wunsch, J. Mol. Bio. 48: 443 (1970); Pearson and Lipman, Methods in Mol. Biol. 24: 307-31 (1988); Higgins and Sharp, Gene 73: 15 237-44 (1988); Higgins and Sharp, CABIOS 5: 151-3 (1989) Corpet et al., Nuc. Acids Res. 16: 10881-90 (1988); Huang et al., Comp. Appl. BioSci. 8: 155-65 (1992); and Pearson et al., Meth. Mol. Biol. 24: 307-31 (1994). The NCBI Basic Local Alignment Search Tool (BLAST) [Altschul 20 et al., J. Mol. Biol. 215: 403-10 (1990) ] is available from several sources, including the National Center for Biological Information (NBCl, Bethesda, Md.) and on the Internet, for use in connection with the sequence analysis programs blastp, blasm, blastx, tblastn and tblastx. BLAST and a description of how to determine sequence identify using the program can be accessed at the official website of NCBI (National Center for Biotechnology Information) under NIH (National Institute of Health).

Recitation of any protein provided herein encompasses a functional variant of the protein. The term "functional variant" of a protein refers to a variant of the protein that retains the ability to be specifically targeted to exosomes.

As used herein, the term "pharmaceutical composition" refers to one or more of the compounds described herein, such as, e.g., an extracellular vesicle mixed or intermingled with, or suspended in one or more other chemical components, such as pharmaceutically-acceptable carriers and excipients. One purpose of a pharmaceutical composition is to facilitate administration of preparations of extracellular vesicles to a subject. The term "pharmaceutically-acceptable" and grammatical variations thereof, refers to compositions, carriers, diluents and reagents capable of administration to or upon a subject without the production of undesirable physiological effects to a degree that prohibits administration of the composition. The term "excipient" or "carrier" refers to an inert substance added to a pharmaceutical composition to further facilitate administration of a compound. The term "pharmaceutically-acceptable carrier" or "pharmaceutically-acceptable excipient" encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound. Included are excipients and carriers that are useful in preparing a pharmaceutical composition and are generally safe, non-toxic, and desirable.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired extracellular vesicles, that have undergone one or more processes of purification, e.g., a selection or an enrichment of the desired extracellular vesicle preparation. In some embodiments, isolating or purifying as used herein is the process of removing, partially removing (e.g. a fraction) of the extracellular vesicles from a sample containing producer cells. In some embodiments, an isolated extracellular vesicle composition has no detectable undesired activity or, alternatively, the level or amount of the undesired activity is at or below an acceptable level or amount. In other embodiments, an isolated extracellular vesicle composition has an amount and/or concentration of desired extracellular vesicles at or above an acceptable amount and/or concentration. In other embodiments, the isolated extracellular vesicle composition is enriched as compared to the starting material (e.g. producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some embodiments, isolated extracellular vesicle preparations are substantially free of residual biological products. In some embodiments, the isolated extracellular vesicle preparations are 100% free, 99% free, 98% free, 97% free, 96% free, or 95% free of any contaminating biological matter. Residual biological products can include abiotic materials (including chemicals) or unwanted nucleic acids, proteins, lipids, or metabolites. Substantially free of residual biological products can also mean that the extracellular vesicle composition contains no detectable producer cells and that only extracellular vesicles are detectable.

The terms "administration," "administering" and variants thereof refer to introducing a composition, such as an extracellular vesicle, or agent into a subject and includes concurrent and sequential introduction of a composition or agent. The introduction of a composition or agent into a subject is by any suitable route, including orally, pulmonarily, intranasally, parenterally (intravenously, intra-arterially, intramuscularly, intraperitoneally, or subcutaneously), rectally, intralymphatically, intrathecally, intratumorally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, the term "modulate," "modulating", "modify," and/or "modulator" generally refers to the ability to alter, by increase or decrease, e.g., directly or indirectly promoting/stimulating/up-regulating or interfering with/inhibiting/down-regulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity.

The term "sufficient amount" means an amount sufficient to produce a desired effect, e.g., an amount sufficient to modulate a condition in the subject.

The term "therapeutically effective amount" is an amount that is effective to ameliorate a symptom of a disease. A therapeutically effective amount can be a "prophylactically effective amount" as prophylaxis can be considered therapy.

As used herein, the term "substantially" or "substantial" refers, e.g., to the presence, level, or concentration of an entity in a particular space, the effect of one entity on another entity, or the effect of a treatment. For example, an activity, level or concentration of an entity is substantially increased if the increase is 2-fold, 3-fold, 4-fold, 5-fold, 10-fold, 50-fold, 100-fold, or 1000-fold relative to a baseline. An activity, level or concentration of an entity is also substantially increased if the increase is 5%, 10%, 20%, 30%, 40%, 50%, 60%, 70%, 80%, 90%, 100%, 200%, or 500% relative to a baseline.

The term "in vivo" refers to processes that occur in a living organism.

The term "mammal" as used herein includes both humans and non-human mammals.

Abbreviations used in this application include the following: "mRNA" refers to messenger RNA, "miRNA" refers to microRNA, "siRNA" refers to small interfering RNA, "antisense RNA" refers to single stranded RNA that is complementary to an mRNA, "shRNA" refers to small or short hairpin RNA, "lncRNA" refers to long non-coding RNA, and "dsDNA" refers to double stranded DNA.

Compositions

Aspects of the subject disclosure include a composition capable of regulating the immune system. The composition comprises an extracellular vesicle comprising a cell membrane, and an immunomodulating component associated with the cell membrane or enclosed within the membrane-bound enclosed volume.

The Extracellular Vesicle

In various embodiments, the composition comprises an extracellular vesicle. In certain embodiments, the extracellular vesicle is a cell-derived vesicle comprising a membrane that encloses an internal space.

In various embodiments, the extracellular vesicle can be a membrane-bound vesicle that has a smaller diameter than the cell from which it is derived. In some embodiments, the extracellular vesicle has a longest dimension between about 20-1000 nm, such as between about 20-100 nm, 20-200 nm, 20-300 nm, 20-400 nm, 20-500 nm, 20-600 nm, 20-700 nm, 20-800 nm, 20-900 nm, 30-100 nm, 30-200 nm, 30-300 nm, 30-400 nm, 30-500 nm, 30-600 nm, 30-700 nm, 30-800 nm, 30-900 nm, 40-100 nm, 40-200 nm, 40-300 nm, 40-400 nm, 40-500 nm, 40-600 nm, 40-700 nm, 40-800 nm, 40-900 nm, 50-150 nm, 50-500 nm, 50-750 nm, 100-200 nm, 100-500 nm, or 500-1000 nm.

In certain embodiments, the extracellular vesicle is an exosome. In certain embodiments, the extracellular vesicle is a nanovesicle. In certain embodiments, the extracellular vesicle is an apoptotic body. In certain embodiments, the extracellular vesicle is a fragment of cell. In certain embodiments, the extracellular vesicle is a vesicle derived from cell by direct or indirect manipulation. In certain embodiments, the extracellular vesicle is a vesiculated organelle. In various embodiments, the extracellular vesicle is a vesicle produced by living cells.

In some embodiments, the extracellular vesicle is derived from a living organism. In some embodiments, the extracellular vesicle is derived from a dead organism. In some embodiments, the extracellular vesicle is derived from an explanted tissue. In some embodiments, the extracellular vesicle is derived from an explanted organ. In some embodiments, the extracellular vesicle is derived from cultured cells. In some of these embodiments, when the extracellular vesicle is generated in a cell culture system, the extracellular vesicle is further isolated (e.g., by separating the extracellular vesicle from the cultured cells). Separation can be achieved by sedimentation. For example, the extracellular vesicle can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$. Separation can also be achieved by affinity purification. For example, the extracellular vesicle can be purified by binding a population comprising extracellular vesicles to a resin, said resin comprising a plurality of ligands that have specific affinity for one or more target proteins on the surface of the extracellular vesicle. The target proteins may be a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc. The target protein may additionally be the immunomodulating component that is displayed on the surface of the exosomes.

In various embodiments, the extracellular vesicle comprises lipids or fatty acids and polypeptides. In certain embodiments, the extracellular vesicle further comprises a sugar. In certain embodiments, the extracellular vesicle further comprises a polynucleotide.

In various embodiments, the extracellular vesicle membrane comprises an interior surface and an exterior surface and encloses an internal space. In some embodiments, the extracellular vesicle further comprises a payload. In certain embodiments, the payload is enclosed within the internal space. In certain embodiments, the payload is displayed on the external surface of the extracellular vesicle. In certain embodiments, the payload is spanning the membrane of the extracellular vesicle. In various embodiments, the payload comprises nucleic acids, proteins, carbohydrates, lipids, small molecules, and/or combinations thereof. In some embodiments, the extracellular vesicle further comprises a receiver.

The Exosome

In various embodiments, the extracellular vesicle is an exosome. In certain embodiments, the exosome is a small membrane-bound vesicle secreted by producer cells.

In some embodiments, the exosome from the producer cell has a longest dimension between about 20-300 nm, such as between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-210 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 nm, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 nm, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 nm, 60-120 nm, 60-110 nm, 60-100 nm, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 nm, 70-120 nm, 70-110 nm, 70-100 nm, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm.

In particularly preferred embodiments, the exosome from the producer cell described herein has a longest dimension between about 30-100 nm. In another preferred embodiment, the exosome from the producer cell has a longest dimension between about 20-300 nm. In another preferred embodiment, the exosome from the producer cell has a longest dimension between about 40-200 nm. In another embodiment, a population of the exosomes described herein comprise a population wherein 90% of the exosomes have a longest dimension 20-300 nm. In another embodiment, a population of the exosomes described herein comprise a population wherein 95% of the exosomes have a longest dimension 20-300 nm. In another embodiment, a population of the exosomes described herein comprise a population wherein 99% of the exosomes have a longest dimension 20-300 nm. In another embodiment, a population of the exosomes described herein comprise a population wherein 90% of the exosomes have a longest dimension 40-200 nm. In another embodiment, a population of the exosomes described herein comprise a population wherein 95% of the exosomes have a longest dimension 40-200 nm. In another embodiment, a population of the exosomes described herein comprise a population wherein 99% of the exosomes have a longest dimension 40-200 nm. In other preferred embodiments, the size of the exosome or population of exosomes described herein is measured according to methods described, infra.

In some embodiments, the exosome is generated by a producer cell. In some embodiments, the membrane of the exosome comprises one or more molecules derived from the producer cell. In some embodiments, the exosome is generated in a cell culture system and isolated (e.g., by separating the exosome from the producer cell). Separation can be achieved by sedimentation. For example, the exosome can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$. Separation can also be achieved by affinity purification. For example, the extracellular vesicle can be purified by binding a population comprising extracellular vesicles to a resin, said resin comprising a plurality of ligands that have specific affinity for one or more target proteins on the surface of the extracellular vesicle. The one or more target protein may be a tetraspanin (e.g., CD63, CD81 and/or CD9), an EWI protein/immunoglobulin superfamily member (e.g., PTGFRN, IGSF8 and/or IGSF3), an integrin (e.g., ITGB1 and/or ITGA4), an ATP transporter protein (e.g., ATP1A1, ATP1A2, ATP1A3, ATP1A4, ATP1B3, ATP2B1, ATP2B2, ATP2B3 and/or ATP2B4), SLC3A2, BSG, or CD98hc. The target protein may additionally be the immunomodulating component that is displayed on the surface of the exosomes.

In some embodiments, the exosome membrane comprises an interior surface and an exterior surface. In certain embodiments, the interior surface faces the inner core of the exosome. In certain embodiments, the exterior surface can be in contact with the endosome, the multivesicular bodies, or the membrane/cytoplasm of a producer cell or a target cell.

In some embodiments, the exosome membrane comprises lipids and fatty acids. In some embodiments, the exosome membrane comprises phospholipids, glycolipids, fatty acids, sphingolipids, phosphoglycerides, sterols, cholesterols, and phosphatidylserines. In some embodiments, the lipid and fatty acid can be one or more of those listed in Table 1.

In certain embodiments, the exosome comprises a lipid bilayer composed of an inner leaflet and an outer leaflet. The composition of the inner and outer leaflet can be determined by transbilayer distribution assays known in the art, see e.g., Kuypers et al. Biohim Biophys Acta 1985 819:170. In some embodiments, the composition of the outer leaflet is between approximately 70-90% choline phospholipids, between approximately 0-15% acidic phospholipids, and between approximately 5-30% phosphatidylethanolamine. In some embodiments, the composition of the inner leaflet is between approximately 15-40% choline phospholipids, between approximately 10-50% acidic phospholipids, and between approximately 30-60% phosphatidylethanolamine.

In some embodiments, the exosome membrane further comprises one or more polypeptide. In certain embodiments, the exosome comprises one or more polypeptide selected from the following list, including but not limited to, spectrin, myosin-like polypeptide, band 3, SLC4A1, actin, actin-like polypeptide, glyceraldehyde 3-P dehydrogenase (G3PD), tetraspanins (e.g., CD63, CD81 and/or CD9), Alix and TSG101, integrins (e.g., ITGB1 and/or ITGA4), selectins, CR1, TNFRI, proteolytic enzymes, glycosylphosphatidylinositol (GPI)-linked proteins or histones, EWI protein/immunoglobulin superfamily members (e.g., PTGFRN, IGSF8 and/or IGSF3), ATP transporter proteins (e.g., ATP1A1, ATP1A2, ATP1A3, ATP1A4, ATP1B3, ATP2B1, ATP2B2, ATP2B3 and/or ATP2B4), SLC3A2, BSG, or CD98hc. In some embodiments, the exosome comprises at least one polypeptide selected from Table 2.

In some embodiments, the exosome comprises polypeptides on its surface. In some embodiments, the exosome is modified to contain the one or more polypeptides. In some embodiments, the producer cell is modified to contain the one or more polypeptides. In some embodiments, the producer cell naturally contains the one or more polypeptides and exosomes derived therefrom also contain the polypeptides. The levels of any desired surface marker can be modified directly on the exosome (e.g., by contacting the complex with recombinantly produced polypeptides to bring about insertion in or conjugation to the membrane of the complex). Alternatively or in addition, the levels of any desired surface marker can be modified directly on the producer cell (e.g., by contacting the complex with recombinantly produced polypeptides to bring about insertion in or conjugation to the membrane of the cell). Alternatively, the producer cell can be modified by transducing an exogenous nucleic acid into the producer cell to express a desired surface marker. The surface marker can already be naturally present on the producer cell, in which case the exogenous construct can lead to overexpression of the marker and increased concentration of the marker in or on the producer cell. Alternatively, a naturally expressed surface marker can be removed from the producer cell (e.g., by inducing gene silencing in the producer cell). The polypeptides can confer different functionalities to the exosome (e.g., specific targeting capabilities, delivery functions (e.g., fusion molecules), enzymatic functions, increased or decreased half-life in vivo, etc.). In some embodiments, the polypeptides include, but are not limited to CD47, CD55, CD49, CD40, CD133, CD59, glypican-1, CD9, CD63, CD81, integrins, selectins, lectins, and cadherins.

In specific embodiments, the exosomes comprise one or more polypeptides on their surface, wherein said polypeptides are selected from a group of proteins that was recently identified to be enriched on the surface of exosomes (described in detail in U.S. Patent Application 62/550,543, which is incorporated herein by reference in its entirety). This group of polypeptides includes prostaglandin F2 receptor negative regulator (PTGFRN); basigin (BSG); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B4)).

In some embodiments, the exosome membrane further comprises one or more polysaccharide, such as glycan.

In some embodiments, the exosome delivers the payload (therapeutic agent) to a target. The payload is a therapeutic agent that acts on a target (e.g., a target cell) that is contacted with the exosome. Contacting can occur in vitro or in a subject. Payloads that can be introduced into an exosome and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, or siRNA), amino acids (e.g., amino acids comprising a detectable moiety or a toxin that disrupt translation), polypeptides (e.g., enzymes), lipids, carbohydrates, and small molecules (e.g., small molecule drugs and toxins).

The exosome can interact with the target cell via membrane fusion and deliver payloads (e.g., therapeutic agents) in an exosome composition to the surface or cytoplasm of a target cell. In some embodiments, membrane fusion occurs between the exosome and the plasma membrane of a target cell. In other embodiments, membrane fusion occurs between the exosome and an endosomal membrane of a target cell.

In some embodiments, the exosome comprises a receiver polypeptide. The receiver polypeptide can be synthetic. In some embodiments, the receiver polypeptide is introduced into the producer cell (e.g., an exogenous nucleic acid that encodes the receiver polypeptide is introduced into the producer cell) or a recombinant receiver polypeptide that is made outside the producer cell (e.g., synthesized by a protein expression system). In some embodiments, the receiver polypeptide (e.g., a recombinantly produced polypeptide) is introduced into the exosome directly (e.g., after the exosome is isolated from the producer cell). In some embodiments, the receiver polypeptide can be on the surface of the exosomes. In some embodiments, the receiver polypeptide is capable of targeting the exosome to a specific target (e.g., a target such as a pathogen, a metabolite, a polypeptide complex or a cell such as non-functional cell or cancer cell) that circulates in the circulatory system of the subject, such as the blood, or a target that resides in a tissue (such as a diseased tissue).

In some embodiments, the exosome is synthetic. For example, the exosome can comprise a payload, such as, e.g., a therapeutic polypeptide, nucleic acid (such as DNA or RNA) or other polynucleotide, polysaccharide or glycan, lipid or fatty acid, large biologic, small molecule or toxin such that the exosome is not naturally occurring. In some embodiments, the exosome is modified (e.g., by introducing a payload or otherwise modifying the content of the complex, such as by changing the protein, lipid or glycan content of the membrane). For example, exosomes are first isolated from a producer cell and then modified as desired, thereby generating synthetic exosomes. In some embodiments, the producer cell is modified. For example, an exogenous nucleic acid, an exogenous polypeptide or small molecule or toxin can be introduced into the producer cell. Alternatively or in addition, the producer cell can otherwise be modified (e.g., by modifying the cellular or membrane content, such as by changing the lipid or glycan content of the cell membrane). Exosomes generated from the modified producer cells comprise one or more of the modifications of the producer cell. The process produces synthetic exosomes. In some embodiments, both the producer cell and the exosome isolated from the producer cell are modified as described herein.

Nanovesicle

In various embodiments, the extracellular vesicle is a nanovesicle. In certain embodiments, the nanovesicle is a cell-derived small vesicle comprising a membrane that encloses an internal space, and which is generated from the cell by direct or indirect manipulation such that the nanovesicle would not be produced by the cell without the manipulation. Appropriate manipulations of the cell include but are not limited to serial extrusion, treatment with alkaline solutions, sonication, or combinations thereof and can, in some instances, result in the destruction of the producer cell.

In various embodiments, the nanovesicle has a longest dimension between about 20-250 nm, such as between about 20-100 nm, 20-150 nm, 20-200 nm, 30-100 nm, 30-150 nm, 30-200 nm, 30-250 nm, 40-100 nm, 40-150 nm, 40-200 nm, 40-250 nm, 50-100 nm, 50-150 nm, 50-200 nm, 50-250 nm, 100-200 nm, or 150-250 nm.

In various embodiments, the nanovesicle is derived from a producer cell. In certain embodiments, the nanovesicle is generated from a producer cell by direct or indirect manipulation. Appropriate manipulations include but are not limited to serial extrusion, treatment with alkaline solutions, sonication, or combinations thereof. In some of these embodiments, the manipulation can result in the destruction of the producer cell. In some preferred embodiments, the population of the nanovesicle is substantially free of vesicles that are derived from producer cells by way of direct budding from the plasma membrane or fusion of the late endosome with the plasma membrane.

In some embodiments, the nanovesicle is isolated from the producer cell based on its size, density, biochemical parameters, or a combination thereof. In certain embodiments, the isolation can be achieved by sedimentation. For example, the nanovesicle can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$.

In various embodiments, the nanovesicle comprises lipids or fatty acids and polypeptides. In certain embodiments, the nanovesicle further comprises a sugar. In certain embodiments, the nanovesicle further comprises a polynucleotide. In some embodiments, the nanovesicle further comprises a receiver. In some embodiments, the nanovesicle further comprises a payload. In some of these embodiments, the payload comprises nucleic acids, proteins, carbohydrates, lipids, small molecules, and/or combinations thereof.

The Immunomodulating Component

In various embodiments, the composition further comprises an immunomodulating component.

In some embodiments, the immunomodulating compound is a protein that is expressed as a translational fusion protein to an exosome surface protein, such that said protein is retained on the surface of the exosome. In certain embodiments, the immunomodulating compound is a membrane protein. In certain embodiments, the immunomodulating compound is a soluble protein. In some embodiments, the exosome surface protein is a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc or a fragment or variant thereof.

In some embodiments, the immunomodulating compound is a soluble protein that is expressed as a translational fusion protein to an exosome surface protein, such that said soluble protein is retained on the surface of the exosome. In some embodiments, the exosome surface protein is a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc or a fragment or variant thereof.

In certain embodiments, the immunomodulating component has anti-tumor activity. In some embodiments, the immunomodulating component regulates the innate immune response. In some of these embodiments, the immunomodulating component targets the natural killer cells. In some other embodiments, the immunomodulating component regulates the adaptive immune response. In some of these embodiments, the immunomodulating component targets the cytotoxic T cells.

In some embodiments, the immunomodulating component is expressed in the producer cell in its full-length form.

In other embodiments, the immunomodulating component is expressed as a translational fusion protein to an exosome surface protein, which results in a higher level of expression of the biologically active portion of the immunomodulating compound on the surface of the exosome. In some embodiments, the immunomodulating compound is a soluble protein that is expressed as a translational fusion protein to an exosome surface protein, such that said soluble protein is retained on the surface of the exosome. In some embodiments, the exosome surface protein is a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc or a fragment or variant thereof.

In some embodiments, the immunomodulating component is an inhibitor for a negative checkpoint regulator. In some embodiments, the immunomodulating component is an inhibitor for a binding partner of a negative checkpoint regulator.

In certain embodiments, the immunomodulating component is an inhibitor of cytotoxic T-lymphocyte-associate protein 4 (CTLA-4). In some of these embodiments, the CTLA-4 inhibitor is a monoclonal antibody of CTLA-4. In certain embodiments, the inhibitor is a fragment of a monoclonal antibody of CTLA-4. In certain embodiments, the antibody fragment is a scFv, (scFv)$_2$, Fab, Fab', and F(ab')$_2$, F(ab1)$_2$, Fv, dAb, or Fd of a monoclonal antibody of CTLA-4. In certain embodiments, the inhibitor is a nanobody, a bispecific antibody, or a multispecific antibody against CTLA-4. In some specific embodiments, the monoclonal antibody is ipilimumab. In some specific embodiments, the monoclonal antibody is tremelimumab.

In certain embodiments, the immunomodulating component is an inhibitor of programmed cell death protein 1 (PD-1). In certain embodiments, the immunomodulating component is an inhibitor of programmed death-ligand 1 (PD-L1). In certain embodiments, the immunomodulating component is an inhibitor of programmed death-ligand 2 (PD-L2). In some embodiments, the inhibitor of PD-1, PD-L1, or PD-L2 is a monoclonal antibody of PD-1, PD-L1, or PD-L2. In certain embodiments, the inhibitor is a fragment of a monoclonal antibody of PD-1, PD-L1, or PD-L2. In certain embodiments, the antibody fragment is a scFv, (scFv)$_2$, Fab, Fab', and F(ab')$_2$, F(ab1)$_2$, Fv, dAb, or Fd of a monoclonal antibody of PD-1, PD-L1, or PD-L2. In certain embodiments, the inhibitor is a nanobody, a bispecific antibody, or a multispecific antibody against PD-1, PD-L1, or PD-L2. In some specific embodiments, the monoclonal antibody is nivolumab. In some specific embodiments, the monoclonal antibody is pembrolizumab. In some specific embodiments, the monoclonal antibody is pidilizumab. In some specific embodiments, the monoclonal antibody is atezolizumab. In some specific embodiments, the monoclonal antibody is avelumab.

In certain embodiments, the immunomodulating component is an inhibitor of lymphocyte-activated gene 3 (LAG3). In some of these embodiments, the inhibitor of LAG3 is a monoclonal antibody of LAG3.

In certain embodiments, the immunomodulating component is an inhibitor of T-cell immunoglobulin mucin-containing protein 3 (TIM-3). In certain embodiments, the immunomodulating component is an inhibitor of B and T lymphocyte attenuator (BTLA). In certain embodiments, the immunomodulating component is an inhibitor of T cell immunoreceptor with Ig and ITIM domains (TIGIT). In certain embodiments, the immunomodulating component is an inhibitor of V-domain Ig suppressor of T cell activation (VISTA). In certain embodiments, the immunomodulating component is an inhibitor of adenosine A2a receptor (A2aR). In certain embodiments, the immunomodulating component is an inhibitor of killer cell immunoglobulin like receptor (KIR). In certain embodiments, the immunomodulating component is an inhibitor of indoleamine 2,3-dioxygenase (IDO). In certain embodiments, the immunomodulating component is an inhibitor of CD20, CD39, or CD73.

In some embodiments, the immunomodulating component is an activator for a positive co-stimulatory molecule. In some embodiments, the immunomodulating component is an activator for a binding partner of a positive co-stimulatory molecule.

In some embodiments, the immunomodulating component is an activator of a TNF receptor superfamily member. In certain embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, GITR, TROY, CD358, TRAMP, and XEDAR. In some embodiments, the immunomodulating component is a TNF superfamily member. In certain embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2.

In some embodiments, the activator of a TNF receptor superfamily member is expressed as a monomeric protein. In some embodiments, the activator of a TNF receptor superfamily member is expressed as trimeric proteins. In some embodiments, the TNF receptor superfamily member is expressed as a monomeric protein. In some embodiments, the TNF receptor superfamily member is expressed as trimeric proteins.

In certain embodiments, the immunomodulating component is an activator of TNF Receptor Superfamily Member 4 (OX40). In some of these embodiments, the activator of OX40 is an agonist antibody of OX40. In some other of these embodiments, the activator of OX40 is OX40 ligand (OX40L).

In certain embodiments, the immunomodulating component is an activator of CD27. In some of these embodiments, the activator of CD27 is an agonist antibody of CD27. In some other of these embodiments, the activator of CD27 is CD27 ligand (CD27L).

In certain embodiments, the immunomodulating component is an activator of CD40. In some of these embodiments, the activator of CD40 is an agonist antibody of CD40. In some other of these embodiments, the activator of CD40 is CD40 ligand (CD40L). In some embodiments, the CD40L is monomeric CD40L. In some embodiments, the CD40L is trimeric CD40L.

In some embodiments, trimeric CD40L is fused to PTGFRN or a fragment thereof. In some embodiments, trimeric CD40L is fused to the N-terminus of PTGFRN or a fragment thereof. In some embodiments, trimeric CD40L is expressed as a fusion protein to PTGFRN, wherein the polypeptide has the sequence of SEQ ID NO: 19 or SEQ ID NO: 20.

In certain embodiments, the immunomodulating component is an activator of glucocorticoid-induced TNFR-related protein (GITR). In some of these embodiments, the activator of GITR is an agonist antibody of GITR. In some other of these embodiments, the activator of GITR is a natural ligand of GITR.

In certain embodiments, the immunomodulating component is an activator of 4-1BB. In some of these embodiments, the activator of 4-1BB is an agonist antibody of 4-1BB. In some other of these embodiments, the activator of 4-1BB is a natural ligand of 4-1BB.

In some embodiments, the immunomodulating component is Fas receptor (Fas). In some of these embodiments, the Fas receptor is displayed on the surface of the extracellular vesicle. In some other embodiments, the immunomodulating component is Fas ligand (FasL). In some of these embodiments, the Fas ligand is displayed on the surface of the extracellular vesicle. In certain embodiments, the immunomodulating component is an antibody of Fas receptor. In certain embodiments, the immunomodulating component is an antibody of Fas ligand.

In some embodiments, the immunomodulating component is an activator of a CD28-superfamily co-stimulatory molecule. In certain embodiments, the CD28-superfamily co-stimulatory molecule is ICOS or CD28. In certain embodiments, the immunomodulating component is ICOSL, CD80, or CD86.

In certain embodiments, the immunomodulating component is an activator of inducible T cell co-stimulator (ICOS). In some of these embodiments, the activator of ICOS is an agonist antibody of ICOS. In some other of these embodiments, the activator of ICOS is ICOS ligand (ICOSL).

In certain embodiments, the immunomodulating component is an activator of CD28. In some of these embodiments, the activator of CD28 is an agonist antibody of CD28. In some other of these embodiments, the activator of CD28 is a natural ligand of CD28. In certain embodiments, the ligand of CD28 is CD80.

In certain embodiments, the composition comprises an inhibitor for a negative checkpoint regulator or an inhibitor for a binding partner of a negative checkpoint regulator and an activator for a positive co-stimulatory molecule or an activator for a binding partner of a positive co-stimulatory molecule.

In certain embodiments, the immunomodulating component is a cytokine. In some embodiments, the cytokine is a soluble cytokine that has been translationally fused to an exosome surface protein or fragment thereof. In some embodiments, the cytokine is interleukin 2 (IL-2). In some embodiments, the cytokine is interleukin 7 (IL-7). In some embodiments, the cytokine is interleukin 12 (IL-12). In some embodiments, the cytokine is interleukin 15 (IL-15).

In certain embodiments, the cytokine is fused to PTGFRN or a fragment thereof. In some embodiments, IL-7 is fused to PTGFRN or a fragment thereof. In some embodiments, IL-7 is fused to the N-terminus of PTGFRN or a fragment thereof. In some embodiments, IL-7 is expressed as a fusion protein to PTGFRN, wherein the polypeptide has the sequence of SEQ ID NO: 1 or SEQ ID NO: 2.

In certain embodiments, the cytokine is fused to PTGFRN or a fragment thereof. In some embodiments, IL-12 is fused to PTGFRN or a fragment thereof. In some embodiments, IL-12 is fused to the N-terminus of PTGFRN or a fragment thereof. In some embodiments, IL-12 is expressed as a fusion protein to PTGFRN, wherein the polypeptide has the sequence of SEQ ID NO: 3, SEQ ID NO: 4, SEQ ID NO: 5, or SEQ ID NO: 6.

In certain embodiments, the cytokine is fused to PTGFRN or a fragment thereof. In some embodiments, IL-15 is fused to PTGFRN or a fragment thereof. In some embodiments, IL-15 is fused to the N-terminus of PTGFRN or a fragment thereof. In some embodiments, IL-15 is expressed as a fusion protein to PTGFRN, wherein the polypeptide has the sequence of SEQ ID NO: 15 or SEQ ID NO: 16.

In some embodiments, the cytokine is an interferon (IFN). In certain embodiments, the interferon is fused to PTGFRN or a fragment thereof. In certain embodiments, the interferon is interferon γ (IFNγ). In some embodiments, IFNγ is fused to PTGFRN or a fragment thereof. In some embodiments, IFNγ is fused to the N-terminus of PTGFRN or a fragment thereof. In some embodiments, IFNγ is expressed as a fusion protein to PTGFRN, wherein the polypeptide has the sequence of SEQ ID NO: 7 or SEQ ID NO: 8.

In some embodiments, the immunomodulating component is a T-cell receptor (TCR) or a derivative thereof. In certain embodiments, the immunomodulating component is a TCR α-chain or a derivative thereof. In certain embodiments, the immunomodulating component is a TCR β-chain or a derivative thereof. In some embodiments, the immunomodulating component is a co-receptor of the T-cell or a derivative thereof.

In some embodiments, the immunomodulating component is a tumor antigen. In certain embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In certain embodiments, the tumor antigen is a carcinoembryonic antigen (CEA). In certain embodiments, the tumor antigen is an epithelial tumor antigen (ETA).

In certain embodiments, the tumor antigen is a mucin. In some of these embodiments, the mucin is a secreted mucin. In some other of these embodiments, the mucin is a transmembrane mucin. In specific embodiments, the tumor antigen is mucin 1 (MUC1). In specific embodiments, the tumor antigen is Tn-MUC1. In specific embodiments, the tumor antigen is mucin 16 (MUC16).

In certain embodiments, the tumor antigen is a melanoma-associated antigen (MAGE). In some of these embodiments, the MAGE is a type-I MAGE. In some other of these embodiments, the MAGE is a type-II MAGE. In specific embodiments, the type-I MAGE is MAGE-A2. In specific embodiments, the type-I MAGE is MAGE-A4.

In certain embodiments, the tumor antigen is alpha-fetoprotein (AFP). In certain embodiments, the tumor antigen is tumor protein p53 (p53). In certain embodiments, the tumor antigen is tyrosinase. In certain embodiments, the tumor antigen is a tyrosinase-related protein (TRP). In some embodiments, the tumor antigen is programmed death ligand 1 (PD-L1) or programmed death ligand 2 (PD-L2). In various embodiments, the tumor antigen is selected from the group consisting of CD4, CD8, CD45, CD80, and CD86.

In some embodiments, the immunomodulating component is a chimeric antigen receptor (CAR) or a derivative thereof. In some embodiments, the CAR binds to one or more of alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In some embodiments, the immunomodulating component is an activator of a T-cell receptor or co-receptor. In certain embodiments, the immunomodulating component is an activator of CD3. In certain embodiments, the activator is a fragment of a monoclonal antibody of CD3. In certain embodiments, the antibody fragment is a scFv, (scFv)$_2$, Fab, Fab', and F(ab')$_2$, F(ab1)$_2$, Fv, dAb, or Fd of a monoclonal antibody against CD3. In certain embodiments, the activator is a nanobody, a bispecific antibody, or a multispecific antibody against CD3. In some embodiments, the anti-CD3 antibody fragment is fused to PTGFRN or a fragment thereof. In some embodiments, the anti-CD3 antibody fragment is fused to the N-terminus of PTGFRN or a fragment thereof. In some embodiments, the anti-CD3 antibody fragment is expressed as a fusion protein to PTGFRN, wherein the polypeptide has the sequence of SEQ ID NO: 18 or SEQ ID NO: 21. In certain embodiments, the immunomodulating component is an activator of CD28. In certain embodiments, the inhibitor is a fragment of a monoclonal antibody of CD28. In certain embodiments, the antibody fragment is a scFv, (scFv)$_2$, Fab, Fab', and F(ab')$_2$, F(ab1)$_2$, Fv, dAb, or Fd of a monoclonal antibody of CD28. In certain embodiments, the inhibitor is a nanobody, a bispecific antibody, or a multispecific antibody against CD28.

In some embodiments, the immunomodulating component is a major histocompatibility complex (MHC) or a derivative thereof. In some of these embodiments, the immunomodulating component is an MHC class I or a derivative thereof. In some of these embodiments, the immunomodulating component is an MHC class II or a derivative thereof. In some of these embodiments, the immunomodulating component is an MHC class III or a derivative thereof.

In some embodiments, the immunomodulating component is a human leukocyte antigen (HLA) or a derivative thereof. In some of these embodiments, the immunomodulating component is an HLA-A, HLA-B, HLA-C, or derivative thereof. In some of these embodiments, the immunomodulating component is an HLA-E, HLA-F, HLA-G, or a derivative thereof. In some of these embodiments, the immunomodulating component is an HLA-DP, HLA-DQ, HLA-DR, or a derivative thereof.

In various embodiments, the immunomodulating component can be a polypeptide, a polynucleotide, a polysaccharide, a lipid, a small molecule, or a toxin.

In some embodiments, the immunomodulating component can be a protein, a peptide, a glycolipid, or a glycoprotein.

In certain embodiments, the immunomodulating component is an agonist. In some of these embodiments, the agonist is an endogenous agonist, such as a hormone, or a neurotransmitter. In some other of these embodiments, the agonist is an exogenous agonist, such as a drug. In some embodiments, the agonist is a physical agonist, which can create an agonist response without binding to the receptor. In some embodiments, the agonist is a superagonist, which can produce a greater maximal response than the endogenous agonist. In certain embodiments, the agonist is a full agonist with full efficacy at the receptor. In certain other embodiments, the agonist is a partial agonist having only partial efficacy at the receptor relative to a full agonist. In some embodiments, the agonist is an inverse agonist that can inhibit the constitutive activity of the receptor. In some embodiments, the agonist is a co-agonist that works with other co-agonists to produce an effect on the receptor. In certain embodiments, the agonist is an irreversible agonist that binds permanently to a receptor through formation of covalent bond. In certain embodiments, the agonist is selective agonist for a specific type of receptor.

In certain embodiments, the immunomodulating component is an antagonist. In some of these embodiments, the antagonist is a competitive antagonist, which reversibly binds to the receptor at the same binding site as the endogenous ligand or agonist without activating the receptor. Competitive antagonist can affect the amount of agonist necessary to achieve a maximal response. In some other of these embodiments, the antagonist is a non-competitive antagonist, which binds to an active site of the receptor or an allosteric site of the receptor. Non-competitive antagonist can reduce the magnitude of the maximum response that can be attained by any amount of agonist. In some other embodiments, the antagonist is an uncompetitive antagonist, which requires receptor activation by an agonist before its binding to a separate allosteric binding site.

In various embodiments, the immunomodulating component comprises an antibody or an antigen-binding fragment. The immunomodulating component can be a full length protein or a fragment thereof. The antibody or antigen-binding fragment can be derived from natural sources, or partly or wholly synthetically produced. In some embodiments, the antibody is a monoclonal antibody. In some of these embodiments, the monoclonal antibody is an IgG antibody. In certain embodiments, the monoclonal antibody is an IgG1, IgG2, IgG3, or IgG4. In some other embodiments, the antibody is a polyclonal antibody. In certain embodiments, the antigen-binding fragment is selected from Fab, Fab', and F(ab')$_2$, F(ab1)$_2$, Fv, dAb, and Fd fragments. In certain embodiments, the antigen-binding fragment is an scFv or (scFv)$_2$ fragment. In certain other embodiments, the antibody or antigen-binding fragment is a Nanobody® (single-domain antibody). In some embodiments, the antibody or antigen-binding fragment is a bispecific or multi-specific antibody.

In various embodiments, the antibody or antigen-binding fragment is fully human. In some embodiments, the antibody or antigen-binding fragment is humanized. In some embodiments, the antibody or antigen-binding fragment is chimeric. In some of these embodiments, the chimeric antibody has non-human V region domains and human C region domains. In some embodiments, the antibody or antigen-binding fragment is non-human, such as murine or veterinary.

In certain embodiments, the immunomodulating component is a polynucleotide. In some of these embodiments, the polynucleotide includes, but is not limited to, an mRNA, a miRNA, an siRNA, an antisense RNA, an shRNA, a lncRNA, and a dsDNA. In some embodiments, the polynucleotide is an RNA (e.g., an mRNA, a miRNA, an siRNA, an antisense RNA, an shRNA, or an lncRNA). In some of these embodiments, when the polynucleotide is an mRNA, it can be translated into a desired polypeptide. In some embodiments, the polynucleotide is a microRNA (miRNA) or pre-miRNA molecule. In some of these embodiments, the miRNA is delivered to the cytoplasm of the target cell, such that the miRNA molecule can silence a native mRNA in the target cell. In some embodiments, the polynucleotide is a small interfering RNA (siRNA) or a short hairpin RNA (shRNA) capable of interfering with the expression of an oncogene or other dysregulating polypeptides. In some of these embodiments, the siRNA is delivered to the cytoplasm of the target cell, such that the siRNA molecule can silence a native mRNA in the target cell. In some embodiments, the polynucleotide is an antisense RNA that is complementary to an mRNA. In some embodiments, the polynucleotide is a long non-coding RNA (lncRNA) capable of regulating gene expression and modulating diseases. In some embodiments, the polynucleotide is a DNA that can be transcribed into an RNA. In some of these embodiments, the transcribed RNA can be translated into a desired polypeptide.

In some embodiments, the immunomodulating component is a protein, a peptide, a glycolipid, or a glycoprotein.

In various embodiments, the composition comprises two or more above mentioned immunomodulating components, including mixtures, fusions, combinations and conjugates, of atoms, molecules, etc. In some embodiments, the composition comprises one, two, three, four, five, six, seven, eight, nine, ten, eleven, or twelve different immunomodulating components associated with the membrane or enclosed within the enclosed volume of said extracellular vesicle. In certain embodiments, the composition comprises a nucleic acid combined with a polypeptide. In certain embodiments, the composition comprises two or more polypeptides conjugated to each other. In certain embodiments, the composition comprises a protein conjugated to a biologically active molecule. In some of these embodiments, the biologically active molecule is a prodrug.

In some embodiments, the composition comprises two different immunomodulating components associated with the membrane or enclosed within the enclosed volume of said extracellular vesicle. In certain embodiments, the two different immunomodulating components are IL-12 and CD40L. In some embodiments, the CD40L and IL-12 are fused to PTGFRN or a fragment thereof respectively. In some embodiments, the CD40L and IL-12 are fused to the N-terminus of PTGFRN or a fragment thereof respectively. In some embodiments, the CD40L and IL-12 are expressed as fusion proteins to PTGFRN, wherein the polypeptides have the sequences of SEQ ID NO: 20 and SEQ ID NO: 3 respectively.

In some embodiments, the composition comprises three different immunomodulating components associated with the membrane or enclosed within the enclosed volume of said extracellular vesicle. In certain embodiments, the two different immunomodulating components are IL-12, CD40L, and FMS-like tyrosine kinase 3 ligand (FLT3L). In some embodiments, the CD40L, IL-12, and FLT3L are fused to PTGFRN or a fragment thereof respectively. In some embodiments, the CD40L, IL-12, and FLT3L are fused to the N-terminus of PTGFRN or a fragment thereof respectively. In some embodiments, the CD40L, IL-12, and FLT3L are expressed as fusion proteins to PTGFRN, wherein the polypeptides have the sequences of SEQ ID NO: 20, SEQ ID NO: 3, and SEQ ID NO: 22 respectively.

The Pharmaceutical Composition

The pharmaceutical compositions generally comprise a plurality of extracellular vesicles and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some embodiments, the pharmaceutical composition comprises one or more therapeutic agents and the extracellular vesicle described herein. In some embodiments, the extracellular vesicles are co-administered with of one or more separate therapeutic agents, wherein co-administration includes administration of the separate therapeutic agent before, after or concurrent with administration of the extracellular vesicles.

Pharmaceutically-acceptable excipients include excipients that are generally safe, non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents can also be incorporated into the compositions. Typically, a pharmaceutical composition is formulated to be compatible with its intended route of administration. The extracellular vesicles can be administered by parenteral, topical, intravenous, oral, subcutaneous, intra-arterial, intradermal, transdermal, rectal, intracranial, intraperitoneal, intranasal, intratumoral, intramuscular route or as inhalants. In certain embodiments, the pharmaceutical composition comprising extracellular vesicles is administered intravenously, e.g. by injection. The extracellular vesicles can optionally be administered in combination with other therapeutic agents that are at least partly effective in treating the disease, disorder or condition for which the extracellular vesicles are intended.

Solutions or suspensions can include the following components: a sterile diluent such as water, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as manitol, sorbitol, and sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the extracellular vesicles in an effective amount and in an appropriate solvent with one or a combination of ingredients enumerated herein, as desired. Generally, dispersions are prepared by incorporating the extracellular vesicles into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The extracellular vesicles can be administered in the form of a depot injection or implant preparation which can be formulated in such a manner to permit a sustained or pulsatile release of the extracellular vesicles.

Systemic administration of compositions comprising extracellular vesicles can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain embodiments the pharmaceutical composition comprising extracellular vesicles is administered intravenously into a subject that would benefit from the pharmaceutical composition. In certain other embodiments, the composition is administered to the lymphatic system, e.g., by intralymphatic injection or by intranodal injection (see e.g., Senti et al., PNAS 105(46): 17908 (2008)), or by intramuscular injection, by subcutaneous administration, by intratumoral injection, by direct injection into the thymus, or into the liver.

In certain embodiments, the pharmaceutical composition comprising extracellular vesicles is administered as a liquid suspension. In certain embodiments, the pharmaceutical composition is administered as a formulation that is capable of forming a depot following administration. In certain preferred embodiments, the depot slowly releases the extracellular vesicles into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the extracellular vesicles described herein and optionally a pharmaceutically active or therapeutic agent. The therapeutic agent can be a biological agent, a small molecule agent, or a nucleic acid agent.

Dosage forms are provided that comprise a pharmaceutical composition comprising the extracellular vesicles described herein. In some embodiments, the dosage form is formulated as a liquid suspension for intravenous injection. In some embodiments, the dosage form is formulated as a liquid suspension for intratumoral injection.

In certain embodiments, the preparation of extracellular vesicles is subjected to radiation, e.g., X rays, gamma rays, beta particles, alpha particles, neutrons, protons, elemental nuclei, UV rays in order to damage residual replication-competent nucleic acids.

In certain embodiments, the preparation of extracellular vesicles is subjected to gamma irradiation using an irradiation dose of more than 1, 5, 10, 15, 20, 25, 30, 35, 40, 50, 60, 70, 80, 90, 100, or more than 100 kGy.

In certain embodiments, the preparation of extracellular vesicles is subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

Methods

Aspects of the subject disclosure also include methods of producing the composition comprising the extracellular vesicle and the immunomodulating component. In some embodiments, the method comprises: obtaining the extracellular vesicle from the producer cell, wherein the producer cell naturally contains the immunomodulating component; and optionally isolating the obtained extracellular vesicle. In some embodiments, the method comprises: modifying a producer cell with the immunomodulating component; obtaining the extracellular vesicle from the modified producer cell; and optionally isolating the obtained extracellular vesicles. In some other embodiments, the method comprises: obtaining the extracellular vesicle from a producer cell; isolating the obtained extracellular vesicles; and modifying the isolated extracellular vesicle with the immunomodulating component. In certain embodiments, the method further comprises formulating the isolated extracellular vesicles into a pharmaceutical composition.

Methods of Producing the Extracellular Vesicles
Methods of Modifying the Producer Cell with the Immunomodulating Component In various embodiments, the method comprises modifying a producer cell with the immunomodulating component.

The producer cell can be a mammalian cell line, a plant cell line, an insect cell line, a fungi cell line, or a prokaryotic cell line. In certain embodiments, the producer cell is a mammalian cell line. The mammalian cell lines include but are not limited to a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, and a mesenchymal stem cell (MSC) cell line. In some preferred embodiments, the mammalian cell line can be HEK-293 cells, BJ human foreskin fibroblast cells, fHDF fibroblast cells, AGE.HN® neuronal precursor cells, CAP® amniocyte cells, adipose mesenchymal stem cells, or RPTEC/TERT1 cells. The producer cell can also be a primary cell. In various embodiments, the primary cell can be a primary mammalian cell, a primary plant cell, a primary insect cell, a primary fungi cell, or a primary prokaryotic cell.

In certain preferred embodiments, the producer cell is an immune cell, such as a dendritic cell, a T cell, a B cell, a natural killer cell (NK cell), an antigen presenting cell, a macrophage, a T helper cell, or a regulatory T cell (Treg cell).

In various embodiments, the immunomodulating component can be expressed in a producer cell from a transgene or mRNA introduced into the producer cell by transfection, viral transduction, electroporation, extrusion, sonication, cell fusion, or other methods that are known to the skilled in the art.

In certain embodiments, the immunomodulating component is introduced to the producer cell by transfection. In some embodiments, the immunomodulating component can be introduced into suitable producer cells using synthetic macromolecules such as cationic lipids and polymers (Papapetrou et al., Gene Therapy 12: S118-S130 (2005)). In some embodiments, the cationic lipids form complexes with the immunomodulating component through charge interactions. In some of these embodiments, the positively charged complexes bind to the negatively charged cell surface and are taken up by the cell by endocytosis. In some other embodiments, a cationic polymer can be used to transfect producer cells. In some of these embodiments, the cationic polymer is polyethylenimine (PEI). In certain embodiments, chemicals such as calcium phosphate, cyclodextrin, or polybrene, can be used to introduce the immunomodulating component to the producer cells. The immunomodulating component can also be introduced into a producer cell using a physical method such as particle-mediated transfection, "gene gun", biolistics, or particle bombardment technology (Papapetrou et al., Gene Therapy 12: S118-S130 (2005)). A reporter gene such as, for example, beta-galactosidase, chloramphenicol acetyltransferase, luciferase, or green fluorescent protein can be used to assess the transfection efficiency of the producer cell.

In certain embodiments, the immunomodulating component is introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In certain embodiments, the immunomodulating component is introduced to the producer cell by electroporation. Electroporation creates transient pores in the cell membrane, allowing for the introduction of various molecules into the cell. In some embodiments, DNA and RNA as well as polypeptides and non-polypeptide therapeutic agents can be introduced into the producer cell by electroporation.

In certain embodiments, the immunomodulating component is introduced to the producer cell by microinjection. In some embodiments, a glass micropipette can be used to inject the immunomodulating component into the producer cell at the microscopic level.

In certain embodiments, the immunomodulating component is introduced to the producer cell by extrusion.

In certain embodiments, the immunomodulating component is introduced to the producer cell by sonication. In some embodiments, the producer cell is exposed to high intensity sound waves, causing transient disruption of the cell membrane allowing loading of an immunomodulating component.

In certain embodiments, the immunomodulating component is introduced to the producer cell by cell fusion. In some embodiments, the immunomodulating component is introduced by electrical cell fusion. In some other embodiments, polyethylene glycol (PEG) is used to fuse the producer cells. In some other embodiments, sendai virus is used to fuse the producer cells.

In some embodiments, the immunomodulating component is introduced to the producer cell by hypotonic lysis. In some of these embodiments, the producer cell is exposed to low ionic strength buffer causing them to burst allowing loading of an immunomodulating component. In some alternative embodiments, controlled dialysis against a hypotonic solution is used to swell the producer cell and to create pores in the producer cell membrane. The producer cell is subsequently exposed to conditions that allow resealing of the membrane.

In some embodiments, the immunomodulating component is introduced to the producer cell by detergent treatment. In certain embodiments, producer cell is treated with a mild detergent which transiently compromises the producer cell membrane by creating pores allowing loading of an immunomodulating component. After producer cells are loaded, the detergent is washed away thereby resealing the membrane.

In some embodiments, the immunomodulating component is introduced to the producer cell by receptor mediated endocytosis. In certain embodiments, producer cells have a surface receptor which upon binding of the immunomodulating component induces internalization of the receptor and the associated immunomodulating component.

In some embodiments, the immunomodulating component is introduced to the producer cell by filtration. In certain embodiments, the producer cells and the immunomodulating component can be forced through a filter of pore size smaller than the producer cell causing transient disruption of the producer cell membrane and allowing the immunomodulating component to enter the producer cell.

In some embodiments, the producer cell is subjected to several freeze thaw cycles, resulting in cell membrane disruption allowing loading of an immunomodulating component.

Methods of Modifying the Extracellular Vesicle with the Immunomodulating Component In various alternative embodiments, the immunomodulating component is introduced directly to the extracellular vesicles after the isolation of the extracellular vesicles.

In certain embodiments, the immunomodulating component is introduced to the extracellular vesicle by transfection. In some embodiments, the immunomodulating component can be introduced into the extracellular vesicles using synthetic macromolecules such as cationic lipids and polymers (Papapetrou et al., Gene Therapy 12: S118-S130 (2005)). In certain embodiments, chemicals such as calcium phosphate, cyclodextrin, or polybrene, can be used to introduce the immunomodulating component to the extracellular vesicles.

In certain embodiments, the immunomodulating component is introduced to the extracellular vesicle by electroporation. In some embodiments, extracellular vesicles are exposed to an electrical field which causes transient holes in the extracellular vesicle membrane, allowing loading of an immunomodulating component.

In certain embodiments, the immunomodulating component is introduced to the extracellular vesicle by microinjection. In some embodiments, a glass micropipette can be used to inject the immunomodulating component directly into the extracellular vesicle at the microscopic level.

In certain embodiments, the immunomodulating component is introduced to the extracellular vesicle by extrusion.

In certain embodiments, the immunomodulating component is introduced to the extracellular vesicle by sonication.

In some embodiments, extracellular vesicles are exposed to high intensity sound waves, causing transient disruption of the extracellular vesicle membrane allowing loading of an immunomodulating component.

In some embodiments, the immunomodulating component can be conjugated to the surface of the extracellular vesicle. Conjugation can be achieved chemically or enzymatically, by methods known in the art.

In some embodiments, the extracellular vesicle comprises an immunomodulating component that is chemically conjugated. Chemical conjugation can be accomplished by covalent bonding of the immunomodulating component to another molecule, with or without use of a linker. The formation of such conjugates is within the skill of artisans and various techniques are known for accomplishing the conjugation, with the choice of the particular technique being guided by the materials to be conjugated. In certain embodiments, polypeptides are conjugated to the extracellular vesicle. In certain other embodiments, non-polypeptides, such as lipids, carbohydrates, nucleic acids, and small molecules, are conjugated to the extracellular vesicle.

In some embodiments, the immunomodulating component is introduced to the extracellular vesicle by hypotonic lysis. In some of these embodiments, the extracellular vesicles are exposed to low ionic strength buffer causing them to burst allowing loading of an immunomodulating component. In some alternative embodiments, controlled dialysis against a hypotonic solution is used to swell the extracellular vesicle and to create pores in the extracellular vesicle membrane. The extracellular vesicle is subsequently exposed to conditions that allow resealing of the membrane.

In some embodiments, the immunomodulating component is introduced to the extracellular vesicle by detergent treatment. In certain embodiments, extracellular vesicles are treated with a mild detergent which transiently compromises the extracellular vesicle membrane by creating pores allowing loading of an immunomodulating component. After extracellular vesicles are loaded, the detergent is washed away thereby resealing the membrane.

In some embodiments, the immunomodulating component is introduced to the extracellular vesicle by receptor mediated endocytosis. In certain embodiments, extracellular vesicles have a surface receptor which upon binding of the immunomodulating component induces internalization of the receptor and the associated immunomodulating component.

In some embodiments, the immunomodulating component is introduced to the extracellular vesicle by mechanical firing. In certain embodiments, extracellular vesicles can be bombarded with an immunomodulating component attached to a heavy or charged particle such as gold microcarriers. In some of these embodiments, the particle can be mechanically or electrically accelerated such that it traverses the extracellular vesicle membrane.

In some embodiments, the immunomodulating component is introduced to the extracellular vesicle by filtration. In certain embodiments, the extracellular vesicles and the immunomodulating component can be forced through a filter of pore size smaller than the extracellular vesicle causing transient disruption of the extracellular vesicle membrane and allowing the immunomodulating component to enter the extracellular vesicle.

In some embodiments, extracellular vesicles are subjected to several freeze thaw cycles, resulting in extracellular vesicle membrane disruption allowing loading of an immunomodulating component.

Methods of Isolating the Extracellular Vesicles

The extracellular vesicles can be isolated from the producer cells. In certain embodiments, the extracellular vesicle is released by the producer cell into the cell culture medium. It is contemplated that all known manners of isolation of extracellular vesicles are deemed suitable for use herein. For example, physical properties of extracellular vesicles can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Alternatively, or additionally, isolation can be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using extracellular vesicle or producer cell-specific surface markers. For example, specific surface markers can be used in immunoprecipitation, FACS sorting, affinity purification, and magnetic separation with bead-bound ligands.

In some embodiments, size exclusion chromatography can be utilized to isolate the extracellular vesicles. Size exclusion chromatography techniques are known in the art. Exemplary, non-limiting techniques are provided herein. In some embodiments, a void volume fraction is isolated and comprises the extracellular vesicles of interest. Further, in some embodiments, the extracellular vesicles can be further isolated after chromatographic separation by centrifugation techniques (of one or more chromatography fractions), as is generally known in the art. In some embodiments, for example, density gradient centrifugation can be utilized to further isolate the extracellular vesicles. In certain embodiments, it can be desirable to further separate the producer cell-derived extracellular vesicles from extracellular vesicles of other origin. For example, the producer cell-derived extracellular vesicles can be separated from non-producer cell-derived extracellular vesicles by immunosorbent capture using an antigen antibody specific for the producer cell.

In some embodiments, the isolation of extracellular vesicles can involve combinations of methods that include, but are not limited to, differential centrifugation, size-based membrane filtration, immunoprecipitation, FACS sorting, and magnetic separation.

Methods of Measuring the Size of Extracellular Vesicles

In some embodiments, the methods described herein comprise measuring the size of extracellular vesicles and/or populations of extracellular vesicles. Generally, extracellular vesicle size is measured as the longest measurable dimension. Generally, the longest measurable dimension of an extracellular vesicle is also referred to as its diameter.

Extracellular vesicle size can be measured using dynamic light scattering (DLS) and/or multiangle light scattering (MALS). Methods of using DLS and/or MALS to measure the size of extracellular vesicles are known to those of skill in the art, and include the nanoparticle tracking assay (NTA, e.g., using a Malvern NanoSight NS300 nanoparticle tracking device). In a specific embodiment, the extracellular vesicle size is determined using a Malvern NanoSight NS300. In some embodiments, the extracellular vesicles described herein have a longest dimension of about 20-300 nm as measured by NTA (e.g., using a Malvern NanoSight NS300). In other embodiments, the extracellular vesicles described herein have a longest dimension of about 40-200 nm as measured by NTA (e.g., using a Malvern NanoSight NS300). In other embodiments, the extracellular vesicle populations described herein comprise a population, wherein 90% of the extracellular vesicles have a longest dimension of about 20-300 nm as measured by NTA (e.g., using a Malvern NanoSight NS300). In other embodiments, the extracellular vesicle populations described herein comprise a population, wherein 95% of the extracellular vesicles have a longest dimension of about 20-300 nm as measured by NTA (e.g., using a Malvern NanoSight NS300). In other embodiments, the extracellular vesicle populations described herein comprise a population, wherein 99% of the extracellular vesicles have a longest dimension of about 20-300 nm as measured by NTA (e.g., using a Malvern NanoSight NS300). In other embodiments, the extracellular vesicle populations described herein comprise a population, wherein 90% of the extracellular vesicles have a longest dimension of about 40-200 nm as measured by NTA (e.g., using a Malvern NanoSight NS300). In other embodiments, the extracellular vesicle populations described herein comprise a population, wherein 95% of the extracellular vesicles have a longest dimension of about 40-200 nm as measured by NTA (e.g., using a Malvern NanoSight NS300). In other embodiments, the extracellular vesicle populations described herein comprise a population, wherein 99% of the extracellular vesicles have a longest dimension of about 40-200 nm as measured by NTA (e.g., using a Malvern NanoSight NS300).

Extracellular vesicle size can be measured using tunable resistive pulse sensing (TRPS). In a specific embodiment, extracellular vesicle size as measured by TRPS is determined using an iZON qNANO Gold. In some embodiments, the extracellular vesicles described herein have a longest dimension of about 20-300 nm as measured by TRPS (e.g., using an iZON qNano Gold). In other embodiments, the extracellular vesicles described herein have a longest dimension of about 40-200 nm as measured by TRPS (e.g., an iZON qNano Gold). In other embodiments, the extracellular vesicle populations described herein comprise a population, wherein 90% of the extracellular vesicles have a longest dimension of about 20-300 nm as measured by TRPS (e.g., using an iZON qNano Gold). In other embodiments, the extracellular vesicle populations described herein comprise a population, wherein 95% of the extracellular vesicles have a longest dimension of about 20-300 nm as measured by TRPS (e.g., using an iZON qNano Gold). In other embodiments, the extracellular vesicle populations described herein comprise a population, wherein 99% of the extracellular vesicles have a longest dimension of about 20-300 nm as measured by TRPS (e.g., using an iZON qNano Gold). In other embodiments, the extracellular vesicle populations described herein comprise a population, wherein 90% of the extracellular vesicles have a longest dimension of about 40-200 nm as measured by TRPS (e.g., using an iZON qNano Gold). In other embodiments, the extracellular vesicle populations described herein comprise a population, wherein 95% of the extracellular vesicles have a longest dimension of about 40-200 nm as measured by TRPS (e.g., using an iZON qNano Gold). In other embodiments, the extracellular vesicle populations described herein comprise a population, wherein 99% of the extracellular vesicles have a longest dimension of about 40-200 nm as measured by TRPS (e.g., using an iZON qNano Gold).

Extracellular vesicles size can be measured using electron microscopy. In some embodiments, the method of electron microscopy used to measure extracellular vesicle size is transmission electron microscopy. In a specific embodiment, the transmission electron microscope used to measure extracellular vesicle size is a Tecnai™ $G^2$ Spirit BioTWIN. Methods of measuring extracellular vesicle size using an electron microscope are well-known to those of skill in the art, and any such method can be appropriate for measuring extracellular vesicle size. In some embodiments, the extracellular vesicles described herein have a longest dimension of about 20-300 nm as measured by a scanning electron microscope (e.g., a Tecnai™ $G^2$ Spirit BioTWIN scanning electron microscope). In other embodiments, the extracellular vesicles described herein have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population, wherein 90% of the extracellular vesicles have a longest dimension of about 20-300 nm as measured by a scanning electron microscope (e.g., a Tecnai™ $G^2$ Spirit BioTWIN scanning electron microscope). In other embodiments, the extracellular vesicle populations described herein comprise a population, wherein 95% of the extracellular vesicles have a longest dimension of about 20-300 nm as measured by a scanning electron microscope (e.g., a Tecnai™ $G^2$ Spirit BioTWIN scanning electron microscope). In other embodiments, the extracellular vesicle populations described herein comprise a population, wherein 99% of the extracellular vesicles have a longest dimension of about 20-300 nm as measured by a scanning electron microscope (e.g., a Tecnai™ $G^2$ Spirit BioTWIN scanning electron microscope). In other embodiments, the extracellular vesicle populations described herein comprise a population wherein 90% of the extracellular vesicles have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population wherein 95% of the extracellular vesicles have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population wherein 99% of the extracellular vesicles have a longest dimension of about 40-200 nm as measured by a scanning electron microscope (e.g., a Tecnai™ $G^2$ Spirit BioTWIN scanning electron microscope).

Methods of Treating Cancer, GvHD, and Autoimmune Disease

Also, provided herein are methods of treating cancer, graft-versus-host-disease (GvHD) and autoimmune disease in a subject.

In various embodiments, the composition is administered to a subject with cancer. In some of these embodiments, the composition can up-regulate an immune response and enhance the tumor targeting of the subject's immune system. In some embodiments, the cancer being treated is characterized by infiltration of leukocytes (T-cells, B-cells, macrophages, dendritic cells, monocytes) into the tumor microenvironment, or so-called "hot tumors" or "inflammatory tumors". In some embodiments, the cancer being treated is characterized by low levels or undetectable levels of leukocyte infiltration into the tumor microenvironment, or so-called "cold tumors" or "non-inflammatory tumors". In some embodiments, the composition is administered in an amount and for a time sufficient to convert a "cold tumor" into a "hot tumor", i.e., said administering results in the infiltration of leukocytes (such as T-cells) into the tumor microenvironment.

In some embodiments, the composition comprising an extracellular vesicle and an immunomodulating component is administered to a subject as a cancer vaccine. In some of these embodiments, the composition is administered to a subject as a personalized cancer vaccine. In some embodiments, the immunomodulating component is a tumor antigen or a peptide derived from a tumor antigen. Examples of suitable tumor antigens include: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived a genome sequence of the subject receiving the composition.

The cancers that can be treated with the composition include but are not limited to the cancers listed in Table 5.

In certain embodiments, the composition is administered to a subject with graft-versus-host disease (GvHD). In some of these embodiments, the composition can down-regulate an immune response and alleviate the symptoms of GvHD. In some specific embodiments, the composition alleviates the symptoms of GvHD through activation of apoptotic signaling. In certain embodiments, the composition for treating GvHD comprises Fas ligand (FasL). In some of these embodiments, the FasL is expressed on the surface of the extracellular vesicle.

In various embodiments, the composition is administered to a subject with an autoimmune disease. In some of these embodiments, the composition can down-regulate an immune response and suppress the immune activity of the subject.

The autoimmune diseases include but are not limited to multiple sclerosis, peripheral neuritis, Sjogren's syndrome, rheumatoid arthritis, alopecia, autoimmune pancreatitis, Behcet's disease, Bullous pemphigoid, Celiac disease, Devic's disease (neuromyelitis optica), Glomerulonephritis, IgA nephropathy, assorted vasculitides, scleroderma, diabetes, arteritis, vitiligo, ulcerative colitis, irritable bowel syndrome, psoriasis, uveitis, and systemic lupus erythematosus.

In some embodiments, the composition is administered intravenously to the circulatory system of the subject. In some embodiments, the composition is infused in suitable liquid and administered into a vein of the subject.

In some embodiments, the composition is administered intra-arterialy to the circulatory system of the subject. In some embodiments, the composition is infused in suitable liquid and administered into an artery of the subject.

In some embodiments, the composition is administered to the subject by intrathecal administration. In some embodiments, the composition is administered via an injection into the spinal canal, or into the subarachnoid space so that it reaches the cerebrospinal fluid (CSF).

In some embodiments, the composition is administered intratumorally into one or more tumors of the subject.

In some embodiments, the composition is administered to the subject by intranasal administration. In some embodiments, the composition can be insufflated through the nose in a form of either topical administration or systemic administration. In certain embodiments, the composition is administered as nasal spray.

In some embodiments, the composition is administered to the subject by intraperitoneal administration. In some embodiments, the composition is infused in suitable liquid and injected into the peritoneum of the subject. In some embodiments, said intraperitoneal administration results in distribution of the composition (e.g., the extracellular vesicles in the composition) to the lymphatics. In some embodiments, said intraperitoneal administration results in distribution of the composition (e.g., the extracellular vesicles in the composition) to the thymus, spleen, and/or bone marrow. In some embodiments, said intraperitoneal administration results in distribution of the composition (e.g., the extracellular vesicles in the composition) to one or more lymph nodes. In some embodiments, said intraperitoneal administration results in distribution of the composition (e.g., the extracellular vesicles in the composition) to one or more of the cervical lymph node, the inguinal lymph node, the mediastinal lymph node, or the sternal lymph node. In some embodiments, said intraperitoneal administration results in distribution of the composition (e.g., the extracellular vesicles in the composition) to the pancreas.

In some embodiments, the composition is administered to the subject by periocular administration. In some embodiments, the composition is injected into the periocular tissues. Periocular drug administration includes the routes of sub-conjunctival, anterior sub-Tenon's, posterior sub-Tenon's, and retrobulbar administration.

In some embodiments, the composition is administered into the same subject by multiple routes of administration. In some embodiments, said multiple routes of administration comprise intravenous administration, intra-arterial administration, intrathecal administration, intranasal administration, intratumoral administration, intraperitoneal administration, and/or periocular administration. In a preferred embodiment, said multiple routes of administration comprise intravenous administration and intraperitoneal administration.

In certain embodiments, the dosage of the extracellular vesicles is between 1 ng to 10 ng, 10 ng to 100 ng, 100 ng to 1 µg, 1 µg to 5 µg, 5 µg to 10 µg, 10 µg to 50 µg, 50 µg to 75 µg, 75 µg to 100 µg, 100 µg to 150 µg, 150 µg to 200 µg, 200 µg to 300 µg, 300 µg to 500 µg, 500 µg to 1 mg, or 1 mg to 10 mg.

The compositions can be administered once to the subject. Alternatively, multiple administrations can be performed over a period of time. For example, two, three, four, five, or more administrations can be given to the subject. In some embodiments, administrations can be given as needed, e.g., for as long as symptoms associated with the disease, disorder or condition persists. In some embodiments, repeated administrations can be indicated for the remainder of the subject's life. Treatment periods can vary and can be, e.g., no longer than a year, six months, three months, two months, one month, two weeks, one week, three days, two days, or no longer than one day.

In certain embodiments, doses of extracellular vesicles are administered at intervals such as once daily, every other day, once weekly, twice weekly, once monthly or twice monthly.

In some embodiments, the pharmaceutical composition is administered at a frequency sufficient to effectively increase the concentration of the immunomodulating component in the target cell or tissue above a level that is associated with a symptom of the disease, disorder or condition.

In some embodiments, the compositions are administered at least twice over a treatment period such that the disease, disorder or condition is treated, or a symptom thereof is ameliorated. In some embodiments, the compositions are administered at least twice over a treatment period such that the disease, disorder or condition is treated or a symptom thereof is prevented. In some embodiments, the pharmaceutical composition is administered a sufficient number of times over a treatment period such that a sufficient amount of immunomodulating component is delivered to the target cell or tissue during the treatment period. In some embodiments, the pharmaceutical composition is administered a sufficient number of times over a treatment period such that a sufficient amount of immunomodulating component is delivered to the target cell or tissue during the treatment period such that one or more symptoms of the disease, disorder or condition is prevented, decreased, ameliorated or delayed. In some embodiments, increasing the immunomodulating component concentration in the target cell or tissue includes increasing the peak concentration, while in others it includes increasing the average concentration. In some embodiments, a substantial increase during the treatment period can be determined by comparing a pretreatment or post-treatment period in the subject, or by comparing measurements made in a population undergoing treatment with a matched, untreated control population.

In some embodiments, the pharmaceutical composition is administered a sufficient number of times per treatment period such that the concentration of immunomodulating component in the target cell or tissue is increased for at least about one week, two weeks, three weeks, four weeks, one month, two months, three months, four months, five months, six months or greater than six months. In some embodiments, the pharmaceutical composition is administered a sufficient number of times per treatment period such that the concentration of immunomodulating component in the target cell or tissue is increased for a period of time at least as long as the treatment period.

In some embodiments, the time interval between repeated administrations within a treatment period is no longer than the period in which the number of extracellular vesicles in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of extracellular vesicles present in the administered pharmaceutical composition.

In some embodiments, the methods further comprise one or multiple doses of non-therapeutic extracellular vesicles prior to the injection of a suitable therapeutic dose of extracellular vesicles harboring a therapeutic agent. In certain embodiments, the non-therapeutic extracellular vesicle is administered separately to and at a different dosage than the therapeutic extracellular vesicles. In certain embodiments, the dosage of the non-therapeutic extracellular vesicle is greater than the dosage of the therapeutic extracellular vesicle. In certain other embodiments, the dosage of the non-therapeutic extracellular vesicle is smaller than the dosage of the therapeutic extracellular vesicle. In certain embodiments, the dosage of the non-therapeutic extracellular vesicle is the same as the therapeutic extracellular vesicle. In various embodiments, the methods of non-therapeutic extracellular vesicles prior to injection of a suitable dose of therapeutic extracellular vesicles reduce the update of the therapeutic extracellular vesicles in the liver, lung, and/or spleen.

An effective amount of the composition is provided based, at least in part, on the target tissue, target cell type, means of administration, physical characteristics of the extracellular vesicle (e.g., size, and in some cases the extent of molecules to be delivered) and other determinants. In general, an effective amount of the composition provides efficient cellular response of the target cell. Increased efficiency can be demonstrated by increased cell transfection (i.e., the percentage of cells transfected with the extracellular vesicle constituents), increased cellular response or reduced innate immune response of the host subject.

The dosing and frequency of the administration of the extracellular vesicles and pharmaceutical compositions thereof can be determined, e.g., by the attending physician based on various factors such as the severity of disease, the patient's age, sex and diet, the severity of any inflammation, time of administration and other clinical factors. In an example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse effects that can appear.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pennsylvania: Mack Publishing Company, 2005); Carey and Sundberg Advanced Organic Chemistry $3^{rd}$ Ed. (Plenum Press) Vols A and B(1992).

Methods

Exosome Purification

Conditioned culture media was collected and centrifuged at 300-800×g for 5 minutes at room temperature to remove cells and large debris. Media supernatant was then supplemented with 1000 U/L Benzonase® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and any residual media was aspirated from the bottom of the tube. The pellet was resuspended in 200-1000 μL, PBS (—Ca —Mg).

To further enrich exosome populations, the pellet was processed via density gradient purification (sucrose or Optiprep™). For sucrose gradient purification, the exosome pellet was layered on top of a sucrose gradient as defined in Table 6 below:

TABLE 6

| Sucrose Density Gradient: | | |
|---|---|---|
| Working Percentage (%) | 65% Stock Vol. (mL) | Milli-Q Vol. (mL) |
| 50 | 3.85 | 1.15 |
| 40 | 3.08 | 1.92 |
| 25 | 1.92 | 3.08 |
| 10 | 0.46 | 2.54 |

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 μL) and stored at 4° C.

For Optiprep™ gradient, a 3-tier sterile gradient was prepared with equal volumes of 10%, 30%, and 45% Optiprep in a 12 mL Ultra-Clear (344059) tube for a SW 41 Ti rotor. The pellet was added to the Optiprep™ gradient and ultracentrifuged at 200,000×g for 16 hours at 4° C. to separate the exosome fraction. The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 μL) and store at 4° C.

Example 1: Engineering Exosomes to Display an Immune Checkpoint Regulator Antibody A human embryonic kidney (HEK) cell line is grown to high density, and the resulting exosomes are isolated from culture medium according to methods known to those of skill in the art (e.g., the methods described herein). Exosomes engineered with cytotoxic T-lymphocyte-associated protein 4 (CTLA-4) antibody are prepared by chemical conjugation according to the techniques known in the art. The exosomes modified with CTLA4 antibody are selected by flow cytometry. At the same time, unmodified exosomes are isolated according to the same standard methods.

The two exosome populations are labeled with a radioactive tracer, and 150 μg of each preparation is injected into live mice (e.g. mouse model of melanoma). The mice receiving either the exosomes displaying the CTLA-4 antibody or the unmodified exosomes are monitored continuously for 30 minutes, and again at four hour intervals by whole-animal PET/CT. Whole-animal imaging allows for real-time, high resolution tracking of labeled exosomes to various tissues.

150 µg of each exosome population are injected into two mouse cohorts intravenously without first labeling with a radioactive tracer. The mice are euthanized five weeks post-administration. The tumor samples are collected and analyzed by immunohistochemistry and real-time PCR.

Example 2: Engineering Exosomes to Display Fas Ligand

Human antigen-presenting cells are transfected with a plasmid encoding a puromycin-resistant selectable marker and Fas ligand. Transfected cells are treated with puromycin, and resistant colonies are selected and assayed for surface expression of Fas ligand by flow cytometry. Stable Fas ligand-expressing cells are grown to high concentration, and the resulting exosomes are isolated from culture medium according to methods known to those of skill in the art (e.g., the methods described herein). At the same time, untransfected producer cells are cultured and the resulting exosomes are isolated according to the same standard methods.

The two exosome populations are labeled with a radioactive tracer, and 150 µg of each preparation is injected into live mice (e.g. mouse model of GvHD). The mice receiving either the exosomes derived from unmodified cells or the exosomes derived from Fas ligand-expressing cells are monitored continuously for 30 minutes, and again at four hour intervals by whole-animal PET/CT. Whole-animal imaging allows for real-time, high resolution tracking of labeled exosomes to various tissues.

Purified exosome populations from unmodified producer cells and producer cells engineered to express Fas ligand are purified according to the methods described herein. 150 µg of each exosome population are injected into two mouse cohorts without first labeling with a radioactive tracer. Animals of both cohorts are euthanized three to five weeks post-administration for immunohistochemical analysis and real-time PCR.

Example 3: Lymphatic Uptake of Exosomes after Intraperitoneal Administration To determine the biodistribution of purified exosomes in vivo, the following experiment was performed:

Conditioned culture media from 293T cells was collected and centrifuged at 300-800×g for 5 minutes at room temperature to remove cells and large debris. Media supernatant was then supplemented with 1000 U/L Benzonase® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and residual media was aspirated from the bottom of the tube. The pellet was then resuspended in 200-1000 µL PBS (—Ca —Mg).

To further enrich exosome populations, the pellet was processed via sucrose density gradient purification as defined in Table 6.

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 µL) and stored at 4° C.

To radiolabel the purified exosomes for in vivo imaging, $1\times10^{11}$ purified exosomes in 100 µL, were diluted with HEPES (200 µL, 0.1M, pH 8.5) and conjugated to p-SCN-Bn-DFO (5 µg) for one hour at 37° C. followed by overnight incubation at 4° C., separately. DFO-exosomes were incubated with 89Zr (7.5mCi) diluted in HEPES (100 µL, 1M, pH 7.3) for one hour at 37° C. and purified on a qEv column. This resulted in a total yield (0.4 mCi of 89Zr-DFO-exosomes in up to 0.8 mL PBS) at 100 µCi/$1\times10^{10}$ exosomes. Quality control (HPLC) was performed prior to release to ensure >95% RCP.

In Vitro Stability

Exosomes (20 µCi/$2\times10^{10}$) were incubated at room temperature in:
 a. Formulation buffer
 b. Mouse serum (10% v/v exosome solution in serum, if possible)

2 hours after initiation of incubation solutions were injected into HPLC to determine stability of tracer.

In Vivo Imaging

Mice (SKH-1, n=8, age 5-8 weeks) were randomized into two groups, weighed and injected (with the second group injected immediately after the first group's dynamic scan is over) with $1\times10^{10}$/g exosomes to give a minimum radioactive dose of 100 µCi/mouse. Group 1 was injected intravenously (IV) while group 2 was injected intraperitoneally (IP).

Mice receive a whole-body PET/CT scan in a 4-mouse hotel using the following schedule: 1 h dynamic (5×60, 5×180, 8×300 seconds) and static imaging at 4 h (20 min), 24 h (Thursday, 20 min) and 48 h (Friday, 30 min). Each imaging time point was followed by CT for anatomical reference.

After the last imaging time point, mice were euthanized and the following organs were collected, weighed and counted in the gamma counter: blood, lung (one), liver (lobe), spleen, pancreas, kidney (one), liver, colon and additional organs of high uptake.

Organs were allowed to decay for 2-3 days if counts were extremely high and counted again.

TABLE 7

| Group (mouse # and type) | Tracer | Injection route | Imaging | Imaging time points |
|---|---|---|---|---|
| 1 (n = 4, SKH-1) | 89Zr-DFO-exosomes (100 µCi, <200 µL) | IV | Whole body PET/CT using a 4 mouse hotel | 1 h dynamic followed by static at 4 h and 24 h (20 min) 48 h (30 min) |
| 2 (n = 4, SKH-1) | 89Zr-DFO-exosomes (100 µCi, <200 µL) | IP | Whole body PET/CT using a 4 mouse hotel | 1 h dynamic followed by static at 4 h and 24 h (20 min) 48 h (30 min) |

Results

The two cohorts of treated mice were imaged 4 hours, 24 hours, and 48 hours after treatment. Whole body PET/CT imaging revealed robust delivery to the livers of all mice in group 1 treated IV (FIG. 1A), and a distinct non-overlapping distribution for mice in group 2 treated IP (FIG. 1B). Organs were dissected and analyzed by radiographic gamma counter, which revealed significant liver and spleen uptake in mice treated IV (FIG. 2). In contrast, for mice treated IP, uptake was primarily observed in the pancreas, spleen, thymus, and lymph nodes, with additional uptake in the liver and ovaries. These results demonstrate that different routes of administration result in substantially different biodistribution profiles. Importantly, IP administration led to significant uptake in the lymphatics, suggesting that IP administration can be a suitable route of administration to reach immune cells.

Example 4: B-Cell Activation by Engineered CD40L Exosomes

CD40L is a member of the tumor necrosis factor (TNF) superfamily primarily expressed on T-cells. The CD40L receptor, CD40, is expressed on antigen presenting cells including macrophages, dendritic cells and B-cells. Signaling through CD40 activates B-cells and induces an antigen-specific response. Activating the CD40 pathway therefore has implications in the development of anti-tumor immunity in a broad array of tumor types. To determine whether engineered exosomes could be generated to induce a specific immunological effect, exosomes were generated from HEK293SF cells transfected with a plasmid containing full-length human CD40L. Transfected cells were put under puromycin selection and resistant cell populations were grown to high density. The resulting exosomes were collected from the conditioned culture medium and purified over an Optiprep™ gradient as described above. Exosomes from unmodified HEK293SF cells were also isolated to be used as a control. Human peripheral blood mononuclear cells (PBMCs) were plated at 150,000 cells per well of a 96-well plate, and incubated with purified CD40L exosomes or native exosomes overnight at 37° C. One sample of PBMCs was incubated with 1 µg/mL of soluble recombinant CD40L-Fc as a positive control. As shown in FIGS. 3A and 3B, CD40L exosomes activated B-cells in a dose-dependent manner, as measured by CD69 expression in two different donor samples. Native exosomes failed to induce B-cell activation. Importantly, the level of B-cell activation by CD40L exosomes was comparable to the activation caused by the CD40L-Fc.

Figure 4A:
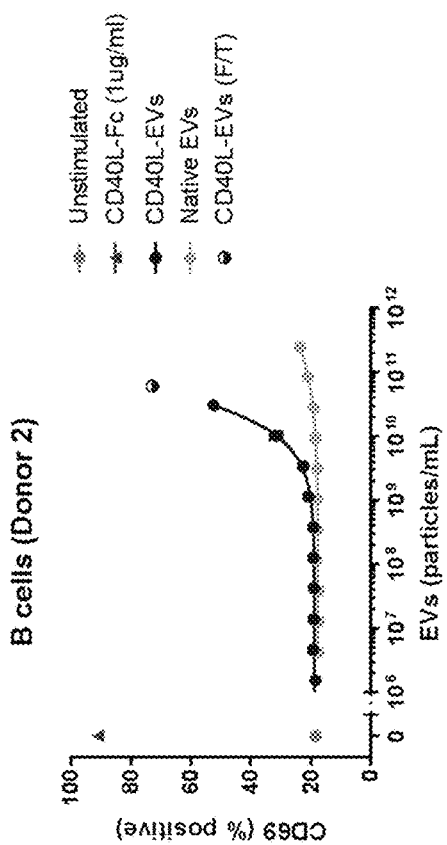
FIGS. 4A and 4B show the effects of B-cell activation of purified B-cells from two human donors after incubation with CD40L-expressing exosomes.
Figure 4B:
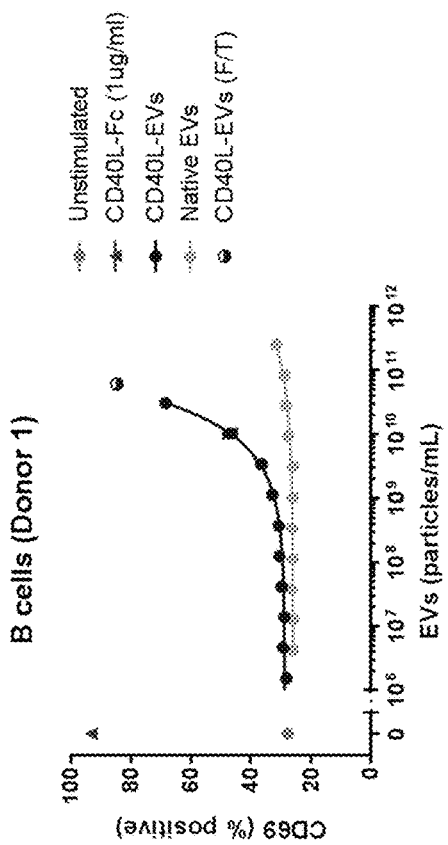

To determine whether the observed exosome-mediated B-cell activation was due to direct activation of B-cells or through trans-acting immune cells, a similar experiment was carried out using purified human B-cells. 50,000 purified human B-cells were plated in a 96-well plate and incubated with either CD40L exosomes, native exosomes, or CD40L-Fc. One sample of high concentration CD40L exosomes was put through a freeze-thaw cycle (CD40L-EVs [F/T]) and tested for B-cell activation as well. As shown in FIGS. 4A and 4B, CD40L exosomes activated purified B-cells from two donors to a similar extent as CD40L-Fc. Native exosomes failed to activate B-cells, while the CD40L exosome freeze-thaw samples successfully activated B-cells, indicating that the effect of CD40L exosomes is mediated directly through B-cells, and that the presence of CD40L is sufficient for B-cell activation. Additionally, the engineered exosomes remain stable and active for at least one freeze-thaw cycle.

Figure 5C:
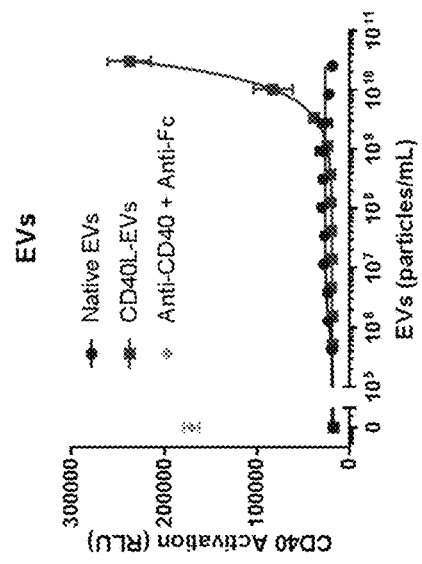
FIG. 5C shows the effects of CD40L-expressing exosomes on a CD40 reporter cell line.
Figure 5B:
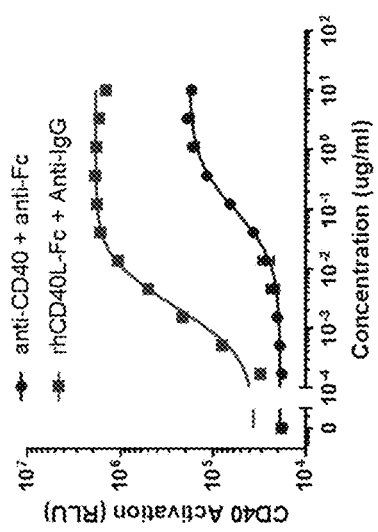
FIG. 5B shows the concentration-dependent activation of a CD40 reporter cell line treated with an anti-CD40 agonistic antibody or recombinant human CD40L.
Figure 5A:
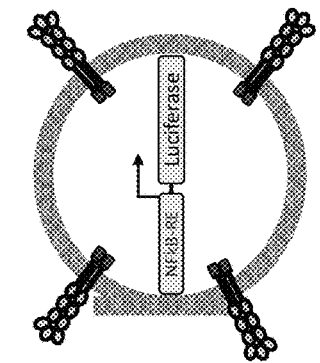
FIG. 5A is a schematic of a CD40 reporter cell line.

To further validate the CD40L exosomes, a reporter system was used to measure the activity of the engineered exosomes. Activation of CD40 pathway results in activation of NF-κB. Using a modified U2OS cell line engineered to overexpress CD40 on its surface and contain a luciferase reporter downstream of the NF-κB promoter (Promega Corporation), CD40 activation was confirmed by incubating the cells in the presence of an agonistic anti-CD40 antibody (BioLegend, Inc.) crosslinked with an anti-Fc antibody (Jackson ImmunoResearch, Inc.) or recombinant human CD40L (ACROBiosystems) cross-linked with an anti-IgG antibody (Jackson ImmunoResearch, Inc.) (FIGS. 5A and 5B). CD40L engineered exosomes were incubated with the engineered cells and resulted in a robust increase in luciferase activity comparable to the effects of anti-CD40+anti-Fc. Importantly, the engineered exosomes did not require a cross-linking antibody, demonstrating that CD40L on the surface of exosomes can form functional CD40L trimers sufficient to activate CD40.

Example 5: T-Cell Activation by Engineered CD80 Exosomes

Figure 6B:
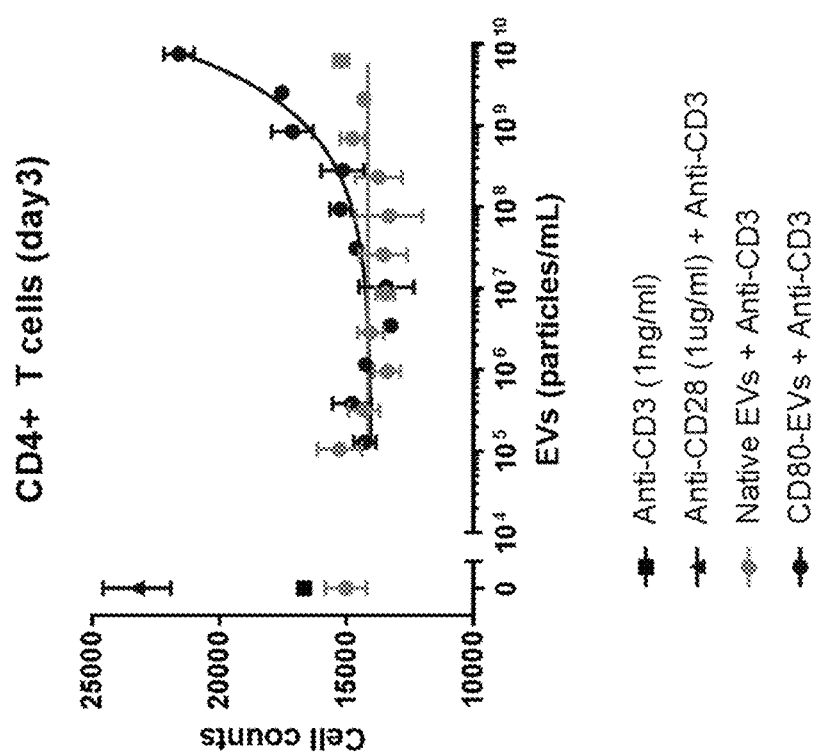
FIGS. 6A and 6B show the effects of T-cell activation in peripheral blood mononuclear cells (PBMCs) with CD80-expressing exosomes.
Figure 6A:
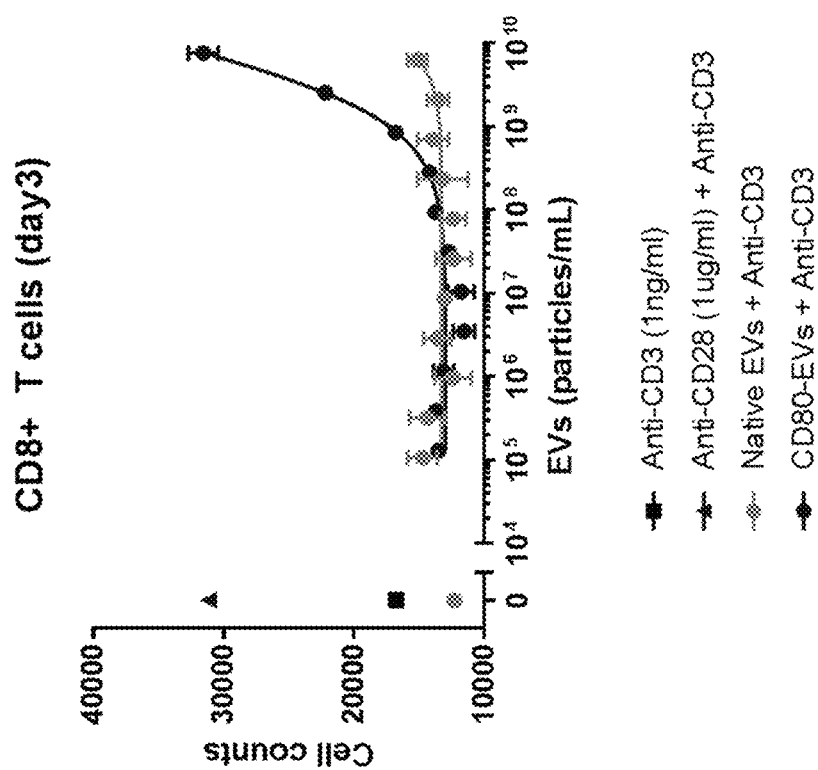

CD80 is expressed on antigen presenting cells and binds to CD28 and CTLA-4 on the surface of T-cells. Stimulation by CD80 (and CD86) through CD28 and CTLA-4 activates T-cells during the initiation of an immune response. To determine whether exosomes could be engineered to activate T-cells, CD80-containing exosomes were generated by transfection and selection of HEK293SF cells as described in Example 4. To validate the activity of CD80 exosomes, human PBMCs were plated at 150,000 cells per well of a 96-well plate, and incubated with (i) purified CD80 exosomes and anti-CD3 antibody, (ii) native exosomes and anti-CD3 antibody, (iii) anti-CD3 antibody alone, or (iv) a combination of anti-CD28 and anti-CD3 antibodies. The samples were incubated at 37° C. for three days and assayed for T-cell counts for both CD4$^+$ T-cells (FIG. 6A) and CD8$^+$ T-cells (FIG. 6B). CD80 exosomes activated T-cells in a dose-dependent manner and to an extent comparable to the positive control of CD3 and CD28 antibodies. In contrast, the native exosomes had no effect on T-cell proliferation.

Figure 7B:
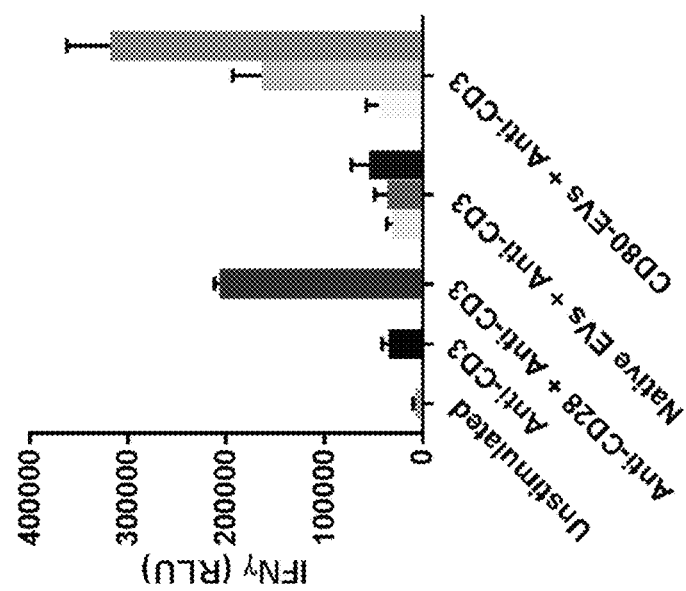
FIGS. 7A and 7B show the effects of CD80-expressing exosomes on IFNγ expression in human PBMCs.
Figure 7A:
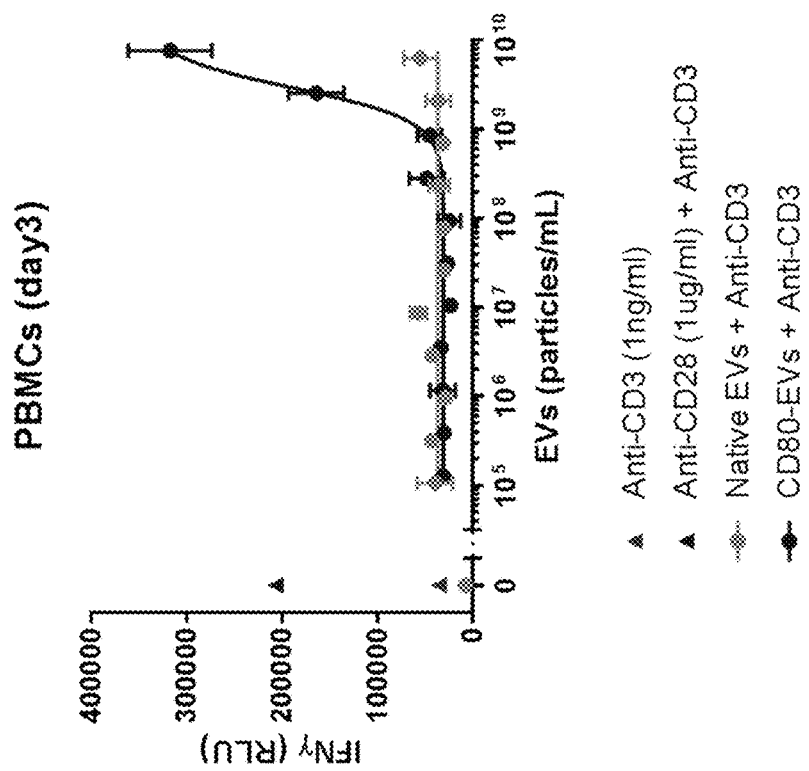

To confirm that CD80 exosomes induce a functional activation of T-cells, IFNγ levels were measured by AlphaLISA in PBMCs incubated with native exosomes and CD80 exosomes with additional anti-CD3 antibody. As shown in FIG. 7A, there was a dose-dependent increase in IFNγ levels for the CD80 exosomes but not for the native exosomes. As shown in FIG. 7B, the highest concentrations of CD80 exosomes resulted in greater IFNγ levels than any other condition, including the positive control (anti-CD28/anti-CD3). These results demonstrate that exosomes can be engineered with specific activity that results in immune cell activation.

Figure 8A:
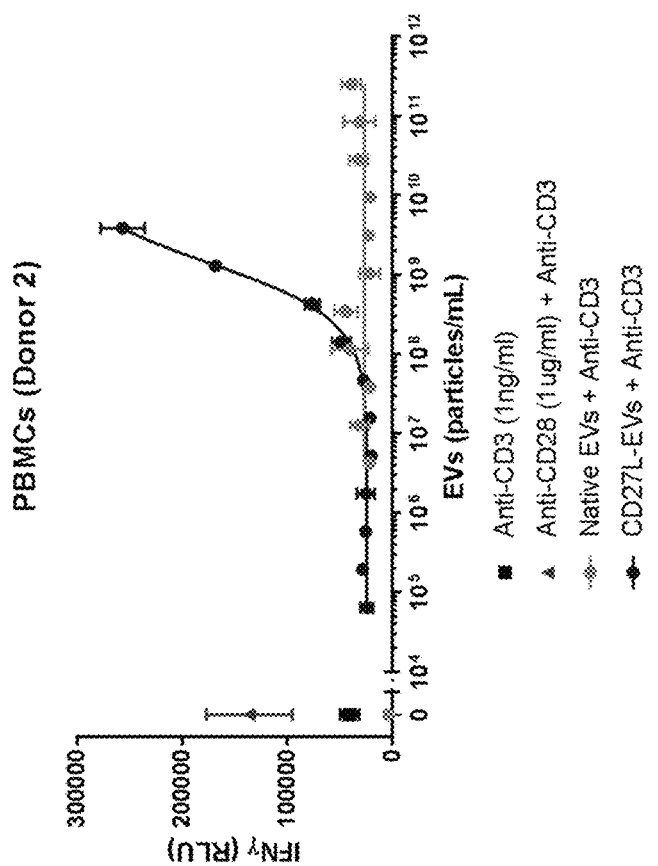
FIGS. 8A and 8B show the effects of CD27L-expressing exosomes on IFNγ expression in human PBMCs from two donors.
Figure 8B:
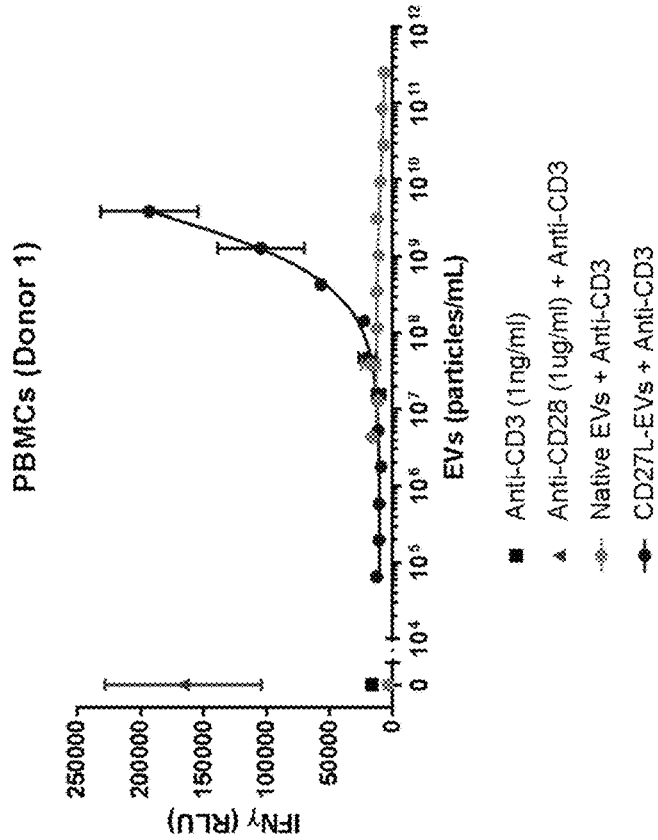
Figure 9A:
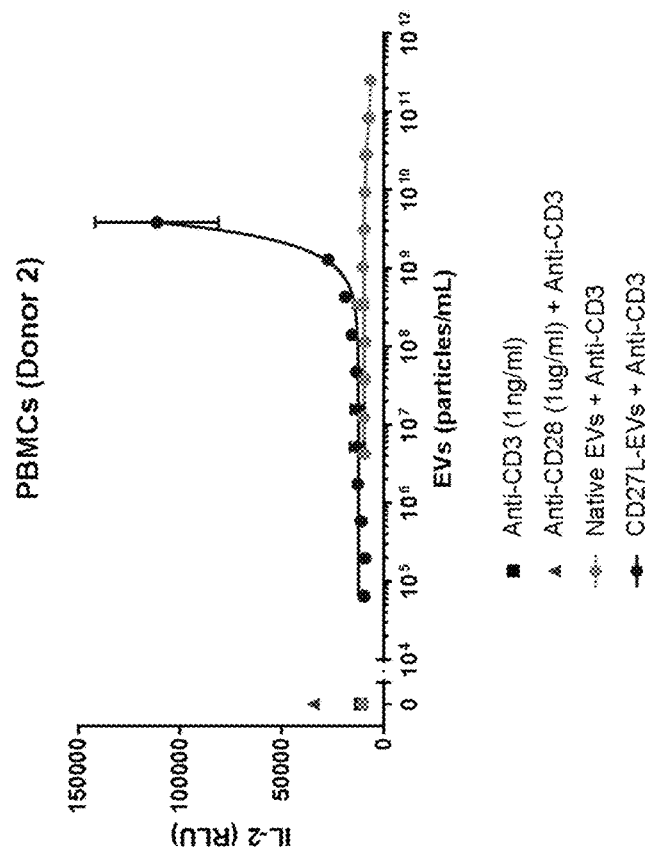
FIGS. 9A and 9B show the effects of CD27L-expressing exosomes on IL-2 expression in human PBMCs from two donors.
Figure 9B:
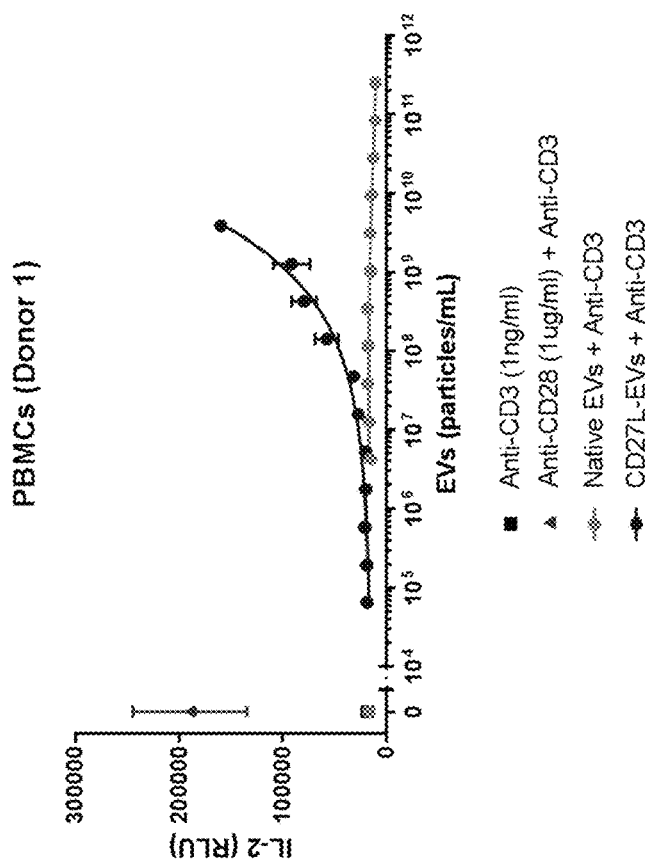
Figure 10A:
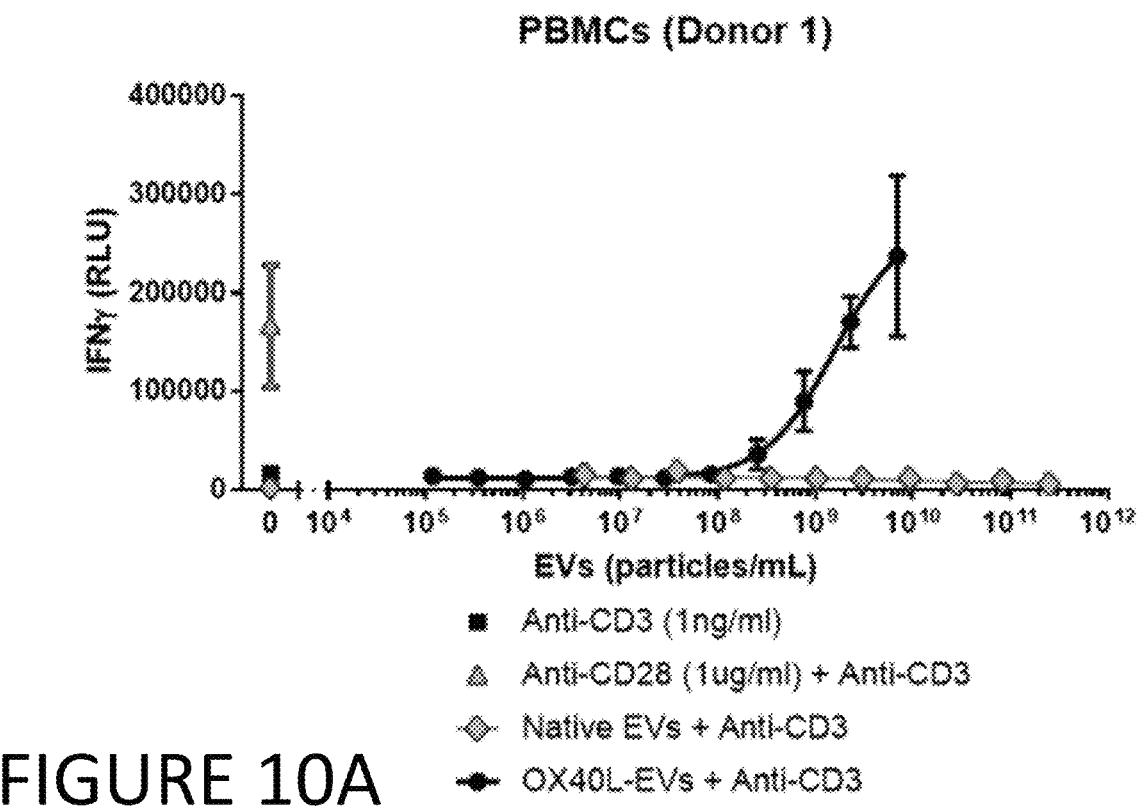
FIGS. 10A and 10B show the effects of OX40L-expressing exosomes on IFNγ expression in human PBMCs from two donors.
Figure 10B:
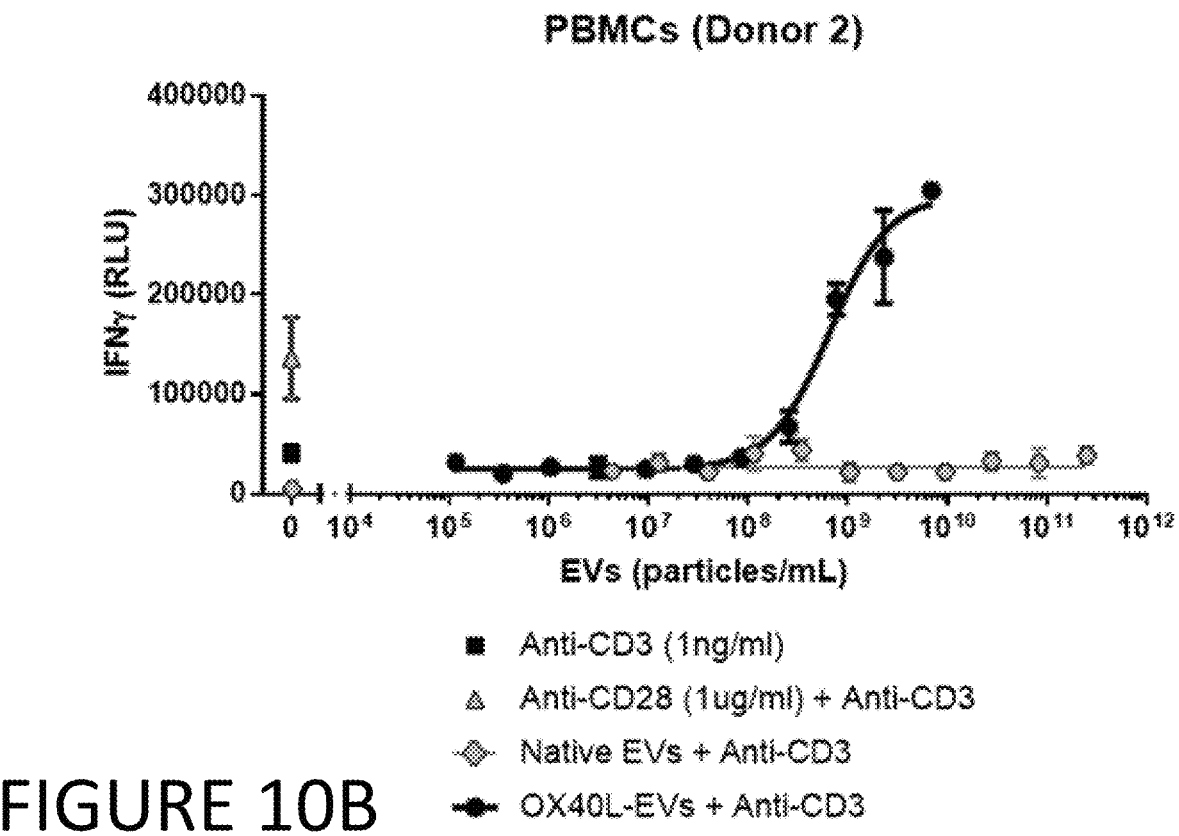
Figure 11A:
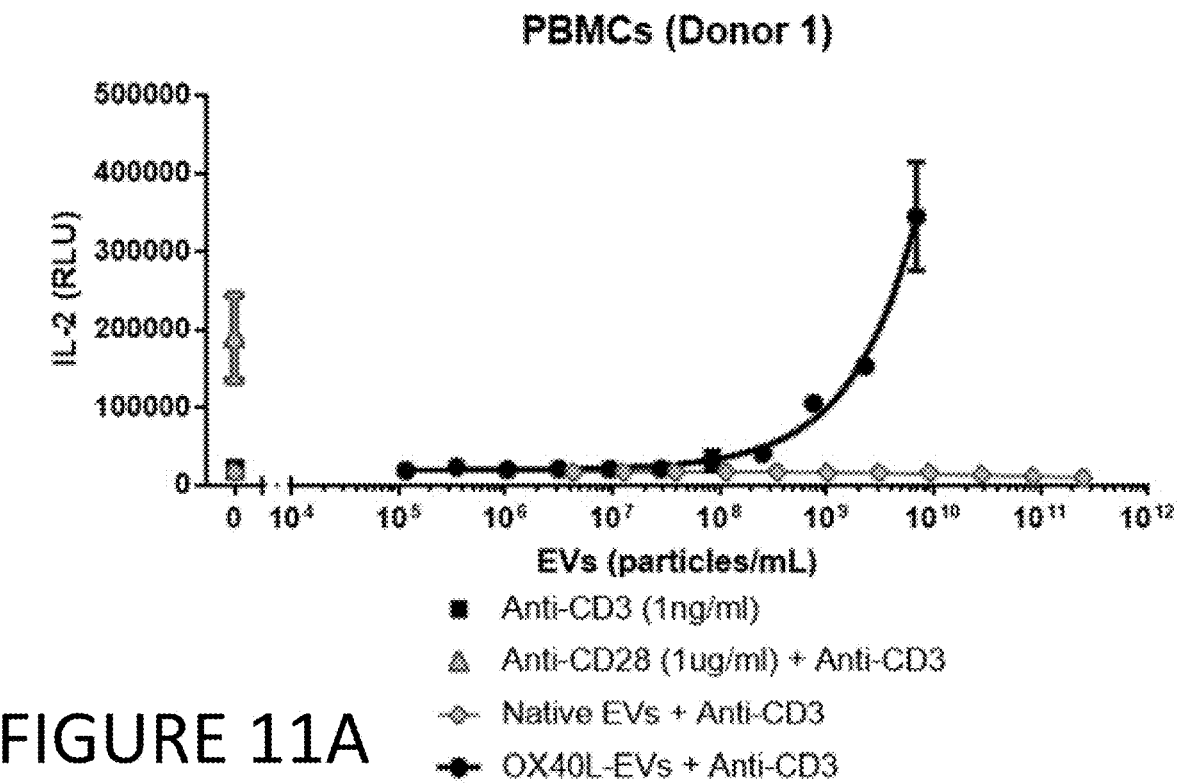
FIGS. 11A and 11B show the effects of OX40L-expressing exosomes on IL-2 expression in human PBMCs from two donors.
Figure 11B:
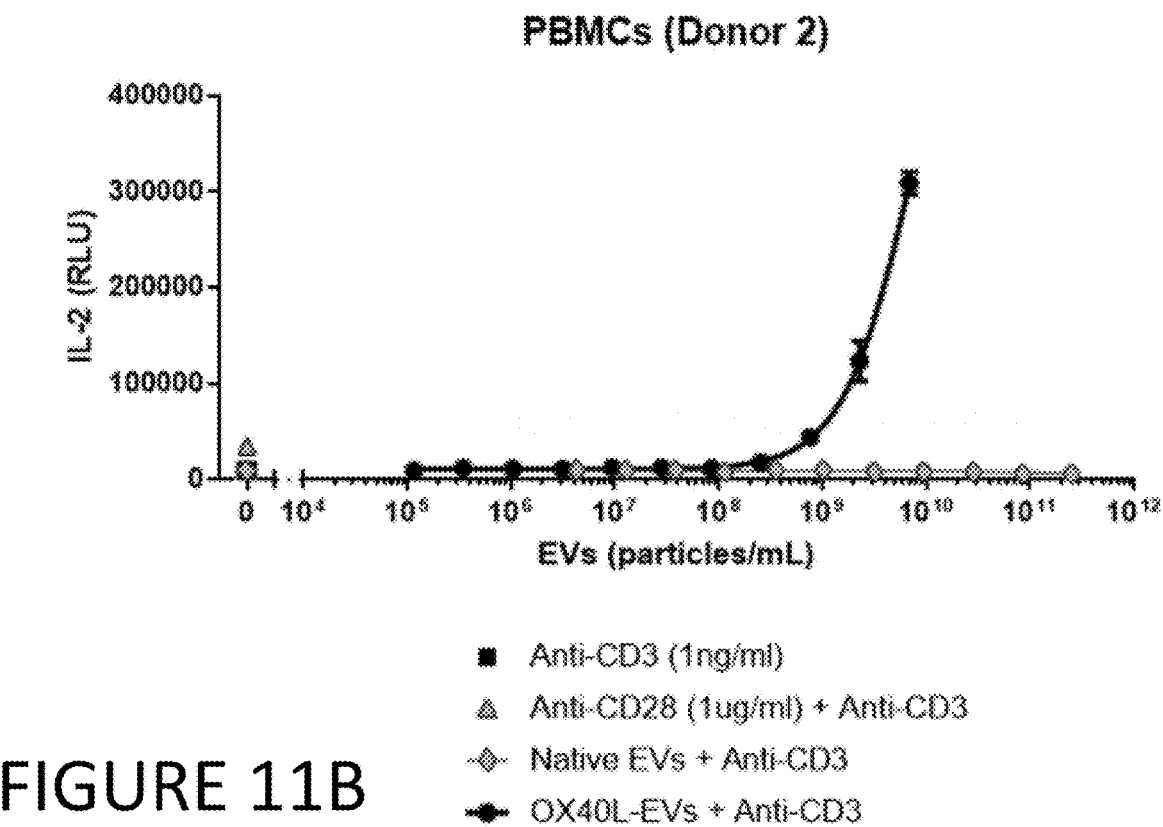

Example 6: Pro-Inflammatory Cytokine Production by Engineered CD27L and OX40L Exosomes CD27L (CD70) and OX40L are members of the TNF super-family, and bind to cognate receptors (CD27 and OX40, respectively) on T-cells. CD27L is expressed by certain populations of T- and B-cells, while OX40L is expressed by certain populations of antigen presenting cells. Signaling through CD27 or OX40 therefore have implications in immuno-oncology, specifically as a method of activating anergic T-cells. To determine whether exosomes could be engineered to induce pro-inflammatory cytokine production in PBMCs, CD27L- and OX40L-containing exosomes were generated by transfection and selection of HEK293SF cells as described in Example 4. To validate the activity of CD27L exosomes, human PBMCs were plated in a 96-well plate, and incubated with purified CD27L exosomes and anti-CD3 antibody, native exosomes and anti-CD3 antibody, anti-CD3 antibody alone, or a combination of anti-CD28 and anti-CD3 antibodies. The samples were incubated at 37 C for two days and assayed for Interferon Gamma (IFNγ) production (FIGS. 8A and 8B) and IL-2 production (FIGS. 9A and 9B) in two different donors. CD27L exosomes induced IFNγ and IL-2 production in a dose-dependent manner and to an extent comparable to (Donor 1) or significantly more than (Donor 2) the positive control of CD3 and CD28 antibodies. In contrast, the native exosomes had no effect on IFNγ or IL-2 production. Similarly, OX40L exosomes were sufficient to induce IFNγ and IL-2 production in two different donors to a similar or greater extent (FIGS. 10A and 10B and FIGS. 11A and 11B).

Figure 12C:
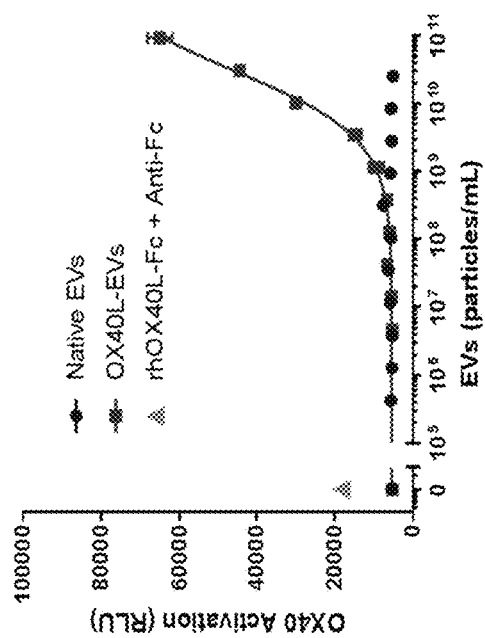
FIG. 12C shows the effects of OX40L-expressing exosomes on an OX40 reporter cell line.
Figure 12B:
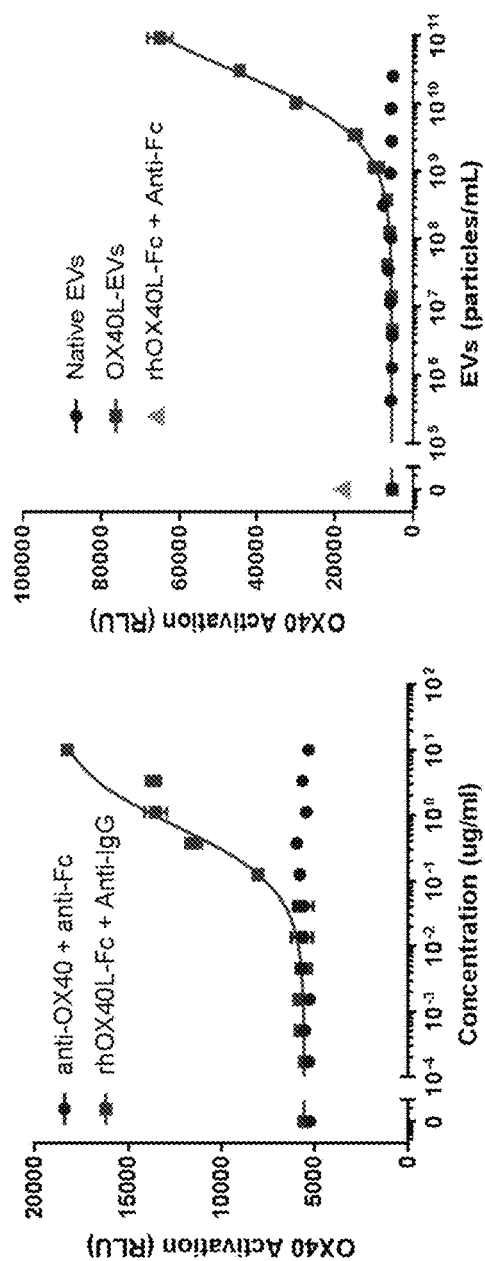
FIG. 12B shows the concentration-dependent activation of an OX40 reporter cell line treated with an anti-OX40 agonistic antibody or recombinant human OX40L.
Figure 12A:
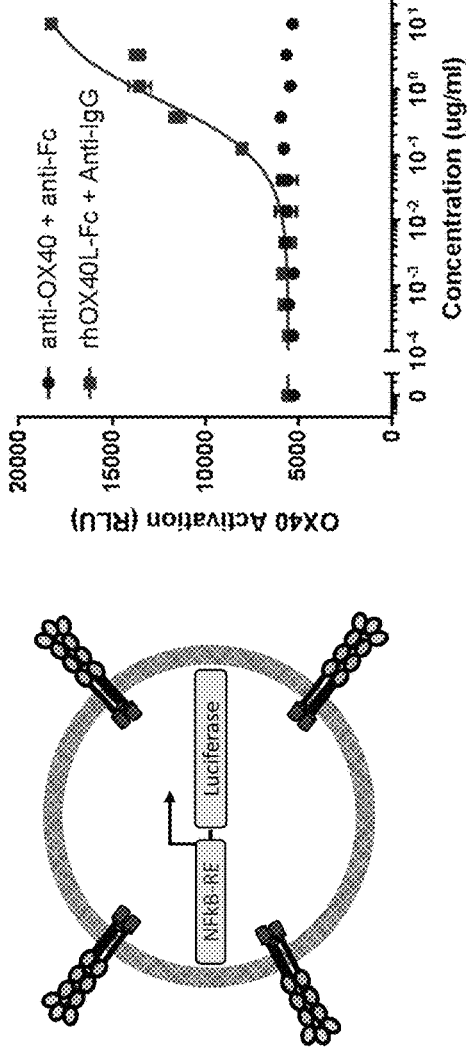
FIG. 12A is a schematic of an OX40 reporter cell line.

To further validate the OX40L exosomes, a report system was used to measure the activity of the engineered exosomes. Activation of the OX40 pathway results in activation of NF-κB. Using a modified Jurkat T-cell line engineered to overexpress OX40 on its surface and contain a luciferase reporter downstream of the NF-κB promoter (Promega Corporation), OX40 activation was confirmed by incubating the cells in the presence of an agonistic anti-OX40 antibody (Biolegend) crosslinked with an anti-Fc antibody (Jackson ImmunoResearch, Inc.) or recombinant human OX40L (AC-ROBiosystems) cross-linked with an anti-IgG antibody (Jackson Immunoresearch) (FIGS. 12A and 12B). The anti-OX40L antibody crosslinked with anti-IgG failed to activate the reporter cells, while the recombinant OX40L cross-linked with anti-Fc led to a robust activation of the reporter gene (FIG. 12B). Strikingly, the engineered OX40L exosomes induced reporter gene expression to a greater extent than either the anti-OX40 antibody or the recombinant OX40L (FIG. 12C). Importantly, the engineered exosomes did not require a cross-linking antibody, demonstrating that OX40L on the surface of exosomes can form functional OX40L trimers sufficient to activate OX40.

Example 7: T-Cell Activation by IL-7 Engineered Exosomes

Figures 13A, 13B:
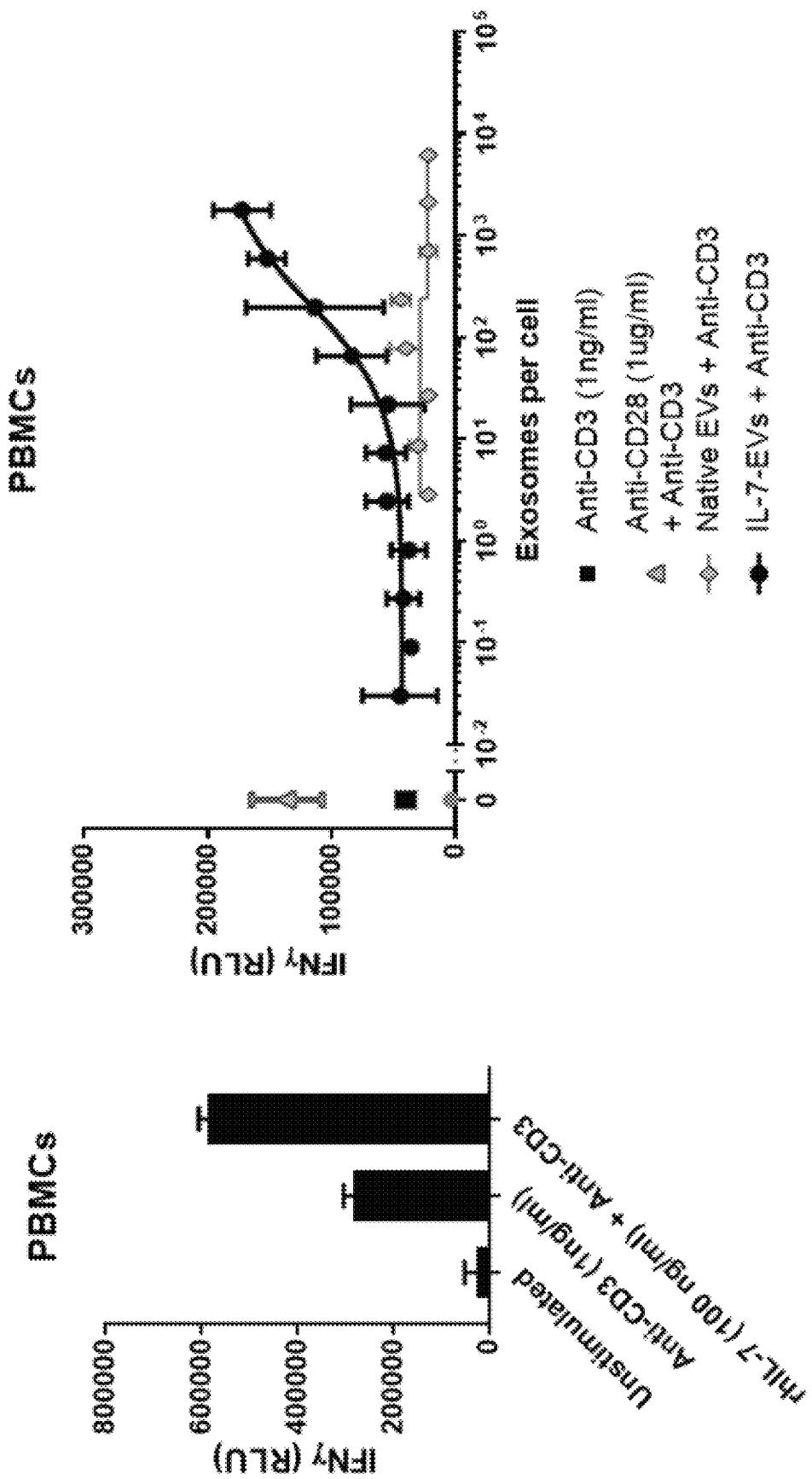
FIGS. 13A and 13B show the effects of IL-7-expressing exosomes in combination with an anti-CD3 antibody on IFNγ expression in human PBMCs.

IL-7 is a cytokine involved in B-cell and T-cell proliferation and has implications in immunotherapy. Specifically, IL-7 may activate T-cells and induce a tumor antigen response in tumors that are poorly infiltrated by leukocytes or in tumor microenvironments that have induced T-cell anergy. IL-7 signaling through the heterodimeric IL-7 receptor induces Interferon Gamma (IFNγ) signaling, which can enhance tumor-specific antigen response by T-cells. To determine whether exosomes could be engineered to induce T-cell activation, IL-7-containing exosomes were generated by transfection and selection of HEK293SF cells with the pDisplay™ plasmid (ThermoFisher) encoding a fusion of IL-7 and PDGF Receptor. The engineered exosomes were purified as described in the Methods. To validate the activity of IL-7 exosomes, human PBMCs were plated in a 96-well plate, and incubated with purified IL-7 exosomes and anti-CD3 antibody, native exosomes and anti-CD3 antibody, anti-CD3 antibody alone, or a combination of anti-CD28 and anti-CD3 antibodies. The samples were incubated at 37° C. for two days and assayed for IFNγ (FIGS. 13A and 13B). IL-7 exosomes in combination with anti-CD3 antibody induced peak IFNγ production to a greater extent than anti-CD3 alone (FIG. 13A). Additionally, IL-7 exosomes induced IFNγ in a dose-dependent manner and to an extent comparable to the positive control of CD3 and CD28 antibodies. In contrast, the native exosomes had no effect on IFNγ production (FIG. 13B).

Figure 14C:
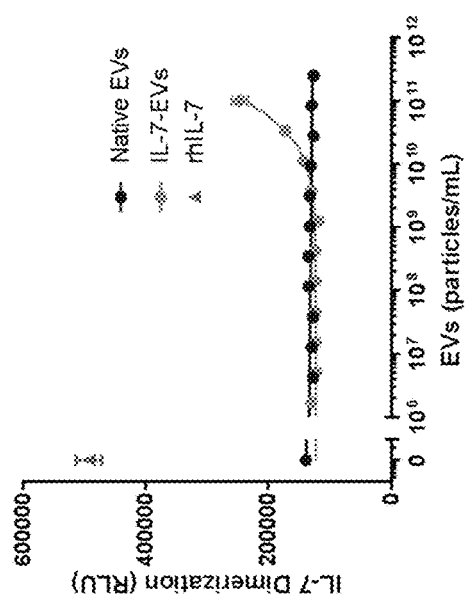
FIG. 14C shows the effects of IL-7-expressing exosomes on an IL-7 receptor reporter cell line.
Figure 14B:
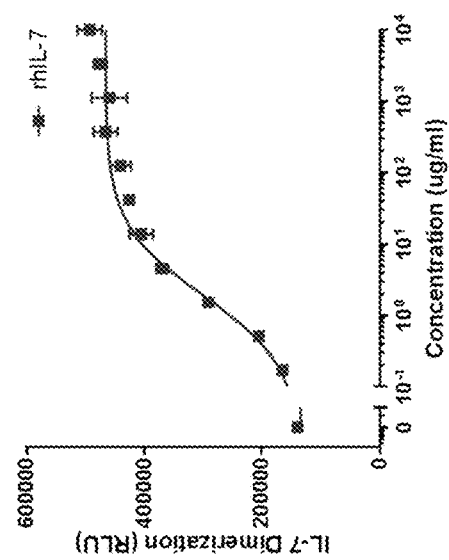
FIG. 14B shows the concentration-dependent activation of an IL-7 receptor reporter cell line treated with recombinant human IL-7.
Figure 14A:
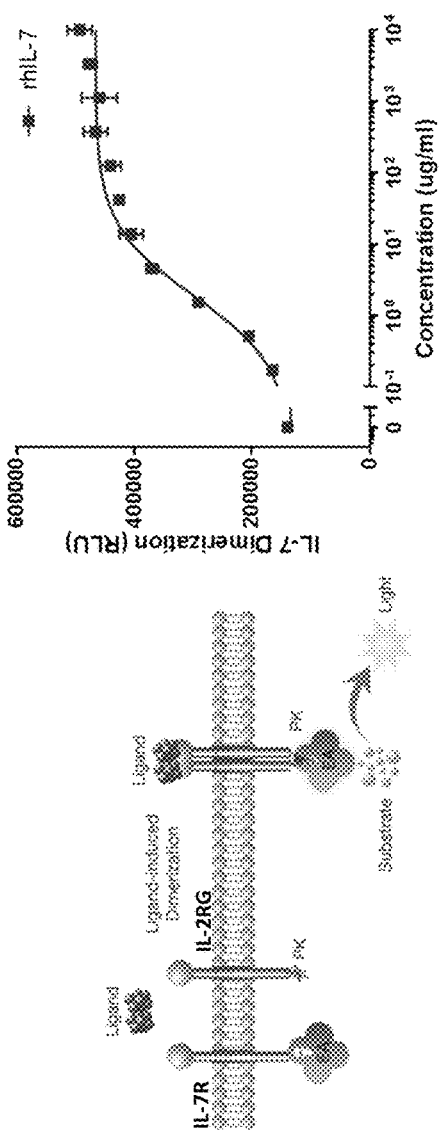
FIG. 14A is a schematic of an IL-7 receptor reporter cell line.

The IL-7 receptor is a heterodimeric complex consisting of IL-7R and IL-2RG, which form a ternary complex in the presence of IL-7 and induces downstream signaling through the JAK/STAT pathway, resulting in cell proliferation. A synthetic cell-based assay was used to measure IL-7 signaling through the IL-7 receptor to assess the functional activity of engineered IL-7 exosomes (DiscoverX Corporation) (FIG. 14A). Recombinant human IL-7 (rhIL-7) was sufficient to increase signaling through the IL-7 receptor (FIG. 14B), and engineered IL-7 exosomes were able to induce signaling through the IL-7 receptor while native exosomes were not (FIG. 14C). These data demonstrate that IL-7-expressing exosomes are sufficient to induce signaling through the IL-7 receptor in vitro.

Figure 15A:
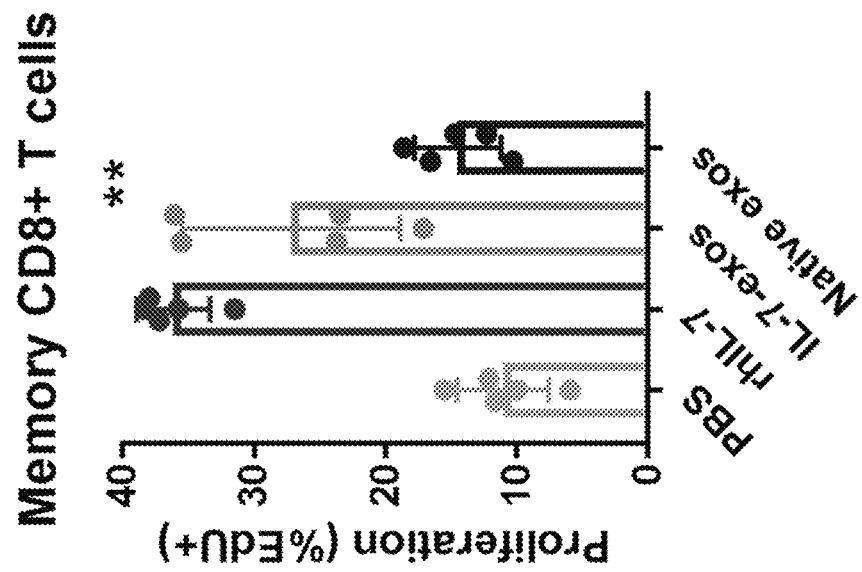
FIGS. 15A and 15B show the effects of IL-7-expressing exosomes on T-cell proliferation in mice in vivo as measured by EdU incorporation.
Figure 15B:
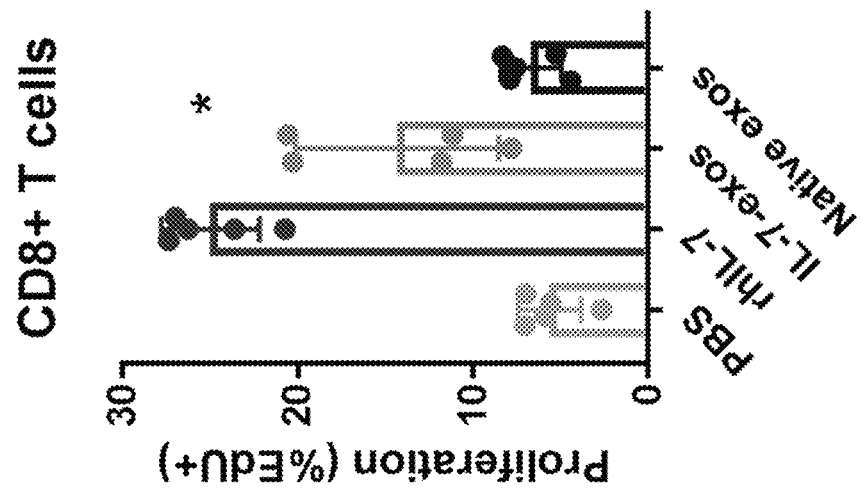

To determine whether the effects of IL-7 exosomes observed in vitro could be recapitulated in an in vivo model, the IL-7 exosomes were administered to C57BL/6 mice. A cohort of 20 mice were separated into the following groups: (1) PBS, (2) recombinant human IL-7 (rhIL-7), (3) IL-7 engineered exosomes, and (4) unmodified native exosomes. Five mice in each group were injected intraperitoneally (IP) with 1 mg of EdU and either PBS, $1\times10^{11}$ native or IL-7 exosomes, or 10 μg of rhIL-7 once daily for three days. Mice were sacrificed, spleens were isolated, and EdU levels were measured in splenic cells by flow cytometry. As shown in FIG. 15A, the percent-positive CD8+ T-cell were significantly increased in the IL-7 exosome mice and the rhIL-7 mice compared to the control cohorts. Although the T-cell counts in IL-7 exosome mice were lower than the rhIL-7 cohort, it is estimated that there was five-fold fewer IL-7 molecules administered in the IL-7 exosome cohort (data not shown). A similar trend was observed for Memory CD8+ T-cells by measuring the levels of the memory marker CD45RO (FIG. 15B).

Figure 16B:
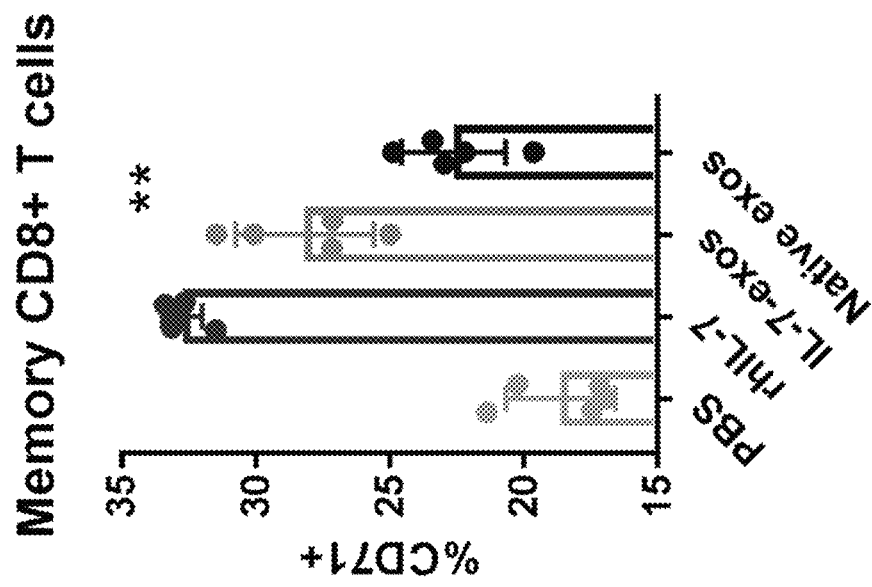
FIGS. 16A and 16B show the effects of IL-7-expressing exosomes on T-cell proliferation in mice in vivo as measured by CD71 positivity.
Figure 16A:
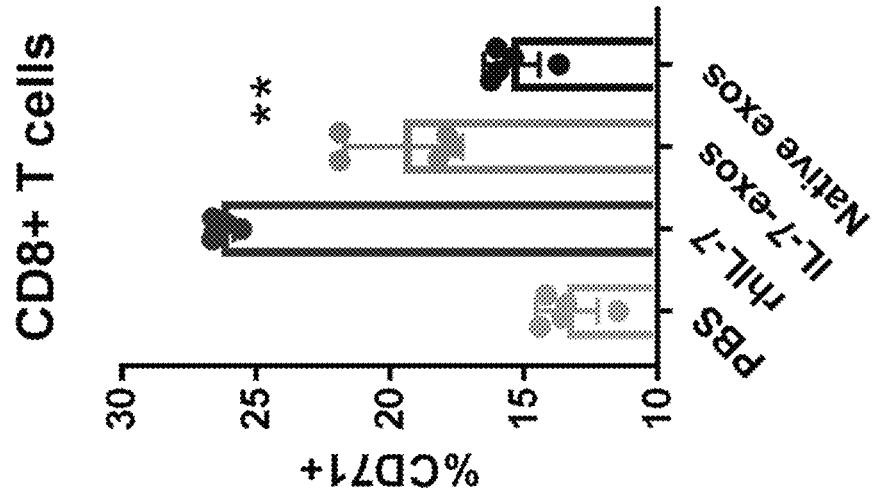

As an orthogonal approach, the levels of CD71 (Transferrin receptor) were measured in splenic cells isolated from exosome-treated mice. CD71 is required for proliferation, and CD71 levels correlate with T-cell number. As shown in FIGS. 15A and 15B, CD8+ T-cell and Memory CD-8+ T-cell numbers followed the same trend as observed in FIGS. 16A and 16B. Together, these data demonstrate that engineered exosomes can induce a specific immune cell effect in vivo, and that this activation can be more potent on a per-molecule basis compared to recombinant agonists.

Example 8: IL-7 Fusion to Proprietary Scaffolds Enhances Specific Activity

Figure 18A:
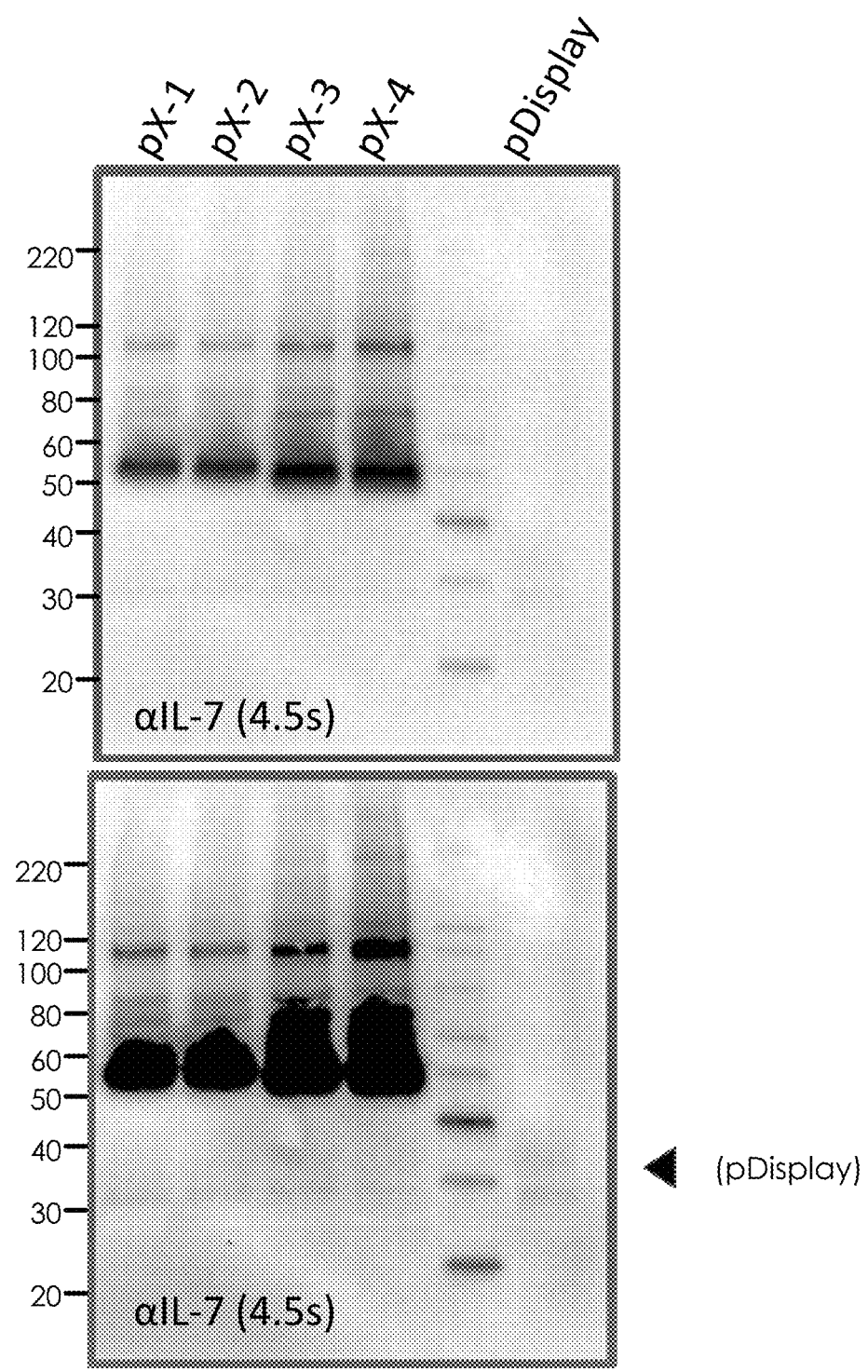
FIG. 18A is a Western blot showing the relative expression of different IL-7 fusion proteins on the surface of purified exosomes.
Figure 18B:
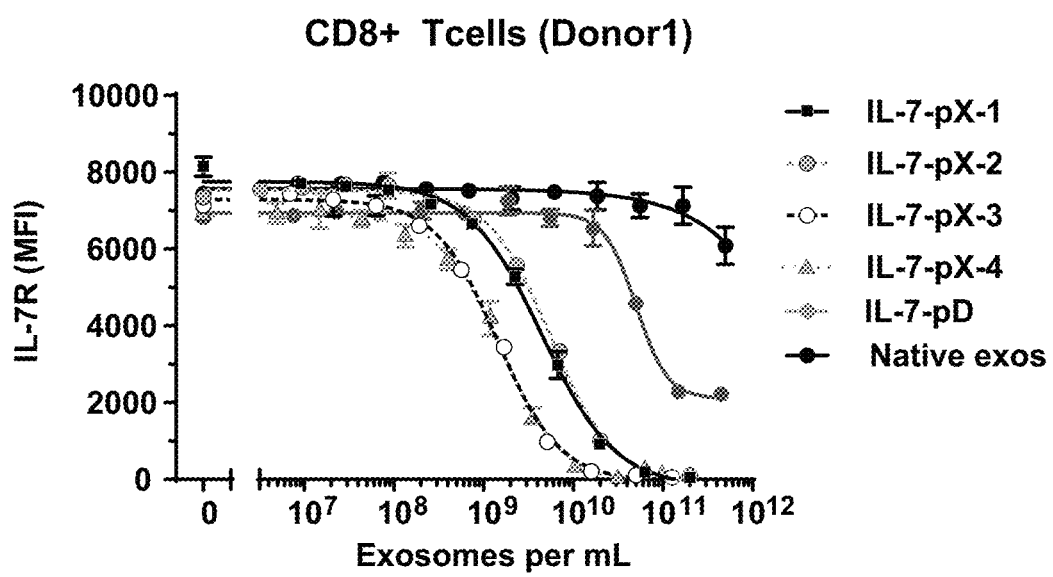
FIG. 18B shows the effects of IL-7-expressing exosomes on IL-7 receptor down-regulation as a model of IL-7-mediated T-cell activation.

To enhance the activity of IL-7 engineered exosomes, the IL-7 sequence was fused to a truncated portion of PTGFRN, a novel exosome transmembrane protein that is highly expressed on the surface of HEK293SF exosomes. IL-7 was expressed as a translational fusion upstream of a short fragment of PTGFRN encompassing the region before the C-terminal-most IgV domain, the transmembrane domain, and the intracellular domain of PTGFRN, as well as a FLAG tag. A series of expression constructs was generated by introducing a series of four amino acid deletions between IL-7 and PTGFRN (FIG. 17A). The resulting constructs were numbered pX-1 through pX-4 (pX-4 complete sequence shown in FIG. 17B). As shown by Western blot analysis using an anti-IL-7 antibody, constructs pX-3 and pX-4 showed the highest levels of expression. The level of IL-7 expression in the PTGFRN backbone was dramatically higher than pDisplay-IL-7, which was used in Example 7 (FIG. 18A). The increased expression of IL-7 suggested that these novel fusion proteins could induce a much greater level of IL-7-mediated T-cell activation. To determine the potency of PTGFRN-IL-7 fusions, an in vitro model of T-cell activation was carried out. Upon IL-7-mediated activation of T-cells, IL-7 receptor (IL-7R) levels decrease in a dose-dependent manner within 24 hours (Ghawazi et al., Immunol Cell Biol. 2013 February; 91(2):149-58). Thus, IL-7R levels were monitored after incubation of PBMCs with various IL-7 engineered exosomes. As shown in FIG. 18B, native exosomes failed to reduce IL-7R levels, while pDisplay-IL-7 exosomes (IL-7-pD) reduced IL-7R levels only at high doses. In contrast, PTGFRN-IL-7 exosomes (IL-7-pX3 to pX4) completely reduced IL-7R levels at much lower doses, demonstrating an increased potency of these engineered exosomes. As a measure of IC50, the PTGFRN-IL-7 exosomes were 20- to 76-fold more potent than the IL-7-pD exosomes (Table 2), demonstrating that increased ligand density is sufficient to increase biological potency. Furthermore, these results demonstrate that specific truncations of PTGFRN may be ideal scaffolds for use in engineering therapeutic exosomes.

TABLE 8

| Exosomes | pX1 | pX2 | pX3 | pX4 | pD |
|---|---|---|---|---|---|
| IC50 (p/ml) | 4.2E+09 | 5.4E+09 | 1.4E+09 | 1.5E+09 | 1.1E+11 |
| Fold increase in potency | 25.6 | 19.8 | 76.5 | 71.0 | N/A |

Example 9: Exosomes Engineered with Anti-CD3 Antibody Fragments

Figure 19B:
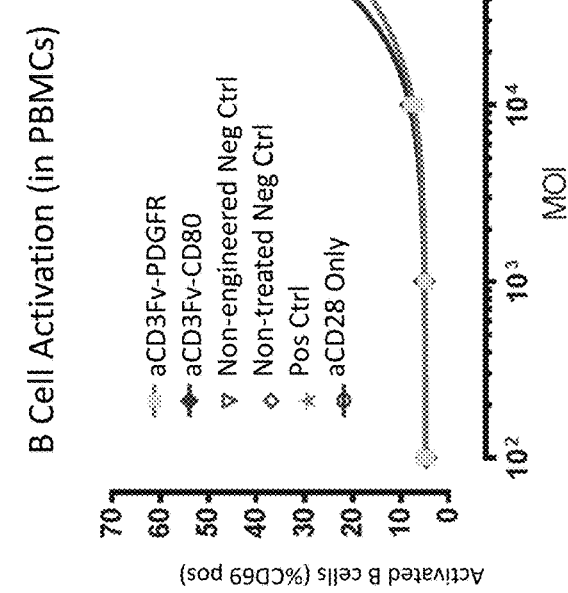
FIG. 19B shows the effects of anti-CD3 scFv exosomes on B-cell activation in PBMCs.
Figure 19A:
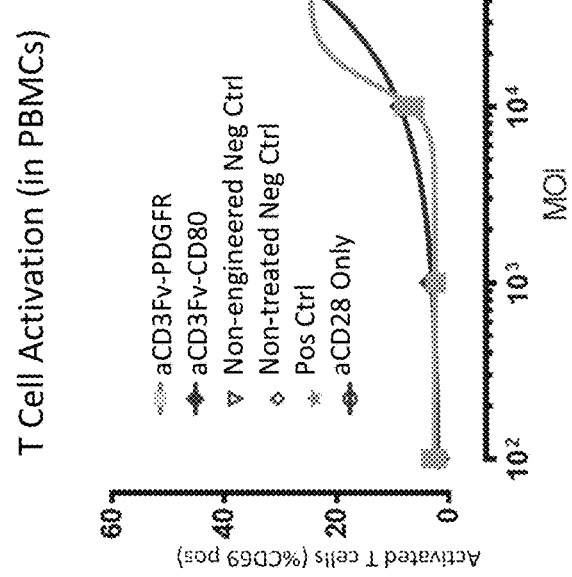
FIG. 19A shows the effects of anti-CD3 scFv exosomes on T-cell activation in PBMCs.
Figure 21B:
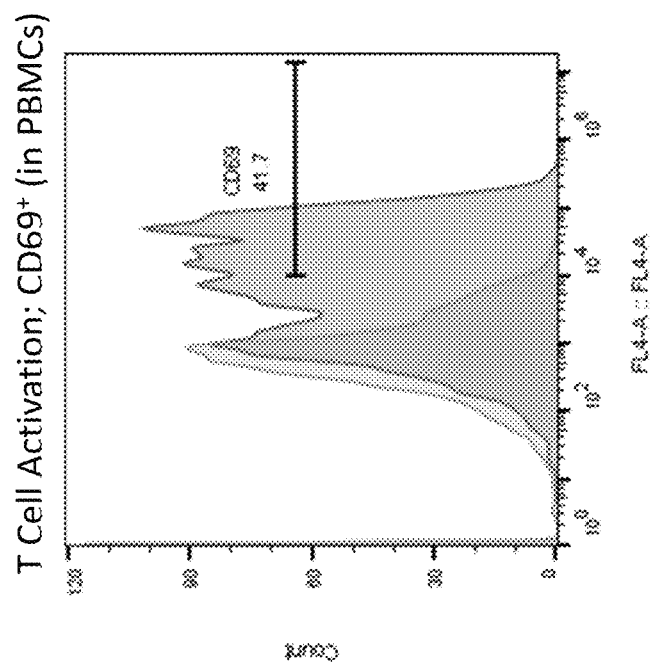
FIG. 21B is a histogram showing the extent of B-cell activation after treatment with anti-CD3 scFv exosomes.
Figure 21A:
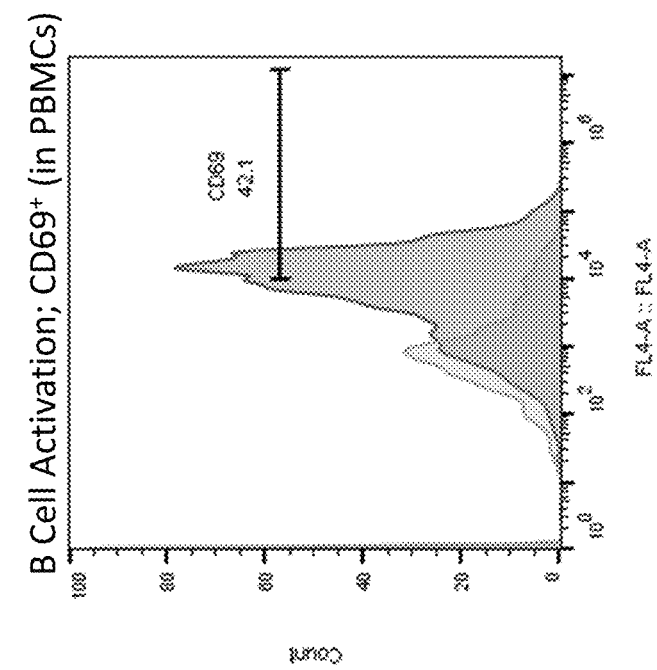
FIG. 21A is a histogram showing the extent of T-cell activation after treatment with anti-CD3 scFv exosomes.

As shown in the previous examples, exosomes can be engineered to overexpress functional endogenous sequences of immunomodulatory proteins. To determine if synthetic agonists can be engineered on the surface of exosomes, anti-CD-3 antibodies were expressed as fusions to either pDisplay as described in Example 4, or the transmembrane domain of CD80. Human PBMCs were plated in a 96-well plate at 100,000 cells per well and incubated overnight with exosomes engineered to express an anti-CD3 single chain Fv (scFv) (FIGS. 19A and 19B) or single chain Fab (scFab) (FIGS. 20A and 20B). As a positive control, PBMCs were incubated with ImmunoCult™ CD3/CD28 Activator (Stem Cell Technologies) according to the manufacturers' protocol. In the presence of anti-CD28 co-stimulation, all engineered exosomes induced T-cell (FIGS. 19A and 20A) and B-cell (FIGS. 19B and 20B) activation comparable to the positive control, while the non-engineered exosome controls did not. To measure the effects of anti-CD3 exosomes on immune cell populations, T-cell and B-cells were assayed for CD69 positivity by flow cytometry. As shown in FIG. 21A, PBMCs incubated with exosomes expressing anti-CD3 scFv fused to the CD80 transmembrane domain led to activation of ~40% of T-cells. Similar effects were observed for the activation of B-cells (FIG. 21B).

Figure 22B:
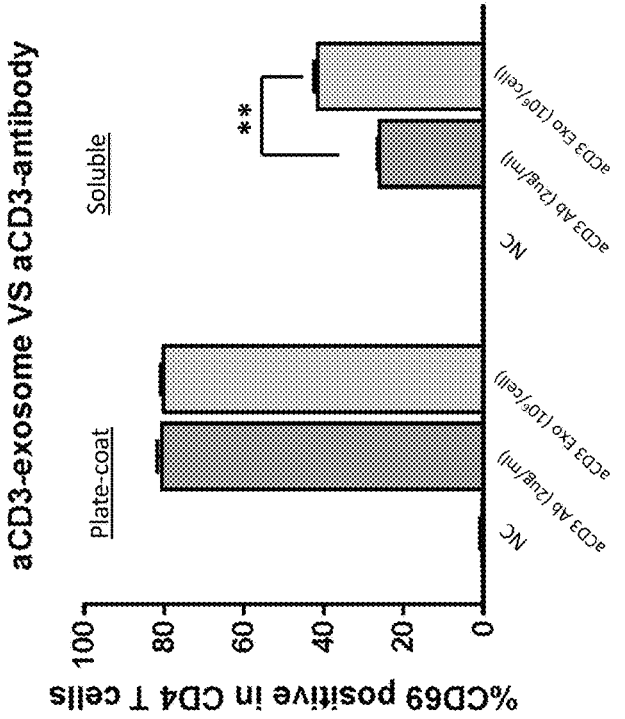
FIG. 22B is a bar chart quantitating the results of a separate experiment carried out as in FIG. 22A.
Figure 22A:
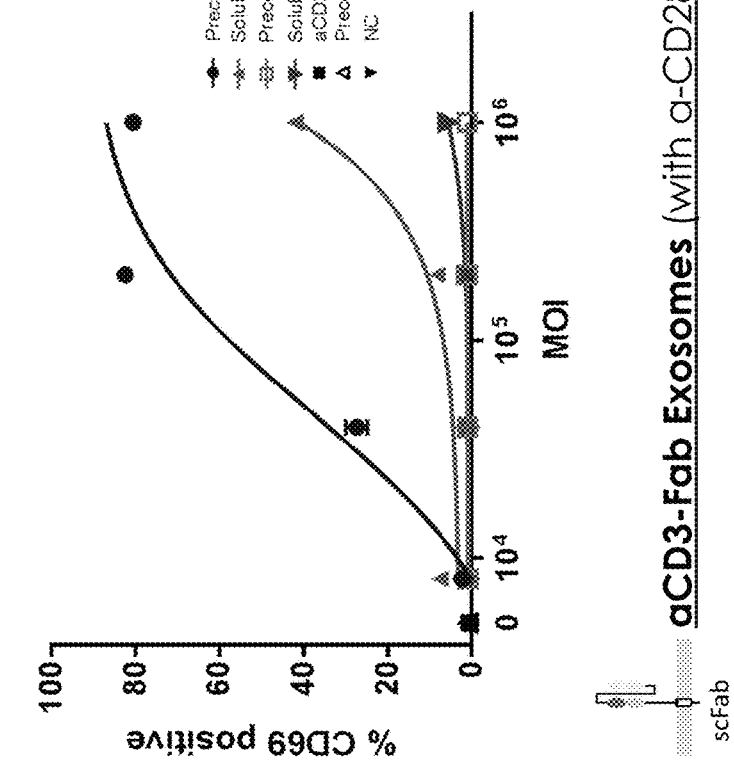
FIG. 22A shows the effects of anti-CD3 scFab exosomes on T-cell activation in a plate-coated activation assay compared to soluble anti-CD3 antibody or plate-coated anti-CD3 antibody.

To determine whether anti-CD-3 exosome-mediated T-cell activation was due to direct T-cell activation or through trans-acting immune cells, activation of purified T-cells was measured. 100,000 purified human T-cells were plated in 96-well format in wells that were pre-coated with a non-targeting antibody or anti-CD3 exosomes in the presence or absence of anti-CD28 antibody, or in wells that were incubated with soluble anti-CD3 exosomes in the presence or absence of anti-CD28 antibody. As shown in FIG. 22A, both soluble and plate-coated anti-CD3 scFv exosomes activated T-cells in the presence of anti-CD28 antibody as measured by CD69 expression. As shown in FIG. 22B, plate-coated anti-CD3 antibody in the presence of anti-CD28 antibody activated T-cells to the same extent as plate-coated anti-CD3 scFv in the presence of anti-CD28 antibody. Strikingly, while soluble anti-CD3 antibody in the presence of anti-CD28 antibody was sufficient to activate ~30% of T-cells, soluble anti-CD3 scFv exosomes in the presence of anti-CD28 antibody activated a significantly higher proportion of T-cells, demonstrating that exosomes engineered to overexpress an antibody fragment can induce higher levels of T-cell activation compared to soluble antibody. Together, these results demonstrate that exosomes can be engineered to overexpress antibody fragments with functional activity against specific cell types.

Example 10: IL-12-PTGFRN Exosomes have Potent Immunomodulatory Activity In Vitro and In Vivo IL-12 is a potent immunostimulatory cytokine produced by antigen presenting cells in response to infection and other antigenic stimulation. IL-12 production by activated dendritic cells, macrophages, and neutrophils induces IFNγ production by both CD8+ and CD4+ T-cells and induces cytotoxic effects of Natural Killer (NK) cells. The combined impact of IL-12 secretion in the tumor microenvironment results in the secretion of Th1 cytokines including IFNγ, leading to tumor cell killing, reprogramming of myeloid-derived suppressor cells (MDSCs) and anti-angiogenic effects. IL-12-mediated anti-tumor effects result in a durable T-cell response and anti-tumor immunity in numerous animal models. IL-12 has previously been tested as an immunotherapy agent in humans but resulted in significant toxicity in renal cell carcinoma patients despite a detectable induction of a robust IFNγ response (Leonard et al., Blood. 1997 Oct. 1; 90(7):2541-8). Exosomes therefore may represent an ideal delivery modality for IL-12 due to the high local concentration of the cytokine and presumed tumor-retained pharmacology.

Figure 23B:
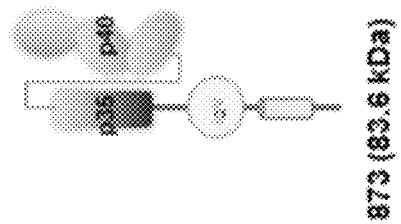
FIG. 23B shows a schematic of a shortened PTGFRN/IL-12 fusion protein.
Figure 23A:
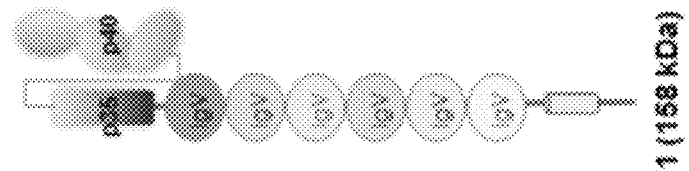
FIG. 23A shows a schematic of a full-length PTGFRN/IL-12 fusion protein.
Figure 24B:
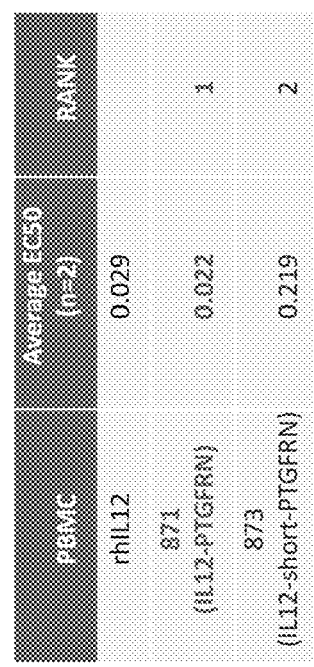
FIG. 24B is a table summarizing the potency of recombinant IL-12 and IL-12-containing exosomes.
Figure 24A:
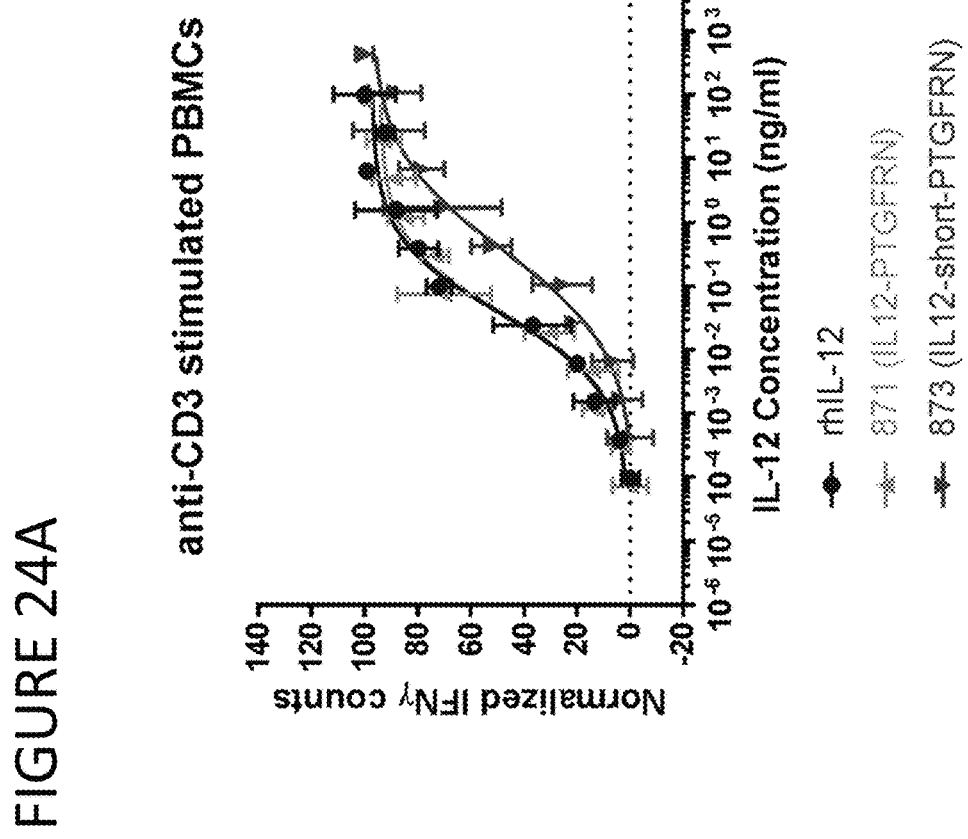
FIG. 24A shows the effects of recombinant human IL-12 or exosomes overexpressing either short or full-length PTGFRN-IL-12 inducing IFNγ in human PBMCs.

IL-12 consists of two domains, p35 and p40. The human IL-12 dimer was encoded as a fusion protein to either full-length PTGFRN (FIG. 23A, construct 871, SEQ ID NO: 3) or a shortened fragment of PTGFRN that enables high-density surface display (FIG. 23B, construct 873, SEQ ID NO: 5), and the constructs were stably expressed in HEK293SF cells. Stable cell lines were grown in chemically defined media and the exosomes from the culture supernatant were purified over an Optiprep™ gradient as described in the Methods. The amount of IL-12 protein on the surface of the exosomes was measured by ELISA and concentration-matched to the rIL-12 for all functional studies. Purified full-length and short hIL-12-PTGFRN exosomes or recombinant hIL-12 (rhIL-12; BioLegend, Catalog No. 573004) were titrated in human PBMCs in the presence of a suboptimal concentration anti-CD3 antibody to induce IFNγ expression. rhIL-12 resulted in robust IFNγ expression with an $EC_{50}$ of 0.029 ng/ml, which was comparable to full-length IL12-PTGFRN, both of which were ~10× more potent than IL12-short-PTGFRN (FIG. 24A-B). These results suggest that IL-12 displayed on the full-length PTGFRN scaffold may be a more potent immunomodulating reagent than the short PTGFRN construct.

Figure 25:
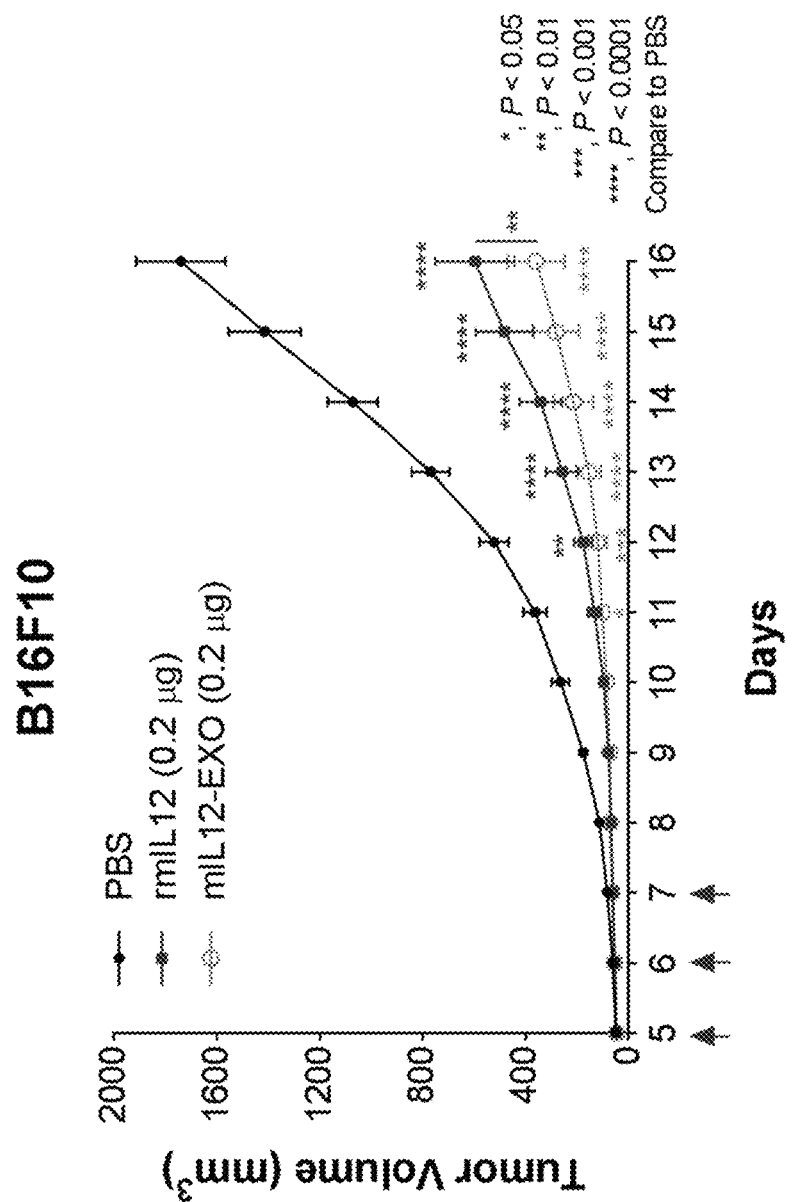
FIG. 25 shows the effects of recombinant IL-12 and IL-12-PTGFRN exosomes on reducing tumor growth in a murine model of melanoma.
Figure 26A:
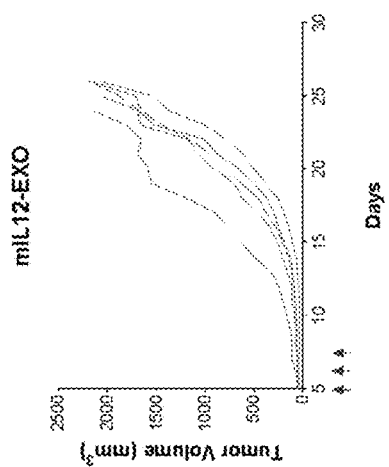
FIG. 26A shows the tumor growth curves for each of the tumor-bearing mice shown in FIG. 25 treated with PBS.
Figure 26B:
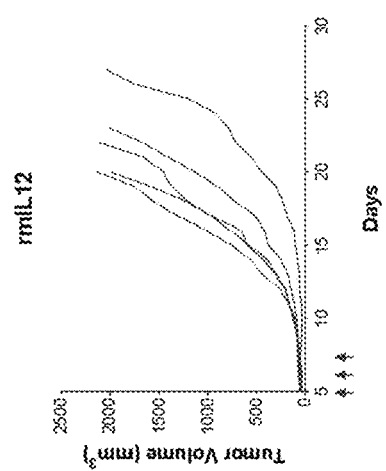
FIG. 26B shows the tumor growth curves for each of the tumor-bearing mice shown in FIG. 25 treated with recombinant IL-12.
Figure 26C:
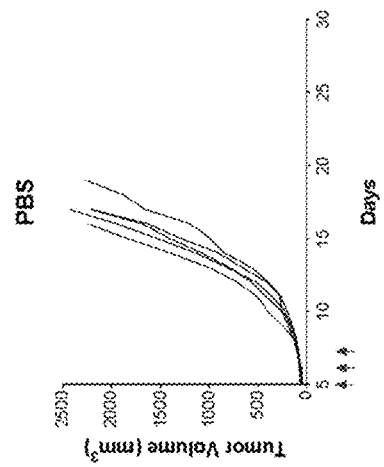
FIG. 26C shows the tumor growth curves for each of the tumor-bearing mice shown in FIG. 25 treated with IL-12-PTGFRN exosomes.
Figure 27:
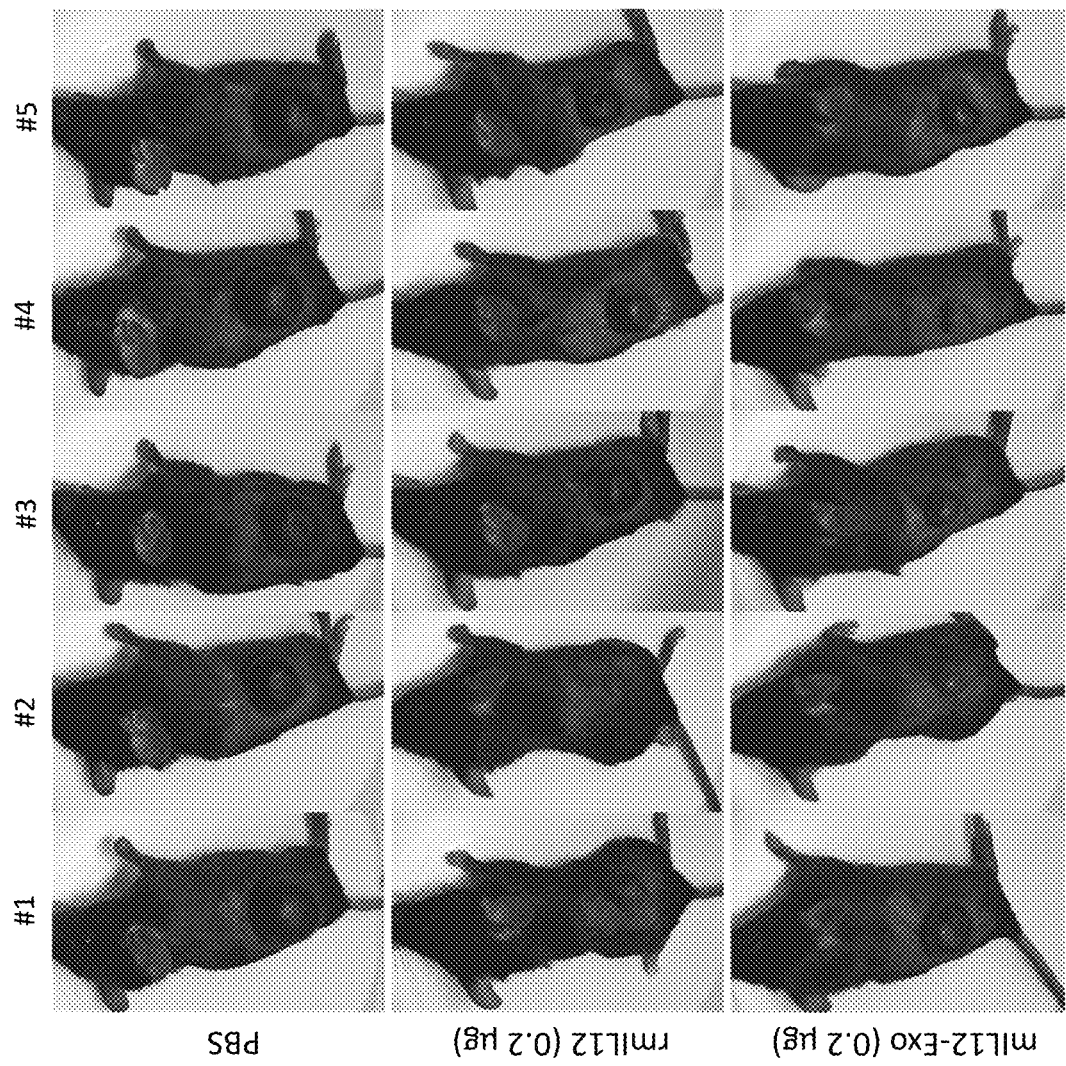
FIG. 27 shows images of all B16F10 tumor-bearing mice in the efficacy study shown in FIG. 25.
Figure 28:
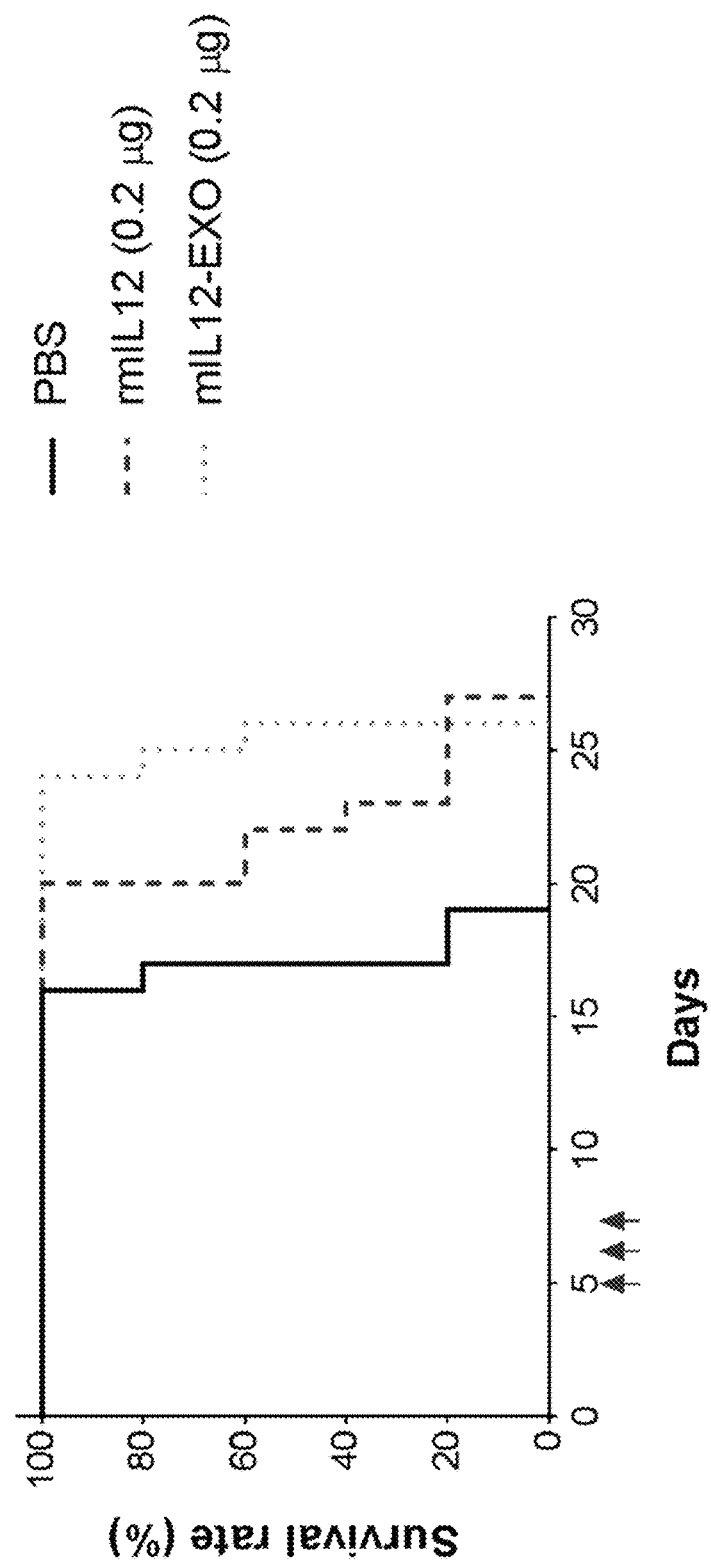
FIG. 28 shows the survival curves of the B16F10 tumor-bearing mice shown in FIG. 25.

Mouse and human IL-12 proteins do not cross-react, and the in vitro data shown in FIG. 24 suggest that mIL-12 fused to full-length PTGFRN would be more a more potent than using the short scaffold of PTGFRN. To determine the potency of mIL-12-PTGFRN exosomes in an in vivo model of cancer, C57BL/6 mice were implanted subcutaneously with $1 \times 10^6$ B16F10 murine melanoma cells (n=5 mice per group). On days 5, 6, and 7 after tumor inoculation the animals were injected intratumorally with PBS, 0.2 µg of recombinant murine IL-12 (mIL12; BioLegend, Catalog No. 577004), or 1×10¹¹ exosomes displaying full-length IL-12-PTGFRN (mIL12-Exosomes; SEQ ID NO: 4). Animals were sacrificed once tumor volumes reached 2,000 mm³. As shown in FIGS. 25-27, tumors in the PBS group grew rapidly while tumors in the rmIL12 and mIL12-Exo groups were dramatically reduced (-65-80% reduction in volume). Importantly, by day 16, tumors in the mIL12-Exo group were smaller than those in the rmIL12 group demonstrating superior efficacy of IL-12 when displayed on the surface of exosomes compared to the soluble cytokine. There was also a survival advantage for the IL-12 treated groups compared to the PBS treated groups (FIG. 28).

Figure 30:
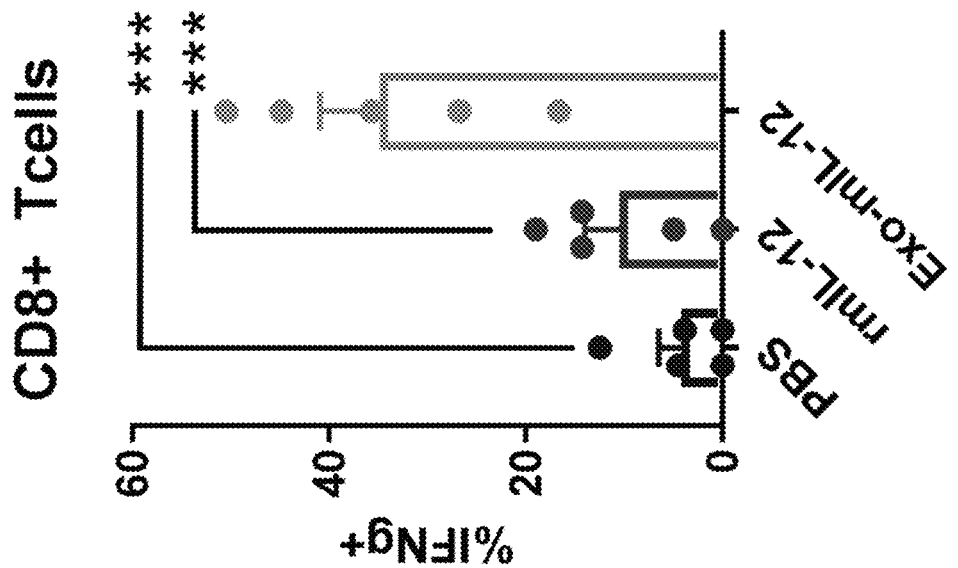
FIG. 30 shows the percent of IFNγ-positive CD8+ splenic T-cells in tumor-bearing mice treated with PBS, rIL-12 or IL-12-PTGFRN exosomes.

To understand the mechanistic advantage of IL-12-PTGFRN-exosomes over rmIL12, Th1 gene expression was profiled in the tumors of the control and treated groups. IFNγ (FIG. 29A), the T-cell chemoattractants CXCL9 (FIG. 29B) and CXCL10 (FIG. 29C), and TGFβ (FIG. 29D) were all increased in the IL-12 treated groups compared to the control group. In most cases, the cytokine signals were higher in the animals treated with mIL12-Exo compared to rmIL-12. IFNγ levels in splenic CD8+ T-cells were measured by flow cytometry, and the Exo-mIL-12-treated mice showed significantly greater signal than either the PBS group or the rmIL-12 group (FIG. 30). Together, these data demonstrate that IL-12 displayed on the surface of an exosome represents a novel and potent immunomodulatory strategy that promotes robust T-cell activation in vitro and can be used to elicit potent anti-tumor effects in an aggressive model of murine melanoma in vivo. Mechanistically, the IL-12 exosomes show superiority over rIL-12, and thus represent a novel, differentiated therapeutic modality in cancer immunotherapy.

Figure 31A:
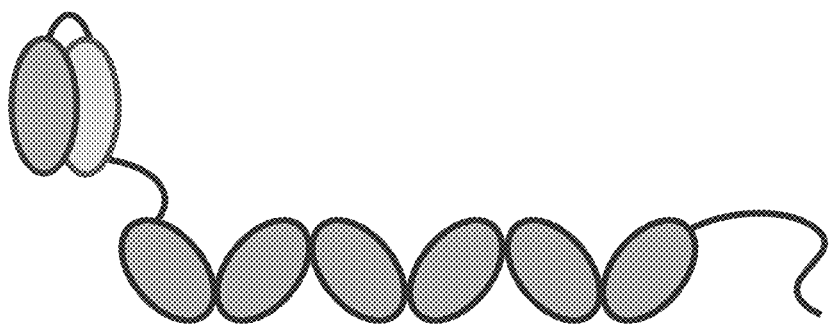
FIG. 31A shows a schematic of a full-length PTGFRN fused to an IFNγ monomer.
Figure 31B:
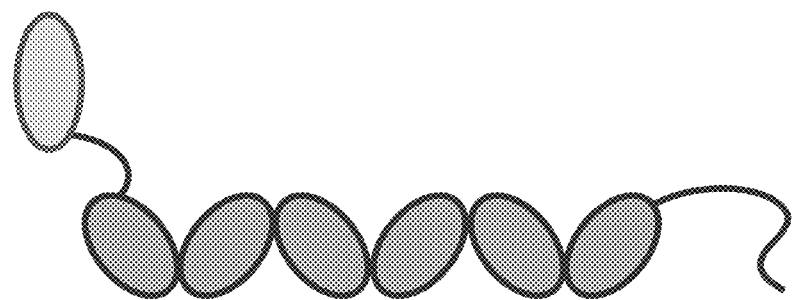
FIG. 31B shows a schematic of a full-length PTGFRN fused to an IFNγ tandem dimer.
Figure 32:
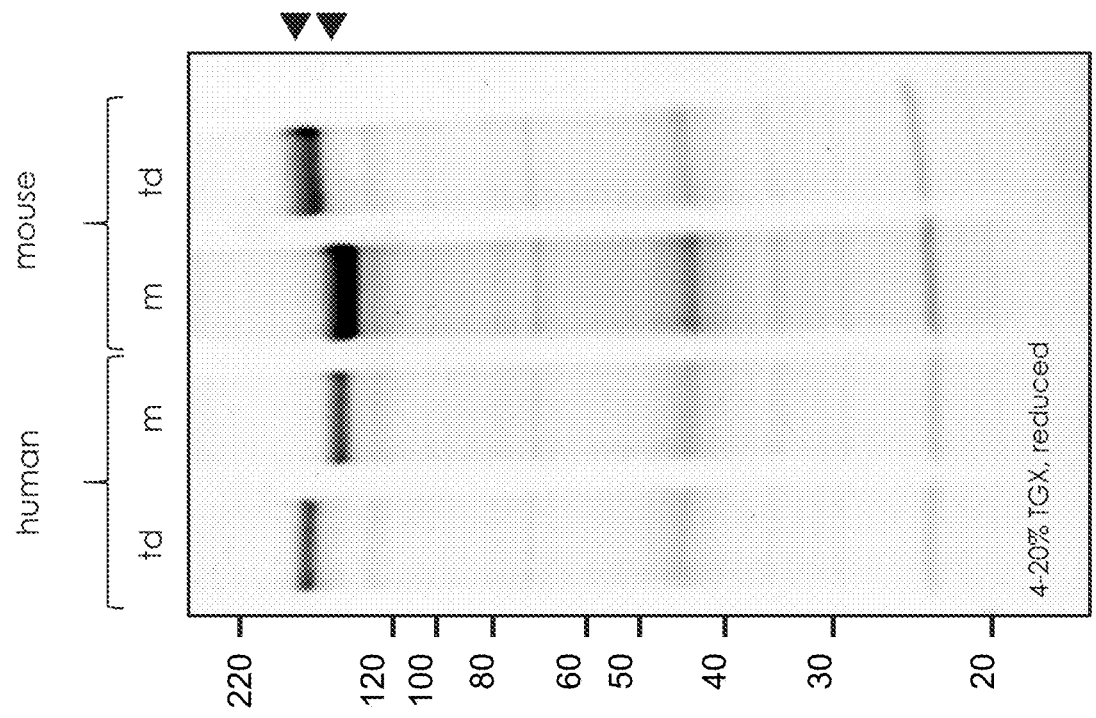
FIG. 32 shows the PAGE analysis results of purified human and mouse monomeric (m) and tandem dimer (td) PTGFRN IFNγ exosomes.

Example 11: Interferon Gamma-Displaying Exosomes Are Potent Immune Cell Activators Interferon gamma (IFNγ) is a cytokine involved in priming innate and adaptive immune responses. It is expressed from a variety of cell types in response to numerous signals including IL-12, and is sufficient to activate NK cells, drive antigen presentation in antigen presenting cells, and promote leukocyte activation and invasion. IFNγ is naturally expressed as a homodimer and is secreted as a soluble factor. IFNγ expressing exosomes were generated by stably transfecting HEK293SF cells with full-length PTGFRN fused to monomeric or dimeric human and mouse IFNγ (FIGS. 31A and 31B, respectively). Exosomes from suspension cell cultures were purified as described above and analyzed by PAGE. Monomeric (m) and tandem dimer (td) PTGFRN IFNγ exosomes were expressed at the predicted molecular weights (arrow heads) at comparable levels (FIG. 32). The purified exosomes were analyzed by ELISA and compared to a standard curve using recombinant IFNγ (Biolegend, Catalog No. 570206) to calculate the number of IFNγ molecules per exosome. The results in Table 9 show the number of IFNγ molecules in each of the four types of purified exosomes. Notably, the tandem dimer IFNγ PTGFRN exosomes contain at least twice as many IFNγ molecules as the monomeric IFNγ PTGFRN exosomes, suggesting that the tandem dimer exosomes are appropriately expressing the dimeric IFNγ constructs.

TABLE 9

| Construct | IFN γ molecules/exosome |
|---|---|
| h-mIFNγ-PTGFRN | 53 |
| h-tdIFNγ-PTGFRN | 173 |
| m-mIFNγ-PTGFRN | 47 |
| m-tdIFNγ-PTGFRN | 113 |

Figure 33:
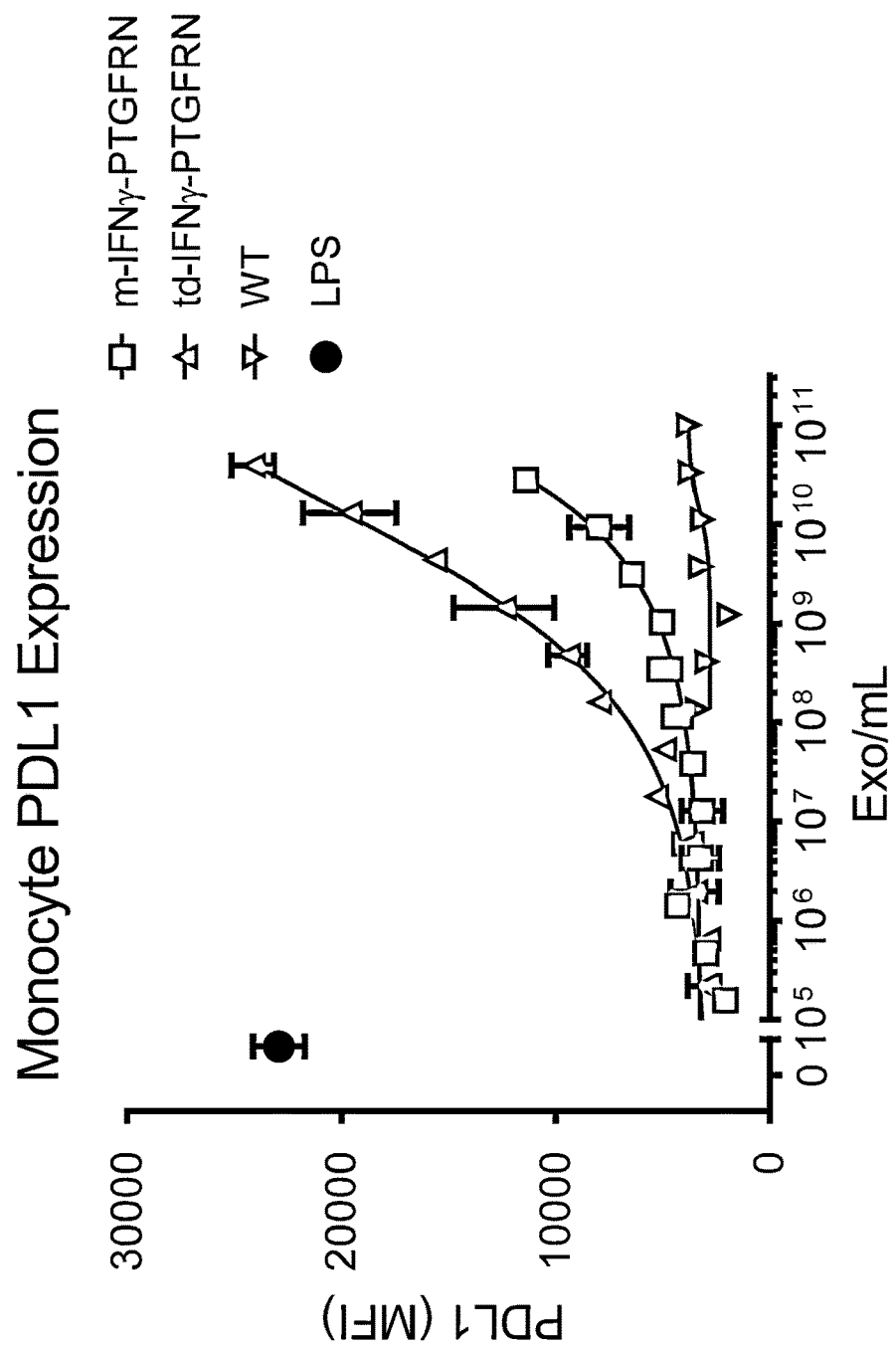
FIG. 33 shows the monocyte PD-L1 expression after addition of native exosomes (WT), monomeric IFNγ PTGFRN exosomes (m-IFNγ-PTGFRN), and tandem dimer IFNγ PTGFRN exosomes (td-IFNγ-PTGFRN) respectively. LPS-induced PD-L1 activation was used as positive control.

Human monomeric and tandem dimer PTGFRN-IFNγ exosomes were incubated with human PBMCs for 24 hours at increasing concentrations. Monocyte activation was measured by PD-L1 expression, a downstream surface protein induced by IFNγ signaling. As shown in FIG. 33, native HEK293SF exosomes (WT) failed to induce PD-L1 expression, while both monomeric and tandem dimer IFNγ PTGFRN exosomes induced PD-L1 in a dose-dependent manner, with greater activation by the tandem dimer IFNγ PTGFRN exosomes. Exosome-mediated PD-L1 activation was comparable to LPS-induced activation (FIG. 33). These data demonstrate that a soluble cytokine, in either monomeric or dimeric format, can be functionally expressed on the surface of an exosome and induce immune cell activation. The use of IFNγ expressing exosomes in immuno-oncology may be useful for the induction of NK and T-cell responses against tumor cells.

Example 12: IL-15 Expressing Exosomes Induce NK Cell Activation

Figure 34:
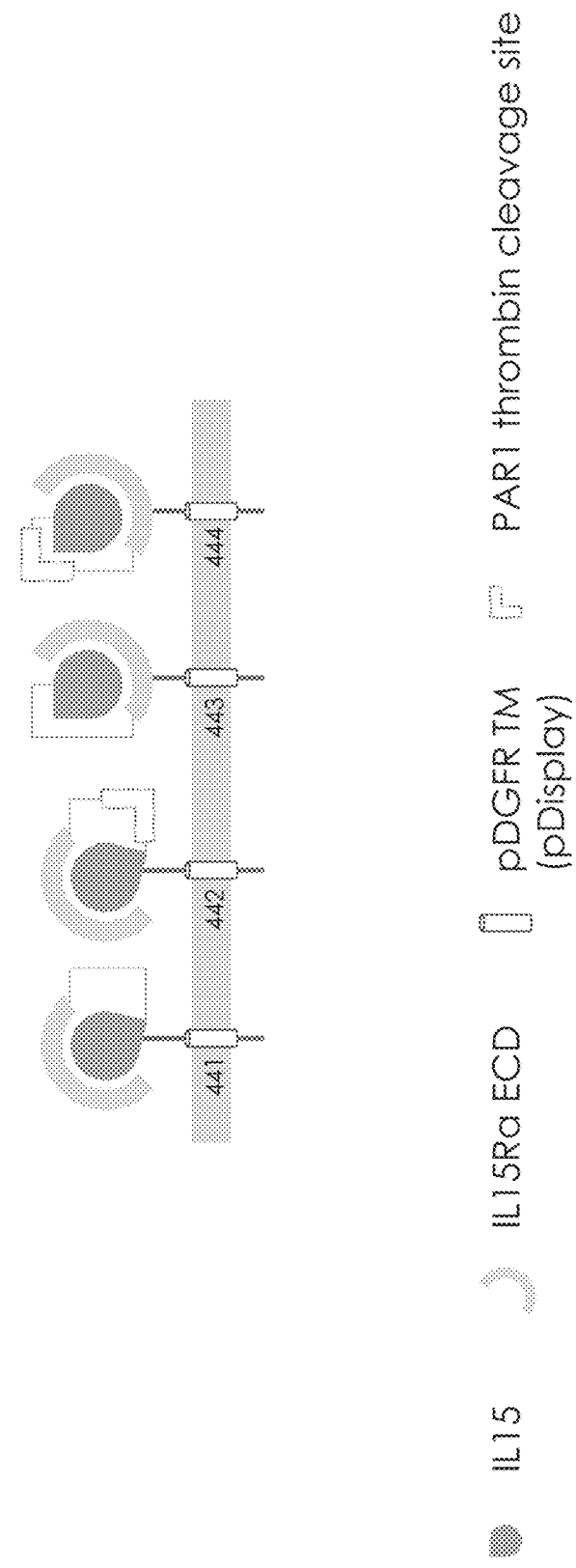
FIG. 34 shows the schematics of 15/IL-15Ra fusion proteins fused to the transmembrane domain of PDGFR.
Figure 35:
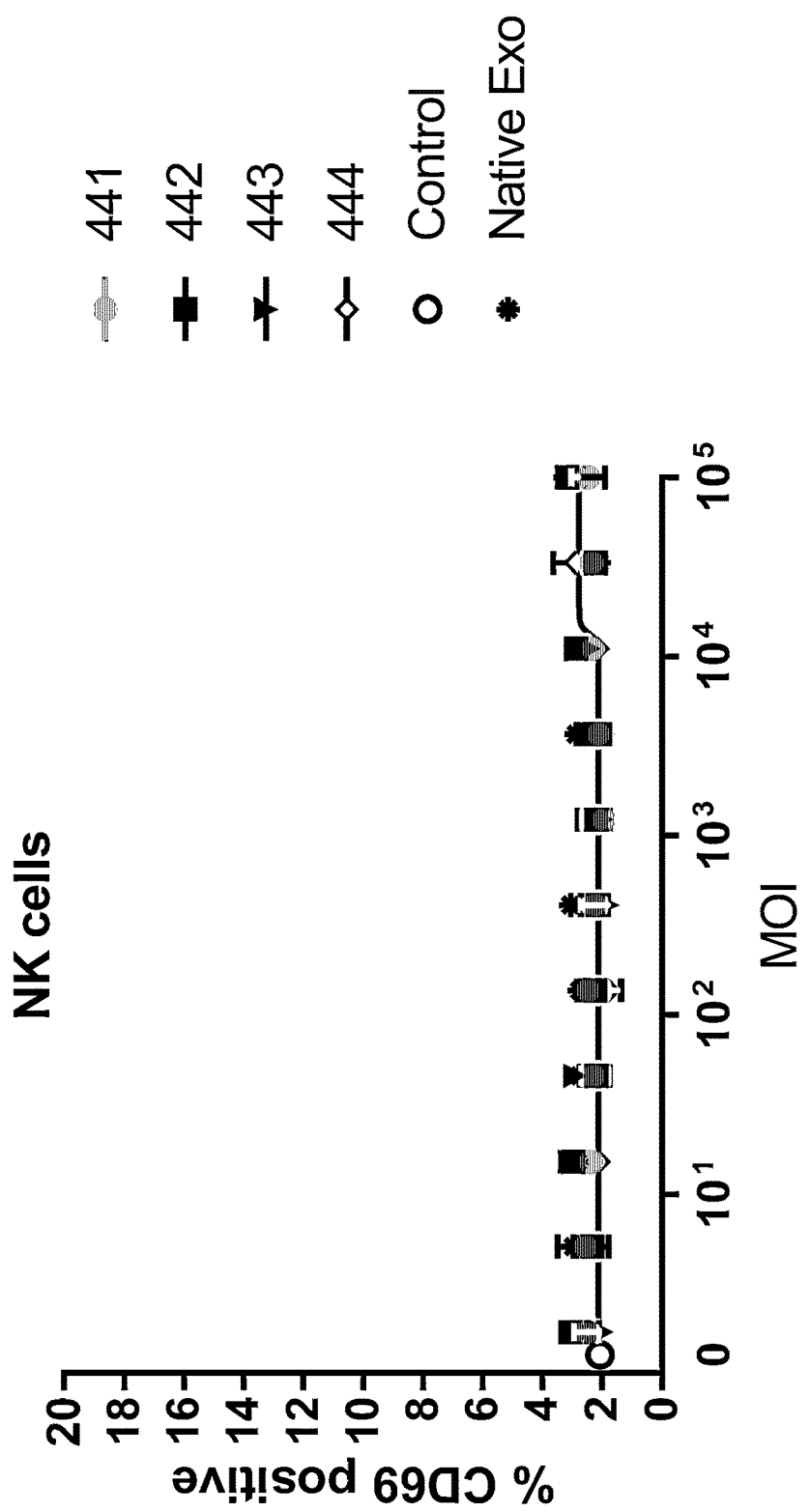
FIG. 35 shows the NK cell activation measured by the percentage of CD69 positive NK cells after the addition of pDisplay IL-15 exosomes.
Figure 36B:
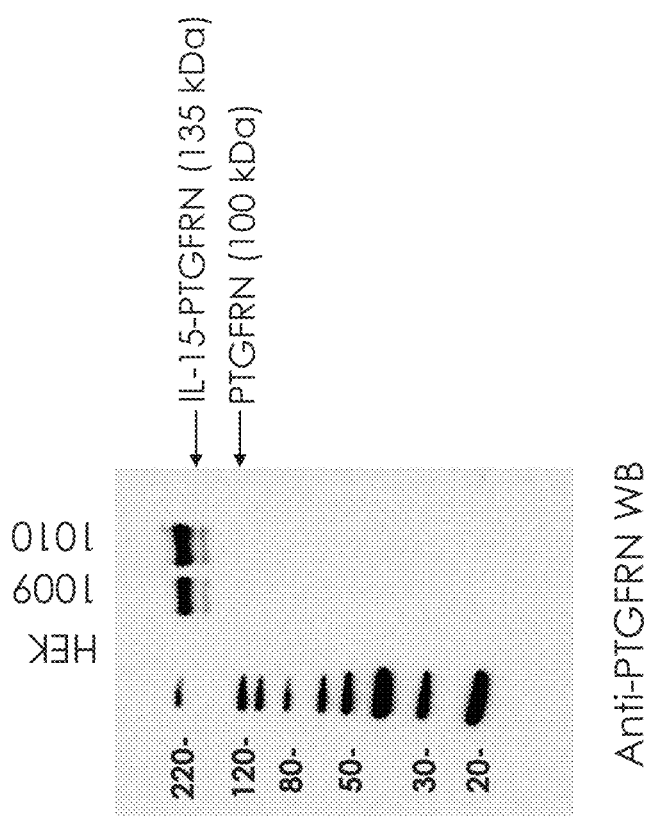
FIG. 36B shows the Western blotting of IL-15 fused to full-length PTGFRN and IL-15 N72D fused to full-length PTGFRN.
Figure 36A:
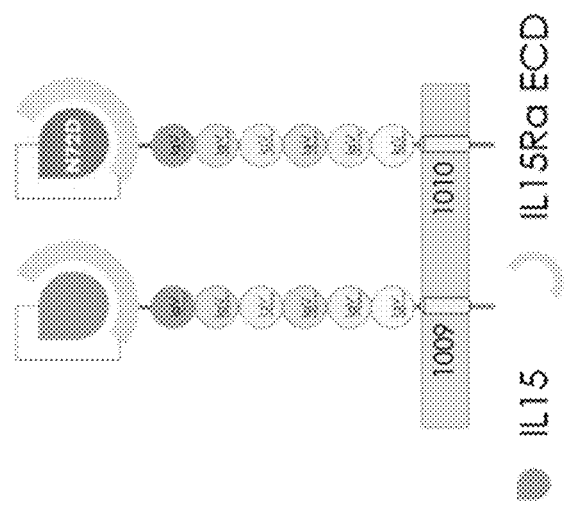
FIG. 36A shows the schematics of IL-15 fused to full-length PTGFRN and IL-15 N72D fused to full-length PTGFRN.
Figure 37:
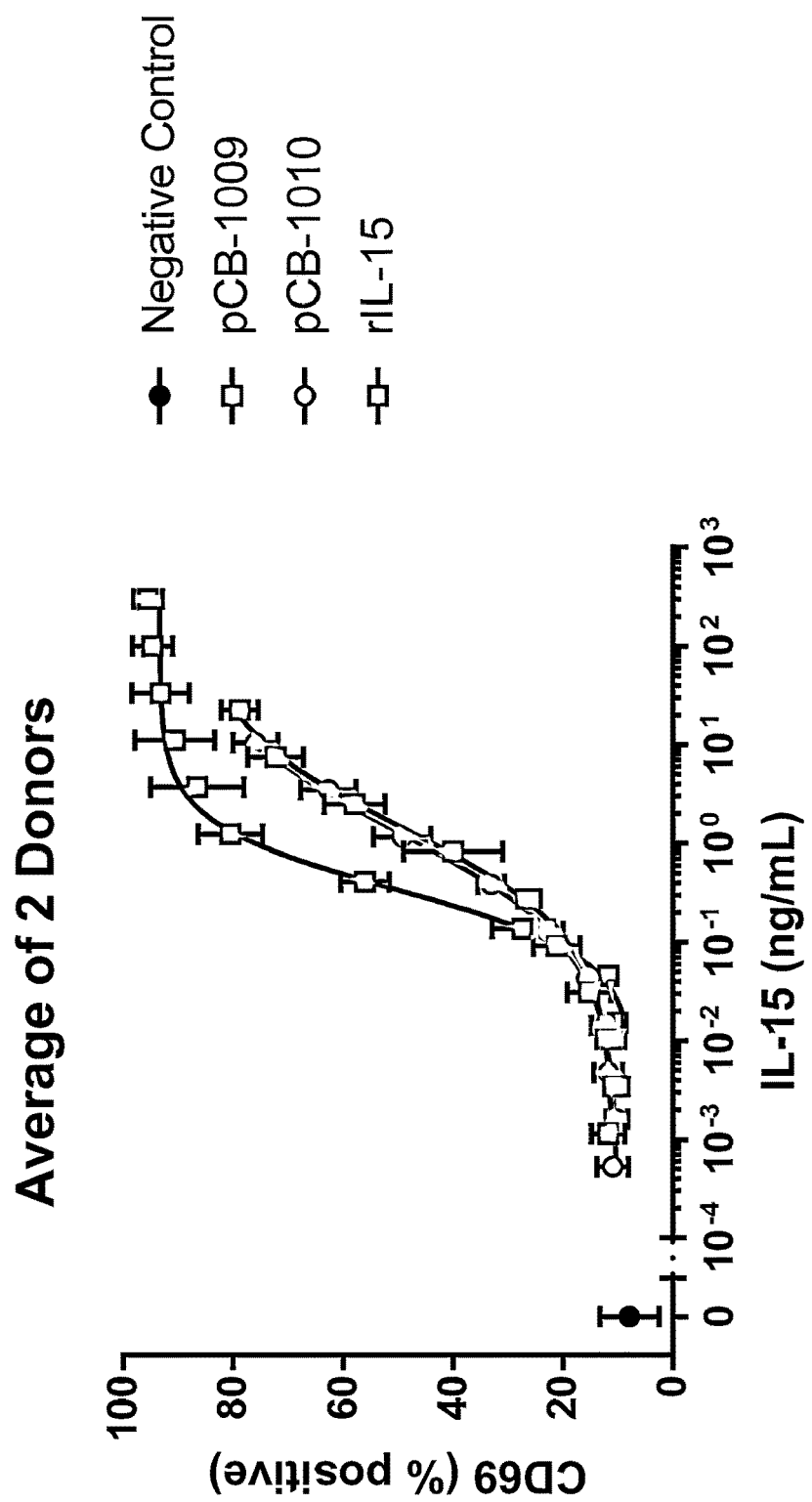
FIG. 37 shows NK cell activation measured by the percentage of CD69 positive NK cells after the addition of IL-15 fused to full-length PTGFRN and IL-15 N72D fused to full-length PTGFRN.

Interleukin 15 (IL-15) is a cytokine produced by mononuclear cells after pathogenic infection. IL-15 can be secreted as a soluble protein or presented as a dimeric membrane-anchored protein bound to IL-15Ra. IL-15 activates NK cells and T-cells and is implicated as a potential therapeutic molecule in immuno-oncology and other immune intervention therapies. IL-15-expressing exosomes were produced by stably transfecting HEK293SF cells with expression plasmids encoding the transmembrane domain of PDGFR (pDisplay) fused to IL-15/IL-15Ra fusion proteins (FIG. 34). Exosomes were purified by Optiprep™ density-gradient ultracentrifugation as described in the Methods above. Purified exosomes were incubated with human PBMCs for 24 hours, and NK cell activation was measured as percent positive for CD69 by flow cytometry. None of the pDisplay IL-15 exosomes induced NK cell activation at doses up to 10⁵ exosomes per cell of PBMC culture (FIG. 35; exosome construct number as in FIG. 34). To investigate whether higher density IL-15 display was required to induce NK cell activation, HEK293SF cells were stably transfected with an expression plasmid encoding IL-15 fused to full-length PTGFRN. Additionally, HEK293SF cells were stably transfected with an expression plasmid encoding a more potent IL-15 fused to full-length PTGFRN (IL-15 N72D, as described in J Immunol. 2009 Sep. 15; 183(6):3598-607; FIG. 36A). Expression was confirmed by anti-PTGFRN Western blotting (FIG. 36B). IL-15 levels were quantified by ELISA (R&D Systems, Catalog No. D1500), normalized to recombinant IL-15 (Biolegend, Catalog No. 570302). The IL-15 PTGFGN exosomes were added to two independent PBMC cultures overnight and compared to concentration-matched recombinant IL-15. All three IL-15 sources induced NK cell activation in PBMCs in a dose-dependent manner as measured by the percentage of NK cells positive for CD69. Furthermore, all constructs were comparable to each other across both donors demonstrating meaningful comparative efficacy (FIG. 37; exosome construct number as in FIG. 36). These data demonstrate that IL-15 can be actively and potently displayed on the surface of exosomes, but this requires high expression levels such as those bestowed by PTGFRN.

Figure 38:
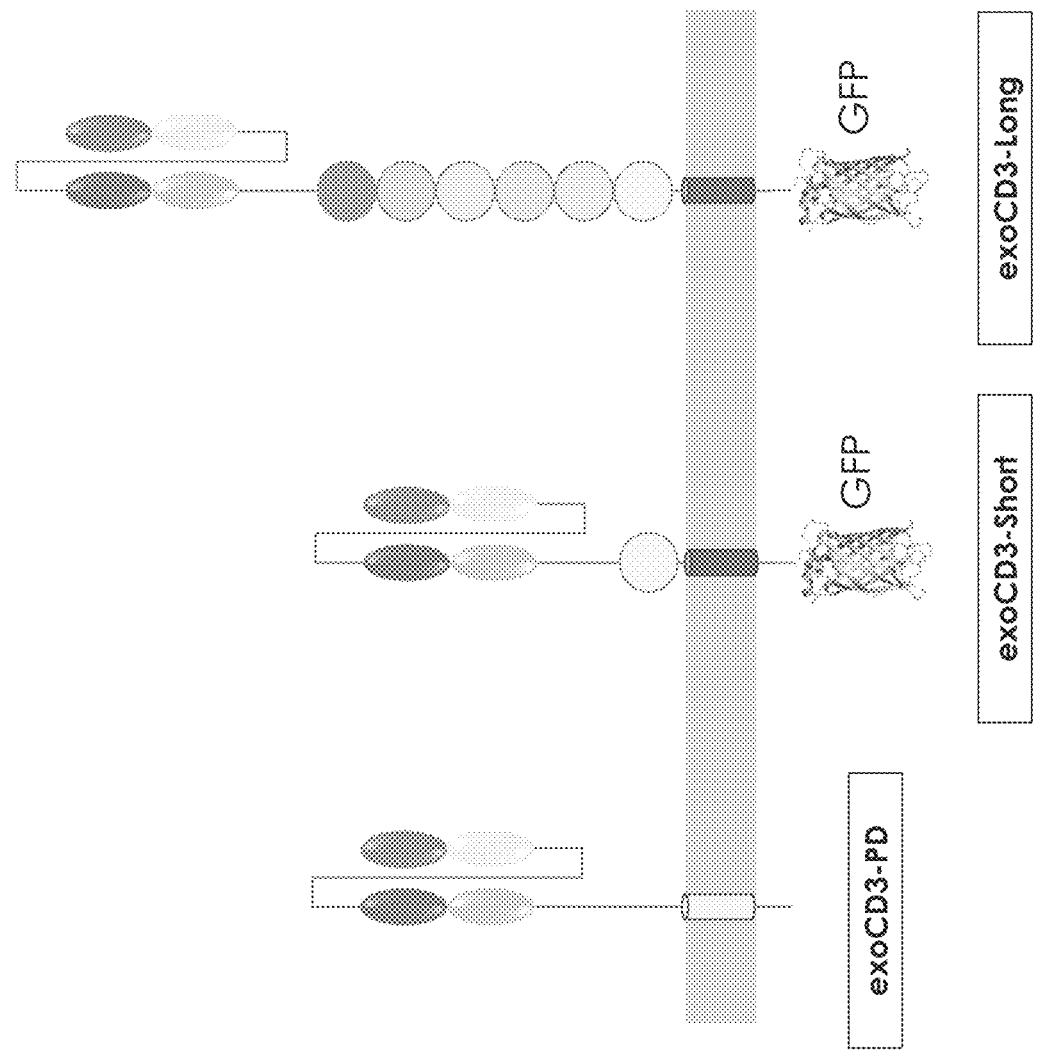
FIG. 38 shows the schematics of anti-CD3 antibody fragment fused to the PDGFR transmembrane region (exoCD3-PD), a full-length PTGFRN (exoCD3-long), and a PTGFRN fragment (exoCD3-short) respectively.
Figure 39:
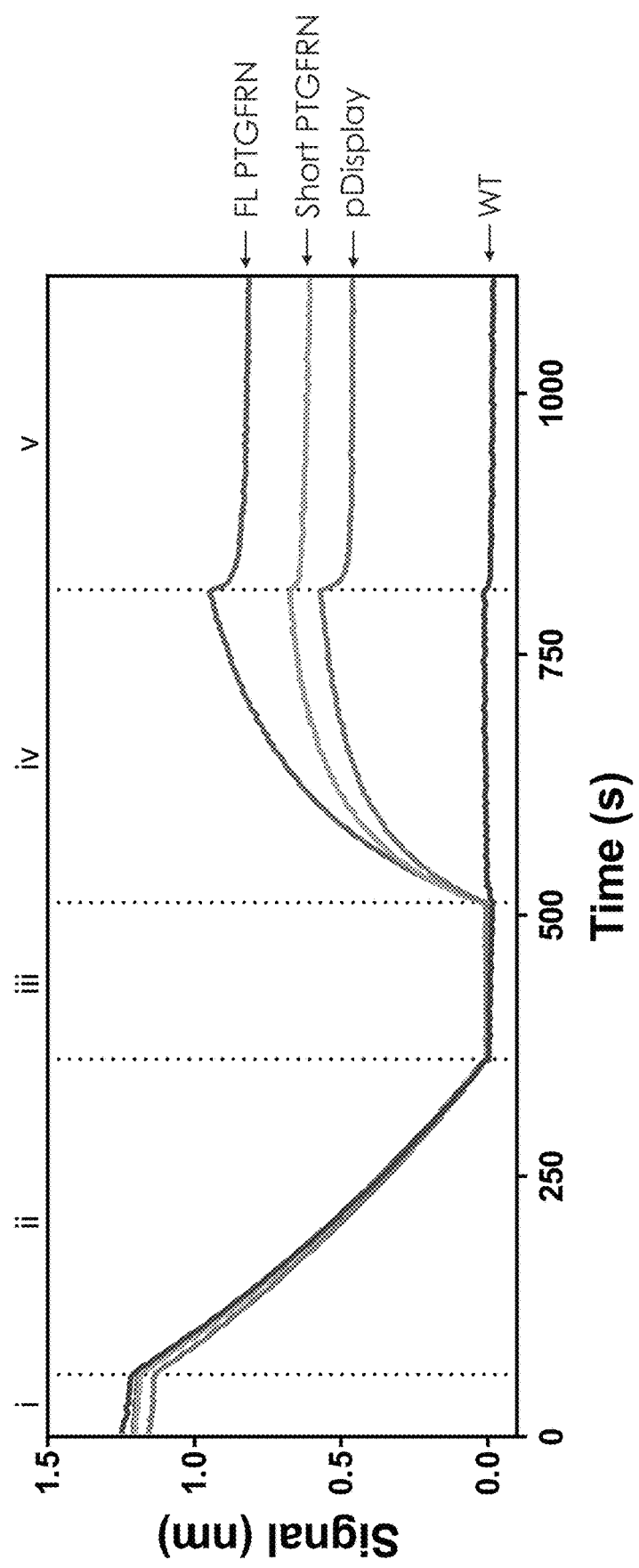
FIG. 39 shows the results of bio-layer interferometry (BLI) after addition of native exosomes (WT), exosomes with anti-CD3 antibody fragment fused to the PDGFR transmembrane region (pDisplay), exosomes with anti-CD3 antibody fragment fused to a full-length PTGFRN (FL PTGFRN), and exosomes with anti-CD3 antibody fragment fused to a PTGFRN fragment (Short PTGFRN), respectively.
Figure 40B:
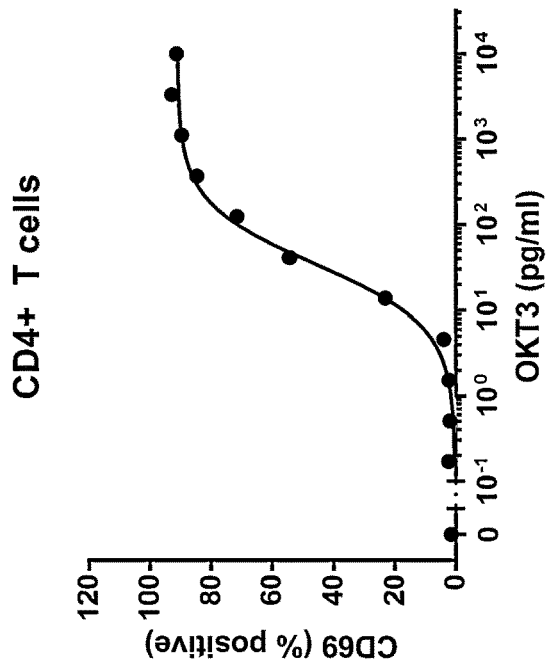
FIG. 40B shows CD4+ T cell activation measured by the percentage of CD69 positive CD4+ T cells after the addition of native exosomes (exoNative) and exosomes with anti-CD3 antibody fragment fused to a PTGFRN fragment (exoCD3-Short), respectively.
Figure 40A:
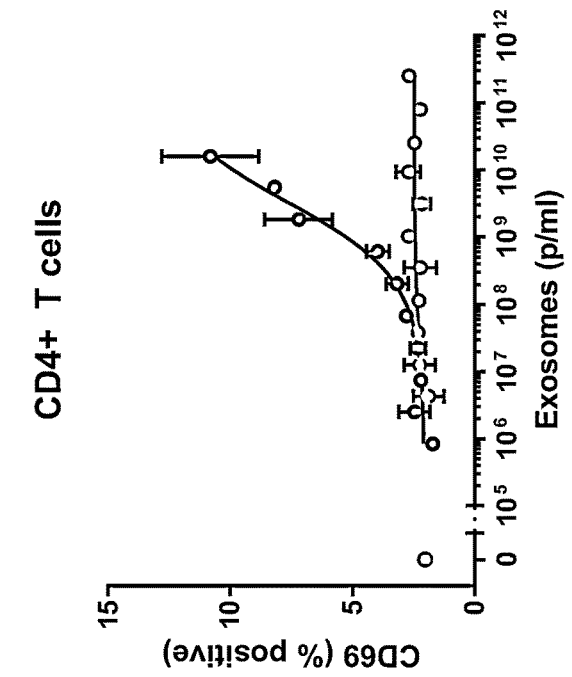
FIG. 40A shows CD4+ T cell activation measured by the percentage of CD69 positive CD4+ T cells after the addition of anti-CD3 antibody fragment.

Example 13: Exosomes Displaying Anti-CD-3 Antibody Fragments on a PTGFRN Scaffold Activate T-Cells The results in Example 9 demonstrate that exosomes displaying anti-CD3 antibody fragments can activate T-cells. To determine whether the PTGFRN scaffold supports this activity, anti-CD3 antibody fragments (OKT3 variants) were fused to the PDGFR transmembrane region (exoCD3-PD), full-length PTGFRN (exoCD3-long), or a PTGFRN fragment (exoCD3-short) and stably expressed in HEK293SF cells (FIG. 38). Exosome binding was confirmed by biolayer interferometry (BLI) using an Octet® RED96 (Pall). A CD3 fragment was bound to the BLI probe (FIG. 39, ii), washed (FIG. 39, iii), and the exosome constructs were added (FIG. 39, iv). Exosomes from WT HEK293SF cells did not bind the BLI probe, but all engineered constructs did. Both PTGFRN fragments bound to the probe with a greater affinity and remained stably bound (FIG. 39, v). Anti-CD3 display exosomes were tested for in vitro activity. T-cell activation was measured by CD69 positivity on CD4+ T-cells as measured by flow cytometry. In contrast to the unmodified native exosomes (exoNative), the exosomes with anti-CD3 fused to the PTGFRN fragment (exoCD3-short) were effective in activating CD4+ T-cells in vitro (FIG. 40).

Example 14: Exosomes Displaying CD40L Are Potent Activators of B-Cells

Figure 41:
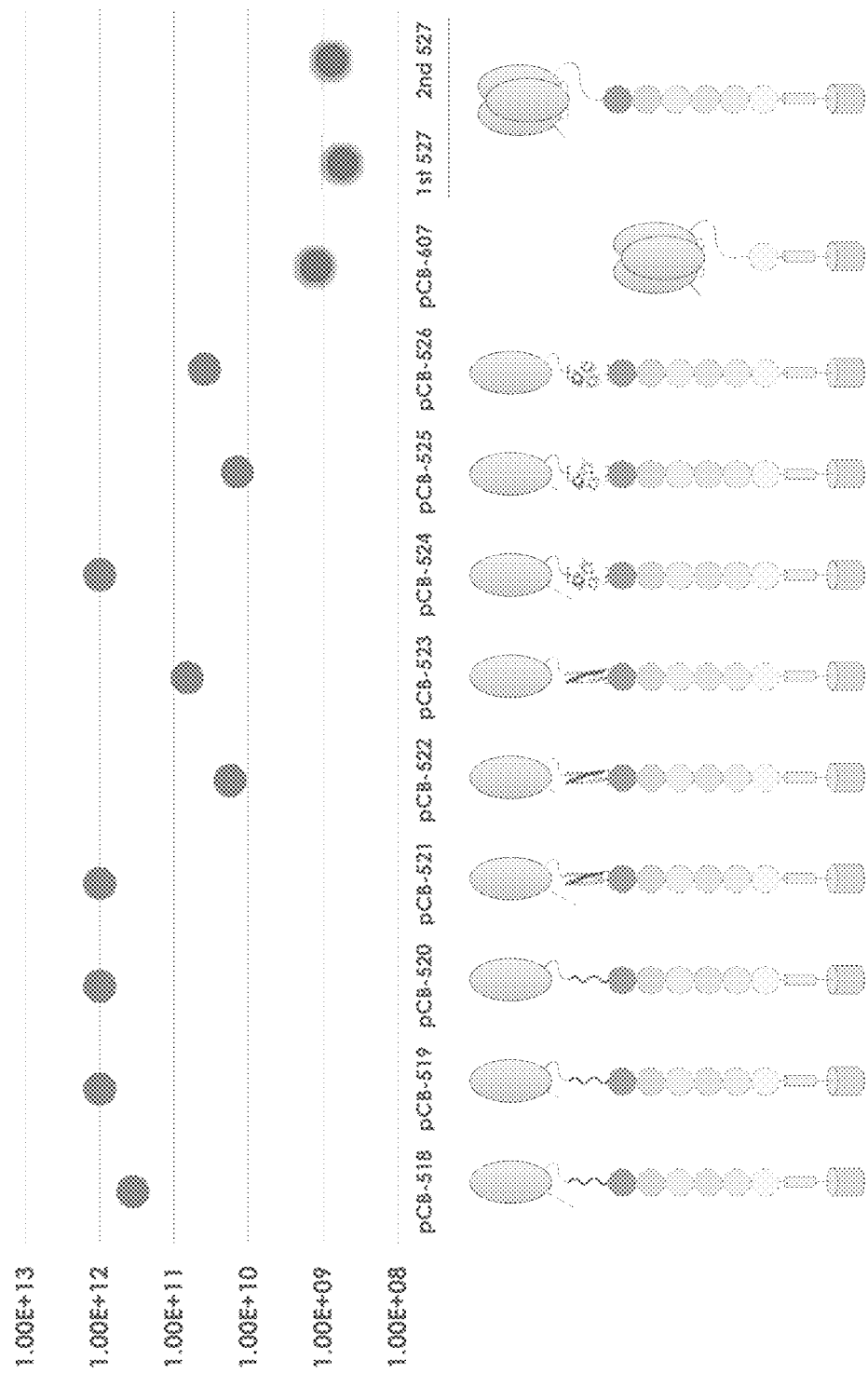
FIG. 41 shows the schematics of CD40L-GFP PTGFRN fusion proteins and the $EC_{50}$ for each construct in the B-cell activation assay measured by CD69 positivity on B-cells.

CD40 ligand (CD40L) is a ligand of the tumor necrosis superfamily (TNFSF) that binds to the costimulatory receptor CD40, which is highly expressed on B-cells and other antigen presenting cells. TNFSF ligand-mediated cellular activation requires the formation of trimeric ligand complexes that form on the cell surface and bind to cognate receptors. To investigate whether exosomes displaying different conformations of CD40L on their surface were sufficient to activate B-cells, over 40 different CD40L expression constructs were designed and individually transfected in HEK293SF cells. CD40L was expressed as a fusion to the transmembrane domain of PDGFR, full-length PTGFRN, and a short single-domain fragment of PTGFRN (FIG. 41A, bottom). CD40L-GFP PTGFRN fusions were expressed as a monomer (pCB-518 to pCB-526) or as a forced trimer (pCB-607 and pCB-527) (FIG. 41A, bottom). To promote trimerization of monomeric CD40L, constructs were designed which expressed a fusion to multimerization domains from TRAF2 (pCB-521 to pCB-523) or Collagen XV (pCB-524 to pCB-526). Among the monomeric CD40L constructs, pCB-518/521/524 contained full-length N-terminal stem sequences from endogenous CD40L; pCB-519/522/525 contained a truncated N-terminal stem sequence from endogenous CD40L; and pCB-520/523/526 contained only the soluble portion of CD40L. Each of the engineered exosome populations was incubated with purified B-cells, isolated from human peripheral blood by using RosetteSep™ Human B Cell Enrichment Cocktail (Stemcell Technologies #15064) and B-cell activation was measured by CD69 positivity on B-cells by flow cytometry. The $EC_{50}$ for each of the constructs was calculated as a function of particles concentration of cell culture and is plotted in the graph shown in FIG. 41, top. Interestingly, all of the monomeric CD40L constructs had modest potency, while the trimeric constructs were at least ten-fold more potent than the monomers (FIG. 41, top). These results demonstrate that monomeric CD40L is a poor activator of B-cells when presented on the surface of exosomes, but that forced trimeric CD40L can induce robust B-cell activation. Furthermore, PTGFRN has been shown to form dimeric structures (PCT/US2018/048026), suggesting that higher order multimeric structures may be forming on the exosome surface to further promote target engagement and immune cell activation.

The results shown in FIG. 41 all employed exosomes containing luminal GFP fused to the C-terminus of PTGFRN. With the goal of generating a tag-less CD40L exosome, the same trimeric CD40L-PTGFRN construct as the lead construct pCB-527 but lacking the C-terminal GFP was stably expressed in HEK293SF cells (pCB-766). The absolute concentration of CD40L on the surface of the engineered exosomes was quantified using ELISA (R&D Systems, Catalog No., DCDL40), as shown in Table 10, below.

TABLE 10

| EC50 | pCB-0766 | pCB-0527 | rhCD40L |
|---|---|---|---|
| particles/mL | 6.63E+08 | 4.53E+08 | N/A |
| ng/mL | 1.68 | 1.89 | 28.51 |

Figure 42B:
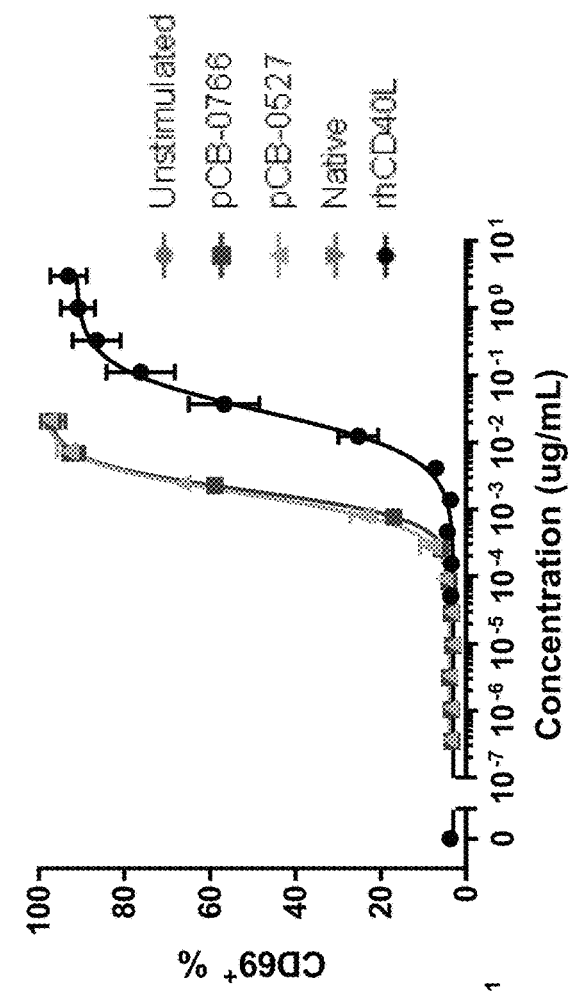
FIG. 42B shows B cell activation measured by the percentage of CD69 positive B cells after the addition of exosomes with trimeric CD40L-PTGFRN constructs pCB-527 and pCB-766 respectively compared to concentration-matched CD40L.
Figure 42A:
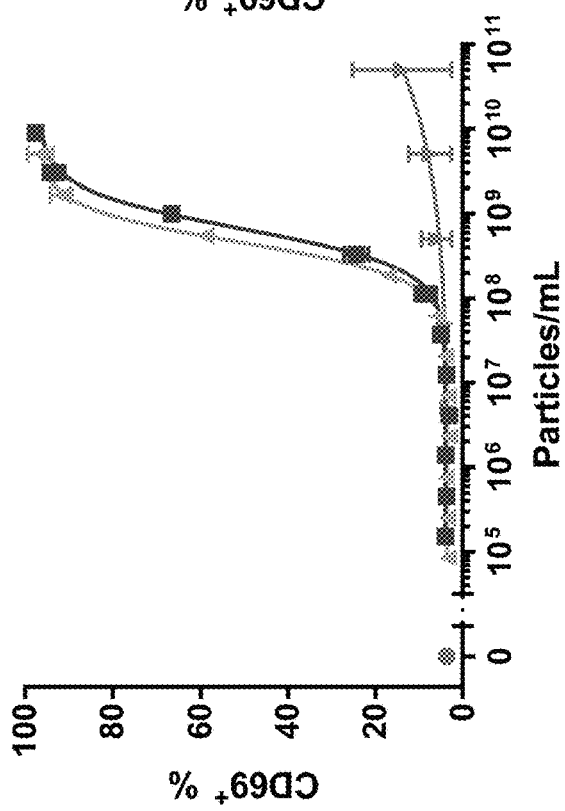
FIG. 42A shows B cell activation measured by the percentage of CD69 positive B cells after the addition of native exosomes, exosomes with trimeric CD40L-PTGFRN constructs pCB-527, and exosomes with trimeric CD40L-PTGFRN constructs pCB-766, respectively.

The purified CD40L-PTGFRN exosomes were tested in B-cell activation assays as described above, compared to concentration-matched recombinant human CD40L (Biolegend, Catalog No. 591702). The GFP-containing and the tag-less CD40L exosomes were comparable B-cell activators when measured as a function of particle number or CD40L concentration (FIG. 42A), and both exosome preparations were more potent than concentration-matched CD40L (FIG. 42B). Native, non-engineered exosomes from HEK293SF cells failed to activate B-cells, demonstrating that the engineered CD40L trimeric constructs on the exosome surface were sufficient to potently activate B-cells.

Figure 43A:
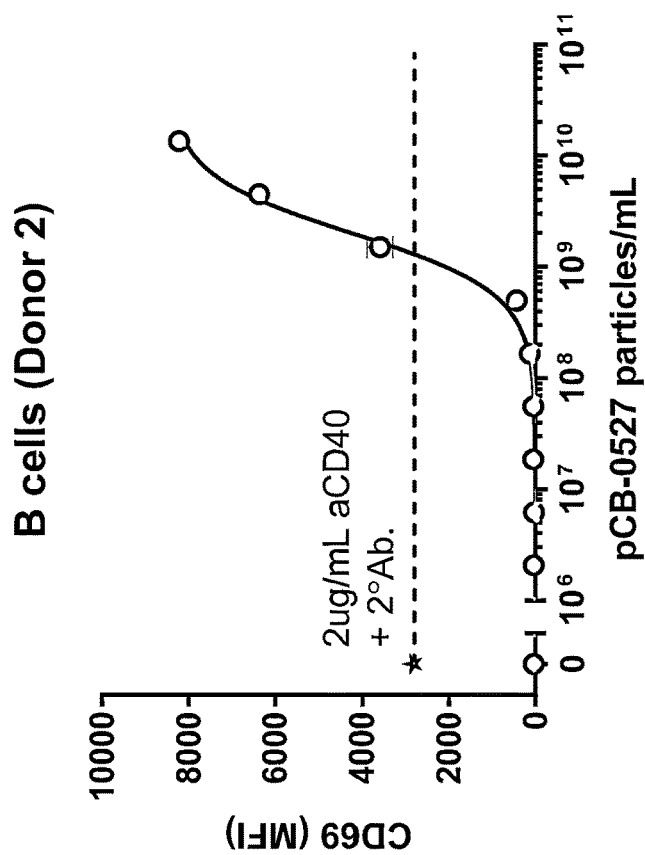
FIG. 43A shows B cell activation in Donor 1 measured by the percentage of CD69 positive B cells after the addition of exosomes with trimeric CD40L-PTGFRN constructs pCB-527.
Figure 43B:
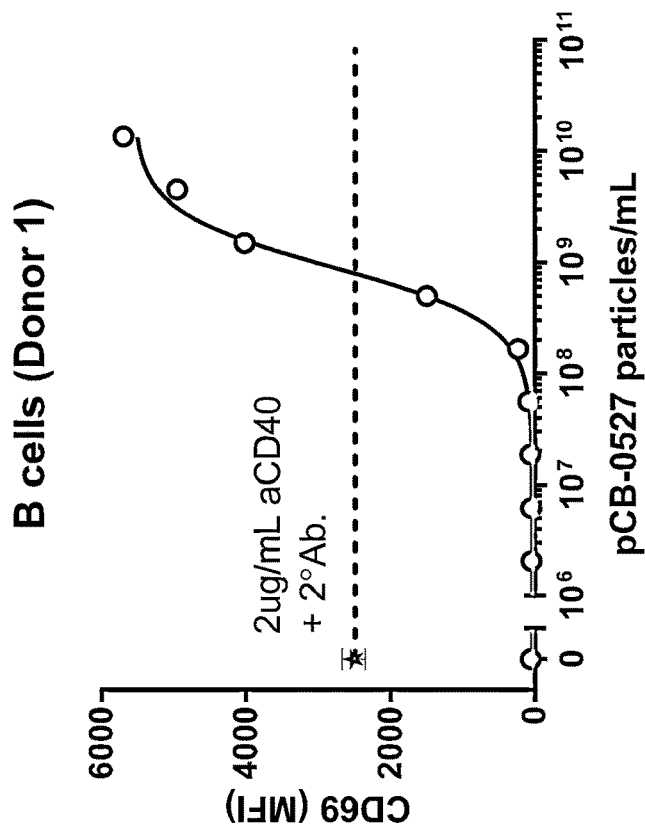
FIG. 43B shows B cell activation in Donor 2 measured by the percentage of CD69 positive B cells after the addition of exosomes with trimeric CD40L-PTGFRN constructs pCB-527.

An alternative modality to agonize CD40 and activate B-cells is to use an agonistic antibody cross-linked with a secondary antibody. To compare the potency of trimeric CD40L-expressing exosomes to an agonistic CD40L antibody, PBMC cultures were incubated with 2 μg/ml anti-CD40L antibody (Biolegend®; Clone 5C3) with a secondary cross-linking antibody (JacksonImmuno Research, Catalog No. 115-006-071). Maximal B-cell activation is shown as the dotted line in FIGS. 43A and 43B. pCB-527 exosomes (PTGFRN-trimeric CD40L-GFP) induced a greater maximal B-cell activation than the cross-linked agonistic antibody in two independent donor PBMC pools (FIGS. 43A and 43B) demonstrating superiority of trimeric CD40L exosomes in activating immune cells.

Example 15: Simultaneous Display of Multiple Immuno-Oncology Molecules on Individual Exosomes The previous examples demonstrate that individual immune-modulating proteins can be displayed on the surface of an exosome and induce functional changes in one or more immune cell types. In certain applications, the use of combinatorially engineered exosomes may be required, i.e., an exosome containing more than one molecule on the exosome surface, each of which is capable of signaling a distinct immune cell pathway. HEK293SF cells were stably transfected with a plasmid expressing both PTGFRN-IL-12 and PTGFRN-CD40L fusion proteins. Exosomes were isolated and purified as described above. Exosomes from unmodified HEK293SF cells were used as negative controls.

To demonstrate simultaneous loading of different ligands, a pull-down co-stain assay was developed:
REAGENTS:
Dynabeads (Thermofisher Exosome-Streptavidin Isolation/Detection Reagent,
  Catalog No. 10608D): $1\times10^7$ beads/mL, 50% slurry
  Isolation buffer: 0.5% BSA/PBS (1:4 from 2% BSA)
  Block buffer: 2% BSA/PBS (1 gr/50 mL, filter)
  Wash 0.5 ml beads with 0.5 ml isolation buffer and resuspend in 0.5 mL isolation buffer
  Add 1 µg biotinylated capture antibody (2.2 ul of 0.5 ug/ul stock)
  1 hr rotation, RT
  Wash 500 µl isolation buffer
  Resuspend in 500 µl block buffer, 10 min rotation RT
  Incubate in 500 µl isolation buffer ($1\times10^7$ beads/mL, 50% slurry)
  Store at 4C
A. Exosome capture and flow
  $1\times10^5$ beads per sample (10 µl beads, 20 µl slurry)
  exosomes per bead; $5\times10^9$ exosomes per sample ($1.2\times10^9$ exosomes/µL stock)
  of each fluorescently labeled detection antibody for flow
  Mix $5\times10^9$ exosomes+20 µl Dynabeads slurry+0.7 ml 0.1% BSA/PBS
PROCEDURE:
1. 120 µl slurry beads, remove sup, add 0.7 ml block buffer, mix, rotate 10 min RT, remove sup
2. Suspend beads in 0.7 ml isolation buffer+25.2 µl exosomes, rotate ON @ 4 C
3. Next day: quick spin exosomes and beads, 5 sec
4. Place tube on magnet, remove sup
5. Block in 700 µl, 10 min rotate RT
6. Place tube on magnet, remove sup
7. Resuspend in 600 µl isolation buffer: 6×100 µl per tube
8. Add 1 µl labeled detection antibody, mix, incubate 30 min @ 4 C in dark
9. Spin 2 min @ 500 g, remove sup
10. Wash 2× isolation buffer
11. Resuspend in 200 µl isolation buffer, run flow.

Figure 44B:
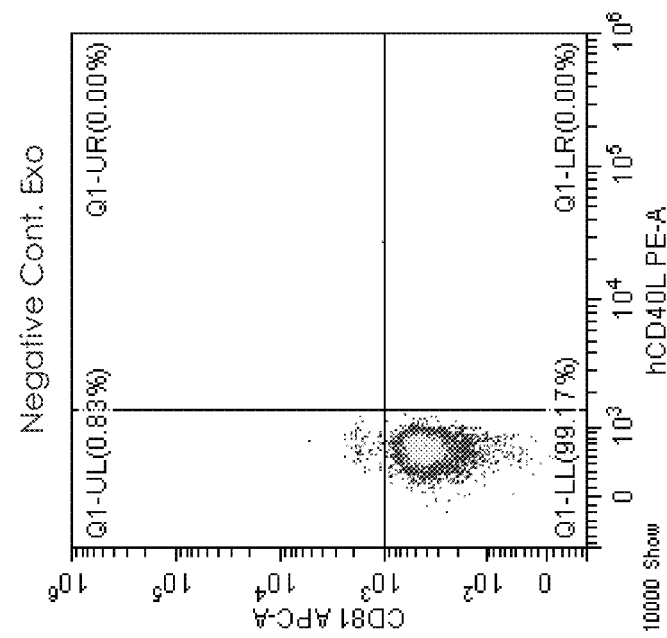
FIG. 44B shows the FACS analysis of native exosomes isolated with anti-CD40L-decorated beads and labeled fluorescent antibodies with against CD81 and CD40L.
Figure 44A:
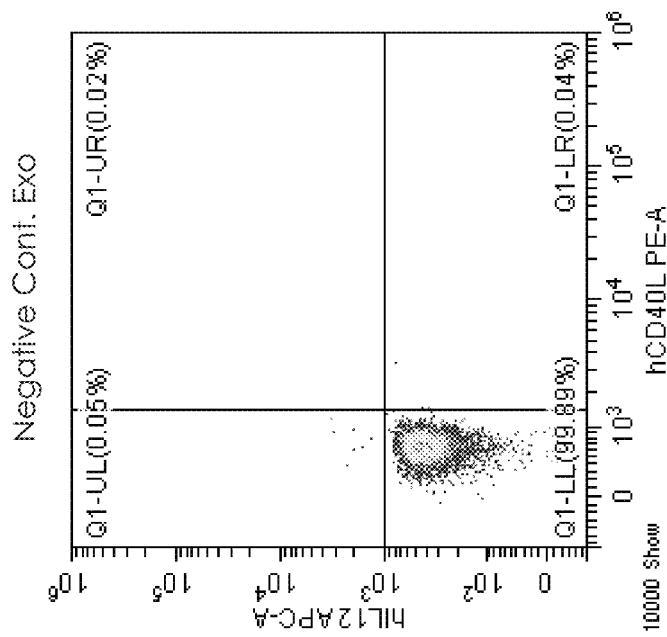
FIG. 44A shows the FACS analysis of native exosomes isolated with anti-CD40L-decorated beads and labeled with fluorescent antibodies against IL-12 and CD40L.
Figure 45B:
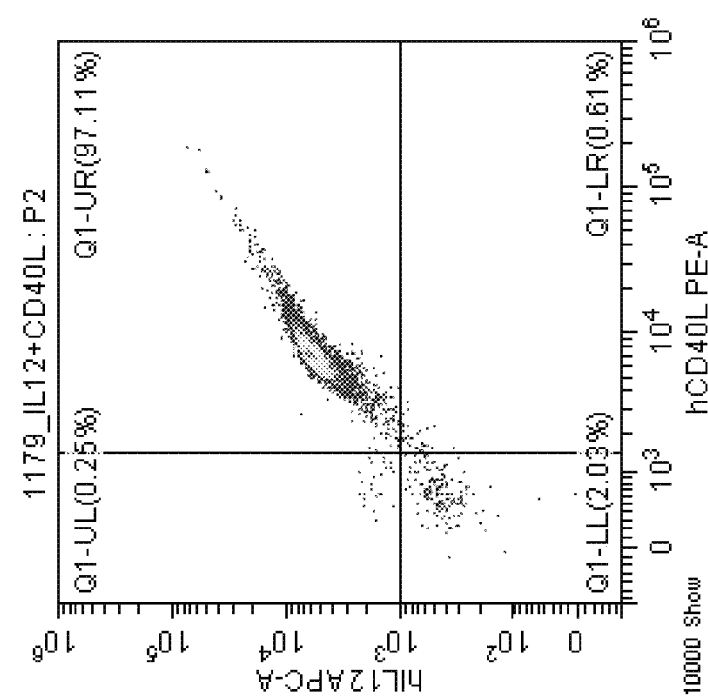
FIG. 45B shows the FACS analysis of PTGFRN-CD40L/IL-12 double engineered exosomes isolated with anti-CD40L-decorated beads and labeled with fluorescent antibodies against IL-12 and CD40L.
Figure 45A:
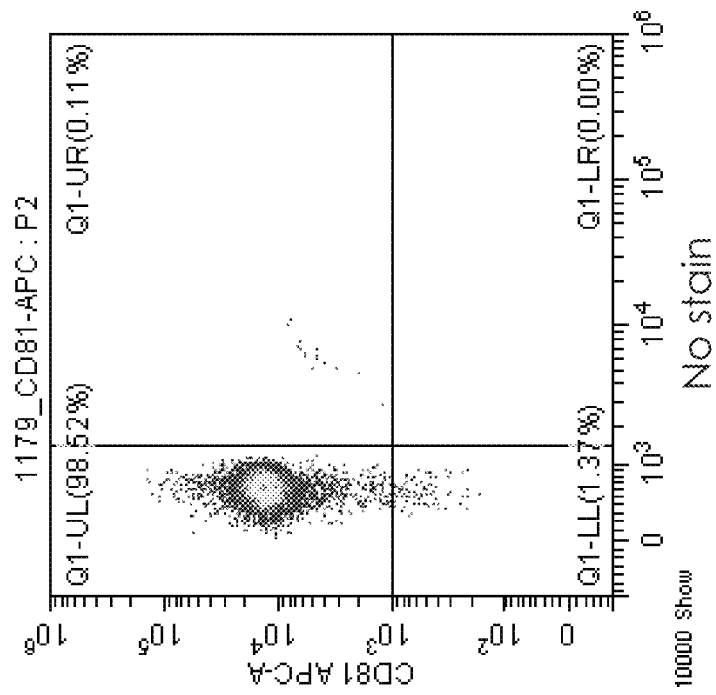
FIG. 45A shows the FACS analysis of PTGFRN-CD40L/IL-12 double engineered exosomes isolated with anti-CD40L-decorated beads and labeled with fluorescent antibody against CD81.
Figure 46B:
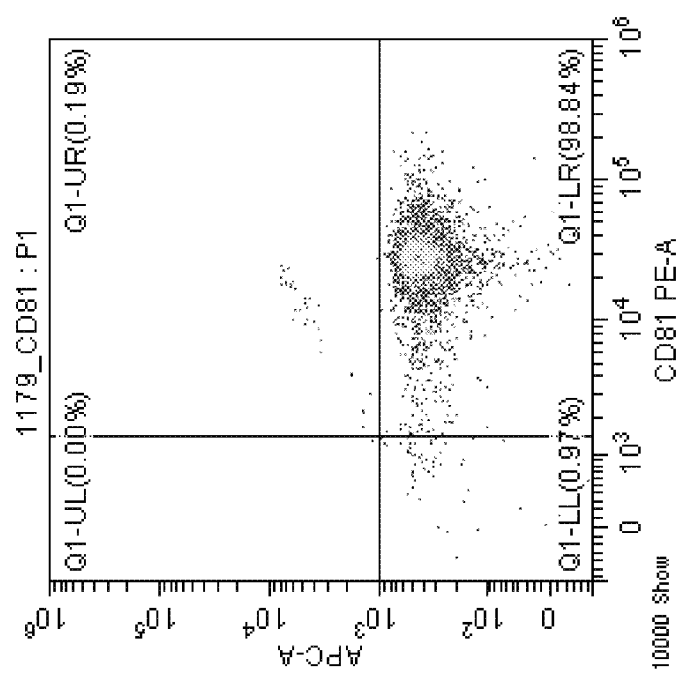
FIG. 46B shows the FACS analysis of PTGFRN-CD40L/IL-12 double engineered exosomes isolated with anti-IL-12-decorated beads and labeled with fluorescent antibody against CD81.
Figure 46A:
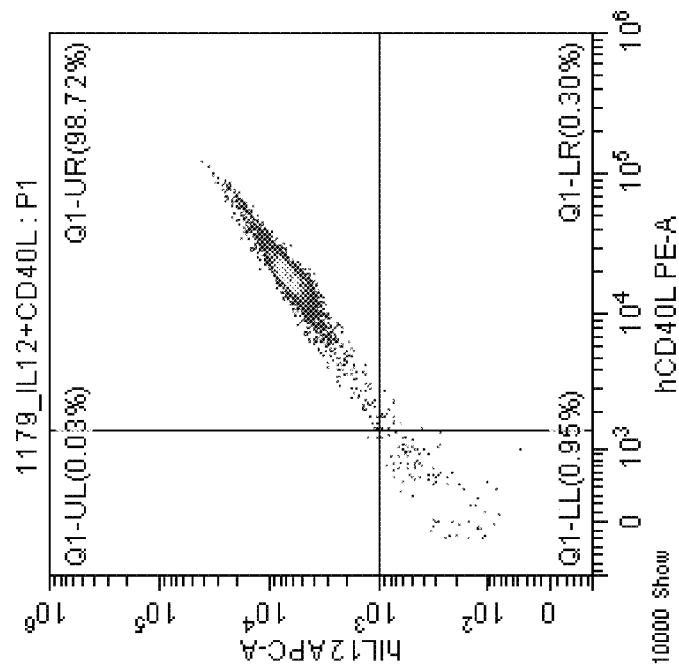
FIG. 46A shows the FACS analysis of PTGFRN-CD40L/IL-12 double engineered exosomes isolated with anti-IL-12-decorated beads and labeled with fluorescent antibodies against IL-12 and CD40L.

Native exosomes were isolated with anti-CD40L-decorated beads and labeled fluorescent antibodies against IL-12 and CD40L (FIG. 44A) or CD81, an exosome marker present on native and engineered exosomes, and CD40L (FIG. 44B). The CD40L beads did not pull down any of the native exosomes, since no fluorescent signal was detected for IL-12, CD40L or CD81. In contrast, PTGFRN-CD40L/IL-12 double engineered exosomes were incubated with anti-CD40L beads and isolated as above. Staining for CD81 (FIG. 45A), IL-12 or CD40L (FIG. 45B) were all detected with the engineered exosomes (greater than 97% of counted beads), indicating that CD40L-mediated isolation could also isolate IL-12 exosomes. Similarly, anti-IL-12-decorated beads were incubated with the IL-12/CD40L engineered exosomes and stained for IL-12, CD40L, and CD81. Greater than 98% of all beads were positive for both CD40L and IL-12 or for CD81 (FIGS. 46A and 46B), demonstrating that the exosomes contained both IL-12 and CD40L on their surface.

Figure 47B:
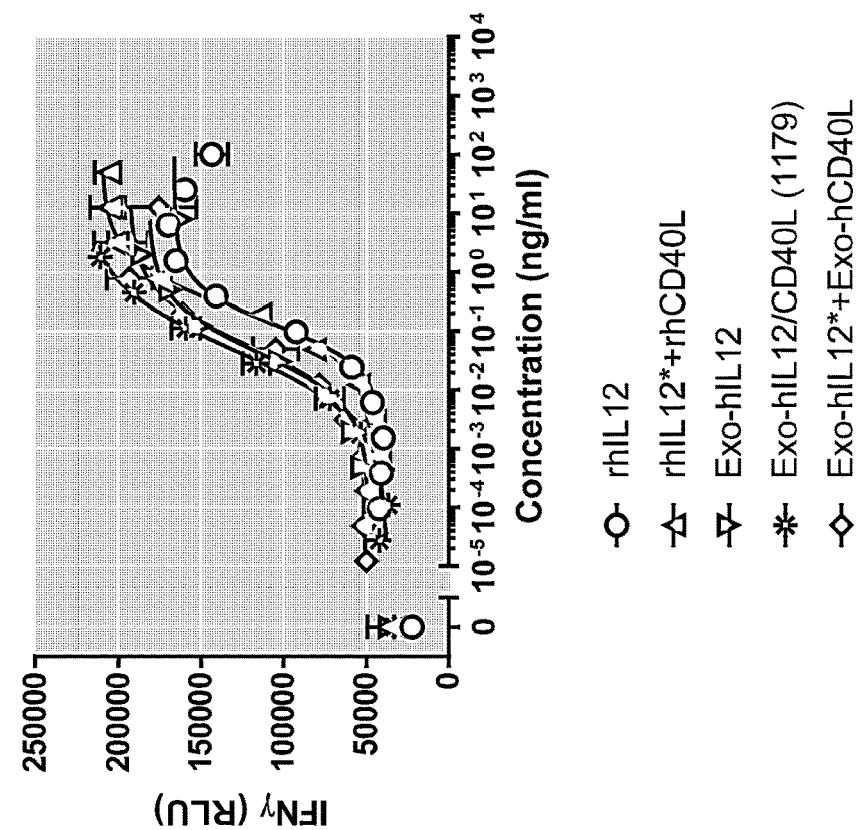
FIG. 47B shows the IFNγ response in Donor 2 human PBMCs after addition of recombinant IL-12, recombinant IL-12 mixed with recombinant CD40L, PTGFRN-IL-12 exosomes, double-positive PTGFRN-CD40L/IL-12 exosomes, and a mixture of PTGFRN-IL-12 exosomes and PTGFRN-CD40L exosomes, respectively.
Figure 47A:
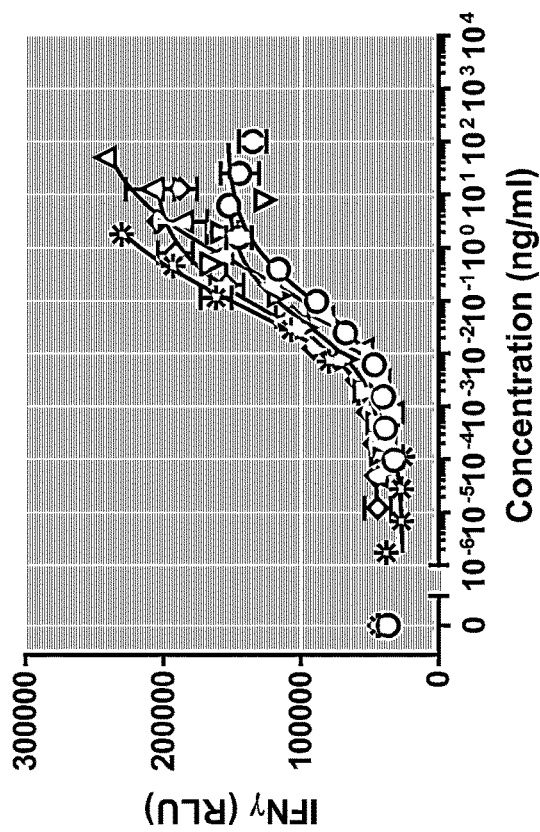
FIG. 47A shows the IFNγ response in Donor 1 human PBMCs after addition of recombinant IL-12, recombinant IL-12 mixed with recombinant CD40L, PTGFRN-IL-12 exosomes, double-positive PTGFRN-CD40L/IL-12 exosomes, and a mixture of PTGFRN-IL-12 exosomes and PTGFRN-CD40L exosomes, respectively.
Figure 49B:
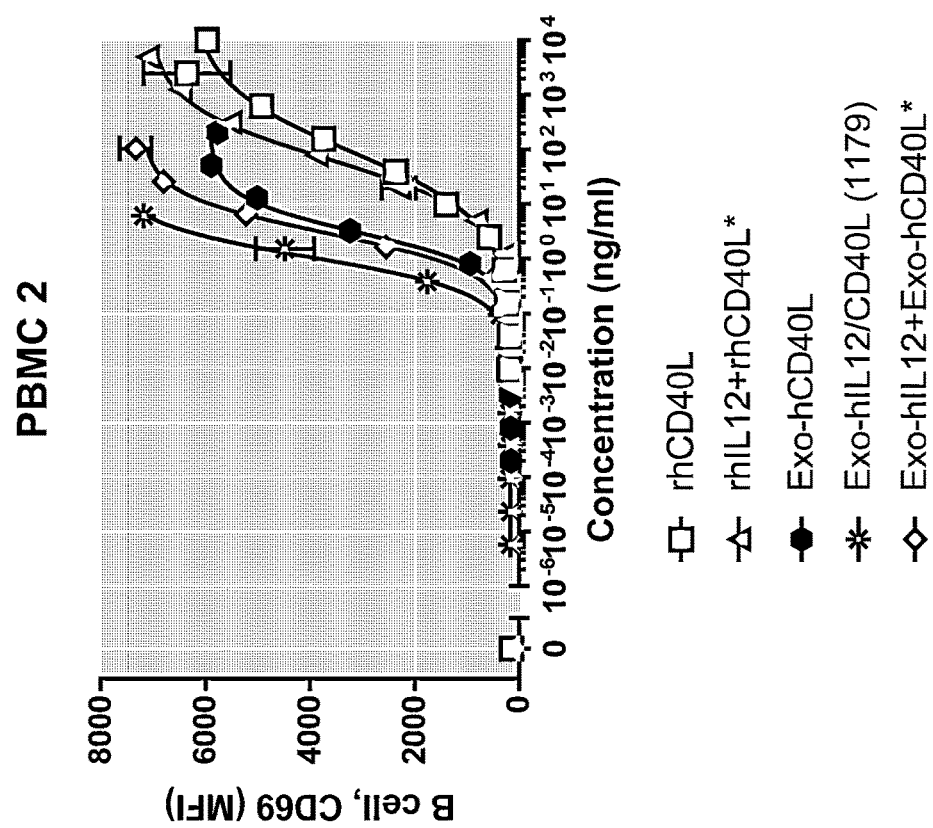
FIG. 49B shows the B cell activation in Donor 2 human PBMCs after addition of recombinant CD40L, recombinant IL-12 mixed with recombinant CD40L, PTGFRN-CD40L exosomes, double-positive PTGFRN-CD40L/IL-12 exosomes, and a mixture of PTGFRN-IL-12 exosomes and PTGFRN-CD40L exosomes, respectively.
Figure 49A:
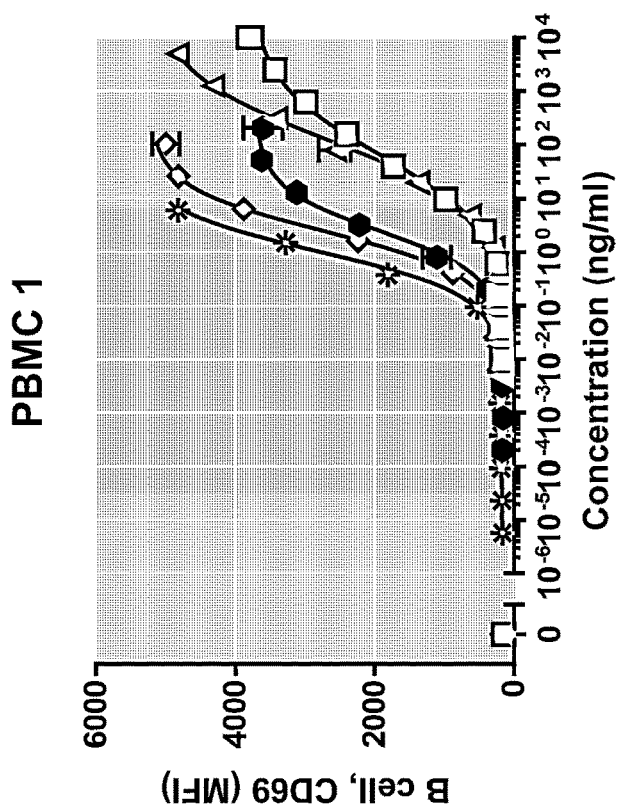
FIG. 49A shows the B cell activation in Donor 1 human PBMCs after addition of recombinant CD40L, recombinant IL-12 mixed with recombinant CD40L, PTGFRN-CD40L exosomes, double-positive PTGFRN-CD40L/IL-12 exosomes, and a mixture of PTGFRN-IL-12 exosomes and PTGFRN-CD40L exosomes, respectively.

IL-12 and CD40L concentration was quantified by ELISA (Abcam Catalog No. ab119517) for testing the engineered exosomes for potency in vitro. Equal concentrations of recombinant IL-12, recombinant IL-12 mixed with recombinant CD40L, PTGFRN-IL-12 exosomes, double-positive PTGFRN-CD40L/IL-12 exosomes, or a mixture of PTGFRN-IL-12 exosomes and PTGFRN-CD40L exosomes were added to human PBMCs at increasing concentrations (rhIL-12—BioLegend, Catalog No. 573004; rhCD40L—Biolegend, Catalog No. 591702). The cells were co-stimulated with anti-CD3 antibody, and IFNγ production was measured by (PerkinElmer, Catalog No. AL217C). As shown in FIGS. 47A and 47B, all IL-12-containing exosome preparations elicited an IFNγ response comparable to the recombinant cytokines. Calculation of the $EC_{50}$ for the various conditions revealed that exosome-associated IL-12 was more potent than concentration-matched IL-12, whether expressed singly or combinatorially on the exosome surface (FIG. 48). Similar results were achieved with recombinant CD40L and singly or doubly engineered CD40L exosomes in the context of B-cell activation (FIGS. 49A and B). Again, the CD40L engineered exosomes were more potent than the soluble recombinant cytokine, and in this case the doubly engineered exosomes were the most potent construct tested in the assay (FIG. 50).

Figure 51A:
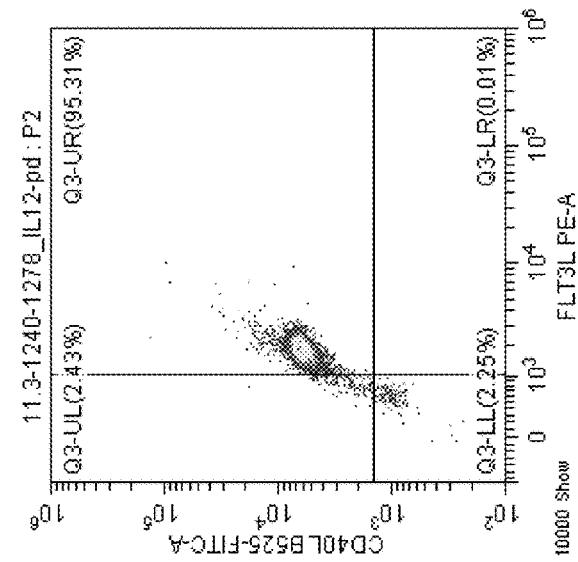
FIG. 51A shows the FACS analysis of PTGFRN-CD40L/IL-12/FLT3L triple engineered exosomes isolated with anti-IL-12-decorated beads and labeled with fluorescent antibodies against IL-12 and CD40L.
Figure 51B:
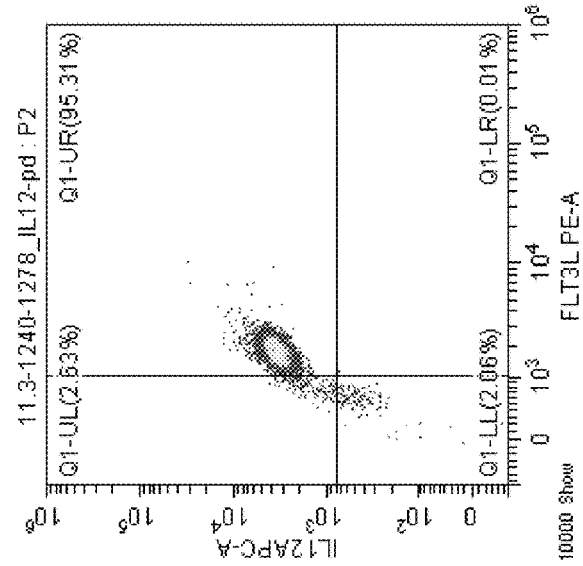
FIG. 51B shows the FACS analysis of PTGFRN-CD40L/IL-12/FLT3L triple engineered exosomes isolated with anti-IL-12-decorated beads and labeled with fluorescent antibodies against IL-12 and FLT3L.
Figure 51C:
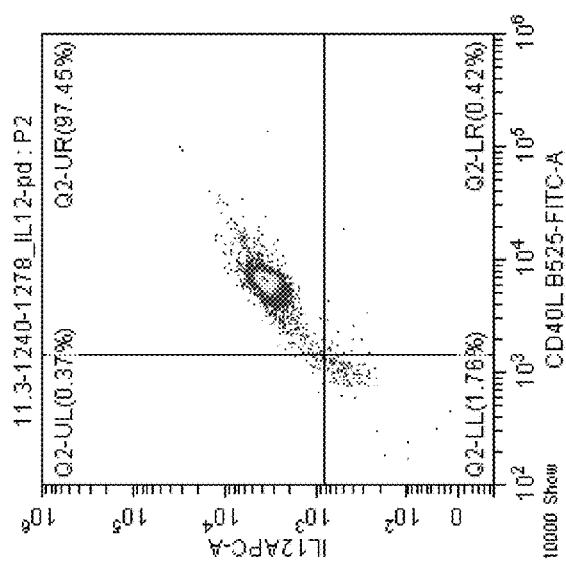
FIG. 51C shows the FACS analysis of PTGFRN-CD40L/IL-12/FLT3L triple engineered exosomes isolated with anti-IL-12-decorated beads and labeled with fluorescent antibodies against CD40L and FLT3L.
Figure 52C:
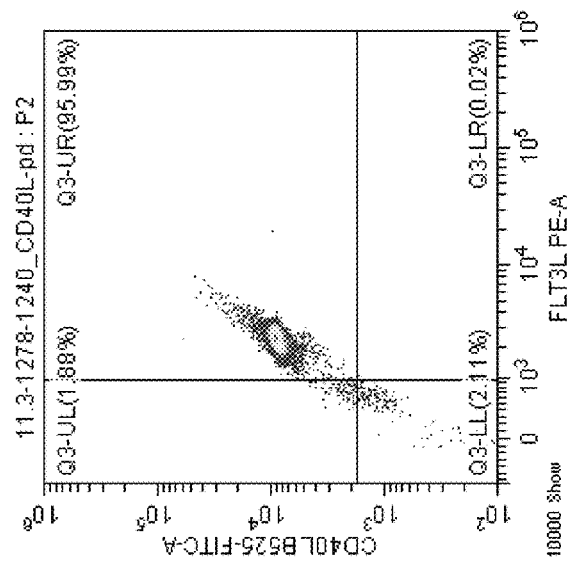
FIG. 52C shows the FACS analysis of PTGFRN-CD40L/IL-12/FLT3L triple engineered exosomes isolated with anti-CD40L-decorated beads and labeled with fluorescent antibodies against CD40L and FLT3L.
Figure 52B:
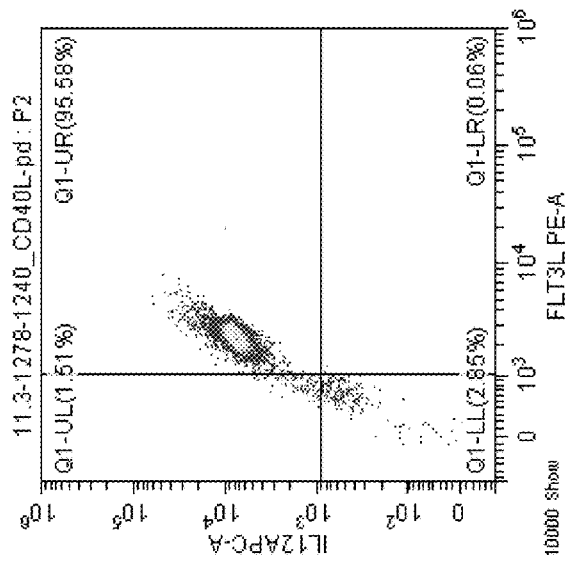
FIG. 52B shows the FACS analysis of PTGFRN-CD40L/IL-12/FLT3L triple engineered exosomes isolated with anti-CD40L-decorated beads and labeled with fluorescent antibodies against IL-12 and FLT3L.
Figure 52A:
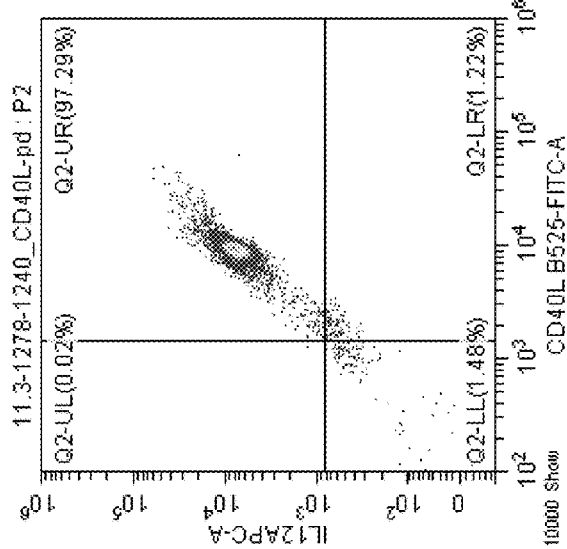
FIG. 52A shows the FACS analysis of PTGFRN-CD40L/IL-12/FLT3L triple engineered exosomes isolated with anti-CD40L-decorated beads and labeled with fluorescent antibodies against IL-12 and CD40L.

To further explore the possibility of combinatorial surface display exosomes, HEK293SF cells were stably transfected with three independent constructs expressing either PTGFRN-IL-12, PTGFRN-CD40L, or PTGFRN-FLT3L fusion proteins. Exosomes were purified and isolated by the affinity bead methods as described above, but were also interrogated for the presence of surface FLT3L using an anti-FLT3L-PE conjugated antibody. Exosomes isolated with anti-IL-12 beads were doubly positive for IL-12 and CD40L (FIG. 51A), IL-12 and FLT3L (Figure MB), and CD40L and FLT3L (Figure MC). Exosomes isolated with anti-CD40L beads were doubly positive for IL-12 and CD40L (FIG. 52A), IL-12 and FLT3L (FIG. 52B), and CD40L and FLT3L (FIG. 52C), confirming that individual exosomes expressed each of the three immunomodulatory ligands. These results demonstrate that multiply engineered immuno-modulatory exosomes are a feasible therapeutic modality, and that they are comparable or more potent than soluble cytokines in immune cell activation.

Although the foregoing invention has been described in some detail by way of illustration and example for purposes of clarity of understanding, it is readily apparent to those of ordinary skill in the art in light of the teachings of this disclosure that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

SEQUENCE LISTING

>SEQ ID NO: 1
MFHVSFRYIFGLPPLILVLLPVASSDCDIEGKDGKQYESVLMVSIDQLLDSMKEIGS
NCLNNEFNFFKRHICDANKEGMFLFRAARKLRQFLKMNSTGDFDLHLLKVSEGTTILLNCTG
QVKGRKPAALGEAQPTKSLEENKSLKEQKKLNDLCFLKRLLQEIKTCWNKILMGTKEHSAGG
GGSDYKDDDDKGGGGSGPIFNASVHSDTPSVIRGDLIKLFCIITVEGAALDPDDMAFDVSWE
AVHSFGLDKAPVLLSSLDRKGIVTTSRRDWKSDLSLERVSVLEFLLQVHGSEDQDFGNYYCS
VTPWVKSPTGSWQKEAEIHSKPVFITVKMDVLNAFKYPLLIGVGLSTVIGLLSCLIGYCSSH
WCCKKEVQETRRERRRLMSMEMD

>SEQ ID NO: 2
MFHVSFRYIFGLPPLILVLLPVASSDCDIEGKDGKQYESVLMVSIDQLLDSMKEIGS
NCLNNEFNFFKRHICDANKEGMFLFRAARKLRQFLKMNSTGDFDLHLLKVSEGTTILLNCTG
QVKGRKPAALGEAQPTKSLEENKSLKEQKKLNDLCFLKRLLQEIKTCWNKILMGTKEHSAGG
GGSGGGGSGPIFNASVHSDTPSVIRGDLIKLFCIITVEGAALDPDDMAFDVSWFAVHSFGLD
KAPVLLSSLDRKGIVTTSRRDWKSDLSLERVSVLEFLLQVHGSEDQDEGNYYCSVTPWVKSP
TGSWQKEAEIHSKPVFITVKMDVLNAFKYPLLIGVGLSTVIGLLSCLIGYCSSHWCCKKEVQ
ETRRERRRLMSMEMD

>hIL-12-PTGERN; 871 (SEQ ID NO: 3)
MCHQQLVISW FSLVFLASPL VAIWELKKDV YVVELDWYPD APGEMVVLTC
DTPEEDGITW TLDQSSEVLG SGKTLTIQVK EFGDAGQYTC HKGGEVLSHS
LLLLHKKEDG IWSTDILKDQ KEPKNKTFLR CEAKNYSGRF TCWWLTTIST
DLTFSVKSSR GSSDPQGVTC GAATLSAERV RGDNKEYEYS VECQEDSACP
AAEESLPIEV MVDAVHKLKY ENYTSSFFIR DIIKPDPPKN LQLKPLKNSR
QVEVSWEYPD TWSTPHSYFS LTFCVQVQGK SKREKKDRVF TDKTSATVIC
RKNASISVRA QDRYYSSSWS EWASVPCSGG SGGGSGGGGS GGGGSGGGSG
GRNLPVATPS D PGMFPCLHHS QNLLRAVSNM LQKARQTLEF YPCTSEEIDH
EDITKDKTST VEACLPLELT KNESCLNSRE TSFITNGSCL ASRKTSFMMA
LCLSSIYEDL KMYQVEFKTM NAKLLMDPKR QIFLDQNMLA VIDELMQALN
FNSETVPQKS SLEEPDEYKT KIKLCILLHA FRIRAVTIDR VMSYLNASSA
GGGGSGGGGS RVVRVPTATL VRVVGTELVI PCNVSDYDGP SEQNFDWSES
SLGSSFVELA STWEVGFPAQ LYQERLQRGE ILLRRTANDA VELHIKNVQP
SDQGHYKCST PSTDATVQGN YEDTVQVKVL ADSLHVGPSA RPPPSLSLRE
GEPFELRCTA ASASPLHTHL ALLWEVHRGP ARRSVLALTH EGRFHPGLGY
EQRYHSGDVR LDTVGSDAYR LSVSRALSAD QGSYRCIVSE WIAEQGNWQE
IQEKAVEVAT VVIQPSVLRA AVPKNVSVAE GKELDLTCNI TTDRADDVRP
EVTWSFSRMP DSTLPGSRVL ARLDRDSLVH SSPHVALSHV DARSYHLLVR
DVSKENSGYY YCHVSLWAPG HNRSWHKVAE AVSSPAGVGV TWLEPDYQVY
LNASKVPGFA DDPTELACRV VDTKSGEANV RFTVSWYYRM NRRSDNVVTS
ELLAVMDGDW TLKYGERSKQ RAQDGDFIFS KEHTDTENER IQRTTEEDRG
NYYCVVSAWT KQRNNSWVKS KDVFSKPVNI FWALEDSVLV VKARQPKPFF
AAGNTFEMTC KVSSKNIKSP RYSVLIMAEK PVGDLSSPNE TKYIISLDQD
SVVKLENWTD ASRVDGVVLE KVQEDEFRYR MYQTQVSDAG LYRCMVTAWS
PVRGSLWREA ATSLSNPIEI DFQTSGPIEN ASVHSDTPSV IRGDLIKLFC
IITVEGAALD PDDMAFDVSW FAVHSFGLDK APVLLSSLDR KGIVTTSRRD
WKSDLSLERV SVLEFLLQVH GSEDQDEGNY YCSVTPWVKS PTGSWQKEAE
IHSKPVFITV KMDVLNAFKY PLLIGVGLST VIGLLSCLIG YCSSHWCCKK
EVQETRRERR RLMSMEMD*

>mIL-12-PTGERN; 872 (SEQ ID NO: 4)
MCPQKLTISW FAIVLLVSPL MAMWELEKDV YVVEVDWTPD APGETVNLTC
DTPEEDDITW TSDQRHGVIG SGKTLTITVK EFLDAGQYTC HKGGETLSHS
HLLLHKKENG IWSTEILKNF KNKTFLKCEA PNYSGRETCS WLVQRNMDLK
FNIKSSSSSP DSRAVTCGMA SLSAEKVILD QRDYEKYSVS CQEDVTCPTA
EETLPIELAL EARQQNKYEN YSTSPFIRDI IKPDPPKNLQ MKPLKNSQVE
VSWEYPDSWS TPHSYFSLKF FVRIQRKKEK MKETEEGCNQ KGAFLVEKTS
TEVQCKGGNV CVQAQDRYYN SSCSKWACVP CRVRSGGSGG GSGGGGSGGG
GSGGGSGGRV IPVSGPARCL SQSRNLLKTT DDMVKTAREK LKHYSCTAED
IDHEDITRDQ TSTLKTCLPL ELHKNESCLA TRETSSTTRG SCLPPQKTSL
MMTLCLGSIY EDLKMYQTEF QAINAALQNH NHQQIILDKG MLVAIDELMQ
SLNHNGETLR QKPPVGEADP YRVKMKLCIL LHAFSTRVVT INRVMGYLSS
ASAGGGGSGG GGSRVVRVPT ATLVRVVGTE LVIPCNVSDY DGPSEQNEDW
SESSLGSSFV ELASTWEVGF PAQLYQERLQ RGEILLRRTA NDAVELHIKN
VQPSDQGHYK CSTPSTDATV QGNYEDTVQV KVLADSLHVG PSARPPPSLS
LREGEPFELR CTAASASPLH THLALLWEVH RGPARRSVLA LTHEGRFHPG
LGYEQRYHSG DVRLDTVGSD AYRLSVSRAL SADQGSYRCI VSEWIAEQGN
WQEIQEKAVE VATVVIQPSV LRAAVPKNVS VAEGKELDLT CNITTDRADD
VRPEVTWSFS RMPDSTLPGS RVLARLDRDS LVHSSPHVAL SHVDARSYHL
LVRDVSKENS GYYYCHVSLW APGHNRSWHK VAEAVSSPAG VGVTWLEPDY
QVYLNASKVP GFADDPTELA CRVVDTKSGE ANVRFTVSWY YRMNRRSDNV
VTSELLAVMD GDWTLKYGER SKQRAQDGDF IFSKEHTDTF NFRIQRTTEE
DRGNYYCVVS AWTKQRNNSW VKSKDVFSKP VNIFWALEDS VLVVKARQPK
PFFAAGNTFE MTCKVSSKNI KSPRYSVLIM AEKPVGDLSS PNETKYIISL
DQDSVVKLEN WTDASRVDGV VLEKVQEDEF RYRMYQTQVS DAGLYRCMVT
AWSPVRGSLW REAATSLSNP IEIDFQTSGP IFNASVHSDT PSVIRGDLIK
LFCIITVEGA ALDPDDMAFD VSWFAVHSFG LDKAPVLLSS LDRKGIVTTS
RRDWKSDLSL ERVSVLEFLL QVHGSEDQDE GNYYCSVTPW VKSPTGSWQK
EAEIHSKPVF ITVKMDVLNA FKYPLLIGVG LSTVIGLLSC LIGYCSSHWC
CKKEVQETRR ERRRLMSMEM D*

SEQUENCE LISTING

>hIL-12-short PTGFRN; 873 (SEQ ID NO: 5)
MCHQQLVISW FSLVFLASPL VAIWELKKDV YVVELDWYPD APGEMVVLTC
DTPEEDGITW TLDQSSEVLG SGKTLTIQVK EFGDAGQYTC HKGGEVLSHS
LLLLHKKEDG IWSTDILKDQ KEPKNKTFLR CEAKNYSGRF TCWWLTTIST
DLTFSVKSSR GSSDPQGVTC GAATLSAERV RGDNKEYEYS VECQEDSACP
AAEESLPIEV MVDAVHKLKY ENYTSSFFIR DIIKPDPPKN LQLKPLKNSR
QVEVSWEYPD TWSTPHSYES LTFCVQVQGK SKREKKDRVF TDKTSATVIC
RKNASISVRA QDRYYSSSWS EWASVPCSGG SGGGSGGGGS GGGGSGGGSG
GRNLPVATPD PGMFPCLHHS QNLLRAVSNM LQKARQTLEF YPCTSEEIDH
EDITKDKTST VEACLPLELT KNESCLNSRE TSFITNGSCL ASRKTSFMMA
LCLSSIYEDL KMYQVEFKTM NAKLLMDPKR QIFLDQNMLA VIDELMQALN
FNSETVPQKS SLEEPDFYKT KIKLCILLHA FRIRAVTIDR VMSYLNASSA
GGGGSGGGGS GPIFNASVHS DTPSVIRGDL IKLFCIITVE GAALDPDDMA
FDVSWFAVHS FGLDKAPVLL SSLDRKGIVT TSRRDWKSDL SLERVSVLEF
LLQVHGSEDQ DEGNYYCSVT PWVKSPTGSW QKEAEIHSKP VFITVKMDVL
NAFKYPLLIG VGLSTVIGLL SCLIGYCSSH WCCKKEVQET RRERRRLMSM
EMD*

>mIL-12-short PTGFRN; 874 (SEQ ID NO: 6)
MCPQKLTISW FAIVLLVSPL MAMWELEKDV YVVEVDWTPD APGETVNLTC
DTPEEDDITW TSDQRHGVIG SGKTLTITVK EFLDAGQYTC HKGGETLSHS
HLLLHKKENG IWSTEILKNF KNKTFLKCEA PNYSGRFTCS WLVQRNMDLK
FNIKSSSSSP DSRAVTCGMA SLSAEKVTLD QRDYEKYSVS CQEDVTCPTA
EETLPIELAL EARQQNKYEN YSTSFFIRDI IKPDPPKNLQ MKPLKNSQVE
VSWEYPDSWS TPHSYFSLKF FVRIQRKKEK MKETEEGCNQ KGAFLVEKTS
TEVQCKGGNV CVQAQDRYYN SSCSKWACVP CRVRSGGSGG GSGGGGSGGG
GSGGGSGGRV IPVSGPARCL SQSRNLLKTT DDMVKTAREK LKHYSCTAED
IDHEDITRDQ TSTLKTCLPL ELHKNESCLA TRETSSTTRG SCLPPQKTSL
MMTLCLGSIY EDLKMYQTEF QAINAALQNH NHQQIILDKG MLVAIDELMQ
SLNHNGETLR QKPPVGEADP YRVKMKLCIL LHAFSTRVVT INRVMGYLSS
ASAGGGGSGG GGSGPIFNAS VHSDTPSVIR GDLIKLFCII TVEGAALDPD
DMAFDVSWFA VHSFGLDKAP VLLSSLDRKG IVTTSRRDWK SDLSLERVSV
LEFLLQVHGS EDQDEGNYYC SVTPWVKSPT GSWQKEAEIH SKPVFITVKM
DVLNAFKYPL LIGVGLSTVI GLLSCLIGYC SSHWCCKKEV QETRRERRRL
MSMEMD*

SEQ ID NO: 7 PTGFRN_IFN_gamma monomer
MGRLASRPLLLALLSLALCRGQDPYVKEAENLKKYFNAGHSDVADNGTLFLGILKN
WKEESDRKIMQSQIVSFYFKLFKNFKDDQSIQKSVETIKEDMNVKFFNSNKKKRDDF
EKLTNYSVTDLNVQRKAIHELIQVMAELSPAAKTGSAGGGGSGGGGSRVVRVPTAT
LVRVVGTELVIPCNVSDYDGPSEQNFDWSFSSLGSSFVELASTWEVGFPAQLYQERL
QRGEILLRRTANDAVELHIKNVQPSDQGHYKCSTPSTDATVQGNYEDTVQVKVLAD
SLHVGPSARPPPSLSLREGEPFELRCTAASASPLHTHLALLWEVHRGPARRSVLALTH
EGRFHPGLGYEQRYHSGDVRLDTVGSDAYRLSVSRALSADQGSYRCIVSEWIAEQG
NWQEIQEKAVEVATVVIQPSVLRAAVPKNVSVAEGKELDLTCNITTDRADDVRPEVT
WSFSRMPDSTLPGSRVLARLDRDSLVHSSPHVALSHVDARSYHLLVRDVSKENSGY
YYCHVSLWAPGHNRSWHKVAEAVSSPAGVGVTWLEPDYQVYLNASKVPGFADDP
TELACRVVDTKSGEANVRFTVSWYYRMNRRSDNVVTSELLAVMDGDWTLKYGER
SKQRAQDGDFIFSKEHTDTFNFRIQRTTEEDRGNYYCVVSAWTKQRNNSWVKSKDV
FSKPVNIFWALEDSVLVVKARQPKPFFAAGNTFEMTCKVSSKNIKSPRYSVLIMAEKP
VGDLSSPNETKYIISLDQDSVVKLENWTDASRVDGVVLEKVQEDEFRYRMYQTQVS
DAGLYRCMVTAWSPVRGSLWREAATSLSNPIEIDFQTSGPIFNASVHSDTPSVIRGDLI
KLFCIITVEGAALDPDDMAFDVSWFAVHSFGLDKAPVLLSSLDRKGIVTTSRRDWKS
DLSLERVSVLEFLLQVHGSEDQDFGNYYCSVTPWVKSPTGSWQKEAEIHSKPVFITV
KMDVLNAFKYPLLIGVGLSTVIGLLSCLIGYCSSHWCCKKEVQETRRERRRLMSME
MD SEQ ID NO: 8 PTGFRN_IFN gamma dimer
MGRLASRPLLLALLSLALCRGQDPYVKEAENLKKYFNAGHSDVADNGTLFLGILKN
WKEESDRKIMQSQIVSFYFKLFKNFKDDQSIQKSVETIKEDMNVKFFNSNKKKRDDF
EKLTNYSVTDLNVQRKAIHELIQVMAELSPAAKTGSGGGSGGSGGSGQDPYVKEAE
NLKKYFNAGHSDVADNGTLFLGILKNWKEESDRKIMQSQIVSFYFKLFKNFKDDQSI
QKSVETIKEDMNVKFFNSNKKKRDDFEKLTNYSVTDLNVQRKAIHELIQVMAELSPA
AKTGSAGGGGSGGGGSRVVRVPTATLVRVVGTELVIPCNVSDYDGPSEQNFDWSFS
SLGSSFVELASTWEVGFPAQLYQERLQRGEILLRRTANDAVELHIKNVQPSDQGHYK
CSTPSTDATVQGNYEDTVQVKVLADSLHVGPSARPPPSLSLREGEPFELRCTAASASP
LHTHLALLWEVHRGPARRSVLALTHEGRFHPGLGYEQRYHSGDVRLDTVGSDAYRL
SVSRALSADQGSYRCIVSEWIAEQGNWQEIQEKAVEVATVVIQPSVLRAAVPKNVSV
AEGKELDLTCNITTDRADDVRPEVTWSFSRMPDSTLPGSRVLARLDRDSLVHSSPHV
ALSHVDARSYHLLVRDVSKENSGYYYCHVSLWAPGHNRSWHKVAEAVSSPAGVGV
TWLEPDYQVYLNASKVPGFADDPTELACRVVDTKSGEANVRFTVSWYYRMNRRSD
NVVTSELLAVMDGDWTLKYGERSKQRAQDGDFIFSKEHTDTFNFRIQRTTEEDRGN
YYCVVSAWTKQRNNSWVKSKDVFSKPVNIFWALEDSVLVVKARQPKPFFAAGNTF
EMTCKVSSKNIKSPRYSVLIMAEKPVGDLSSPNETKYIISLDQDSVVKLENWTDASRV
DGVVLEKVQEDEFRYRMYQTQVSDAGLYRCMVTAWSPVRGSLWREAATSLSNPIEI
DFQTSGPIFNASVHSDTPSVIRGDLIKLFCIITVEGAALDPDDMAFDVSWFAVHSFGLD

```
KAPVLLSSLDRKGIVTTSRRDWKSDLSLERVSVLEFLLQVHGSEDQDFGNYYCSVTP
WVKSPTGSWQKEAEIHSKPVFITVKMDVLNAFKYPLLIGVGLSTVIGLLSCLIGYCSS
HWCCKKEVQETRRERRRLMSMEMD

SEQ ID NO: 9 PTGFRN_IFN gamma mouse monomer
MGRLASRPLLLALLSLALCRGRHGTVIESLESLNNYFNSSGIDVEEKSLFLDIWRNWQ
KDGDMKILQSQIISFYLRLFEVLKDNQAISNNISVIESHLITTFFSNSKAKKDAFMSIAK
FEVNNPQVQRQAFNELIRVVHQLLPESSLRSAGGGGSGGGGSRVVRVPTATLVRVV
GTELVIPCNVSDYDGPSEQNFDWSFSSLGSSFVELASTWEVGFPAQLYQERLQRGEIL
LRRTANDAVELHIKNVQPSDQGHYKCSTPSTDATVQGNYEDTVQVKVLADSLHVGP
SARPPPSLSLREGEPFELRCTAASASPLHTHLALLWEVHRGPARRSVLALTHEGRFHP
GLGYEQRYHSGDVRLDTVGSDAYRLSVSRALSADQGSYRCIVSEWIAEQGNWQEIQ
EKAVEVATVVIQPSVLRAAVPKNVSVAEGKELDLTCNITTDRADDVRPEVTWSFSR
MPDSTLPGSRVLARLDRDSLVHSSPHVALSHVDARSYHLLVRDVSKENSGYYYCHV
SLWAPGHNRSWHKVAEAVSSPAGVGVTWLEPDYQVYLNASKVPGFADDPTELACR
VVDTKSGEANVRFTVSWYYRMNRRSDNVVTSELLAVMDGDWTLKYGERSKQRAQ
DGDFIFSKEHTDTFNFRIQRTTEEDRGNYYCVVSAWTKQRNNSWVKSKDVFSKPVNI
FWALEDSVLVVKARQPKPFFAAGNTFEMTCKVSSKNIKSPRYSVLIMAEKPVGDLSS
PNETKYIISLDQDSVVKLENWTDASRVDGVVLEKVQEDEFRYRMQTQVSDAGLYR
CMVTAWSPVRGSLWREAATSLSNPIEIDFQTSGPIFNASVHSDTPSVIRGDLIKLFCIIT
VEGAALDPDDMAFDVSWFAVHSFGLDKAPVLLSSLDRKGIVTTSRRDWKSDLSLER
VSVLEFLLQVHGSEDQDFGNYYCSVTPWVKSPTGSWQKEAEIHSKPVFITVKMDVL
NAFKYPLLIGVGLSTVIGLLSCLIGYCSSHWCCKKEVQETRRERRRLMSMEMD SEQ ID NO: 10 PTGFRN_IFN gamma mouse dimer
MGRLASRPLLLALLSLALCRGRHGTVIESLESLNNYFNSSGIDVEEKSLFLDIWRNWQ
KDGDMKILQSQIISFYLRLFEVLKDNQAISNNISVIESHLITTFFSNSKAKKDAFMSIAK
FEVNNPQVQRQAFNELIRVVHQLLPESSLRGSGGSGGSGGSGGSGHGTVIESLESLNNYFN
SSGIDVEEKSLFLDIWRNWQKDGDMKILQSQIISFYLRLFEVLKDNQAISNNISVIESH
LITTFFSNSKAKKDAFMSIAKFEVNNPQVQRQAFNELIRVVHQLLPESSLRSAGGGGS
GGGGSRVVRVPTATLVRVVGTELVIPCNVSDYDGPSEQNFDWSFSSLGSSFVELAST
WEVGFPAQLYQERLQRGEILLRRTANDAVELHIKNVQPSDQGHYKCSTPSTDATVQ
GNYEDTVQVKVLADSLHVGPSARPPPSLSLREGEPFELRCTAASASPLHTHLALLWE
VHRGPARRSVLALTHEGRFHPGLGYEQRYHSGDVRLDTVGSDAYRLSVSRALSADQ
GSYRCIVSEWIAEQGNWQEIQEKAVEVATVVIQPSVLRAAVPKNVSVAEGKELDLTC
NITTDRADDVRPEVTWSFSRMPDSTLPGSRVLARLDRDSLVHSSPHVALSHVDARSY
HLLVRDVSKENSGYYYCHVSLWAPGHNRSWHKVAEAVSSPAGVGVTWLEPDYQV
YLNASKVPGFADDPTELACRVVDTKSGEANVRFTVSWYYRMNRRSDNVVTSELLA
VMDGDWTLKYGERSKQRAQDGDFIFSKEHTDTFNFRIQRTTEEDRGNYYCVVSAWT
KQRNNSWVKSKDVFSKPVNIFWALEDSVLVVKARQPKPFFAAGNTFEMTCKVSSKN
IKSPRYSVLIMAEKPVGDLSSPNETKYIISLDQDSVVKLENWTDASRVDGVVLEKVQE
DEFRYRMQTQVSDAGLYRCMVTAWSPVRGSLWREAATSLSNPIEIDFQTSGPIFNA
SVHSDTPSVIRGDLIKLFCIITVEGAALDPDDMAFDVSWFAVHSFGLDKAPVLLSSLD
RKGIVTTSRRDWKSDLSLERVSVLEFLLQVHGSEDQDFGNYYCSVTPWVKSPTGSW
QKEAEIHSKPVFITVKMDVLNAFKYPLLIGVGLSTVIGLLSCLIGYCSSHWCCKKEVQ
ETRRERRRLMSMEMD SEQ ID NO: 11 IL-15 441
MAPRRARGCRTLGLPALLLLLLLRPPATRGITCPPPMSVEHADIWVKSYSLYSRERYI
CNSGFKRKAGTSSLTECVLNKATNVAHWTTPSLKCIRDPALVHQRPAPPSTVTTAGV
TPQPESLSPSGKEPAASSPSSNNTAATTAAIVPGSQLMPSKSPSTGTTEISSHESSHGTP
SQTTAKNWELTASASHQPPGVYPQGHSDTTGGSGGGSGGGGSGGGGSGGGSGGSN
WVNVISDLKKIEDLIQSMHIDATLYTESDVHPSCKVTAMKCFLLELQVISLESGDASI
HDTVENLIILANNSLSSNGNVTESGCKECEELEEKNIKEFLQSFVHIVQMFINTSSADY
KDDDDKFEGGGGSGGGGSAVGQDTQEVIVVPHSLPFKVVVISAILALVVLTIISLIILI
MLWQKKPRSGLLTGRT SEQ ID NO: 12 IL-15 442
MAPRRARGCRTLGLPALLLLLLLRPPATRGHHHHHHITCPPPMSVEHADIWVKSYSL
YSRERYICNSGFKRKAGTSSLTECVLNKATNVAHWTTPSLKCIRDPALVHQRPAPPST
VTTAGVTPQPESLSPSGKEPAASSPSSNNTAATTAAIVPGSQLMPSKSPSTGTTEISSHE
SSHGTPSQTTAKNWELTASASHQPPGVYPQGHSDTTGGSGGGSGGGGSTLDPRSFLL
RNPNDKYEPFWEDEEKNESGGGGSGGGSGGSNWVNVISDLKKIEDLIQSMHIDATLY
TESDVHPSCKVTAMKCFLLELQVISLESGDASIHDTVENLIILANNSLSSNGNVTESGC
KECEELEEKNIKEFLQSFVHIVQMFINTSSADYKDDDDKFEGGGGSGGGGSAVGQDT
QEVIVVPHSLPFKVVVISAILALVVLTIISLIILIMLWQKKPRSGLLTGRT SEQ ID NO: 13 IL-15 443
METDTLLLWVLLLWVPGSTGNWVNVISDLKKIEDLIQSMHIDATLYTESDVHPSCKV
TAMKCFLLELQVISLESGDASIHDTVENLIILANNSLSSNGNVTESGCKECEELEEKNI
KEFLQSFVHIVQMFINTSGGSGGGGSGGGGSGGGGSGGGGSGGSITCPPPMSVEHADIW
VKSYSLYSRERYICNSGFKRKAGTSSLTECVLNKATNVAHWTTPSLKCIRDPALVHQ
RPAPPSTVTTAGVTPQPESLSPSGKEPAASSPSSNNTAATTAAIVPGSQLMPSKSPSTG
TTEISSHESSHGTPSQTTAKNWELTASASHQPPGVYPQGHSDTTSADYKDDDDKFEG
GGGSGGGGSAVGQDTQEVIVVPHSLPFKVVVISAILALVVLTIISLIILIMLWQKKPRS
GLLTGRT
```

SEQUENCE LISTING

SEQ ID NO: 14 IL-15 444
METDTLLLWVLLLWVPGSTGNWVNVISDLKKIEDLIQSMHIDATLYTESDVHPSCKV
TAMKCFLLELQVISLESGDASIHDTVENLIILANNSLSSNGNVTESGCKECEELEEKNI
KEFLQSFVHIVQMFINTSDYKDDDDKGGSGGGSGGGGSTLDPRSFLLRNPNDKYEPF
WEDEEKNESGGGGSGGGSGGSITCPPPMSVEHADIWVKSYSLYSRERYICNSGFKRK
AGTSSLTECVLNKATNVAHWTTPSLKCIRDPALVHQRPAPPSTVTTAGVTPQPESLSP
SGKEPAASSPSSNNTAATTAAIVPGSQLMPSKSPSTGTTEISSHESSHGTPSQTTAKNW
ELTASASHQPPGVYPQGHSDTTSAFEGGGGSGGGGSAVGQDTQEVIVVPHSLPFKVV
VISAILALVVLTIISLIILIMLWQKKPRSGLLTGRTHHHHHH

SEQ ID NO: 15 IL-15 1009
METDTLLLWVLLLWVPGSTGNWVNVISDLKKIEDLIQSMHIDATLYTESDVHPSCKV
TAMKCFLLELQVISLESGDASIHDTVENLIILANNSLSSNGNVTESGCKECEELEEKNI
KEFLQSFVHIVQMFINTSGGSSGSGSGSTGTSSSGTGTSAGTTGTSASTSGSGSGGGGG
SGGGGSAGGTATAGASSGSITCPPPMSVEHADIWVKSYSLYSRERYICNSGFKRKAG
TSSLTECVLNKATNVAHWTTPSLKCIRDPALVHQRPAPPSTVTTAGVTPQPESLSPSG
KEPAASSPSSNNTAATTAAIVPGSQLMPSKSPSTGTTEISSHESSHGTPSQTTAKNWEL
TASASHQPPGVYPQGHSDTTSAGGGGSGGGGSRVVRVPTATLVRVVGTELVIPCNVS
DYDGPSEQNFDWSFSSLGSSFVELASTWEVGFPAQLYQERLQRGEILLRRTANDAVE
LHIKNVQPSDQGHYKCSTPSTDATVQGNYEDTVQVKVLADSLHVGPSARPPPSLSLR
EGEPFELRCTAASASPLHTHLALLWEVHRGPARRSVLALTHEGRFHPGLGYEQRYHS
GDVRLDTVGSDAYRLSVSRALSADQGSYRCIVSEWIAEQGNWQEIQEKAVEVATVV
IQPSVLRAAVPKNVSVAEGKELDLTCNITTDRADDVRPEVTWSFSRMPDSTLPGSRV
LARLDRDSLVHSSPHVALSHVDARSYHLLVRDVSKENSGYYYCHVSLWAPGHNRS
WHKVAEAVSSPAGVGVTWLEPDYQVYLNASKVPGFADDPTELACRVVDTKSGEAN
VRFTVSWYYRMNRRSDNVVTSELLAVMDGDWTLKYGERSKQRAQDGDFIFSKEHT
DTFNFRIQRTTEEDRGNYYCVVSAWTKQRNNSWVKSKDVFSKPVNIFWALEDSVLV
VKARQPKPFFAAGNTFEMTCKVSSKNIKSPRYSVLIMAEKPVGDLSSPNETKYIISLD
QDSVVKLENWTDASRVDGVVLEKVQEDEFRYRMYQTQVSDAGLYRCMVTAWSPV
RGSLWREAATSLSNPIEIDFQTSGPIFNASVHSDTPSVIRGDLIKLFCIITVEGAALDPD
DMAFDVSWFAVHSFGLDKAPVLLSSLDRKGIVTTSRRDWKSDLSLERVSVLEFLLQV
HGSEDQDFGNYYCSVTPWVKSPTGSWQKEAEIHSKPVFITVKMDVLNAFKYPLLIGV
GLSTVIGLLSCLIGYCSSHWCCKKEVQETRRERRRLMSMEMD

SEQ ID NO: 16 IL-15 1010
METDTLLLWVLLLWVPGSTGNWVNVISDLKKIEDLIQSMHIDATLYTESDVHPSCKV
TAMKCFLLELQVISLESGDASIHDTVENLIILANDSLSSNGNVTESGCKECEELEEKNI
KEFLQSFVHIVQMFINTSGGSSGSGSGSTGTSSSGTGTSAGTTGTSASTSGSGSGGGGG
SGGGGSAGGTATAGASSGSITCPPPMSVEHADIWVKSYSLYSRERYICNSGFKRKAG
TSSLTECVLNKATNVAHWTTPSLKCIRDPALVHQRPAPPSTVTTAGVTPQPESLSPSG
KEPAASSPSSNNTAATTAAIVPGSQLMPSKSPSTGTTEISSHESSHGTPSQTTAKNWEL
TASASHQPPGVYPQGHSDTTSAGGGGSGGGGSRVVRVPTATLVRVVGTELVIPCNVS
DYDGPSEQNFDWSFSSLGSSFVELASTWEVGFPAQLYQERLQRGEILLRRTANDAVE
LHIKNVQPSDQGHYKCSTPSTDATVQGNYEDTVQVKVLADSLHVGPSARPPPSLSLR
EGEPFELRCTAASASPLHTHLALLWEVHRGPARRSVLALTHEGRFHPGLGYEQRYHS
GDVRLDTVGSDAYRLSVSRALSADQGSYRCIVSEWIAEQGNWQEIQEKAVEVATVV
IQPSVLRAAVPKNVSVAEGKELDLTCNITTDRADDVRPEVTWSFSRMPDSTLPGSRV
LARLDRDSLVHSSPHVALSHVDARSYHLLVRDVSKENSGYYYCHVSLWAPGHNRS
WHKVAEAVSSPAGVGVTWLEPDYQVYLNASKVPGFADDPTELACRVVDTKSGEAN
VRFTVSWYYRMNRRSDNVVTSELLAVMDGDWTLKYGERSKQRAQDGDFIFSKEHT
DTFNFRIQRTTEEDRGNYYCVVSAWTKQRNNSWVKSKDVFSKPVNIFWALEDSVLV
VKARQPKPFFAAGNTFEMTCKVSSKNIKSPRYSVLIMAEKPVGDLSSPNETKYIISLD
QDSVVKLENWTDASRVDGVVLEKVQEDEFRYRMYQTQVSDAGLYRCMVTAWSPV
RGSLWREAATSLSNPIEIDFQTSGPIFNASVHSDTPSVIRGDLIKLFCIITVEGAALDPD
DMAFDVSWFAVHSFGLDKAPVLLSSLDRKGIVTTSRRDWKSDLSLERVSVLEFLLQV
HGSEDQDFGNYYCSVTPWVKSPTGSWQKEAEIHSKPVFITVKMDVLNAFKYPLLIGV
GLSTVIGLLSCLIGYCSSHWCCKKEVQETRRERRRLMSMEMD

SEQ ID NO: 17 pDisplay-anti-CD3
MKIICLALVALLLTAQPAMAEIVLTQSPATLSLSPGERATLSCRASQSVSSYLAWYQQ
KPGQAPRLLIYDASNRATGIPARFSGSGSGTDFTLTISSLEPEDFAVYYCQQRSNWPPL
TFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFN
RGECGGSSGSGSGSTGTSSSGTGTSAGTTGTSASTSGSGSGGGGSGGGGSAGGTAT
AGASSGSQVQLVESGGGVVQPGRSLRLSCAASGFKFSGYGMHWVRQAPGKGLEWV
AVIWYDGSKKYYVDSVKGRFTISRDNSKNTLYLQMNSLRAEDTAVYYCARQMGY
WHFDLWGRGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVE
PKSCDKTHTGGSGGGSGGGGSGGGSGGGSGGSAVGQDTQEVIVVPHSLPFKVVVIS
AILALVVLTIISLIILIMLWQKKPRDYKDDDDK SEQ ID NO: 18 PTGFRN-anti-CD3
MKIICLALVALLLTAQPAMAEIVLTQSPATLSLSPGERATLSCRASQSVSSYLAWYQQ
KPGQAPRLLIYDASNRATGIPARFSGSGSGTDFTLTISSLEPEDFAVYYCQQRSNWPPL
TFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFN
RGECGGSSGSGSGSTGTSSSGTGTSAGTTGTSASTSGSGSGGGGSGGGGSAGGTAT

SEQUENCE LISTING

```
AGASSGSQVQLVESGGGVVQPGRSLRLSCAASGFKFSGYGMHWVRQAPGKGLEWV
AVIWYDGSKKYYVDSVKGRFTISRDNSKNTLYLQMNSLRAEDTAVYYCARQMGY
WHFDLWGRGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVE
PKSCDKTHTGGSGGGSGGGGSGGGGSGGGSGGSRVVRVPTATLVRVVGTELVIPCN
VSDYDGPSEQNFDWSFSSLGSSFVELASTWEVGFPAQLYQERLQRGEILLRRTANDA
VELHIKNVQPSDQGHYKCSTPSTDATVQGNYEDTVQVKVLADSLHVGPSARPPPSLS
LREGEPFELRCTAASASPLHTHLALLWEVHRGPARRSVLALTHEGRFHPGLGYEQRY
HSGDVRLDTVGSDAYRLSVSRALSADQGSYRCIVSEWIAEQGNWQEIQEKAVEVAT
VVIQPSVLRAAVPKNVSVAEGKELDLTCNITTDRADDVRPEVTWSFSRMPDSTLPGS
RVLARLDRDSLVHSSPHVALSHVDARSYHLLVRDVSKENSGYYYCHVSLWAPGHN
RSWHKVAEAVSSPAGVGVTWLEPDYQVYLNASKVPGFADDPTELACRVVDTKSGE
ANVRFTVSWYYRMNRRSDNVVTSELLAVMDGDWTLKYGERSKQRAQDGDFIFSKE
HTDTFNFRIQRTTEEDRGNYYCVVSAWTKQRNNSWVKSKDVFSKPVNIFWALEDSV
LVVKARQPKPFFAAGNTFEMTCKVSSKNIKSPRYSVLIMAEKPVGDLSSPNETKYIISL
DQDSVVKLENWTDASRVDGVVLEKVQEDEFRYRMYQTQVSDAGLYRCMVTAWSP
VRGSLWREAATSLSNPIEIDFQTSGPIFNASVHSDTPSVIRGDLIKLFCIITVEGAALDP
DDMAFDVSWFAVHSFGLDKAPVLLSSLDRKGIVTTSRRDWKSDLSLERVSVLEFLLQ
VHGSEDQDFGNYYCSVTPWVKSPTGSWQKEAEIHSKPVFITVKMDVLNAFKYPLLIG
VGLSTVIGLLSCLIGYCSSHWCCKKEVQETRRERRRLMSMEMDTGGSGGSVSKGEEL
FTGVVPILVELDGDVNGHKFSVSGEGEGDATYGKLTLKFICTTGKLPVPWPTLVTTL
TYGVQCFSRYPDHMKQHDFFKSAMPEGYVQERTIFFKDDGNYKTRAEVKFEGDTLV
NRIELKGIDFKEDGNILGHKLEYNYNSHNVYIMADKQKNGIKVNFKIRHNIEDGSVQ
LADHYQQNTPIGDGPVLLPDNHYLSTQSKLSKDPNEKRDHMVLLEFVTAAGITLGM
DELYKDYKDDDDK

SEQ ID NO: 19 PTGFRN_CD40L trimer mouse
METDTLLLWVLLLWVPGSTGMQRGDEDPQIAAHVVSEANSNAASVLQWAKKGYY
TMKSNLVMLENGKQLTVKREGLYYVYTQVTFCSNREPSSQRPFIVGLWLKPSSGSER
ILLKAANTHSSSQLCEQQSVHLGGVFELQAGASVFVNVTEASQVIHRVGFSSFGLLKL
GSGGSGGSGGSGMQRGDEDPQIAAHVVSEANSNAASVLQWAKKGYYTMKSNLVM
LENGKQLTVKREGLYYVYTQVTFCSNREPSSQRPFIVGLWLKPSSGSERILLKAANTH
SSSQLCEQQSVHLGGVFELQAGASVFVNVTEASQVIHRVGFSSFGLLKLGSGGSGGS
GGGSGMQRGDEDPQIAAHVVSEANSNAASVLQWAKKGYYTMKSNLVMLENGKQLT
VKREGLYYVYTQVTFCSNREPSSQRPFIVGLWLKPSSGSERILLKAANTHSSSQLCEQ
QSVHLGGVFELQAGASVFVNVTEASQVIHRVGFSSFGLLKLSAGGGGSGGGGSRVV
RVPTATLVRVVGTELVIPCNVSDYDGPSEQNFDWSFSSLGSSFVELASTWEVGFPAQ
LYQERLQRGEILLRRTANDAVELHIKNVQPSDQGHYKCSTPSTDATVQGNYEDTVQ
VKVLADSLHVGPSARPPPSLSLREGEPFELRCTAASASPLHTHLALLWEVHRGPARRS
VLALTHEGRFHPGLGYEQRYHSGDVRLDTVGSDAYRLSVSRALSADQGSYRCIVSE
WIAEQGNWQEIQEKAVEVATVVIQPSVLRAAVPKNVSVAEGKELDLTCNITTDRAD
DVRPEVTWSFSRMPDSTLPGSRVLARLDRDSLVHSSPHVALSHVDARSYHLLVRDVS
KENSGYYYCHVSLWAPGHNRSWHKVAEAVSSPAGVGVTWLEPDYQVYLNASKVP
GFADDPTELACRVVDTKSGEANVRFTVSWYYRMNRRSDNVVTSELLAVMDGDWT
LKYGERSKQRAQDGDFIFSKEHTDTFNFRIQRTTEEDRGNYYCVVSAWTKQRNNSW
VKSKDVFSKPVNIFWALEDSVLVVKARQPKPFFAAGNTFEMTCKVSSKNIKSPRYSV
LIMAEKPVGDLSSPNETKYIISLDQDSVVKLENWTDASRVDGVVLEKVQEDEFRYRM
YQTQVSDAGLYRCMVTAWSPVRGSLWREAATSLSNPIEIDFQTSGPIFNASVHSDTPS
VIRGDLIKLFCIITVEGAALDPDDMAFDVSWFAVHSFGLDKAPVLLSSLDRKGIVTTS
RRDWKSDLSLERVSVLEFLLQVHGSEDQDFGNYYCSVTPWVKSPTGSWQKEAEIHS
KPVFITVKMDVLNAFKYPLLIGVGLSTVIGLLSCLIGYCSSHWCCKKEVQETRRERRR
LMSMEMD SEQ ID NO: 20 PTGFRN_CD40L trimer human
METDTLLLWVLLLWVPGSTGMQKGDQNPQIAAHVISEASSKTTSVLQWAEKGYYT
MSNNLVTLENGKQLTVKRQGLYYIYAQVTFCSNREASSQAPFIASLCLKSPGRFERIL
LRAANTHSSAKPCGQQSIHLGGVFELQPGASVFVNVTDPSQVSHGTGFTSFGLLKLG
SGGSGGSGGSGMQKGDQNPQIAAHVISEASSKTTSVLQWAEKGYYTMSNNLVTLEN
GKQLTVKRQGLYYIYAQVTFCSNREASSQAPFIASLCLKSPGRFERILLRAANTHSSA
KPCGQQSIHLGGVFELQPGASVFVNVTDPSQVSHGTGFTSFGLLKLGSGGSGGSGGS
GMQKGDQNPQIAAHVISEASSKTTSVLQWAEKGYYTMSNNLVTLENGKQLTVKRQ
GLYYIYAQVTFCSNREASSQAPFIASLCLKSPGRFERILLRAANTHSSAKPCGQQSIHL
GGVFELQPGASVFVNVTDPSQVSHGTGFTSFGLLKLSAGGGGSGGGGSRVVRVPTAT
LVRVVGTELVIPCNVSDYDGPSEQNFDWSFSSLGSSFVELASTWEVGFPAQLYQERL
QRGEILLRRTANDAVELHIKNVQPSDQGHYKCSTPSTDATVQGNYEDTVQVKVLAD
SLHVGPSARPPPSLSLREGEPFELRCTAASASPLHTHLALLWEVHRGPARRSVLALTH
EGRFHPGLGYEQRYHSGDVRLDTVGSDAYRLSVSRALSADQGSYRCIVSEWIAEQG
NWQEIQEKAVEVATVVIQPSVLRAAVPKNVSVAEGKELDLTCNITTDRADDVRPEVT
WSFSRMPDSTLPGSRVLARLDRDSLVHSSPHVALSHVDARSYHLLVRDVSKENSGY
YYCHVSLWAPGHNRSWHKVAEAVSSPAGVGVTWLEPDYQVYLNASKVPGFADDP
TELACRVVDTKSGEANVRFTVSWYYRMNRRSDNVVTSELLAVMDGDWTLKYGER
SKQRAQDGDFIFSKEHTDTFNFRIQRTTEEDRGNYYCVVSAWTKQRNNSWVKSKDV
FSKPVNIFWALEDSVLVVKARQPKPFFAAGNTFEMTCKVSSKNIKSPRYSVLIMAEKP
VGDLSSPNETKYIISLDQDSVVKLENWTDASRVDGVVLEKVQEDEFRYMYQTQVS
DAGLYRCMVTAWSPVRGSLWREAATSLSNPIEIDFQTSGPIFNASVHSDTPSVIRGDLI
KLFCIITVEGAALDPDDMAFDVSWFAVHSFGLDKAPVLLSSLDRKGIVTTSRRDWKS
```

SEQUENCE LISTING

```
DLSLERVSVLEFLLQVHGSEDQDFGNYYCSVTPWVKSPTGSWQKEAEIHSKPVFITV
KMDVLNAFKYPLLIGVGLSTVIGLLSCLIGYCSSHWCCKKEVQETRRERRRLMSME
MD

SEQ ID NO: 21 PTGFRN_short-anti-CD3
MKIICLALVALLLTAQPAMAEIVLTQSPATLSLSPGERATLSCRASQSVSSYLAWYQQ
KPGQAPRLLIYDASNRATGIPARFSGSGSGTDFTLTISSLEPEDFAVYYCQQRSNWPPL
TFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFN
RGECGGSSGSGSGSTGTSSSGTGTSAGTTGTSASTSGSGSGGGGSGGGGSAGGTAT
AGASSGSQVQLVESGGGVVQPGRSLRLSCAASGFKFSGYGMHWVRQAPGKGLEWV
AVIWYDGSKKYYVDSVKGRFTISRDNSKNTLYLQMNSLRAEDTAVYYCARQMGY
WHFDLWGRGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDKKVE
PKSCDKTHTGGSGGSGGGGSGGGGSGGGSGGSGPIFNASVHSDTPSVIRGDLIKLFC
IITVEGAALDPDDMAFDVSWFAVHSFGLDKAPVLLSSLDRKGIVTTSRRDWKSDLSL
ERVSVLEFLLQVHGSEDQDFGNYYCSVTPWVKSPTGSWQKEAEIHSKPVFITVKMD
VLNAFKYPLLIGVGLSTVIGLLSCLIGYCSSHWCCKKEVQETRRERRRLMSMEMDTG
GSGGGVSKGEELFTGVVPILVELDGDVNGHKFSVSGEGEGDATYGKLTLKFICTTGK
LPVPWPTLVTTLTYGVQCFSRYPDHMKQHDFFKSAMPEGYVQERTIFFKDDGNYKT
RAEVKFEGDTLVNRIELKGIDFKEDGNILGHKLEYNYNSHNVYIMADKQKNGIKVNF
KIRHNIEDGSVQLADHYQQNTPIGDGPVLLPDNHYLSTQSKLSKDPNEKRDHMVLLE
FVTAAGITLGMDELYKDYKDDDDK SEQ ID NO: 22 FLT3L-PTGFRN
MTVLAPAWSPTTYLLLLLLLSSGLSGTQDCSFQHSPISSDFAVKIRELSDYLLQDYPVT
VASNLQDEELCGGLWRLVLAQRWMERLKTVAGSKMQGLLERVNTEIHFVTKCAFQ
PPPSCLRFVQTNISRLLQETSEQLVALKPWITRQNFSRCLELQCQPDSSTLPPPWSPRPL
EATAPTAPQPPSAGGGGSGGGGSRVVRVPTATLVRVVGTELVIPCNVSDYDGPSEQN
FDWSFSSLGSSFVELASTWEVGFPAQLYQERLQRGEILLRRTANDAVELHIKNVQPSD
QGHYKCSTPSTDATVQGNYEDTVQVKVLADSLHVGPSARPPPSLSLREGEPFELRCT
AASASPLHTHLALLWEVHRGPARRSVLALTHEGRFHPGLGYEQRYHSGDVRLDTVG
SDAYRLSVSRALSADQGSYRCIVSEWIAEQGNWQEIQEKAVEVATVVIQPSVLRAAV
PKNVSVAEGKELDLTCNITTDRADDVRPEVTWSFSRMPDSTLPGSRVLARLDRDSLV
HSSPHVALSHVDARSYHLLVRDVSKENSGYYYCHVSLWAPGHNRSWHKVAEAVSS
PAGVGVTWLEPDYQVYLNASKVPGFADDPTELACRVVDTKSGEANVRFTVSWYYR
MNRRSDNVVTSELLAVMDGDWTLKYGERSKQRAQDGDFIFSKEHTDTFNFRIQRTT
EEDRGNYYCVVSAWTKQRNNSWVKSKDVFSKPVNIFWALEDSVLVVKARQPKPFF
AAGNTFEMTCKVSSKNIKSPRYSVLIMAEKPVGDLSSPNETKYIISLDQDSVVKLENW
TDASRVDGVVLEKVQEDEFRYRMYQTVQSDAGLYRCMVTAWSPVRGSLWREAAT
SLSNPIEIDFQTSGPIFNASVHSDTPSVIRGDLIKLFCIITVEGAALDPDDMAFDVSWFA
VHSFGLDKAPVLLSSLDRKGIVTTSRRDWKSDLSLERVSVLEFLLQVHGSEDQDFGN
YYCSVTPWVKSPTGSWQKEAEIHSKPVFITVKMDVLNAFKYPLLIGVGLSTVIGLLSC
LIGYCSSHWCCKKEVQETRRERRRLMSMEMD
```

Tables

TABLE 1

| Exosome lipids | |
|---|---|
| Lysobisphosphatidic acid | Ganglioside GM3 24:1 |
| Sphingomyelin (SM) | Ganglioside GM3 16:0 |
| Ganglioside GM3 | PE40:5 |
| Phosphatidylserine (PS) | PE40:6 |
| Phosphatidylinositol (PI) | PE38:3 |
| Phosphatidylcholine (PC) | PE38:4 |
| Phosphatidylethanolamine (PE) | PE36:1 |
| Lysophosphatidylcholine (LPC) | PE36:2 |
| Cholesterol (Chol) | PE34:1 |
| Diacylglycerol (DG) | PE34:2 |
| PI18:0/20:3 | PE-ether38:5 |
| PI18:0/20:4 | PE-ether38:6 |
| PI18:0/18:1 | PE-ether34:1 |
| PI18:1/18:1 | PE-ether34:2 |
| PI18:0/16:0 | PC34:1 |
| PA18:0/18:1 | PC36:4 |
| PS18:0/18:1 | PC34:3 |
| BMP18:0/18:1 | PC32:0 |
| BMP18:1/18:1 | PC30:0 |
| BMP18:1/16:0 | SM24:1 |
| CL(18:1)3/16:1 | SM16:0 |
| CL(18:1)2/(16:1)2 | Dihydrosphingomyelin16:0 |

TABLE 2

| Exosome polypeptides | | | |
|---|---|---|---|
| ACLY | TCP1 | ACTR1A | LY75 |
| ACTB | PRDX2 | THOC4 | ABCC1 |
| ACTG1 | TSPAN6 | INADL | MYO1E |
| ALB | CCT3 | CTDSPL | NACA |
| ALDOA | TSTA3 | ZMPSTE24 | NAP1L4 |
| ALDOB | TUBA3C | DNAJA2 | NCL |
| AKR1B1 | HIST1H2AK | NDRG1 | NEDD8 |
| AMBP | HIST1H2AJ | RAPGEF3 | YBX1 |
| ANPEP | HIST1H2AB | SPON2 | PA2G4 |
| ANXA2 | HIST2H2AC | UBAC1 | PECAM1 |
| ANXA3 | IFITM1 | N4BP2L2 | PFAS |
| ANXA4 | PDXK | CAP1 | SERPINB9 |
| ANXA5 | LIN7A | VAT1 | PI4KA |
| ANXA6 | BUB3 | NEBL | PLAT |
| ANXA7 | MAP4K4 | DCTN2 | PLCG2 |
| ANXA11 | EDIL3 | ARPC1A | PPA1 |
| | ATP6AP2 | C6orf108 | PPP2CA |
| CAPZB | PSME3 | SMC2 | PRKCB |
| CD63 | TUBB3 | AHSA1 | PSMA6 |
| CD81 | IFITM3 | STAMBP | PSMA7 |
| CKB | ACAA2 | PMVK | PSMB8 |
| CLU | CCT7 | GIPC1 | PSMB9 |
| CLIC1 | CCT4 | HBS1L | PSMD7 |
| TPP1 | IFITM2 | NCKAP1 | PSME1 |
| CLTC | GNA13 | ALDH1L1 | PTPRA |
| CNP | RUVBL2 | FTCD | RAC2 |

TABLE 2-continued

Exosome polypeptides

| | | | |
|---|---|---|---|
| COL6A1 | PRSS23 | FGL2 | RPL3 |
| CR1 | ACOT7 | CFHR3 | RPL4 |
| CTNND1 | CCT5 | MMP24 | RPL5 |
| ACE | DIP2C | COPS8 | RPL11 |
| DDT | ASCC3L1 | CKAP4 | RPL22 |
| DEFA1 | TNIK | C10orf116 | RPL24 |
| DEFA3 | NEDD4L | SLC27A2 | RPL27 |
| DNAH8 | NCSTN | MID2 | RPL30 |
| DPEP1 | TSPAN15 | KIF3A | RPL28 |
| DPP4 | PLXNB2 | NUDT5 | RPL31 |
| EEF1A1 | SDCBP2 | TREH | RPL34 |
| EEF2 | IGKV1-5 | CEP250 | RPL35A |
| EGF | IGHV4-31 | PDCD10 | RPL37A |
| EIF5A | IGKV3-20 | PADI2 | RPS2 |
| ENO1 | IGKV2-24 | PACSIN2 | RPS3A |
| ENO3 | MINK1 | CHP | RPS5 |
| ENPEP | IGKα | SNF8 | RPS9 |
| STOM | VPS36 | DDX19B | RPS19 |
| EPS8 | DERA | SCN11A | RPS25 |
| FABP3 | GOLGA7 | LYPLA2 | RPS26 |
| FGA | KRT76 | PARK7 | RPS28 |
| MLANA | EIF3EIP | COBLL1 | RPS29 |
| FN1 | LSR | CNKSR2 | RSU1 |
| FTL | TUBA8 | ENPP4 | SARS |
| FUS | RAB4B | RAB3GAP1 | SLAMF1 |
| GAA | SETD4 | AKR7A3 | SLC1A4 |
| GAPDH | TOLLIP | SPEN | SLC2A3 |
| GDI2 | PLEKHB2 | GANAB | SNRPD2 |
| GGT1 | VPS37C | MGRN1 | SPINK1 |
| GLB1 | LIN7C | CUX2 | SPN |
| GLG1 | H2AFJ | DNAJC13 | STK10 |
| GNA11 | CAND1 | ZCCHC11 | STXBP3 |
| GNAI1 | PLSCR3 | PHF15 | TALDO1 |
| GNAI2 | KIAA1199 | KIAA0841 | TNFAIP3 |
| GNAI3 | GNB4 | ARHGEF12 | TPM3 |
| GNAS | MYH14 | COTL1 | TPM4 |
| GNB1 | TSPAN14 | ANGPTL2 | TYK2 |
| GNB2 | NCALD | DDAH2 | VIM |
| GNG7 | REG4 | HEBP2 | WARS |
| SFN | VPS25 | CD2AP | WAS |
| GPI | TUBB6 | PLD3 | LAT2 |
| GSTA1 | TUBA1C | TMEM2 | HIST1H2BL |
| GSTA2 | TNKS1BP1 | SH3BP4 | STX7 |
| GSTA3 | FAM125B | BHMT2 | CPNE1 |
| GSTM3 | LRSAM1 | GCA | RPL14 |
| GSTP1 | HIST3H2A | MXRA5 | PDCD5 |
| GUSB | TUBA3E | AHCTF1 | SYNGR2 |
| HIST1H2AD | TUBA3D | PTPN23 | RPL23 |
| HLA-A | DCD | DAK | RAB9A |
| HLA-B | HIST4H4 | ACOT11 | IGSF2 |
| HLA-DQB1 | ALDH16A1 | APPL1 | EEF1E1 |
| HLA-DRA | RPS4Y2 | PHGDH | SCAMP2 |
| HLA-DRB1 | MYL6B | TIAM2 | SCAMP3 |
| HLA-DRB5 | BRI3BP | KCNG2 | DPP3 |
| HPGD | AGR3 | CYFIP2 | ARPC1B |
| HRAS | EEF1AL3 | GHITM | PDIA4 |
| HSPA1A | KRT28 | C11orf54 | WASF2 |
| HSPA1B | KRT24 | DBNL | ANP32B |
| HSPA8 | RPLP0-like | ATAD2 | PAICS |
| HSP90AA1 | RPSAP15 | PHPT1 | AHCYL1 |
| | RANP1 | C16orf80 | VAMP5 |
| KRT1 | PCSK9 | OLA1 | 41891 |
| KRT9 | METRNL | ZDHHC1 | HSPH1 |
| KRT10 | LOC284889 | SNX12 | SUB1 |
| LDHA | KRT6C | PSAT1 | CDC37 |
| LDHB | KRT79 | NT5C | CORO1A |
| TACSTD1 | RAB43 | EHD2 | CD300A |
| MCAM | KRT27 | TAX1BP3 | TMC6 |
| MDH1 | ACTBL2 | CRNN | RFTN1 |
| MEP1A | RP11-631M21.2 | NOX3 | SCRIB |
| MSN | TUBB2B | ATP6V0A4 | SERBP1 |
| 2-Sep | KRT77 | ITSN2 | TTLL3 |
| PGAM1 | AGRN | GEMIN4 | CACYBP |
| PGK1 | RAB15 | LAP3 | SIT1 |
| PKM2 | LOC388524 | CRYL1 | SLC43A3 |
| PPP1CA | LOC388720 | MYO15A | PILRA |
| | HSP90AB2P | ATP6V1D | RPL26L1 |
| PTPRC | ACTBL3 | SNX9 | MPP6 |
| RAN | LOC442497 | PCYOX1 | GNG2 |
| RDX | A26C1A | ANKFY1 | TMED9 |
| SDCBP | HIST2H4B | UFC1 | DOCK10 |
| STX3 | hCG_1757335 | FAM49B | C3orf10 |
| STXBP1 | HLA-A29.1 | CUTA | MYO1G |
| STXBP2 | LOC653269 | ATP6V1H | FLJ21438 |
| TPI1 | A26C1B | VPS24 | SLC38A1 |
| EZR | LOC100128936 | CMPK1 | FERMT3 |
| YWHAE | LOC100130553 | UPB1 | ITFG3 |
| TUBA1A | LOC100133382 | CLIC5 | HIST1H2AH |
| WDR1 | LOC100133739 | MUPCDH | SLAMF6 |
| PDCD6IP | AP2A2 | CLIC6 | TMC8 |
| GPA33 | ALDH3B1 | SIAE | LOC153364 |
| TUBA1B | FASLG | CPVL | SVIP |
| TUBB2C | ATP4A | RHOF | TMEM189-UBE2V1 |
| CAPN7 | CAPS | ARL15 | hCG_16001 |
| DDAH1 | COL12A1 | ZNHIT6 | FABP5L7 |
| PGLS | DMBT1 | GIPC2 | Del(X)1Brd |
| SAMM50 | DSP | PCDH24 | ABP1 |
| CLIC4 | EGFR | VPS13C | ACTN3 |
| CHMP2B | EPHA5 | CC2D1A | AFM |
| ULK3 | EPHB1 | EPS8L1 | AKT1 |
| RNF11 | FAT | C10orf18 | ALDH3A2 |
| VPS4A | HSD17B4 | CHCHD3 | ALOX12P2 |
| ARFIP1 | L1CAM | C2orf18 | ANXA2P1 |
| CHMP2A | LAMA5 | C17orf80 | KRT33B |
| SMPDL3B | MUC4 | EPN3 | MYOC |
| PACSIN3 | NOTCH1 | UACA | SERPINE1 |
| EHD4 | PPP2R1B | VPS13D | PIK3CA |
| EHD3 | PTPRF | APPL2 | NRP1 |
| HEBP1 | SORT1 | ARL8B | SPRY1 |
| VPS28 | SERPINB3 | DDX19A | EMILIN1 |
| DCXR | SELP | NAGK | LRG1 |
| RHCG | FSCN1 | ITLN1 | AZGP1P1 |
| CHMP5 | TGFB1 | CCDC132 | LOC728533 |
| VTA1 | CLTCL1 | OTUB1 | ALDH7A1 |
| RAB14 | CHST1 | CDK5RAP2 | AXL |
| GPRC5B | EIF3I | MBD5 | CFB |
| CAB39 | TNFSF10 | SLC22A11 | C1S |
| RAB8B | MAP7 | SUSD2 | CAT |
| TM7SF3 | COPB2 | SUCNR1 | CD47 |
| MXRA8 | HEPH | BDH2 | CD151 |
| C11orf59 | | NIT2 | CDH13 |
| MOBKL1B | CIB1 | RPL23AP13 | CFTR |
| UEVLD | SLC34A2 | FAM20C | CEACAM8 |
| TSNAXIP1 | SLC6A14 | SLC12A9 | AP1S1 |
| GPRC5C | DIP2A | RAB25 | CLTA |
| GNG12 | TNPO3 | SMURF1 | CNGB1 |
| BAIAP2L1 | FER1L3 | TMEM27 | COL1A1 |
| MUC13 | CNTLN | RAB22A | COL1A2 |
| CHMP1B | TUBB4Q | NDRG3 | COL2A1 |
| SLC44A2 | KIF15 | ERMN | COL3A1 |
| CPNE5 | SERINC1 | TAOK1 | COL4A1 |
| TMBIM1 | PDIA2 | KIAA1529 | COL4A2 |
| EPS8L3 | EPS8L2 | RNF213 | COL4A3 |
| MMRN2 | PLVAP | WIZ | COL5A1 |
| TTYH3 | MYADM | ACE2 | COL5A2 |
| SLC44A4 | MUC16 | PLEKHA1 | COL7A1 |
| RAB1B | KRT25 | SCPEP1 | COMP |
| RAB33B | SERINC5 | AASDHPPT | CPS1 |
| RBP5 | LOC440264 | FIGNL1 | CSF1 |
| C5orf32 | AGT | PBLD | VCAN |
| ABHD14B | ALPP | KIF9 | SLC25A10 |
| MOBKL1A | APOA2 | LEPRE1 | CTBP2 |
| ARRDC1 | APOB | RAB17 | CTNNA2 |
| | APOE | IKZF5 | DCTN1 |
| FAM125A | SERPING1 | MMP25 | DECR1 |
| SNX18 | C1QB | MPP5 | DNASE1L1 |
| CHMP4B | C1R | TEKT3 | ENG |
| MITD1 | C4A | ALDH8A1 | STX2 |
| S100A16 | C4B | SLC13A3 | ETFB |
| CPNE3 | C4BPA | DUSP26 | F2R |
| C1orf58 | C4BPB | GGCT | F8 |
| GLIPR2 | CD5L | TMEM38A | ACSL1 |
| TUBB | FCN1 | C1orf16 | FAP |
| ATP6V1C2 | FCN2 | GDPD3 | FBLN1 |
| FTLL1 | FGB | OR2A4 | FBN1 |

TABLE 2-continued

Exosome polypeptides

| | | | |
|---|---|---|---|
| PEF1 | FGG | FAM65A | FBN2 |
| SERPINA3 | GRIN1 | NARG1L | FEN1 |
| ACP2 | MSH6 | CHMP6 | FLT1 |
| ACPP | HBA1 | DYNC2H1 | FUCA2 |
| ACTA2 | HBA2 | PRKRIP1 | GAS6 |
| ACTC1 | ITGA2B | GSTCD | GDI1 |
| ACTG2 | PPARG | PIP4K2C | GLDC |
| ACY1 | PDLIM7 | CYBRD1 | GNAL |
| APCS | CD274 | FUZ | GRM2 |
| APOD | A1BG | ARMC9 | GRM3 |
| APRT | ACAT1 | NAT13 | GRM7 |
| AQP1 | ACO1 | COASY | GSTM1 |
| AQP2 | ADCY1 | UBXN6 | GSTM5 |
| ARF1 | ADFP | COL18A1 | H2AFX |
| ARF3 | ADH5 | BHLHB9 | HBE1 |
| ARF4 | ADH6 | WNT5B | HMGCS2 |
| ARF5 | PARP4 | CAB39L | TNC |
| ARF6 | AHSG | ITM2C | IDH3B |
| RHOA | AK1 | LOC81691 | IFRD1 |
| ARL3 | ALAD | AMN | ITGA5 |
| ASAH1 | ALCAM | SH3BGRL3 | ITGB5 |
| ASS1 | ALDH2 | C9orf58 | ITPR2 |
| FXYD2 | ALDH9A1 | BCL2L12 | KRT84 |
| BHMT | ALDOC | RAB34 | LAMB1 |
| BST2 | ALK | TBC1D10A | LCN1 |
| C3 | ALOX12 | GPR98 | LGALS8 |
| CA2 | ALPL | HDHD2 | LMNA |
| CA4 | ANXA13 | ARL6 | LOXL2 |
| CALB1 | AOX1 | IQCG | LTBP2 |
| CALR | APAF1 | C2orf16 | MAP1A |
| CD9 | APOA4 | PARD6B | MAT1A |
| CD59 | SHROOM2 | TXNDC17 | MC1R |
| HSPA5 | RHOB | ABCC11 | MCC |
| HSPA6 | ARHGAP1 | FAM40A | ME1 |
| HSP90AB1 | ARHGDIB | SCIN | MECP2 |
| HSPD1 | ARSE | SCRN2 | MAP3K1 |
| IDH1 | ARSF | ZNF486 | MFAP4 |
| KNG1 | ASL | ACY3 | SCGB2A1 |
| KRAS | ASNA1 | C11orf52 | ALDH6A1 |
| LAMP1 | ATIC | CRB3 | MOS |
| LGALS3BP | ATP6V1A | C20orf114 | CITED1 |
| LRP2 | ATP6V1B1 | NAPRT1 | NEFH |
| MAN1A1 | ATP6V1B2 | RG9MTD2 | OPRM1 |
| RAB8A | ATP6V0C | SAT2 | OTC |
| MIF | ATP6V1C1 | KIF12 | OXTR |
| MME | ATP6V1E1 | MAL2 | PAPPA |
| MUC1 | ATP6V0A1 | OSBPL1A | PC |
| MYH9 | ATP6AP1 | VASN | PCOLCE |
| NAGLU | AZU1 | SLC22A12 | PDGFRB |
| NONO | BCR | ACSM1 | PFKFB3 |
| NPM1 | BGN | TTC18 | PGAM2 |
| NRAS | BLMH | GSTO2 | SERPINE2 |
| P2RX4 | BLVRA | CLRN3 | PLP2 |
| P4HB | BLVRB | LRRK2 | PPP1CC |
| PEBP1 | BPI | C12orf59 | SRGN |
| SERPINA5 | BTG1 | LOC124220 | MAP2K6 |
| PFN1 | BTN1A1 | SLC5A10 | PSMB7 |
| PFN2 | TSPO | CCDC105 | PSMB10 |
| ABCB1 | C1QC | C1orf93 | PTK7 |
| SERPINA1 | CAPN5 | ARL8A | PTPRK |
| PIGR | C5 | LOC128192 | PZP |
| PIK3C2B | C9 | GALM | RAD21 |
| PKD1 | PTTG1IP | LRRC15 | RASA1 |
| PLSCR1 | CACNA2D1 | LOC131691 | RDH5 |
| PODXL | CALML3 | H1FOO | RPL18 |
| CTSA | CAMK4 | ENPP6 | RPL29 |
| PPIA | CAMP | CMBL | RPS10 |
| PSAP | CAPG | MUM1L1 | RPS24 |
| PSMB3 | CAPN1 | C20orf117 | S100A13 |
| PTBP1 | CAPN2 | SIRPA | SAA4 |
| PTPRJ | CAPZA2 | PLEKHA7 | ATXN1 |
| RAB1A | CD14 | A2ML1 | CLEC11A |
| RAB2A | CD80 | C16orf89 | SDC2 |
| RAB3B | CD36 | TOM1L2 | SMARCA4 |
| RAB5A | SCARB2 | KIF18B | SPOCK1 |
| RAB5B | CD40 | C19orf18 | STAT1 |
| RAB13 | CDC2 | PM20D1 | STC1 |
| RAB27B | CEL | PROM2 | SURF4 |
| RAB5C | CETP | GPR155 | SYT1 |
| RAC1 | CTSC | SLC36A2 | TAGLN |
| RALB | AP2M1 | VPS37D | TCN1 |
| RAP1B | CSN1S1 | SLC5A12 | TERF1 |
| RBM3 | CSN2 | SLC5A8 | TGFB2 |
| RNASE2 | CSN3 | EML5 | TSPAN4 |
| S100A6 | ACSL3 | TBC1D21 | TSN |
| S100A11 | FOLR1 | ZNF114 | TSNAX |
| S100P | B4GALT1 | ANO6 | COL14A1 |
| SLC1A1 | GNAQ | SLC5A9 | WNT5A |
| SLC2A5 | HBB | CRTC2 | ZNF134 |
| SLC12A1 | HBD | C20orf106 | PXDN |
| SLC12A3 | CFH | TMEM192 | SMC1A |
| SNCG | HLA-G | ARMC3 | OFD1 |
| SNRPD1 | HP | NAPEPLD | COPS3 |
| SOD1 | HPR | C10orf30 | STC2 |
| SRI | IGHA1 | ATP6V0D2 | ADAM9 |
| TF | IGJ | STXBP4 | CREG1 |
| THBS1 | IGLC1 | C17orf61 | CDK5R2 |
| THY1 | IGLC2 | TXNDC8 | TNFSF18 |
| TMPRSS2 | IGLC3 | LRRC57 | MPZL1 |
| TSG101 | LAMC1 | HSPA12A | SEMA5A |
| TUBB2A | LPA | MAGI3 | CLDN1 |
| UBE2N | LPL | C11orf47 | RGN |
| UMOD | LRP1 | SLC39A5 | SLC16A3 |
| UPK2 | LTF | C12orf51 | ARHGEF1 |
| VTN | TACSTD2 | SLC46A3 | LRRFIP2 |
| EIF4H | MBL2 | VMO1 | TAAR2 |
| YWHAB | MYH8 | SLC26A11 | CRIPT |
| YWHAG | NEB | LOC284422 | ENTPD4 |
| YWHAZ | PON1 | CRB2 | IFT140 |
| NPHS2 | PKN2 | HIST2H2AB | RNF40 |
| RAB7A | PROS1 | FAM151A | RB1CC1 |
| PSCA | MASP1 | SLC6A19 | PSMD6 |
| CUBN | RELN | PKD1L3 | MRC2 |
| BBOX1 | PTX3 | LOC342897 | HDAC5 |
| RAB11A | RARS | EGFL11 | RASA4 |
| NAPA | SILV | SERINC2 | SLC25A13 |
| PROM1 | THBS2 | PDDC1 | PSMD14 |
| FCGBP | TLR2 | SLCO4C1 | TFG |
| CPNE3 | TTN | SFT2D2 | CDIPT |
| MGAM | TTR | C9orf69 | CRTAP |
| GPRC5A | TYRP1 | LOC377711 | UNC13B |
| RAB11B | VWF | OR11L1 | ARL6IP5 |
| VAMP3 | CLIP2 | RAB19 | TGOLN2 |
| SLC9A3R1 | XDH | LOC440335 | POSTN |
| ITM2B | APOL1 | HIST2H2BF | CLPX |
| NAPSA | FCN3 | LOC441241 | TSPAN9 |
| VPS4B | SELENBP1 | KPRP | TMED10 |
| RAB3D | SMC3 | HSP90AB6P | SLC38A3 |
| PRDX6 | DDX21 | LOC643751 | IL1RAPL1 |
| KIAA0174 | CCPG1 | LOC651536 | GALNT5 |
| PDCD6 | ABCG2 | LOC652968 | PRR4 |
| ARPC4 | SFI1 | AEBP1 | ITGA11 |
| TSPAN1 | MVP | AMY1A | CLASP2 |
| PDZK1IP1 | AKAP9 | AMY1B | EPB41L3 |
| NUTF2 | PRG4 | AMY1C | KIAA0467 |
| FLOT1 | AKR1A1 | AMY2A | DULLARD |
| HRSP12 | ABCA7 | ANGPT1 | NOMO1 |
| A2M | COLEC10 | APLP2 | KIAA0146 |
| ACP1 | GNB5 | APP | SLC39A14 |
| ACTA1 | MMRN1 | AQP5 | DNPEP |
| ACTN4 | CLASP1 | AZGP1 | CASP14 |
| ACTN1 | SYNE1 | CEACAM1 | STX12 |
| ACTN2 | NIPBL | BMP3 | BRMS1 |
| ADAM10 | CHRDL2 | CA6 | ABI3BP |
| AHCY | HSPB8 | DDR1 | PLEKHG3 |
| ALDH1A1 | ANGPTL4 | CAPNS1 | FBXW8 |
| SLC25A4 | NIN | COL6A2 | GAPDHS |
| SLC25A5 | ZNF571 | COPA | GREM1 |
| SLC25A6 | LRP1B | CPD | DKK3 |
| ANXA1 | CNDP2 | DLD | SRPX2 |
| ANXA2P2 | DNAH7 | ETFA | IGHV3-11 |
| APOA1 | HCN3 | GLUD1 | IGHV3-7 |
| ARHGDIA | EXOC4 | HSD17B10 | IGLV4-3 |
| ARVCF | SNX25 | IMPDH2 | IGLV3-21 |
| | TC2N | HTATIP2 | IGLV1-40 |
| | HAPLN3 | MARVELD2 | ST6GALNAC6 |

TABLE 2-continued

Exosome polypeptides

| | | | |
|---|---|---|---|
| ATP1B1 | CD163L1 | CST4 | COPS4 |
| ATP5A1 | HRNR | CST5 | HERC5 |
| ATP5B | P704P | CTSB | NUSAP1 |
| ATP5I | CD24 | CTSD | PLUNC |
| ATP5O | COL6A3 | DAG1 | PPME1 |
| B2M | COL15A1 | DSG2 | MBD3 |
| CALM1 | COMT | ECM1 | SLC38A2 |
| CALM2 | CP | EIF4G1 | FAM64A |
| CALM3 | CPN2 | EXT2 | GTPBP2 |
| CANX | CRABP2 | FAT2 | DIRAS2 |
| CAPZA1 | CRK | GPC4 | DCHS2 |
| CD2 | CRYAB | FOLH1 | QPCTL |
| CD247 | CRYM | FUT2 | PARP16 |
| CD86 | CSE1L | FUT3 | TMEM51 |
| CD37 | CSK | FUT6 | MCM10 |
| CD44 | CSTB | FUT8 | CHST12 |
| CD53 | CTH | GLRX | LYAR |
| CDC42 | CTNS | GPC1 | ODZ3 |
| CDH1 | CTSD | GPX3 | WDR52 |
| CFL1 | CTSG | IGHA2 | ASH1L |
| CFL2 | DDB1 | IGHVα | UNC45A |
| COX4I1 | DDC | IGLα | SLC7A10 |
| COX5B | DDX3X | IVL | PNO1 |
| CLDN3 | DDX5 | KRT12 | CD248 |
| CSPG4 | CFD | LAMA4 | AHRR |
| CSRP1 | DNM2 | LAMB2 | ZBTB4 |
| CST3 | DPYS | LGALS7 | SPTBN4 |
| CTNNA1 | DSC2 | LMAN1 | LGR6 |
| CTNNB1 | DSG3 | LPO | RNF123 |
| NQO1 | ECE1 | LTBP3 | PRDM16 |
| DYNC1H1 | MEGF8 | DNAJB9 | PARVG |
| EEF1A2 | ELA2 | MEST | RMND5A |
| EFNB1 | SERPINB1 | MGAT1 | FAT4 |
| CTTN | EPHX2 | MGP | FLJ13197 |
| EPHB4 | FBL | MUC5AC | TREML2 |
| ERBB2 | EVPL | MUC7 | SVEP1 |
| F5 | F11 | NEU1 | OBFC1 |
| FASN | FABP1 | NUCB1 | ZNF614 |
| FKBP1A | ACSL4 | NUCB2 | FLJ22184 |
| FLNA | FAH | FURIN | DBF4B |
| FLNB | EFEMP1 | PAM | CD276 |
| G6PD | FBP1 | PLG | CMIP |
| GCNT2 | FKBP4 | FXYD3 | ADAMTS12 |
| PDIA3 | FKBP5 | PLOD2 | SPACA1 |
| GSN | FRK | PLTP | VANGL1 |
| HADHA | FTH1 | PON3 | SPRY4 |
| HLA-DMB | FUCA1 | PPP1CB | HYI |
| HLA-E | GABRB2 | PRELP | FAM108A1 |
| HNRNPA2B1 | GALK1 | DNAJC3 | TMEM47 |
| HNRNPH2 | GBE1 | HTRA1 | MYCBPAP |
| HSPA1L | GDF2 | RARRES1 | RAB6C |
| HSPA2 | GFRA1 | SAA1 | FAM71F1 |
| HSPA4 | GK2 | SAA2 | ZNF503 |
| HSPA7 | GLO1 | SEPP1 | PARP10 |
| HSPA9 | GLUL | SFRP1 | SHANK3 |
| HSP90AA4P | GM2A | ST3GAL1 | LACRT |
| HSP90AA2 | GNG5 | SLC5A5 | TRIM41 |
| HSP90AB3P | GOT1 | SLC9A1 | OXNAD1 |
| HSPE1 | GPD1 | SLC20A2 | LDHAL6B |
| HSPG2 | GPM6A | SLPI | LOC92755 |
| ICAM1 | GPT | SRPR | CACNA2D4 |
| ITGA6 | GPX4 | STAU1 | ARHGAP18 |
| ITGA2 | GRB2 | HSPA13 | AHNAK2 |
| ITGAV | GRID1 | TGFBI | RPLP0P2 |
| | GSR | TGM1 | PGLYRP2 |
| ITGB2 | GSS | TGM3 | RAB39B |
| ITGB4 | GSTM2 | YES1 | GYLTL1B |
| JUP | HGD | HIST2H2AA3 | KRT74 |
| CD82 | HINT1 | HIST2H2BE | SLAIN1 |
| KPNB1 | HNMT | GALNT4 | LOC122589 |
| KRT2 | HNRNPL | B4GALT3 | NLRP8 |
| KRT5 | HPD | TNFSF13 | PODN |
| KRT8 | HPX | TNFSF12 | C5orf24 |
| KRT13 | HRG | ANGPTL1 | CD109 |
| KRT14 | DNAJA1 | GCNT3 | TRIM40 |
| KRT15 | HSPB1 | TM9SF2 | GPR112 |
| KRT16 | DNAJB1 | DDX23 | KRT72 |
| KRT18 | CFI | ADAMTS3 | VTI1A |
| KRT19 | IGF2R | GPR64 | SYT9 |
| LAMP2 | IGFALS | LHFPL2 | KRT80 |
| LGALS4 | IL1RN | ST3GAL6 | CCDC64B |
| LYZ | IRF6 | PRDX4 | ATP8B3 |
| | ITGA1 | MAN1A2 | C1orf84 |
| MFGE8 | EIF6 | OS9 | LOC149501 |
| MMP7 | ITGB8 | MGAT4A | LOC150786 |
| MYH10 | ITIH4 | TWF2 | WDR49 |
| MYL6 | KHK | CLCA4 | NEK10 |
| MYO1C | KIFC3 | TXNDC4 | STOML3 |
| MYO1D | KLK1 | PLCB1 | SASS6 |
| NME1 | LBP | CES3 | DCLK2 |
| NME2 | LCN2 | B3GAT3 | FREM3 |
| PRDX1 | LCP1 | TOR1B | C9orf91 |
| PCBP1 | LTA4H | IGHV3OR16-13 | TREML2P |
| CHMP1A | BCAM | IGLV2-11 | CCDC129 |
| SERPINF1 | MAN2A1 | IGLV1-44 | PAN3 |
| PHB | MDH2 | IGKV3D-15 | MAMDC2 |
| PPIB | MFI2 | IGKV4-1 | RCOR2 |
| PRKAR2A | MLLT3 | C1GALT1C1 | LOC283412 |
| PRKDC | MLLT4 | RACGAP1 | LOC283523 |
| PSMA2 | MNDA | EFEMP2 | NOMO2 |
| QSOX1 | MPO | DUOX2 | SEC14L4 |
| PYGB | MPST | SDF4 | LCN1L1 |
| RAB6A | MYO1B | CYB5R1 | LOC286444 |
| RALA | MSRA | ERAP1 | TAS2R60 |
| RAP1A | MTAP | NUDT9 | KRT18P19 |
| RPL6 | MTHFD1 | FAM3B | LOC343184 |
| RPL8 | MYH3 | FAM20A | LOC345041 |
| RPLP1 | MYO5B | FAM55D | GNAT3 |
| RPLP2 | MYO6 | ANO1 | POLN |
| RPN1 | NID1 | LRRC16A | LOC376693 |
| RPS3 | NKX6-1 | TTC17 | ARMS2 |
| RPS7 | NQO2 | PDGFC | LOC387867 |
| RPS13 | NP | PCDHGB5 | LOC388339 |
| RPS14 | NPC1 | CCL28 | FLG2 |
| RPS15A | NPHS1 | UGCGL1 | LOC388707 |
| RPS18 | NRF1 | SEMA3G | LOC389141 |
| RPS20 | NT5E | CORO1B | LOC390183 |
| RPS21 | PAFAH1B1 | NDRG2 | KRT8P9 |
| RPS27A | PAFAH1B2 | KIAA1324 | LOC391777 |
| RRAS | PCBD1 | TXNDC16 | LOC391833 |
| S100A10 | PCK1 | ARHGAP23 | LOC399942 |
| SDC1 | PDCD2 | MUTED | LOC400389 |
| SDC4 | PDE8A | TINAGL1 | LOC400578 |
| SLC1A5 | ENPP3 | TOR3A | LOC400750 |
| SLC2A1 | SLC26A4 | VWA1 | LOC400963 |
| | PDZK1 | CHID1 | FLJ21767 |
| SLC12A2 | PEPD | TMEM109 | LOC401817 |
| SLC16A1 | PFKL | GAL3ST4 | NOMO3 |
| SPTBN1 | PGD | THSD4 | LOC439953 |
| SSBP1 | PGM1 | UXS1 | RPL12P6 |
| SSR4 | SLC25A3 | TXNDC5 | LOC440589 |
| TBCA | SERPINA4 | CRISPLD1 | LOC440917 |
| TCEB1 | SERPINB6 | LOXL4 | LOC440991 |
| TFRC | SERPINB13 | GNPTG | LOC441876 |
| TKT | PIK3C2A | SCGB3A1 | LOC442308 |
| TSPAN8 | PIP | CHST14 | DIPAS |
| TPM1 | PKD2 | C1QTNF1 | LOC643300 |
| HSP90B1 | PKLR | C1QTNF3 | LOC643358 |
| TUBA4A | PKHD1 | SLC26A9 | LOC643531 |
| TUFM | PLCD1 | FAM129A | RPSAP8 |
| TXN | PLOD1 | HIST2H3C | LOC644464 |
| UBA52 | PLS1 | TPRG1L | LOC644745 |
| UBB | UBL3 | TMPRSS11B | LOC645018 |
| UBC | PPL | C20orf70 | LOC645548 |
| UBA1 | PPP1R7 | PPM1L | LOC646127 |
| UBE2V2 | PRCP | GBP6 | LOC646316 |
| UGDH | PRKCA | KRT78 | LOC646359 |
| UQCRC2 | PRKCD | SLC37A2 | LOC646785 |
| VCP | PRKCH | NPNT | LOC646875 |
| VIL1 | PRKCI | KRT73 | LOC646949 |
| YWHAH | PRKCZ | HIST2H3A | LOC647000 |
| CXCR4 | PRNP | VWA2 | LOC647285 |
| SLC7A5 | PRSS8 | GSTK1 | LOC650405 |
| HIST1H4I | PRTN3 | SBSN | LOC650901 |
| HIST1H4A | PSMA1 | C5orf46 | LOC652493 |
| HIST1H4D | PSMA3 | LRRC26 | LOC652797 |

TABLE 2-continued

Exosome polypeptides

| | | | |
|---|---|---|---|
| HIST1H4F | PSMA4 | C4orf40 | LOC653162 |
| HIST1H4K | PSMA5 | LOC440786 | PPIAL3 |
| HIST1H4J | PSMB1 | SCFV | LOC653232 |
| HIST1H4C | PSMB2 | LGALS7B | HSPBL2 |
| HIST1H4H | PSMB5 | HIST2H3D | LOC728002 |
| HIST1H4B | PSMB6 | ACAT2 | LOC728088 |
| HIST1H4E | PSMC5 | ACTL6A | LOC728576 |
| HIST1H4L | PSMD12 | ADK | LOC728590 |
| HIST2H4A | PSME2 | ANXA8L2 | LOC728791 |
| TAGLN2 | PTPN6 | | LOC728979 |
| RUVBL1 | PTPN13 | | ANG |
| VAMP8 | PTPRO | | BDNF |
| SNAP23 | QDPR | CAV1 | CALU |
| IQGAP1 | RAB27A | CD70 | CCR4 |
| KRT75 | RAP1GDS1 | CS | CCR5 |
| TJP2 | RBL2 | DARS | CSF2 |
| ROCK2 | RBP4 | DHX9 | CSF3 |
| ARPC3 | RENBP | DPYSL2 | DCN |
| ACTR3 | RFC1 | EEF1D | EPO |
| LRPPRC | RHEB | EPRS | F3 |
| TRAP1 | RNH1 | FDPS | GPC5 |
| TUBB4 | RNPEP | FLNC | GDF1 |
| GNB2L1 | ROBO2 | XRCC6 | GDF9 |
| BAIAP2 | RP2 | GFPT1 | GFRA3 |
| HYOU1 | RPS11 | HIST1H1B | GRN |
| AGR2 | RREB1 | HIST1H2BB | CXCL2 |
| OLFM4 | RYR1 | H3F3A | GZMA |
| CCT2 | S100A4 | H3F3B | HIST1H2BD |
| ATP5L | S100A8 | HNRNPF | HGF |
| CCT8 | S100A9 | HNRNPK | IFNG |
| SLC12A7 | SERPINB4 | IARS | IGFBP3 |
| MASP2 | SCN10A | LAMA3 | IGFBP4 |
| IQGAP2 | SEC13 | LAMB3 | IGFBP6 |
| RAB10 | SECTM1 | LAMC2 | IGFBP7 |
| PRDX3 | SH3BGRL | LGALS1 | IL1RAP |
| EHD1 | SHMT1 | NBR1 | IL3 |
| TMED2 | SHMT2 | MARS | IL5 |
| LMAN2 | SLC3A1 | MX1 | IL6ST |
| YWHAQ | SLC4A1 | PFKP | IL7 |
| GCN1L1 | SLC5A1 | PLAU | IL8 |
| RAB35 | SLC5A2 | PSMB4 | IL10 |
| DSTN | SLC6A13 | PSMC2 | IL11 |
| UPK1A | SLC9A3 | PSMC4 | IL13 |
| PHB2 | SLC15A2 | PSMD2 | IL15RA |
| RRAS2 | SLC25A1 | PSMD13 | INHBA |
| SEC31A | SLC22A2 | PYGL | INHBB |
| CLSTN1 | SLC22A5 | RPL10 | IPO5 |
| PTGR1 | SMO | RPL15 | LIF |
| RAB21 | SORD | STX4 | LRP6 |
| CYFIP1 | SORL1 | TARS | LTBP1 |
| SLC44A1 | SPAST | CLDN5 | MMP1 |
| CORO1C | SPR | TPBG | MMP2 |
| MTCH2 | SPRR3 | XPO1 | MMP3 |
| QPCT | SRC | XRCC5 | MMP10 |
| PRDX5 | ST13 | BAT1 | NBL1 |
| SND1 | STK11 | HIST1H2BG | TNFRSF11B |
| F11R | VAMP7 | HIST1H2BF | OSM |
| LIMA1 | SYPL1 | HIST1H2BE | PDGFA |
| RAB6B | SERPINA7 | HIST1H2BI | PRKCSH |
| KRT20 | TECTA | HIST1H2BC | CCL2 |
| VPS35 | TGM4 | HIST1H4G | CCL7 |
| TOMM22 | TGFBR3 | EIF3A | CCL20 |
| AKR1B10 | TGM2 | EIF3B | SFRP4 |
| S100A14 | TLN1 | EIF3C | SOD3 |
| DIP2B | DNAJC7 | SLC5A6 | SPARC |
| RAP2C | UBE2G1 | HIST2H2AA4 | TIMP1 |
| FAM129B | UPK1B | LOC728358 | TIMP2 |
| | UGP2 | LOC730839 | TIMP3 |
| AHNAK | UPK3A | LOC100126583 | ICAM5 |
| VPS37B | UTRN | AARS | TNFRSF1A |
| TUBA4B | VASP | AK2 | VEGFC |
| ARPC5L | VCL | APEH | GDF5 |
| EPPK1 | VDAC1 | FAS | HIST3H3 |
| ADSL | VDAC3 | BAX | HIST1H2AI |
| AP2A1 | XPNPEP2 | FMNL1 | HIST1H2AL |
| RHOC | BTG2 | CASP9 | HIST1H2AC |
| RHOG | GCS1 | CD19 | HIST1H2AM |
| ASNS | BAT2 | MS4A1 | HIST1H2BN |

TABLE 2-continued

Exosome polypeptides

| | | | |
|---|---|---|---|
| | PTP4A2 | CD22 | HIST1H2BM |
| CAD | DYSF | TNFRSF8 | HIST1H2BH |
| CBR1 | EEA1 | SCARB1 | HIST1H2BO |
| CBR3 | STK24 | ENTPD1 | HIST1H3A |
| CCT6A | CUL4B | CD48 | HIST1H3D |
| CDH17 | CUL3 | CD58 | HIST1H3C |
| CEACAM5 | ATRN | CD74 | HIST1H3E |
| COPB1 | CDC42BPA | CD79B | HIST1H3I |
| CLDN4 | PPFIA2 | CD97 | HIST1H3G |
| CLDN7 | AKR7A2 | 41889 | HIST1H3J |
| CRYZ | PPAP2A | CR2 | HIST1H3H |
| CD55 | ABCB11 | CSNK2B | HIST1H3B |
| EEF1G | MAP2K1IP1 | DBI | FADD |
| EPHA2 | EIF3H | DHCR7 | IL1RL2 |
| EIF4A1 | SLC4A4 | DLG1 | FGF18 |
| EIF4A2 | SNX3 | DOCK2 | FGF16 |
| ENO2 | MYH13 | DUT | HIST1H3F |
| SLC29A1 | NAPG | ECH1 | HIST1H2AG |
| EPHB2 | FBP2 | VAPA | HIST1H2BJ |
| EPHB3 | SCEL | H2AFY | NRG2 |
| ESD | SUCLA2 | PDIA4 | GDF3 |
| F7 | GGH | EIF4A3 | FGF19 |
| FLOT2 | PROZ | ACTR1B | GDF11 |
| GARS | SQSTM1 | OPTN | FST |
| GMDS | AP1M1 | NAMPT | LASS1 |
| GNB3 | RAB7L1 | MPZL2 | HPSE |
| HIST1H2AE | WASL | STIP1 | ESM1 |
| HLA-C | PLOD3 | PKP3 | DKK1 |
| HLA-H | PGLYRP1 | POFUT2 | IL17B |
| HPCAL1 | KALRN | QPRT | IL19 |
| | CLIC3 | WBP2 | TNFRSF12A |
| IGHα | BAZ1B | ERO1L | IL23A |
| IGHG1 | SPAG9 | H2AFY2 | FGFRL1 |
| IGHG2 | SLC13A2 | RCC2 | TREM1 |
| IGHG3 | ATP6V0D1 | RTN4 | IL1F9 |
| IGHG4 | HGS | GLT25D1 | CXCL16 |
| IGHM | AP4M1 | RNASE7 | IL22RA1 |
| IGKC | ATP6V1F | FCRLA | HIST1H2BK |
| ITGA3 | PTER | H2AFV | HIST3H2BB |
| KRT3 | TRIP10 | MRLC2 | LOC440093 |
| KRT4 | SLC9A3R2 | PAGE2 | PGAM4 |
| KRT6A | SLIT2 | HIST1H2BA | PC-3 |
| KRT6B | SLC22A6 | SNX33 | LOC729500 |
| KRT7 | KL | PTRF | KRT18P26 |
| KRT17 | KIF3B | HIST2H2BC | S100A11P |
| RPSA | SLC22A8 | ANXA8 | LOC729679 |
| LFNG | GRHPR | NME1-NME2 | KRT17P3 |
| LGALS3 | SLC22A13 | EIF2S1 | RCTPI1 |
| LRP4 | TMPRSS11D | EIF2S3 | LOC729903 |
| CD46 | GSTO1 | EIF4E | RP11-556K13.1 |
| MICA | NPEPPS | EPB41L2 | LOC100129982 |
| MYH11 | TMEM59 | EVI2B | LOC100130100 |
| NARS | ATP6V1G1 | FCER2 | LOC100130446 |
| NEDD4 | CDC42BPB | FGR | LOC100130562 |
| RPL10A | CREB5 | FH | LOC100130624 |
| PCNA | CROCC | GART | LOC100130711 |
| PLEC1 | DHX34 | GOT2 | LOC100130819 |
| PLXNA1 | TMEM63A | NCKAP1L | LOC100131713 |
| PPP2R1A | SLK | HLA-DPB1 | LOC100131863 |
| PSMC6 | RUSC2 | HLA-DQA1 | LOC100132795 |
| PSMD3 | OXSR1 | HNRNPA1 | LOC100133211 |
| PSMD11 | SLC23A1 | HNRNPC | LOC100133690 |
| RAC3 | DOPEY2 | HPRT1 | SET |
| RAP2A | ABI1 | ICAM3 | CCT6B |
| RAP2B | GNPDA1 | INSR | ACTR3B |
| RPL12 | TOM1 | EIF3E | PSMA8 |
| RPLP0 | ABCB6 | ITGAL | ARP11 |
| RPS4X | ABCC9 | ITGB3 | BCHE |
| RPS4Y1 | HUWE1 | ITGB7 | H2AFZ |
| RPS8 | ARPC5 | ITIH2 | SNRPE |
| RPS16 | ACTR2 | STMN1 | TFPI |
| SPTAN1 | TSPAN3 | LCK | ADAMTS1 |
| VAMP1 | ARPC2 | LSP1 | GDF15 |

TABLE 3

Polypeptide payloads and receivers

| Ankyrin repeat proteins | | Fibronectins | Lyases |
|---|---|---|---|
| General Classes | | | |
| Antibodies | Complement receptors | GPI-linked polypeptides | Nanobodies |
| Aptamers | Cyclic peptides | HEAT repeat proteins | Nucleic Acids |
| ARM repeat proteins | DARPins | Hydrolases | Polypeptides |
| Carbohydrates | DNAses | Kinases | Single-chain variable fragments (scFv) |
| Cell surface receptors | Enzymes | Lipoproteins | Tetratri copeptide repeat proteins |
| Complement | | | |
| C1 inhibitor | C4 binding protein | CR3 | Factor I |
| C3 Beta chain Receptor | CD59 | CR4 | Homologous restriction factor |
| C3aR | CR1 | Decay-accelerating factor (DAF) | Membrane cofactor protein (MCP) |
| C3eR | CR2 | Factor H | PRELP |
| Enzymes | | | |
| triacylglycerol lipase | bile-acid-CoA hydrolase | feruloyl esterase | phosphatidate phosphatase |
| (S)-methylmalonyl-CoA hydrolase | bis(2-ethylhexyl)phthalate esterase | formyl-CoA hydrolase | phosphatidylglycero phosphatase |
| [acyl-carrier-protein] phosphodiesterase | bisphosphoglycerate phosphatase | fructose-bisphosphatase | phosphatidylinositol deacylase |
| [phosphorylase] phosphatase | Carboxylic-Ester Hydrolases | fumarylacetoacetase | phosphodiesterase I |
| 1,4-lactonase | carboxymethylenebutenolidase | fusarinine-C ornithinesterase | phosphoglycerate phosphatase |
| 11-cis-retinyl-palmitate hydrolase | cellulose-polysulfatase | galactolipase | phosphoglycolate phosphatase |
| 1-alkyl-2-acetylglycerophosphocholine esterase | cephalosporin-C deacetylase | gluconolactonase | phosphoinositide phospholipase C |
| 2'-hydroxybiphenyl-2-sulfinate desulfinase | cerebroside-sulfatase | glucose-1-phosphatase | phospholipase A1 |
| 2-pyrone-4,6-dicarboxylate lactonase | cetraxate benzylesterase | glucose-6-phosphatase | phospholipase A2 |
| 3',5'-bisphosphate nucleotidase | chlorogenate hydrolase | glutathione thiolesterase | phospholipase C |
| 3-hydroxyisobutyryl-CoA hydrolase | chlorophyllase | glycerol-1-phosphatase | phospholipase D |
| 3'-nucleotidase | cholinesterase | glycerol-2-phosphatase | phosphonoacetaldehyde hydrolase |
| 3-oxoadipate enol-lactonase | choline-sulfatase | glycerophosphocholine phosphodiesterase | phosphonoacetate hydrolase |
| 3-phytase | choloyl-CoA hydrolase | Glycosidases, i.e. enzymes that hydrolyse O- and S-glycosyl compounds | phosphonopyruvate hydrolase |
| 4-hydroxybenzoyl-CoA thioesterase | chondro-4-sulfatase | glycosulfatase | phosphoprotein phosphatase |
| 4-methyloxaloacetate esterase | chondro-6-sulfatase | Glycosylases | Phosphoric-diester hydrolases |
| 4-phytase | citrate-lyase deacetylase | histidinol-phosphatase | Phosphoric-monoester hydrolases |
| 4-pyridoxolactonase | cocaine esterase | hormone-sensitive lipase | Phosphoric-triester hydrolases |
| 5'-nucleotidase | cutinase | Hydrolysing N-glycosyl compounds | phosphoserine phosphatase |
| 6-acetylglucose deacetylase | cyclamate sulfohydrolase | Hydrolysing S-glycosyl compounds | poly(3-hydroxybutyrate) depolymerase |
| 6-phosphogluconolactonase | Cysteine endopeptidases | hydroxyacylglutathione hydrolase | poly(3-hydroxyoctanoate) depolymerase |
| a-amino-acid esterase | Cysteine-type carboxypeptidases | hydroxybutyrate-dimer hydrolase | polyneuridine-aldehyde esterase |
| a-Amino-acyl-peptide hydrolases | D-arabinonolactonase | hydroxymethylglutaryl-CoA hydrolase | protein-glutamate methylesterase |

TABLE 3-continued

Polypeptide payloads and receivers

| Ankyrin repeat proteins | | Fibronectins | Lyases |
|---|---|---|---|
| acetoacetyl-CoA hydrolase | deoxylimonate A-ring-lactonase | iduronate-2-sulfatase | quorum-quenching N-acyl-homoserine lactonase |
| acetoxybutynylbithiophene deacetylase | dGTPase | inositol-phosphate phosphatase | retinyl-palmitate esterase |
| acetylajmalineesterase | dihydrocoumarin hydrolase | juvenile-hormone esterase | Serine dehyrdatase or serine hydroxymethyl transferase |
| acetylalkylglycerol acetylhydrolase | Dipeptidases | kynureninase | Serine endopeptidases |
| acetylcholinesterase | Dipeptide hydrolases | L-arabinonolactonase | serine-ethanolamine-phosphate phosphodiesterase |
| acetyl-CoA hydrolase | Dipeptidyl-peptidases and tripeptidyl-peptidases | limonin-D-ring-lactonase | Serine-type carboxypeptidases |
| acetylesterase | Diphosphoric-monoester hydrolases | lipoprotein lipase | S-formylglutathione hydrolase |
| acetylpyruvate hydrolase | disulfoglucosamine-6-sulfatase | L-rhamnono-1,4-lactonase | sialate O-acetylesterase |
| acetylsalicylate deacetylase | dodecanoyl-[acyl-carrier-protein] hydrolase | lysophospholipase | sinapine esterase |
| acetylxylan esterase | Endodeoxyribonucleases producing 3'-phosphomonoesters | mannitol-1-phosphatase | Site specific endodeoxyribo-nucleases: cleavage is not sequence specific |
| acid phosphatase | Endodeoxyribonucleases producing 5'-phosphomonoesters | Metallocarboxypeptidases | Site-specific endodeoxyribo-nucleases that are specific for altered bases. |
| Acting on acid anhydrides to catalyse transmembrane movement of substances | Endopeptidases of unknown catalytic mechanism | Metalloendopeptidases. | Site-specific endodeoxyribo-nucleases: cleavage is sequence specific |
| Acting on acid anhydrides to facilitate cellular and subcellular movement | Endoribonucleases producing 3'-phosphomonoesters | methylphosphothioglycerate phosphatase | sphingomyelin phosphodiesterase |
| Acting on GTP to facilitate cellular and subcellular movement | Endoribonucleases producing 5'-phosphomonoesters | methylumbelliferyl-acetate deacetylase | S-succinylglutathione hydrolase |
| Acting on phosphorus-nitrogen bonds | Endoribonucleases that are active with either ribo- or deoxyribonucleic acids and produce 3'-phosphomonoesters | monoterpene e-lactone hydrolase | steroid-lactonase |
| Acting on sulfur-nitrogen bonds | Endoribonucleases that are active with either ribo- or deoxyribonucleic acids and produce 5'-phosphomonoesters | N-acetylgalactosamine-4-sulfatase | sterol esterase |
| actinomycin lactonase | Enzymes acting on acid anhydrides | N-acetylgalactosamine-6-sulfatase | steryl-sulfatase |
| acylcarnitine hydrolase | Enzymes Acting on carbon-carbon bonds | N-acetylgalactosaminoglycan deacetylase | succinyl-CoA hydrolase |
| acyl-CoA hydrolase | Enzymes acting on carbon-nitrogen bonds, other than peptide bonds | N-acetylglucosamine-6-sulfatase | sucrose-phosphate phosphatase |
| acylglycerol lipase | Enzymes acting on carbon-phosphorus bonds | N-sulfoglucosamine sulfohydrolase | sugar-phosphatase |

TABLE 3-continued

Polypeptide payloads and receivers

| Ankyrin repeat proteins | Fibronectins | Lyases |
|---|---|---|
| acyloxyacyl hydrolase | Enzymes acting on carbon-sulfur bonds | oleoyl-[acyl-carrier-protein] hydrolase | Sulfuric-ester hydrolases |
| acylpyruvate hydrolase | Enzymes Acting on ether bonds | Omega peptidases | tannase |
| ADAMTS13 | Enzymes acting on halide bonds | orsellinate-depside hydrolase | Thioester hydrolases |
| Adenosine deaminase | Enzymes acting on peptide bonds (peptidases) | oxaloacetase | Thioether and trialkylsulfonium hydrolases |
| adenylyl-[glutamate-ammonia ligase] hydrolase | Enzymes acting on phosphorus-nitrogen bonds | palmitoyl[protein] hydrolase | Threonine endopeptidases |
| ADP-dependent medium-chain-acyl-CoA hydrolase | Enzymes acting on sulfur-nitrogen bonds | palmitoyl-CoA hydrolase | thymidine phosphorylase |
| ADP-dependent short-chain-acyl-CoA hydrolase | Enzymes acting on sulfur-sulfur bonds | pectinesterase | trehalose-phosphatase |
| ADP-phosphoglycerate phosphatase | Ether hydrolases. | Peptidyl peptide hydrolases | triacetate-lactonase |
| alkaline phosphatase | Exodeoxyribonucleases producing 5'-phosphomonoesters | Peptidyl-amino-acid hydrolases | Triphosphoric-monoester hydrolases |
| all-trans-retinyl-palmitate hydrolase | Exonucleases that are active with either ribo- or deoxyribonucleic acids and produce 3'-phosphomonoesters | Peptidylamino-acid hydrolases or acylamino-acid hydrolases | trithionate hydrolase |
| aminoacyl-tRNA hydrolase | Exonucleases that are active with either ribo- or deoxyribonucleic acids and produce 5'-phosphomonoesters | Peptidyl-dipeptidases | tropinesterase |
| Aminopeptidases | Exoribonucleases producing 3'-phosphomonoesters | phenylacetyl-CoA hydrolase | ubiquitin thiolesterase |
| arylesterase | Exoribonucleases producing 5'-phosphomonoesters. | Phenylalanine ammonia lyase | UDP-sulfoquinovose synthase |
| arylsulfatase | Factor IX | Phenylalanine hydroxylase | uricase |
| Asparaginase | Factor VIII | pheophorbidase | uronolactonase |
| Aspartic endopeptidases | fatty-acyl-ethyl-ester synthase | phloretin hydrolase | wax-ester hydrolase |
| | b-diketone hydrolase | phorbol-diester hydrolase | xylono-1,4-lactonase |

TABLE 4

Targets

General Classes of Targets

| | | | |
|---|---|---|---|
| Microbes | Polypeptides | DNA | Amino Acids |
| Fungi | Toxins | RNA | Prions |
| Bacteria | Lipids | Parasites | Cytokines |
| Virus | Cells | Cellular Debris | |

Infectious Disease-Related Targets

| | | | |
|---|---|---|---|
| Lipopolysaccharides | Cell invasion protein | Intermedilysin | Secreted effector protein sptP |
| Zona occludens toxin | Cholera enterotoxin | Invasion protein sipA | Seeligeriolysin |
| Actin polymerization protein RickA | Cysteine protease | Iota toxin component Ia | Serine protease |
| Actin polymerization protein RickA | Cytolethal distending toxin | Ivanolysin | Shiga toxin |

TABLE 4-continued

| Targets | | | |
|---|---|---|---|
| Adenosine monophosphate-protein transferase vopS | Cytolysin | LepB | Sphingomyelinase |
| adenylate cyclase | Cytotoxic necrotizing factor | Lethal factor | Staphylokinase |
| Adenylate cyclase ExoY | Cytotoxin | Leukotoxin | Streptokinase |
| ADP-ribosyltransferase enzymatic component | Dermonecrotic toxin | Listeriolysin | Streptolysin |
| Aerolysin | Deubiquitinase | Microbial collagenase | Streptopain |
| Alpha-toxin | Diphtheria toxin | Outer membrane protein IcsA autotransporter | Suilysin |
| Alveolysin | Enterohemolysin | Panton-Valentine Leucocidin F | Superantigen |
| Alveolysin | Enterotoxin | Perfringolysin | T3SS secreted effector EspF |
| Anthrolysin O | Epidermal cell differentiation inhibitor | Pertussis toxin | Tetanus toxin |
| Arp2/3 complex-activating protein rickA | Exoenzyme | Phospholipase | Tir |
| Binary ADP-ribosyltransferase CDT toxin | Exotoxin | Plasminogen activator | TolC |
| Botulinum neurotoxin | G-nucleotide exchange factor | Pneumolysin | Toxic shock syndrome toxin |
| C2 toxin, component II | Guanine nucleotide exchange factor sopE | Protective antigen | Zink-carboxypeptidase |
| CagA | Heat stable enterotoxin | Protein kinase | Zink-carboxypeptidase |
| Calmodulin-sensitive adenylate cyclase | IgA-specific serine endopeptidase autotransporter | Pyolysin | Zn-dependent peptidase |
| Cell cycle inhibiting factor | Inositol phosphate phosphatase sopB | RTX toxin | |
| Lipid & Cell Targets | | | |
| Circulating tumor cells | very low density lipid (VLDL) | triglycerides | Fatty acids |
| Metastases | high density lipoprotein | chylomicrons | Cholesterol |
| Eukaryotic cells | low density lipoprotein | apolipoproteins | |

TABLE 5

| Cancers | | | |
|---|---|---|---|
| Acute lymphoblastic leukaemia (ALL) | Colorectal cancer | Macroglobulinemia, Waldenström | Pleuropulmonary Blastoma, Childhood |
| Acute myeloid leukaemia (AML) | Craniopharyngioma, Childhood | Male Breast Cancer | Pregnancy and Breast Cancer |
| Adrenocortical Carcinoma | Cutaneous T-Cell Lymphoma | Malignant Fibrous Histiocytoma of Bone and Osteosarcoma | Primary Central Nervous System (CNS) Lymphoma |
| AIDS-Related Kaposi Sarcoma | Ductal Carcinoma In Situ (DCIS) | Melanoma | Prostate Cancer |
| AIDS-Related lymphoma | Embryonal Tumors, Childhood | Merkel Cell Carcinoma | Rare cancers |
| Anal Cancer | Endometrial Cancer | Mesothelioma | Rectal Cancer |
| Appendix Cancer | Ependymoma, Childhood | Metastatic Squamous Neck Cancer with Occult Primary | Renal cell carcinoma |
| Astrocytomas, Childhood | Epithelial cancer | Midline Tract Carcinoma Involving NUT Gene | Renal Pelvis and Ureter, Transitional Cell Cancer |
| Atypical Teratoid/Rhabdoid Tumor, Childhood | Esophageal Cancer | Molar pregnancy | Retinoblastoma |
| Basal Cell Carcinoma | Esthesioneuroblastoma, Childhood | Mouth and oropharyngeal cancer | Rhabdomyosarcoma |

TABLE 5-continued

| Cancers | | | |
|---|---|---|---|
| Bile duct cancer | Ewing sarcoma | Multiple Endocrine Neoplasia Syndromes, Childhood | Salivary Gland Cancer |
| Bladder cancer | Extragonadal Germ Cell Tumor | Multiple Myeloma/Plasma Cell Neoplasm | Sarcoma |
| Bone cancer | Extrahepatic Bile Duct Cancer | Mycosis Fungoides | Secondary cancers |
| Bowel cancer | Eye Cancer | Myelodysplastic Syndromes | Sézary Syndrome |
| Brain Stem Glioma, Childhood | Gallbladder Cancer | Myelodysplastic/Myeloproliferative Neoplasms | Skin Cancer |
| Brain tumours | Gastric cancer | Myeloproliferative Disorders, Chronic | Skin cancer (non melanoma) |
| Breast cancer | Gastrointestinal Carcinoid Tumor | Nasal Cavity and Paranasal Sinus Cancer | Small Cell Lung Cancer |
| Bronchial Tumors, Childhood | Germ Cell Tumor | Nasopharyngeal cancer | Small Intestine Cancer |
| Burkitt Lymphoma | Gestational trophoblastic tumours (GTT) | Neuroblastoma | Soft Tissue Sarcoma |
| Cancer of unknown primary | Glioma | Non-Hodgkin Lymphoma | Squamous Cell Carcinoma |
| Cancer spread to bone | Hairy cell leukaemia | Non-Small Cell Lung Cancer | Squamous Neck Cancer with Occult Primary, Metastatic |
| Cancer spread to brain | Head and neck cancer | Oesophageal cancer | Stomach (Gastric) Cancer |
| Cancer spread to liver | Heart Cancer, Childhood | Oral Cancer | Stomach cancer |
| Cancer spread to lung | Hepatocellular (Liver) Cancer | Oral Cavity Cancer | T-Cell Lymphoma, Cutaneous - see Mycosis Fungoides and Sézary Syndrome |
| Carcinoid Tumor | Histiocytosis, Langerhans Cell | Oropharyngeal Cancer | Testicular cancer |
| Carcinoma of Unknown Primary | Hodgkin Lymphoma | Osteosarcoma (Bone Cancer) | Throat Cancer |
| Cardiac (Heart) Tumors, Childhood | Hypopharyngeal Cancer | Osteosarcoma and Malignant Fibrous Histiocytoma | Thymoma and Thymic Carcinoma |
| Central Nervous System Atypical Teratoid/Rhabdoid Tumor, Childhood | Intraocular Melanoma | Ovarian Cancer | Thyroid Cancer |
| Central Nervous System Embryonal Tumors, Childhood | Islet Cell Tumors, Pancreatic Neuroendocrine Tumors | Pancreatic Cancer | Transitional Cell Cancer of the Renal Pelvis and Ureter |
| Central Nervous System, Childhood | Kidney cancer | Pancreatic Neuroendocrine Tumors (Islet Cell Tumors) | Unknown primary cancer |
| Cervical cancer | Langerhans Cell Histiocytosis | Papillomatosis, Childhood | Ureter and Renal Pelvis, Transitional Cell Cancer |
| Chordoma, Childhood | Laryngeal Cancer | Paraganglioma | Urethral Cancer |
| Choriocarcinoma | Leukemia | Parathyroid Cancer | Uterine Cancer, Endometrial |
| Chronic Lymphocytic Leukemia (CLL) | Lip and Oral Cavity Cancer | Penile Cancer | Uterine Sarcoma |
| Chronic myeloid leukaemia (CML) | Liver cancer | Pharyngeal Cancer | Vaginal cancer |
| Chronic Myeloproliferative Disorders | Lobular Carcinoma In Situ (LCIS) | Pheochromocytoma | Vulvar Cancer |
| Colon cancer | Low Malignant Potential Tumor | Pituitary Tumor | Waldenström Macroglobulinemia |
| Lymphoma | Lung Cancer | Plasma Cell Neoplasm/Multiple Myeloma | Wilms Tumor |

What is claimed is:

1. An exosome comprising a fusion protein which is present on an exterior surface of the exosome, wherein the fusion protein comprises (i) an immunomodulating component and (ii) a prostaglandin F2 receptor negative regulator (PTGFRN) or a functional fragment thereof, and wherein the immunomodulating component comprises a cytokine.

2. The exosome of claim 1, wherein the PTGFRN comprises the full-length PTGFRN.

3. The exosome of claim 1, wherein the functional fragment of the PTGFRN comprises the region before the C-terminal-most IgV domain, the transmembrane domain, and the intracellular domain of PTGFRN.

4. A composition comprising the exosome of claim 1, and a pharmaceutically acceptable carrier.

5. The exosome of claim 1, wherein the cytokine comprises an interleukin-12 (IL-12) protein or an interleukin-15 (IL-15) protein.

6. The exosome of claim 5, wherein the cytokine is fused to the N-terminus of the PTGFRN or functional fragment thereof.

7. The exosome of claim 5, wherein the cytokine is an IL-12 protein and the fusion comprises the amino acid sequence set forth in SEQ ID NO: 3, SEQ ID NO: 4, SEQ ID NO: 5, or SEQ ID NO: 6.

8. The exosome of claim 7, wherein the PTGFRN or functional fragment thereof comprises: (i) amino acid residues 561-1,418 of SEQ ID NO: 3; (ii) 564-1,421 of SEQ ID NO: 4; (iii) amino acid residues 561-753 of SEQ ID NO: 5; or (iv) amino acid residues 563-756 of SEQ ID NO: 6.

9. The exosome of claim 8, wherein the one or more additional immunomodulating components comprise (i) an inhibitor for a negative checkpoint regulator or an inhibitor for a binding partner of a negative checkpoint regulator; (ii) an activator for a positive costimulatory molecule or an activator for a binding partner of a positive co-stimulatory molecule; (iii) a cytokine or a binding partner of a cytokine; (iv) a T-cell receptor (TCR), a T-cell co-receptor, a major histocompatibility complex (MHC), a human leukocyte antigen (HLA), or a derivative thereof; (v) an activator of a T-cell receptor or co-receptor; (vi) a tumor antigen; (vii) an agonist or an antagonist; (viii) an antibody or an antigen-binding fragment; (ix) a polynucleotide; (x) a protein, a peptide, a glycolipid, or a glycoprotein; or (xi) combinations thereof.

10. A composition comprising the exosome of claim 7, and a pharmaceutically acceptable carrier.

11. The exosome of claim 5, wherein the cytokine is an IL-15 protein and the fusion protein comprises the amino acid sequence set forth in SEQ ID NO: 15 or SEQ ID NO: 16.

12. The exosome of claim 11, wherein the PTGFRN or functional fragment thereof comprises: (i) amino acid residues 561-1,418 of SEQ ID NO: 3; (ii) 564-1,421 of SEQ ID NO: 4; (iii) amino acid residues 561-753 of SEQ ID NO: 5; or (iv) amino acid residues 563-756 of SEQ ID NO: 6.

13. A composition comprising the exosome of claim 11, and a pharmaceutically acceptable carrier.

14. The exosome of claim 5, which comprises one or more additional immunomodulating components.

15. The exosome of claim 14, wherein the one or more additional immunomodulating components comprise a CD40L, a FLT3L, or both.

16. The exosome of claim 15, wherein (a) the CD40L is present on the exterior surface of the exosome as a fusion protein, (b) the FLT3L is present on the exterior surface of the exosome as a fusion protein, or (c) both (a) and (b).

17. The exosome of claim 16, wherein the fusion protein comprising the CD40L comprises the amino acid sequence set forth in SEQ ID NO: 19 or SEQ ID NO: 20.

18. The exosome of claim 16, wherein the fusion protein comprising the FLT3L comprises the amino acid sequence set forth in SEQ ID NO: 22.

19. A composition comprising the exosome of claim 14, and a pharmaceutically acceptable carrier.

20. A composition comprising the exosome of claim 5, and a pharmaceutically acceptable carrier.

* * * * *

SEQUENCE LISTING

```
Sequence total quantity: 26
SEQ ID NO: 1              moltype = AA  length = 390
FEATURE                   Location/Qualifiers
source                    1..390
                          mol_type = protein
                          organism = synthetic construct
SEQUENCE: 1
MFHVSFRYIF GLPPLILVLL PVASSDCDIE GKDGKQYESV LMVSIDQLLD SMKEIGSNCL   60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEHSAG  180
GGGSDYKDDD DKGGGGSGPI FNASVHSDTP SVIRGDLIKL FCIITVEGAA LDPDDMAFDV  240
SWFAVHSFGL DKAPVLLSSL DRKGIVTTSR RDWKSDLSLE RVSVLEFLLQ VHGSEDQDFG  300
NYYCSVTPWV KSPTGSWQKE AEIHSKPVFI TVKMDVLNAF KYPLLIGVGL STVIGLLSCL  360
IGYCSSHWCC KKEVQETRRE RRRLMSMEMD                                  390

SEQ ID NO: 2              moltype = AA  length = 382
FEATURE                   Location/Qualifiers
source                    1..382
                          mol_type = protein
                          organism = synthetic construct
SEQUENCE: 2
MFHVSFRYIF GLPPLILVLL PVASSDCDIE GKDGKQYESV LMVSIDQLLD SMKEIGSNCL   60
NNEFNFFKRH ICDANKEGMF LFRAARKLRQ FLKMNSTGDF DLHLLKVSEG TTILLNCTGQ  120
VKGRKPAALG EAQPTKSLEE NKSLKEQKKL NDLCFLKRLL QEIKTCWNKI LMGTKEHSAG  180
GGGSGGGGSG PIFNASVHSD TPSVIRGDLI KLFCIITVEG AALDPDDMAF DVSWFAVHSF  240
GLDKAPVLLS SLDRKGIVTT SRRDWKSDLS LERVSVLEFL LQVHGSEDQD FGNYYCSVTP  300
WVKSPTGSWQ KEAEIHSKPV FITVKMDVLN AFKYPLLIGV GLSTVIGLLS CLIGYCSSHW  360
CCKKEVQETR RERRRLMSME MD                                          382

SEQ ID NO: 3              moltype = AA  length = 1418
FEATURE                   Location/Qualifiers
source                    1..1418
                          mol_type = protein
                          organism = synthetic construct
SEQUENCE: 3
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKDRVF TDKTSATVIC   300
RKNASISVRA QDRYYSSSWS EWASVPCSGG SGGGSGGGGS GGGGSGGGSG GRNLPVATPD  360
PGMFPCLHHS QNLLRAVSNM LQKARQTLEF YPCTSEEIDH EDITKDKTST VEACLPLELT  420
KNESCLNSRE TSFITNGSCL ASRKTSFMMA LCLSSIYEDL KMYQVEFKTM NAKLLMDPKR  480
QIFLDQNMLA VIDELMQALN FNSETVPQKS SLEEPDFYKT KIKLCILLHA FRIRAVTIOR  540
VMSYLNASSA GGGGSGGGGS RVVRVPTATL VRVVGTELVI PCNVSDYDGP SEQNFDWSFS  600
SLGSSFVELA STWEVGFPAQ LYQERLQRGE ILLRRTANDA VELHIKNVQP SDQGHYKCST  660
PSTDATVQGN YEDTVQVKVL ADSLHVGPSA RPPPSLSLRE GEPFELRCTA ASASPLHTHL  720
ALLWEVHRGP ARRSVLALTH EGRFHPGLGY EQRYHSGDVR LDTVGSDAYR LSVSRALSAD  780
QGSYRCIVSE WIAEQGNWQE IQEKAVEVAT VVIQPSVLRA AVPKNVSVAE GKELDLTCNI  840
TTDRADDVRP EVTWSFSRMP DSTLPGSRVL ARLDRDSLVH SSPHVALSHV DARSYHLLVR  900
DVSKENSGYY CHVSLWAPG HNRSWHKVAE AVSSPAGVGV TWLEPDYQVY LNASKVPGFA   960
DDPTELACRV VDTKSGEANV RFTVSWYYRM NRRSDNVVTS ELLAVMDGDW TLKYGERSKQ 1020
RAQDGDFIFS KEHTDFNFR IQRTTEEDRG NYYCVVSAWT KQRNNSWVKS KDVFSKPVNI  1080
FWALEDSVLV VKARQPKPFF AAGNTFEMTC KVSSKNIKSP RYSVLIMAEK PVGDLSSPNE 1140
TKYIISLDQD SVVKLENWTD ASRVDGVVLE KVQEDEFRYR MYQTQVSDAG LYRCMVTAWS 1200
PVRGSLWREA ATSLSNPIEI DFQTSGPIFN ASVHSDTPSV IRGDLIKLFC IITVEGAALD 1260
PDDMAFDVSW FAVHSFGLDK APVLLSSLDR KGIVTTSRRD WKSDLSLERV SVLEFLLQVH 1320
GSEDQDFGNY YCSVTPWVKS PTGSWQKEAE IHSKPVFITV KMDVLNAFKY PLLIGVGLST 1380
VIGLLSCLIG YCSSHWCCKK EVQETRRERR RLMSMEMD                        1418

SEQ ID NO: 4              moltype = AA  length = 1421
FEATURE                   Location/Qualifiers
source                    1..1421
                          mol_type = protein
                          organism = synthetic construct
SEQUENCE: 4
MCPQKLTISW FAIVLLVSPL MAMWELEKDV YVVEVDWTPD APGETVNLTC DTPEEDDITW   60
TSDQRHGVIG SGKTLTITVK EFLDAGQYTC HKGGETLSHS HLLLHKKENG IWSTEILKNF  120
KNKTFLKCEA PNYSGRFTCS WLVQRNMDLK FNIKSSSSSP DSRAVTCGMA SLSAEKVTLD  180
QRDYEKYSVS CQEDVTCPTA EETLPIELAL EARQQNKYEN YSTSFFIRDI IKPDPPKNLQ  240
MKPLKNSQVE VSWEYPDSWS TPHSYFSLKF FVRIQRKKEK MKETEEGCNQ KGAFLVEKTS  300
TEVQCKGGNV CVQAQDRYYN SSCSKWACVP CRVRSGGSGG GSGGGGSGGG GSGGGSGGRV  360
IPVSGPARCL SQSRNLLKTT DDMVKTAREK LKHYSCTAED IDHEDITRDQ TSTLKTCLPL  420
ELHKNESCLA TRETSSTTRG SCLPPQKTSL MMTLCLGSIY EDLKMYQTEF QAINAALQNH  480
NHQQIILDKG MLVAIDELMQ SLNHNGETLR QKPPVGEADP YRVKMKLCIL HAFSTRVVT   540
INRVMGYLSS ASAGGGGSGG GGSRVVRVPT ATLVRVVGTE LVIPCNVSDY DGPSEQNFDW  600
SFSSLGSSFV ELASTWEVGF PAQLYQERLQ RGEILLRRTA NDAVELHIKN VQPSDQGHYK  660
CSTPSTDATV QGNYEDTVQV KVLADSLHVG PSARPPPSLS LREGEPFELR CTAASASPLH  720
```

```
THLALLWEVH RGPARRSVLA LTHEGRFHPG LGYEQRYHSG DVRLDTVGSD AYRLSVSRAL   780
SADQGSYRCI VSEWIAEQGN WQEIQEKAVE VATVVIQPSV LRAAVPKNVS VAEGKELDLT   840
CNITTDRADD VRPEVTWSFS RMPDSTLPGS RVLARLDRDS LVHSSPHVAL SHVDARSYHL   900
LVRDVSKENS GYYYCHVSLW APGHNRSWHK VAEAVSSPAG VGVTWLEPDY QVYLNASKVP   960
GFADDPTELA CRVVDTKSGE ANVRFTVSWY YRMNRRSDNV VTSELLAVMD GDWTLKYGER  1020
SKQRAQDGDF IFSKEHTDTF NFRIQRTTEE DRGNYYCVVS AWTKQRNNSW VKSKDVFSKP  1080
VNIFWALEDS VLVVKARQPK PFFAAGNTFE MTCKVSSKNI KSPRYSVLIM AEKPVGDLSS  1140
PNETKYIISL DQDSVVKLEN WTDASRVDGV VLEKVQEDEF RYRMYQTQVS DAGLYRCMVT  1200
AWSPVRGSLW REAATSLSNP IEIDPQTSGP IFNASVHSDT PSVIRGDLIK LFCIITVEGA  1260
ALDPDDMAFD VSWFAVHSFG LDKAPVLLSS LDRKGIVTTS RRDWKSDLSL ERVSVLEFLL  1320
QVHGSEDQDF GNYYCSVTPW VKSPTGSWQK EAEIHSKPVF ITVKMDVLNA FKYPLLIGVG  1380
LSTVIGLLSC LIGYCSSHWC CKKEVQETRR ERRRLMSMEM D                      1421

SEQ ID NO: 5            moltype = AA  length = 753
FEATURE                 Location/Qualifiers
source                  1..753
                        mol_type = protein
                        organism = synthetic construct
SEQUENCE: 5
MCHQQLVISW FSLVFLASPL VAIWELKKDV YVVELDWYPD APGEMVVLTC DTPEEDGITW    60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCSGG SGGGSGGGGS GGGGSGGGSG GRNLPVATPD   360
PGMFPCLHHS QNLLRAVSNM LQKARQTLEF YPCTSEEIDH EDITKDKTST VEACLPLELT   420
KNESCLNSRE TSFITNGSCL ASRKTSFMMA LCLSSIYEDL KMYQVEFKTM NAKLLMDPKR   480
QIFLDQNMLA VIDELMQALN FNSETVPQKS SLEEPDFYKT KIKLCILLHA FRIRAVTIDR   540
VMSYLNASSA GGGGSGGGGS GPIFNASVHS DTPSVIRGDL IKLFCIITVE GAALDPDDMA   600
FDVSWFAVHS FGLDKAPVLL SSLDRKGIVT TSRRDWKSLS SLERVSVLEF LLQVHGSEDQ   660
DFGNYYCSVT PWVKSPTGSW QKEAEIHSKP VFITVKMDVL NAFKYPLLIG VGLSTVIGLL   720
SCLIGYCSSH WCCKKEVQET RRERRRLMSM EMD                               753

SEQ ID NO: 6            moltype = AA  length = 756
FEATURE                 Location/Qualifiers
source                  1..756
                        mol_type = protein
                        organism = synthetic construct
SEQUENCE: 6
MCPQKLTISW FAIVLLVSPL MAMWELEKDV YVVEVDWTPD APGETVNLTC DTPEEDDITW    60
TSDQRHGVIG SGKTLTITVK EFLDAGQYTC HKGGETLSHS HLLLHKKENG IWSTEILKNF   120
KNKTFLKCEA PNYSGRFTCS WLVQRNMDLK FNIKSSSSSP DSRAVTCGMA SLSAEKVTLD   180
QRDYEKYSVS CQEDVTCPTA EETLPIELAL EARQQNKYEN YSTSFFIRDI IKPDPPKNLQ   240
MKPLKNSQVE VSWEYPDSWS TPHSYFSLKF FVRIQRKKEK MKETEEGCNQ KGAFLVEKTS   300
TEVQCKGGNV CVQAQDRYYN SSCSKWACVP CRVRSGGSGG GSGGGGSGGG GSGGGSGGRV   360
IPVSGPARCL SQSRNLLKTT DDMVKTAREK LKHYSCTAED IDHEDITRDQ TSTLKTCLPL   420
ELHKNESCLA TRETSSTTRG SCLPPQKTSL MMTLCLGSYI EDLKMYQTEF QAINAALQNH   480
NHQQIILDKG MLVAIDELMQ SLNHNGETLR QKPPVGEADP YRVKMKLCIL LHAFSTRVVT   540
INRVMGYLSS ASAGGGGSGG GGSGPIFNAS VHSDTPSVIR GDLIKLFCII TVEGAALDPD   600
DMAFDVSWFA VHSFGLDKAP VLLSSLDRKG IVTTSRRDWK SDLSLERVSV LEFLLQVHGS   660
EDQDFGNYYC SVTPWVKSPT GSWQKEAEIH SKPVFITVKM DVLNAFKYPL LIGVGLSTVI   720
GLLSCLIGYC SSHWCCKKEV QETRRERRRL MSMEMD                            756

SEQ ID NO: 7            moltype = AA  length = 1018
FEATURE                 Location/Qualifiers
source                  1..1018
                        mol_type = protein
                        organism = synthetic construct
SEQUENCE: 7
MGRLASRPLL LALLLSLALCR GQDPYVKEAE NLKKYFNAGH SDVADNGTLF LGILKNWKEE    60
SDRKIMQSQI VSFYFKLFKN FKDDQSIQKS VETIKEDMNV KFFNSNKKKR DDFEKLTNYS   120
VTDLNVQRKA IHELIQVMAE LSPAAKTGSA GGGGSGGGGS RVVRVPTATL VRVVGTELVI   180
PCNVSDYDGP SEQNFDWSFS SLGSSFVELA STWEVGFPAQ LYQERLQRGE ILLRRTANDA   240
VELHIKNVQP SDQGHYKCST PSTDATVQGN YEDTVQVKVL ADSLVHGPSA RPPPSLSLRE   300
GEPFELRCTA ASASPLHTHL ALLWEVHRGP ARRSVLATH EGRFHPGLGY EQRYHSGDVR   360
LDTVGSDAYR LSVSRALSAD QGSYRCIVSE WIAEQGNWQE IQEKAVEVAT VVIQPSVLRA   420
AVPKNVSVAE GKELDLTCNI TTDRADDVRP EVTWSFSRMP DSTLPGSRVL ARLDRDSLVH   480
SSPHVALSHV DARSYHLLVR DVSKENSGYY YCHVSLWAPG HNRSWHKVAE AVSSPAGVGV   540
TWLEPDYQVY LNASKVPGFA DDPTELACRV VDTKSGEANV RFTVSWYYRM NRRSDNVVTS   600
ELLAVMDGDW TLKYGERSKQ RAQDGDFIFS KEHTDTFNFR IQRTTEEDRG NYYCVVSAWT   660
KQRNNSWVKS KDVFSKPVNI FWALEDSVLV VKARQPKPFF AAGNTFEMTC KVSSKNIKSP   720
RYSVLIMAEK PVGDLSSPNE TKYIISLDQD SVVKLENWTD ASRVDGVVLE KVQEDEFRYR   780
MYQTQVSDAG LYRCMVTAWS PVRGSLWREA ATSLSNPIEI DPQTSGPIFN ASVHSDTPSV   840
IRGDLIKLFC IITVEGAALD PDDMAFDVSW FAVHSFGLDK APVLLSSLDR KGIVTTSRRD   900
WKSDLSLERV SVLEFLLQVH GSEDQDFGNY YCSVTPWVKS PTGSWQKEAE IHSKPVFITV   960
KMDVLNAFKY PLLIGVGLST VIGLLSCLIG YCSSHWCCKK EVQETRRERR RLMSMEMD   1018

SEQ ID NO: 8            moltype = AA  length = 1157
FEATURE                 Location/Qualifiers
```

```
source                  1..1157
                        mol_type = protein
                        organism = synthetic construct
SEQUENCE: 8
MGRLASRPLL LALLSLALCR GQDPYVKEAE NLKKYFNAGH SDVADNGTLF LGILKNWKEE    60
SDRKIMQSQI VSFYFKLFKN FKDDQSIQKS VETIKEDMNV KFFNSNKKKR DDFEKLTNYS   120
VTDLNVQRKA IHELIQVMAE LSPAAKTGGS GGSGGSGGSG QDPYVKEAEN LKKYFNAGHS   180
DVADNGTLFL GILKNWKEES DRKIMQSIV SFYFKLFKNF KDDQSIQKSV ETIKEDMNVK    240
FFNSNKKKRD DFEKLTNYSV TDLNVQRKAI HELIQVMAEL SPAAKTGSAG GGGSGGGGSR   300
VVRVPTATLV RVVGTELVIP CNVSDYDGPS EQNFDWSFSS LGSSFVELAS TWEVGFPAQL   360
YQERLQRGEI LLRRTANDAV ELHIKNVQPS DQGHYKCSTP STDATVQGNY EDTVQVKVLA   420
DSLHVGPSAR PPPSLSLREG EPFELRCTAA SASPLHTHLA LLWEVHRGPA RRSVLALTHE   480
GRFHPGLGYE QRYHSGDVRL DTVGSDAYRL SVSRALSADQ GSYRCIVSEW IAEQGNWQEI   540
QEKAVEVATV VIQPSVLRAA VPKNVSVAEG KELDLTCNIT TDRADDVRPE VTWSFSRMPD   600
STLPGSRVLA RLDRDSLVHS SPHVALSHVD ARSYHLLVRD VSKENSGYYY CHVSLWAPGH   660
NRSWHKVAEA VSSPAGVGVT WLEPDYQVYL NASKVPGFAD DPTELACRVV DTKSGEANVR   720
FTVSWYYRMN RRSDNVVTSE LLAVMDGDWT LKYGERSKQR AQDGDFIFSK EHTDTFNFRI   780
QRTTEEDRGN YYCVVSAWTK QRNNSWVKSK DVFSKPVNIF WALEDSVLVV KARQPKPFFA   840
AGNTFEMTCK VSSSKNIKSPR YSVLIMAEKP VGDLSSPNET KYIISLDQDS VVKLENWTDA   900
SRVDGVVLEK VQEDEFRYRM YQTQVSDAGL YRCMVTAWSP VRGSLWREAA TSLSNPIEID   960
FQTSGPIFNA SVHSDTPSVI RGDLIKLFCI ITVEGAALDP DDMAFDVSWF AVHSFGLDKA  1020
PVLLSSLDRK GIVTTSRRDW KSDLSLERVS VLEFLLQVHG SEDQDFGNYY CSVTPWVKSP  1080
TGSWQKEAEI HSKPVFITVK MDVLNAFKYP LLIGVGLSTV IGLLSCLIGY CSSHWCCKKE  1140
VQETRRERRR LMSMEMD                                                 1157

SEQ ID NO: 9            moltype = AA  length = 1018
FEATURE                 Location/Qualifiers
source                  1..1018
                        mol_type = protein
                        organism = synthetic construct
SEQUENCE: 9
MGRLASRPLL LALLSLALCR GRHGTVIESL ESLNNYFNSS GIDVEEKSLF LDIWRNWQKD    60
GDMKILQSQI ISFYLRLFEV LKDNQAISNN ISVIESHLIT TFFSNSKAKK DAFMSIAKFE   120
VNNPQVQRQA FNELIRVVHQ LLPESSLRSA GGGGSGGGSS HGTVIESLES LNNYFNSSGI   180
PCNVSDYDGP SEQNFDWSFS SLGSSFVELA STWEVGFPAQ LYQERLQRGE ILLRRTANDA   240
VELHIKNVQP SDQGHYKCST PSTDATVQGN YEDTVQVKVL ADSLHVGPSA RPPPSLSLRE   300
GEPFELRCTA ASASPLHTHL ALLWEVHRGP ARRSVLALTH EGRFHPGLGY EQRYHSGDVR   360
LDTVGSDAYR LSVSRALSAD QGSYRCIVSE WIAEQGNWQE IQEKAVEVAT VVIQPSVLRA   420
AVPKNVSVAE GKELDLTCNI TTDRADDVRP EVTWSFSRMP DSTLPGSRVL ARLDRDSLVH   480
SSPHVALSHV DARSYHLLVR DVSKENSGYY YCHVSLWAPG HNRSWHKVAE AVSSPAGVGV   540
TWLEPDYQVY LNASKVPGFA DDPTELACRV VDTKSGEANV RFTVSWYYRM NRRSDNVVTS   600
ELLAVMDGDW TLKYGERSKQ RAQDGDFIFS KEHTDTFNFR IQRTTEEDRG NYYCVVSAWT   660
KQRNNSWVKS KDVFSKPVNI FWALEDSVLV VKARQPKPFF AAGNTFEMTC KVSSSKNIKSP   720
RYSVLIMAEK PVGDLSSPNE TKYIISLDQD SVVKLENWTD ASRVDGVVLE KVQEDEFRYR   780
MYQTQVSDAG LYRCMVTAWS PVRGSLWREA ATSLSNPIEI DFQTSGPIFN ASVHSDTPSV   840
IRGDLIKLFC IITVEGAALD PDDMAFDVSW FAVHSFGLDK APVLLSSLDR KGIVTTSRRD   900
WKSDLSLERV SVLEFLLQVH GSEDQDFGNY YCSVTPWVKS PTGSWQKEAE IHSKPVFITV   960
KMDVLNAFKY PLLIGVGLST VIGLLSCLIG YCSSHWCCKK EVQETRRERR RLMSMEMD    1018

SEQ ID NO: 10           moltype = AA  length = 1156
FEATURE                 Location/Qualifiers
source                  1..1156
                        mol_type = protein
                        organism = synthetic construct
SEQUENCE: 10
MGRLASRPLL LALLSLALCR GRHGTVIESL ESLNNYFNSS GIDVEEKSLF LDIWRNWQKD    60
GDMKILQSQI ISFYLRLFEV LKDNQAISNN ISVIESHLIT TFFSNSKAKK DAFMSIAKFE   120
VNNPQVQRQA FNELIRVVHQ LLPESSLRGS GGSGGSGGSG HGTVIESLES LNNYFNSSGI   180
DVEEKSLFLD IWRNWQKDGD MKILQSQIIS FYLRLFEVLK DNQAISNNVI SIESHLITTF   240
FSNSKAKKDA FMSIAKFEVN NPQVQRQAFN ELIRVVHQLL PESSLRSAGG GGSGGGGSRV   300
VRVPTATLVR VVGTELVIPC NVSDYDGPSE QNFDWSFSSL GSSFVELAST WEVGFPAQLY   360
QERLQRGEIL LRRTANDAVE LHIKNVQPSD QGHYKCSTPS TDATVQGNYE DTVQVKVLAD   420
SLHVGPSARP PPSLSLREGE PFELRCTAAS ASPLHTHLAL LWEVHRGPAR RSVLALTHEG   480
RFHPGLGYEQ RYHSGDVRLD TVGSDAYRLS VSRALSADQG SYRCIVSEWI AEQGNWQEIQ   540
EKAVEVATVV IQPSVLRAAV PKNVSVAEGK ELDLTCNITT DRADDVRPEV TWSFSRMPDS   600
TLPGSRVLAR LDRDSLVHSS PHVALSHVDA RSYHLLVRDV SKENSGYYYC HVSLWAPGHN   660
RSWHKVAEAV SSPAGVGVTW LEPDYQVYLN ASKVPGFADD PTELACRVVD TKSGEANVRF   720
TVSWYYRMNR RSDNVVTSEL LAVMDGDWTL KYGERSKQRA QDGDFIFSKE HTDTFNFRIQ   780
RTTEEDRGNY YCVVSAWTKQ RNNSWVKSKD VFSKPVNIFW ALEDSVLVVK ARQPKPFFAA   840
GNTFEMTCKV SSSKNIKSPRY SVLIMAEKPV GDLSSPNETK YIISLDQDSV VKLENWTDAS   900
RVDGVVLEKV QEDEFRYRMY QTQVSDAGLY RCMVTAWSPV RGSLWREAAT SLSNPIEIDF   960
QTSGPIFNAS VHSDTPSVIR GDLIKLFCII TVEGAALDPD DMAFDVSWFA VHSFGLDKAP  1020
VLLSSLDRKG IVTTSRRDWK SDLSLERVSV LEFLLQVHGS EDQDFGNYYC SVTPWVKSPT  1080
GSWQKEAEIH SKPVFITVKM DVLNAFKYPL LIGVGLSTVI GLLSCLIGYC SSHWCCKKEV  1140
QETRRERRRL MSMEMD                                                  1156

SEQ ID NO: 11           moltype = AA  length = 422
FEATURE                 Location/Qualifiers
source                  1..422
```

```
                              mol_type = protein
                              organism = synthetic construct
SEQUENCE: 11
MAPRRARGCR TLGLPALLLL LLLRPPATRG ITCPPPMSVE HADIWVKSYS LYSRERYICN    60
SGFKRKAGTS SLTECVLNKA TNVAHWTTPS LKCIRDPALV HQRPAPPSTV TTAGVTPQPE   120
SLSPSGKEPA ASSPSSNNTA ATTAAIVPGS QLMPSKSPST GTTEISSHES SHGTPSQTTA   180
KNWELTASAS HQPPGVYPQG HSDTTGGSGG GSGGGGSGGG GSGGGGSGGSN WVNVISDLKK   240
IEDLIQSMHI DATLYTESDV HPSCKVTAMK CFLLELQVIS LESGDASIHD TVENLIILAN   300
NSLSSNGNVT ESGCKECEEL EEKNIKEFLQ SFVHIVQMFI NTSSADYKDD DDKFEGGGGS   360
GGGGSAVGQD TQEVIVVPHS LPFKVVVISA ILALVVLTII SLIILIMLWQ KKPRSGLLTG   420
RT                                                                  422

SEQ ID NO: 12        moltype = AA  length = 456
FEATURE              Location/Qualifiers
source               1..456
                     mol_type = protein
                     organism = synthetic construct
SEQUENCE: 12
MAPRRARGCR TLGLPALLLL LLLRPPATRG HHHHHHITCP PPMSVEHADI WVKSYSLYSR    60
ERYICNSGFK RKAGTSSLTE CVLNKATNVA HWTTPSLKCI RDPALVHQRP APPSTVTTAG   120
VTPQPESLSP SGKEPAASSP SSNNTAATTA AIVPGSQLMP SKSPSTGTTE ISSHESSHGT   180
PSQTTAKNWE LTASASHQPP GVYPQGHSDT TGGSGGSGG GGSTLDPRSF LLRNPNDKYE    240
PFWEDEEKNE SGGGGSGGGS GGSNWVNVIS DLKKIEDLIQ SMHIDATLYT ESDVHPSCKV   300
TAMKCFLLEL QVISLESGDA SIHDTVENLI ILANNSLSSN GNVTESGCKE CEELEEKNIK   360
EFLQSFVHIV QMFINTSSAD YKDDDDKFEG GGSGGGGSA VGQDTQEVIV VPHSLPFKVV   420
VISAILALVV LTIISLIILI MLWQKKPRSG LLTGRT                             456

SEQ ID NO: 13        moltype = AA  length = 412
FEATURE              Location/Qualifiers
source               1..412
                     mol_type = protein
                     organism = synthetic construct
SEQUENCE: 13
METDTLLLWV LLLWVPGSTG NWVNVISDLK KIEDLIQSMH IDATLYTESD VHPSCKVTAM    60
KCFLLELQVI SLESGDASIH DTVENLIILA NNSLSSNGNV TESGCKECEE LEEKNIKEFL   120
QSFVHIVQMF INTSGGSGGG SGGGGSGGGG SGGGSGGSIT CPPPMSVEHA DIWVKSYSLY   180
SRERYICNSG FKRKAGTSSL TECVLNKATN VAHWTTPSLK CIRDPALVHQ RPAPPSTVTT   240
AGVTPQPESL SPSGKEPAAS SPSSNNTAAT TAAIVPGSQL MPSKSPSTGT TEISSHESSH   300
GTPSQTTAKN WELTASASHQ PPGVYPQGHS DTTSADYKDD DDKFEGGGGS GGGGSAVGQD   360
TQEVIVVPHS LPFKVVVISA ILALVVLTII SLIILIMLWQ KKPRSGLLTG RT            412

SEQ ID NO: 14        moltype = AA  length = 446
FEATURE              Location/Qualifiers
source               1..446
                     mol_type = protein
                     organism = synthetic construct
SEQUENCE: 14
METDTLLLWV LLLWVPGSTG NWVNVISDLK KIEDLIQSMH IDATLYTESD VHPSCKVTAM    60
KCFLLELQVI SLESGDASIH DTVENLIILA NNSLSSNGNV TESGCKECEE LEEKNIKEFL   120
QSFVHIVQMF INTSDYKDDD DKGGSGGGSG GGGSTLDPRS FLLRNPNDKY EPFWEDEEKN   180
ESGGGGSGGG SGGSITCPPP MSVEHADIWV KSYSLYSRER YICNSGFKRK AGTSSLTECV   240
LNKATNVAHW TTPSLKCIRD PALVHQRPAP PSTVTTAGVT PQPESLSPSG KEPAASSPSS   300
NNTAATTAAI VPGSQLMPSK SPSTGTTEIS SHESSHGTPS QTTAKNWELT ASASHQPPGV   360
YPQGHSDTTS AFEGGGGSGG GGSAVGQDTQ EVIVVPHSLP FKVVVISAIL ALVVLTIISL   420
IILIMLWQKK PRSGLLTGRT HHHHHH                                       446

SEQ ID NO: 15        moltype = AA  length = 1239
FEATURE              Location/Qualifiers
source               1..1239
                     mol_type = protein
                     organism = synthetic construct
SEQUENCE: 15
METDTLLLWV LLLWVPGSTG NWVNVISDLK KIEDLIQSMH IDATLYTESD VHPSCKVTAM    60
KCFLLELQVI SLESGDASIH DTVENLIILA NNSLSSNGNV TESGCKECEE LEEKNIKEFL   120
QSFVHIVQMF INTSGGSSGS GSGSTGTSSS GTGTSAGTTG TSASTSGSGS GGGGSGGGG   180
SAGGTATAGA SSGSITCPPP MSVEHADIWV KSYSLYSRER YICNSGFKRK AGTSSLTECV   240
LNKATNVAHW TTPSLKCIRD PALVHQRPAP PSTVTTAGVT PQPESLSPSG KEPAASSPSS   300
NNTAATTAAI VPGSQLMPSK SPSTGTTEIS SHESSHGTPS QTTAKNWELT ASASHQPPGV   360
YPQGHSDTTS AGGGGSGGGG SRVVRVPTAT LVRVVGTELV IPCNVSDYDG PSEQNFDWSF   420
SSLGSSFVEL ASTWEVGFPA QLYQERLQRG EILLRRTAND AVELHIKNVQ PSDQGHYKCS   480
TPSTDATVQG NYEDTVQVKV LADSLHVGPS ARPPPSLSLR EGEPFELRCT AASASPLHTH   540
LALLWEVHRG PARRRSVLALT HEGRFHPGLG YEQRYHSGDV RLDTVGSDAY RLSVSRALSA   600
DQGSYRCIVS EWIAEQGNWQ EIQEKAVEVA TVVIQPSVLR AAVPKNVSVA EGKELDLTCN   660
ITTDRADDVR PEVTWSFSRM PDSTLPGSRV LARLDRDSLV HSSPHVALSH VDARSYHLLV   720
RDVSKENSGY YYCHVSLWAP GHNRSWHKVA EAVSSPAGVG VTWLEPDYQV YLNASKVPGF   780
ADDPTELACR VVDTKSGEAN VRFTVSWYYR MNRRSDNVVT SELLAVMDGD WTLKYGERSK   840
QRAQDGDFIF SKEHTDTFNF RIQRTTEEDR GNYYCVVSAW TKQRNNSWVK SKDVFSKPVN   900
IFWALEDSVL VVKARQPKPF FAAGNTFEMT CKVSSKNIKS PRYSVLIMAE KPVGDLSSPN   960
ETKYIISLDQ DSVVKLENWT DASRVDGVVL EKVQEDEFRY RMYQTQVSDA GLYRCMVTAW  1020
```

```
SPVRGSLWRE AATSLSNPIE IDFQTSGPIF NASVHSDTPS VIRGDLIKLF CIITVEGAAL    1080
DPDDMAFDVS WFAVHSFGLD KAPVLLSSLD RKGIVTTSRR DWKSDLSLER VSVLEFLLQV    1140
HGSEDQDFGN YYCSVTPWVK SPTGSWQKEA EIHSKPVFIT VKMDVLNAFK YPLLIGVGLS    1200
TVIGLLSCLI GYCSSHWCCK KEVQETRRER RRLMSMEMD                          1239

SEQ ID NO: 16           moltype = AA  length = 1239
FEATURE                 Location/Qualifiers
source                  1..1239
                        mol_type = protein
                        organism = synthetic construct
SEQUENCE: 16
METDTLLLWV LLLWVPGSTG NWVNVISDLK KIEDLIQSMH IDATLYTESD VHPSCKVTAM    60
KCFLLELQVI SLESGDASIH DTVENLIILA NDSLSSNGNV TESGCKECEE LEEKNIKEFL    120
QSFVHIVQMF INTSGSSGS GSGSTGTSSS GTGTSAGTTG TSASTSGSGS GGGGSGGGG      180
SAGGTATAGA SSGSITCPPP MSVEHADIWV KSYSLYSRER YICNSGFKRK AGTSSLTECV    240
LNKATNVAHW TTPSLKCIRD PALVHQRPAP PSTVTTAGVT PQPESLSPSG KEPAASSPSS    300
NNTAATTAAI VPGSQLMPSK SPSTGTTEIS SHESSHGPSR QTTAKNWELT ASASHQPPGV    360
YPQGHSDTTS AGGGGSGGGG SRVVRVPTAT LVRVVGTELV IPCNVSDYDG PSEQNFDWSF    420
SSLGSSFVEL ASTWEVGFPA QLYQERLQRG EILLRRTAND AVELHIKNVQ PSDQGHYKCS    480
TPSTDATVQG NYEDTVQVKV LADSLHVGPS ARPPPSLSLR EGEPFELRCT AASASPLHTH    540
LALLWEVHRG PARRSVLALT HEGRFHPGLG YEQRYHSGDV RLDTVGSDAY RLSVSRALSA    600
DQGSYRCIVS EWIAEQGNWQ EIQEKAVEVA TVVIQPSVLR AAVPKNVSVA EGKELDLTCN    660
ITTDRADDVR PEVTWSFSRM PDSTLPGSRV LARLDRDSLV HSSPHVALSH VDARSYHLLV    720
RDVSKENSGY YYCHVSLWAP GHNRSWHKVA EAVSSPAGVG VTWLEPDYQV YLNASKVPGF    780
ADDPTELACR VVDTKSGEAN VRFTVSWYYR MNRRSDNVVT SELLAVMDGD WTLKYGERSK    840
QRAQDGDFIF SKEHTDTFNF RIQRTTEEDR GNYYCVVSAW TKQRNNSWVK SKDVFSKPVN    900
IFWALEDSVL VVKARQPKPF FAAGNTFEMT CKVSSKNIKS PRYSVLIMAE KPVGDLSSPN    960
ETKYIISLDQ DSVVKLENWT DASRVDGVVL EKVQEDEFRY RMYQTQVSDA GLYRCMVTAW    1020
SPVRGSLWRE AATSLSNPIE IDFQTSGPIF NASVHSDTPS VIRGDLIKLF CIITVEGAAL    1080
DPDDMAFDVS WFAVHSFGLD KAPVLLSSLD RKGIVTTSRR DWKSDLSLER VSVLEFLLQV    1140
HGSEDQDFGN YYCSVTPWVK SPTGSWQKEA EIHSKPVFIT VKMDVLNAFK YPLLIGVGLS    1200
TVIGLLSCLI GYCSSHWCCK KEVQETRRER RRLMSMEMD                          1239

SEQ ID NO: 17           moltype = AA  length = 602
FEATURE                 Location/Qualifiers
source                  1..602
                        mol_type = protein
                        organism = synthetic construct
SEQUENCE: 17
MKIICLALVA LLLTAQPAMA EIVLTQSPAT LSLSPGERAT LSCRASQSVS SYLAWYQQKP    60
GQAPRLLIYD ASNRATGIPA RFSGSGSGTD FTLTISSLEP EDFAVYYCQQ RSNWPPLTFG    120
GGTKVEIKRT VAAPSVFIFP PSDEQLKSGT ASVVCLLNNF YPREAKVQWK VDNALQSGNS    180
QESVTEQDSK DSTYSLSSTL TLSKADYEKH KVYACEVTHQ GLSSPVTKSF NRGECGGSSG    240
SGSGSTGTSS SGTGTSAGTT GTSASTSGSG SGGGGGSGGG GSAGGTATAG ASSGSQVQLV    300
ESGGGVVQPG RSLRLSCAAS GFKFSGYGMH WVRQAPGKGL EWVAVIWYDG SKKYYVDSVK    360
GRFTISRDNS KNTLYLQMNS LRAEDTAVYY CARQMGYWHF DLWGRGTLVT VSSASTKGPS    420
VFPLAPSSKS TSGGTAALGC LVKDYFPEPV TVSWNSGALT SGVHTFPAVL QSSGLYSLSS    480
VVTVPSSSLG TQTYICNVNH KPSNTKVDKK VEPKSCDKTH TGGSGGGSGG GGSGGGGSGG    540
GSGGGSAVGQD TQEVIVVPHS LPFKVVVISA ILALVVLTII SLIILIMLWQ KKPRDYKDDD    600
DK                                                                  602

SEQ ID NO: 18           moltype = AA  length = 1656
FEATURE                 Location/Qualifiers
source                  1..1656
                        mol_type = protein
                        organism = synthetic construct
SEQUENCE: 18
MKIICLALVA LLLTAQPAMA EIVLTQSPAT LSLSPGERAT LSCRASQSVS SYLAWYQQKP    60
GQAPRLLIYD ASNRATGIPA RFSGSGSGTD FTLTISSLEP EDFAVYYCQQ RSNWPPLTFG    120
GGTKVEIKRT VAAPSVFIFP PSDEQLKSGT ASVVCLLNNF YPREAKVQWK VDNALQSGNS    180
QESVTEQDSK DSTYSLSSTL TLSKADYEKH KVYACEVTHQ GLSSPVTKSF NRGECGSSG     240
SGSGSTGTSS SGTGTSAGTT GTSASTSGSG SGGGGGSGGG GSAGGTATAG ASSGSQVQLV    300
ESGGGVVQPG RSLRLSCAAS GFKFSGYGMH WVRQAPGKGL EWVAVIWYDG SKKYYVDSVK    360
GRFTISRDNS KNTLYLQMNS LRAEDTAVYY CARQMGYWHF DLWGRGTLVT VSSASTKGPS    420
VFPLAPSSKS TSGGTAALGC LVKDYFPEPV TVSWNSGALT SGVHTFPAVL QSSGLYSLSS    480
VVTVPSSSLG TQTYICNVNH KPSNTKVDKK VEPKSCDKTH TGGSGGGSGG GGSGGGGSGG    540
GSGGSRVVRV PTATLVRVVG TELVIPCNVS DYDGPSEQNF DWSFSSLGSS FVELASTWEV    600
GFPAQLYQER LQRGEILLRR TANDAVELHI KNVQPSDQGH YKCSTPSTDA TVQGNYEDTV    660
QVKVLADSLH VGPSARPPPS LSLREGEPFE LRCTAASASP LHTHLALLWE VHRGPARRSV    720
LALTHEGRFH PGLGYEQRYH SGDVRLDTVG SDAYRLSVSR ALSADQGSYR CIVSEWIAEQ    780
GNWQEIQEKA VEVATVVIQP SVLRAAVPKN VSVAEGKELD LTCNITTDRA DDVRPEVTWS    840
FSRMPDSTLP GSRVLARLDR DSLVHSSPHV ALSHVDARSY HLLVRDVSKE NSGYYYCHVS    900
LWAPGHNRSW HKVAEAVSSP AGVGVTWLEP DYQVYLNASK VPGFADDPTE LACRVVDTKS    960
GEANVRFTVS WYYRMNRRSD NVVTSELLAV MDGDWTLKYG ERSKQRAQDG DFIFSKEHTD    1020
TFNFRIQRTT EEDRGNYYCV VSAWTKQRNN SWVKSKDVFS KPVNIFWALE DSVLVVKARQ    1080
PKPFFAAGNT FEMTCKVSSK NIKSPRYSVL IMAEKPVGDL SSPNETKYII SLDQDSVVKL    1140
ENWTDASRVD GVVLEKVQED EFRYRMYQTQ VSDAGLYRCM VTAWSPVRGS LWREAATSLS    1200
NPIEIDFQTS GPIFNASVHS DTPSVIRGDL IKLFCIITVE GAALDPDDMA FDVSWFAVHS    1260
FGLDKAPVLL SSLDRKGIVT TSRRDWKSDL SLERVSVLEF LLQVHGSEDQ DFGNYYCSVT    1320
```

```
PWVKSPTGSW QKEAEIHSKP VFITVKMDVL NAFKYPLLIG VGLSTVIGLL SCLIGYCSSH  1380
WCCKKEVQET RRERRRLMSM EMDTGGSGGS VSKGEELFTG VVPILVELDG DVNGHKFSVS  1440
GEGEGDATYG KLTLKFICTT GKLPVPWPTL VTTLTYGVQC FSRYPDHMKQ HDFFKSAMPE  1500
GYVQERTIFF KDDGNYKTRA EVKFEGDTLV NRIELKGIDF KEDGNILGHK LEYNYNSHNV  1560
YIMADKQKNG IKVNFKIRHN IEDGSVQLAD HYQQNTPIGD GPVLLPDNHY LSTQSKLSKD  1620
PNEKRDHMVL LEFVTAAGIT LGMDELYKDY KDDDDK                            1656

SEQ ID NO: 19          moltype = AA  length = 1361
FEATURE                Location/Qualifiers
source                 1..1361
                       mol_type = protein
                       organism = synthetic construct
SEQUENCE: 19
METDTLLLWV LLLWVPGSTG MQRGDEDPQI AAHVVSEANS NAASVLQWAK KGYYTMKSNL   60
VMLENGKQLT VKREGLYYVY TQVTFCSNRE PSSQRPFIVG LWLKPSSGSE RILLKAANTH  120
SSSQLCEQQS VHLGGVFELQ AGASVFVNVT EASQVIHRVG FSSFGLLKLG SGGSGGSGGS  180
GMQRGDEDPQ IAAHVVSEAN SNAASVLQWA KKGYYTMKSN LVMLENGKQL TVKREGLYYV  240
YTQVTFCSNR EPSSQRPFIV GLWLKPSSGS ERILLKAANT HSSSQLCEQQ SVHLGGVFEL  300
QAGASVFVNV TEASQVIHRV GFSSFGLLKL GSGGSGGSGG SGMQRGDEDP QIAAHVVSEA  360
NSNAASVLQW AKKGYYTMKS NLVMLENGKQ LTVKREGLYY VYTQVTFCSN REPSSQRPFI  420
VGLWLKPSSG SERILLKAAN THSSSQLCEQ QSVHLGGVFE LQAGASVFVN VTEASQVIHR  480
VGFSSFGLLK LSAGGGGSGG GGSRVVRVPT ATLVRVVGTE LVIPCNVSDY DGPSEQNFDW  540
SFSSLGSSFV ELASTWEVGF PAQLYQERLQ RGEILLRRTA NDAVELHIKN VQPSDQGHYK  600
CSTPSTDATV QGNYEDTVQV KVLADSLHVG PSARPPPSLS LREGEPFELR CTAASASPLH  660
THLALLWEVH RGPARRSVLA LTHEGRFHPG LGYEQRYHSG DVRLDTVGSD AYRLSVSRAL  720
SADQGSYRCI VSEWIAEQGN WQEIQEKAVE VATVVIQPSV LRAAVPKNVS VAEGKELDLT  780
CNITTDRADD VRPEVTWSFS RMPDSTLPGS RVLARLDRDS LVHSSPHVAL SHVDARSYHL  840
LVRDVSKENS GYYYCHVSLW APGHNRSWHK VAEAVSSPAG VGVTWLEPDY QVYLNASKVP  900
GFADDPTELA CRVVDTKSGE ANVRFTVSWY YRMNRRSDNV VTSELLAVMD GDWTLKYGER  960
SKQRAQDGDF IFSKEHTDTF NFRIQRTTEE DRGNYYCVVS AWTKQRNNSW VKSKDVFSKP 1020
VNIFWALEDS VLVVKARQPK PFFAAGNTFE MTCKVSSKNI KSPRYSVLIM AEKPVGDLSS 1080
PNETKYIISL DQDSVVKLEN WTDASRVDGV VLEKVQEDEF RYRMYQTQVS DAGLYRCMVT 1140
AWSPVRGSLW REAATSLSNP IEIDFQTSGP IFNASVHSDT PSVIRGDLIK LFCIITVEGA 1200
ALDPDDMAFD VSWFAVHSFG LDKAPVLLSS LDRKGIVTTS RRDWKSDLSL ERVSVLEFLL 1260
QVHGSEDQDF GNYYCSVTPW VKSPTGSWQK EAEIHSKPVF ITVKMDVLNA FKYPLLIGVG 1320
LSTVIGLLSC LIGYCSSHWC CKKEVQETRR ERRRLMSMEM D                    1361

SEQ ID NO: 20          moltype = AA  length = 1361
FEATURE                Location/Qualifiers
source                 1..1361
                       mol_type = protein
                       organism = synthetic construct
SEQUENCE: 20
METDTLLLWV LLLWVPGSTG MQKGDQNPQI AAHVISEASS KTTSVLQWAE KGYYTMSNNL   60
VTLENGKQLT VKRQGLYYIY AQVTFCSNRE ASSQAPFIAS LCLKSPGRFE RILLRAANTH  120
SSAKPCGQQS IHLGGVFELQ PGASVFVNVT DPSQVSHGTG FTSFGLLKLG SGGSGGSGGS  180
GMQKGDQNPQ IAAHVISEAS KTTSVLQWAE KGYYTMSNN LVTLENGKQL TVKRQGLYYI  240
YAQVTFCSNR EASSQAPFIA SLCLKSPGRF ERILLRAANT HSSAKPCGQQ SIHLGGVFEL  300
QPGASVFVNV TDPSQVSHGT GFTSFGLLKL GSGGSGGSGG SGMQKGDQNP QIAAHVISEA  360
SSKTTSVLQW AEKGYYTMSN NLVTLENGKQ LTVKRQGLYY IYAQVTFCSN REASSQAPFI  420
ASLCLKSPGR FERILLRAAN THSSAKPCGQ QSIHLGGVFE LQPGASVFVN VTDPSQVSHG  480
TGFTSFGLLK LSAGGGGSGG GGSRVVRVPT ATLVRVVGTE LVIPCNVSDY DGPSEQNFDW  540
SFSSLGSSFV ELASTWEVGF PAQLYQERLQ RGEILLRRTA NDAVELHIKN VQPSDQGHYK  600
CSTPSTDATV QGNYEDTVQV KVLADSLHVG PSARPPPSLS LREGEPFELR CTAASASPLH  660
THLALLWEVH RGPARRSVLA LTHEGRFHPG LGYEQRYHSG DVRLDTVGSD AYRLSVSRAL  720
SADQGSYRCI VSEWIAEQGN WQEIQEKAVE VATVVIQPSV LRAAVPKNVS VAEGKELDLT  780
CNITTDRADD VRPEVTWSFS RMPDSTLPGS RVLARLDRDS LVHSSPHVAL SHVDARSYHL  840
LVRDVSKENS GYYYCHVSLW APGHNRSWHK VAEAVSSPAG VGVTWLEPDY QVYLNASKVP  900
GFADDPTELA CRVVDTKSGE ANVRFTVSWY YRMNRRSDNV VTSELLAVMD GDWTLKYGER  960
SKQRAQDGDF IFSKEHTDTF NFRIQRTTEE DRGNYYCVVS AWTKQRNNSW VKSKDVFSKP 1020
VNIFWALEDS VLVVKARQPK PFFAAGNTFE MTCKVSSKNI KSPRYSVLIM AEKPVGDLSS 1080
PNETKYIISL DQDSVVKLEN WTDASRVDGV VLEKVQEDEF RYRMYQTQVS DAGLYRCMVT 1140
AWSPVRGSLW REAATSLSNP IEIDFQTSGP IFNASVHSDT PSVIRGDLIK LFCIITVEGA 1200
ALDPDDMAFD VSWFAVHSFG LDKAPVLLSS LDRKGIVTTS RRDWKSDLSL ERVSVLEFLL 1260
QVHGSEDQDF GNYYCSVTPW VKSPTGSWQK EAEIHSKPVF ITVKMDVLNA FKYPLLIGVG 1320
LSTVIGLLSC LIGYCSSHWC CKKEVQETRR ERRRLMSMEM D                    1361

SEQ ID NO: 21          moltype = AA  length = 991
FEATURE                Location/Qualifiers
source                 1..991
                       mol_type = protein
                       organism = synthetic construct
SEQUENCE: 21
MKIICLALVA LLLTAQPAMA EIVLTQSPAT LSLSPGERAT LSCRASQSVS SYLAWYQQKP   60
GQAPRLLIYD ASNRATGIPA RFSGSGSGTD FTLTISSLEP EDFAVYYCQQ RSNWPPLTFG  120
GGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGECGGSSG  240
SGSGSTGSS SGTGTSAGTT GTSASTSGSG SGGGGGSGGG GSAGGTATAG ASSGSQVQLV  300
ESGGGVVQPG RSLRLSCAAS GFKFSGYGMH WVRQAPGKGL EWVAVIWYDG SKKYYVDSVK  360
```

```
GRFTISRDNS KNTLYLQMNS LRAEDTAVYY CARQMGYWHF DLWGRGTLVT VSSASTKGPS  420
VFPLAPSSKS TSGGTAALGC LVKDYFPEPV TVSWNSGALT SGVHTFPAVL QSSGLYSLSS  480
VVTVPSSSLG TQTYICNVNH KPSNTKVDKK VEPKSCDKTH TGGSGGGSGG GGSGGGGSGG  540
GSGGGSGPIFN ASVHSDTPSV IRGDLIKLFC IITVEGAALD PDDMAFDVSW FAVHSFGLDK  600
APVLLSSLDR KGIVTTSRRD WKSDLSLERV SVLEFLLQVH GSEDQDFGNY YCSVTPWVKS  660
PTGSWQKEAE IHSKPVFITV KMDVLNAFKY PLLIGVGLST VIGLLSCLIG YCSSHWCCKK  720
EVQETRRERR RLMSMEMDTG GSGGGSVSKGE ELFTGVVPIL VELDGDVNGH KFSVSGEGEG  780
DATYGKLTLK FICTTGKLPV PWPTLVTTLT YGVQCFSRYP DHMKQHDFFK SAMPEGYVQE  840
RTIFFKDDGN YKTRAEVKFE GDTLVNRIEL KGIDFKEDGN ILGHKLEYNY NSHNVYIMAD  900
KQKNGIKVNF KIRHNIEDGS VQLADHYQQN TPIGDGPVLL PDNHYLSTQS KLSKDPNEKR  960
DHMVLLEFVT AAGITLGMDE LYKDYKDDDD K                                991

SEQ ID NO: 22         moltype = AA  length = 1055
FEATURE               Location/Qualifiers
source                1..1055
                      mol_type = protein
                      organism = synthetic construct
SEQUENCE: 22
MTVLAPAWSP TTYLLLLLLL SSGLSGTQDC SFQHSPISSD FAVKIRELSD YLLQDYPVTV   60
ASNLQDEELC GGLWRLVLAQ RWMERLKTVA GSKMQGLLER VNTEIHFVTK CAFQPPPSCL  120
RFVQTNISRL LQETSEQLVA LKPWITRQNF SRCLELQCQP DSSTLPPPWS PRPLEATAPT  180
APQPPSAGGG GSGGGGSRVV RVPTATLVRV VGTELVIPCN VSDYDGPSEQ NFDWSFSSLG  240
SSFVELASTW EVGFPAQLYQ ERLQRGEILL RRTANDAVEL HIKNVQPSDQ GHYKCSTPST  300
DATVQGNYED TVQVKVLADS LHVGPSARPP PSLSLREGEP FELRCTAASA SPLHTHLALL  360
WEVHRGPARR SVLALTHEGR FHPGLGYEQR YHSGDVRLDT VGSDAYRLSV SRALSADQGS  420
YRCIVSEWIA EQGNWQEIQE KAVEVATVVI QPSVLRAAVP KNVSVAEGKE LDLTCNITTD  480
RADDVRPEVT WSFSRMPDST LPGSRVLARL DRDSLVHSSP HVALSHVDAR SYHLLVRDVS  540
KENSGYYYCH VSLWAPGHNR SWHKVAEAVS SPAGVGVTWL EPDYQVYLNA SKVPGFADDP  600
TELACRVVDT KSGEANVRFT VSWYYRMNRR SDNVVTSELL AVMDGDWTLK YGERSKQRAQ  660
DGDFIFSKEH TDTFNPRIQR TTEEDRGNYY CVVSAWTKQR NNSWVKSKDV FSKPVNIFWA  720
LEDSVLVVKA RQPKPFFAAG NTFEMTCKVS SKNIKSPRYS VLIMAEKPVG DLSSPNETKY  780
IISLDQDSVV KLENWTDASR VDGVVLEKVQ EDEFRYRMYQ TQVSDAGLYR CMVTAWSPVR  840
GSLWREAATS LSNPIEIDFQ TSGPIFNASV HSDTPSVIRG DLIKLFCIIT VEGAALDPDD  900
MAFDVSWFAV HSFGLDKAPV LLSSLDRKGI VTTSRRDWKS DLSLERVSVL EFLLQVHGSE  960
DQDFGNYYCS VTPWVKSPTG SWQKEAEIHS KPVFITVKMD VLNAFKYPLL IGVGLSTVIG 1020
LLSCLIGYCS SHWCCKKEVQ ETRRERRRLM SMEMD                           1055

SEQ ID NO: 23         moltype = AA  length = 38
FEATURE               Location/Qualifiers
source                1..38
                      mol_type = protein
                      organism = synthetic construct
SEQUENCE: 23
EHSAGGGGSD YKDDDDKGGG GSLSNPIEID FQTSGPIF                           38

SEQ ID NO: 24         moltype = AA  length = 34
FEATURE               Location/Qualifiers
source                1..34
                      mol_type = protein
                      organism = synthetic construct
SEQUENCE: 24
EHSAGGGGSD YKDDDDKGGG GSIEIDFQTS GPIF                               34

SEQ ID NO: 25         moltype = AA  length = 30
FEATURE               Location/Qualifiers
source                1..30
                      mol_type = protein
                      organism = synthetic construct
SEQUENCE: 25
EHSAGGGGSD YKDDDDKGGG GSFQTSGPIF                                    30

SEQ ID NO: 26         moltype = AA  length = 26
FEATURE               Location/Qualifiers
source                1..26
                      mol_type = protein
                      organism = synthetic construct
SEQUENCE: 26
EHSAGGGGSD YKDDDDKGGG GSGPIF                                        26
```